United States Patent
Yin et al.

(10) Patent No.: US 11,800,872 B2
(45) Date of Patent: Oct. 31, 2023

(54) SYSTEMS, METHODS AND COMPOSITION OF USING RNASE III MUTANTS TO PRODUCE SRNA TO CONTROL HOST PATHOGEN INFECTION

(71) Applicant: Pebble Labs Inc., Los Alamos, NM (US)

(72) Inventors: Guohua Yin, Los Alamos, NM (US); Erick Scott Lebrun, White Rock, NM (US); Timothy S. Travers, Los Alamos, NM (US)

(73) Assignee: Pebble Labs Inc., Los Alamos, NM (US)

( * ) Notice: Subject to any disclaimer, the term of this patent is extended or adjusted under 35 U.S.C. 154(b) by 123 days.

(21) Appl. No.: 17/044,237

(22) PCT Filed: Apr. 1, 2019

(86) PCT No.: PCT/US2019/025261
§ 371 (c)(1),
(2) Date: Sep. 30, 2020

(87) PCT Pub. No.: WO2019/191785
PCT Pub. Date: Oct. 3, 2019

(65) Prior Publication Data
US 2021/0017523 A1    Jan. 21, 2021

Related U.S. Application Data
(60) Provisional application No. 62/651,143, filed on Mar. 31, 2018.

(51) Int. Cl.
*C12N 9/22* (2006.01)
*A01N 63/60* (2020.01)
*C12N 15/113* (2010.01)

(52) U.S. Cl.
CPC .............. *A01N 63/60* (2020.01); *C12N 9/22* (2013.01); *C12N 15/113* (2013.01); *C12N 2310/14* (2013.01); *C12N 2320/51* (2013.01); *C12Y 301/26003* (2013.01)

(58) Field of Classification Search
None
See application file for complete search history.

(56) References Cited

U.S. PATENT DOCUMENTS

| | | |
|---|---|---|
| 2002/0078473 A1 | 6/2002 | Estruch et al. |
| 2007/0155684 A1 | 7/2007 | Maina et al. |
| 2011/0151558 A1 | 6/2011 | Brown et al. |
| 2016/0201103 A1 | 7/2016 | Yamazaki et al. |

FOREIGN PATENT DOCUMENTS

| | | |
|---|---|---|
| WO | 0121200 A1 | 3/2001 |
| WO | 2014/110205 A1 | 7/2014 |

OTHER PUBLICATIONS

Sun et al. Biochemistry 43:13054-62 (Year: 2004).*
Xiao et al. RNA 15: 984-991 (Year: 2009).*
Jin Lan et al: "The molecular mechanism of dsRNA processing by a bacterial Dicer", Nucleic Acids Research, vol. 47, No. 9, Mar. 27, 2019 (Mar. 27, 2019), pp. 4707-4720, XP055875288, GB ISSN: 0305-1048, DOI: 10.1093/nar/gkz208 * the whole document.
Ourt Donald L. et al: "RNase III: Genetics and Function; Structure and Mechanism", Annual Review of Genetics., vol. 47, No. 1, Nov. 23, 2013 (Nov. 23, 2013), pp. 405-431, XP055875298, us ISSN: 0066-4197, DOI: 10.1146/annurev-genet-110711-155618 Retrieved from the Internet: URL:https://www.annualreviews.org/doi/pdf/10.1146/annurev-genet-110711-155618> * abstract; figure 4 *.
European Supplemental Search Report in EP Application No. 19774947 dated Jan. 12, 2022, 11 pages.
International Search Report and Written Opinion dated Aug. 16, 2019 in International Application No. PCT/US19/25261, 15 pages.
Tenllado et al. Crude extracts of bacterially expressed dsRNA can be used to protect plants against virus infections. BMC Biotechnol Mar. 20, 2003 vol. 3 No. 3 pp. 1-11. Especially abstract.
Office Action in corresponding Thai Patent Application Serial No. 2001005605, dated Feb. 2, 2023 (English translation attached).
Office Action in corresponding Colombian Patent Application Serial No. NC2020/0013533, dated Jan. 16, 2023 (English translation attached).
Office Action in corresponding Indonesia Patent Application Serial No. P00202008057, dated Jan. 5, 2023.(English translation attached).
Office Action in corresponding Chinese Patent Application Serial No. 201980036281.7, dated Mar. 3, 2023 (Machine translation attached).

* cited by examiner

*Primary Examiner* — Brian Whiteman
(74) *Attorney, Agent, or Firm* — Hovey Williams LLP

(57) ABSTRACT

The current invention includes systems, methods and compositions for the generation of sRNA molecules using select RNase III mutants. In one preferred embodiment, invention includes systems, methods and compositions for the generation of sRNA molecules using RNase III mutants to control a host pathogen through the production and diffusion of sRNA molecules that may initiate an RNAi pathway response directed to a host pathogen. Additional embodiments of the current invention include systems, methods and compositions for the DICER-independent generation of sRNA molecules using select RNase III mutants.

20 Claims, 37 Drawing Sheets
Specification includes a Sequence Listing.

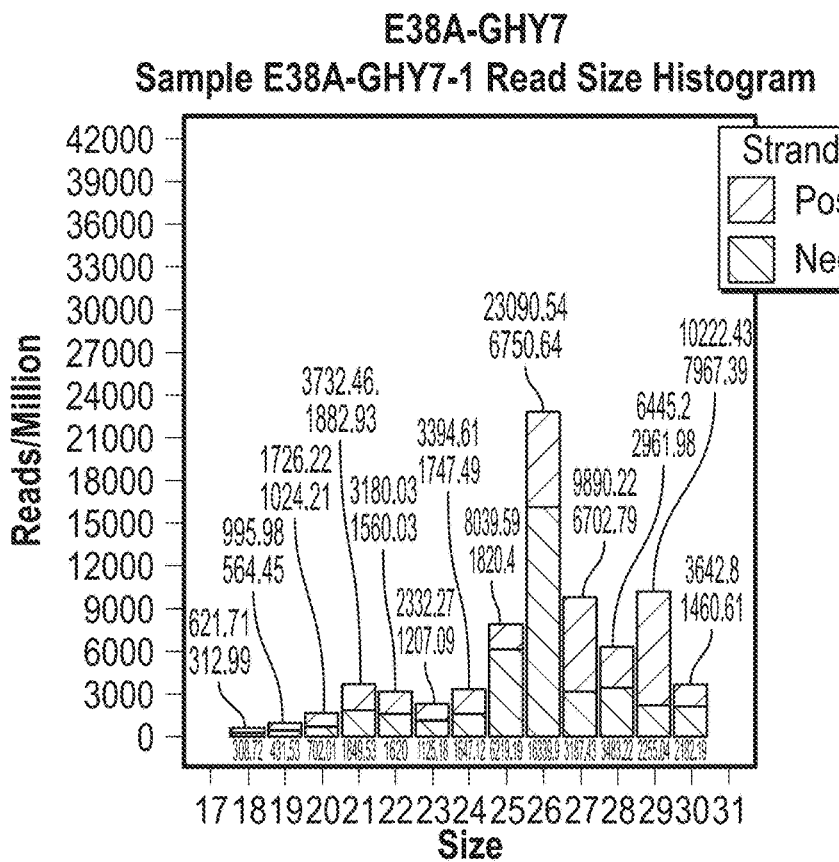
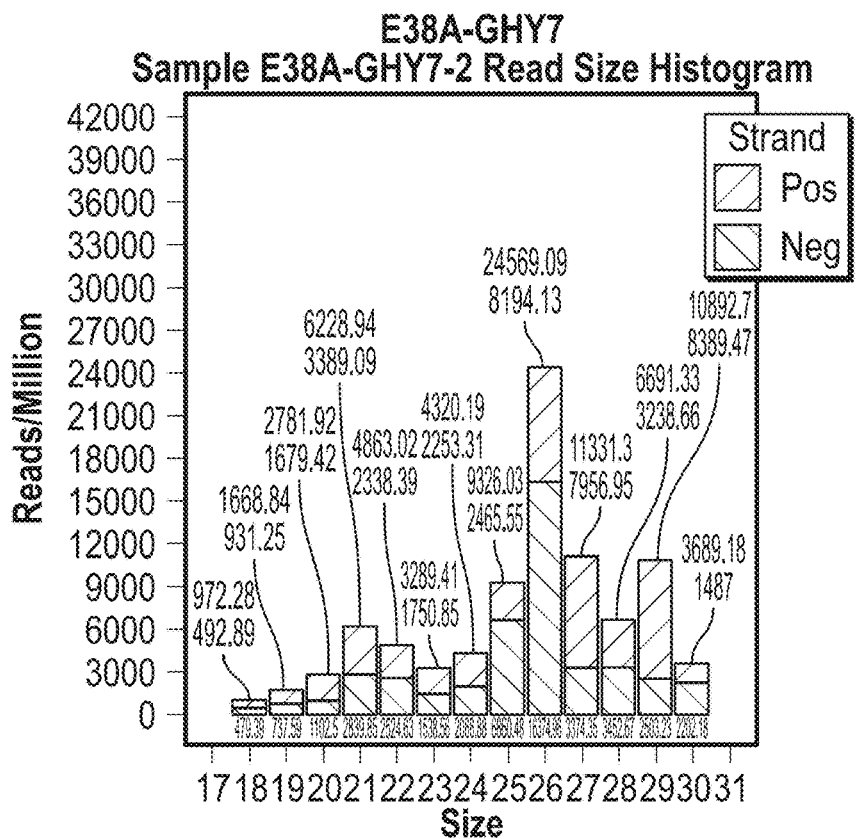
FIG. 24A-B

C
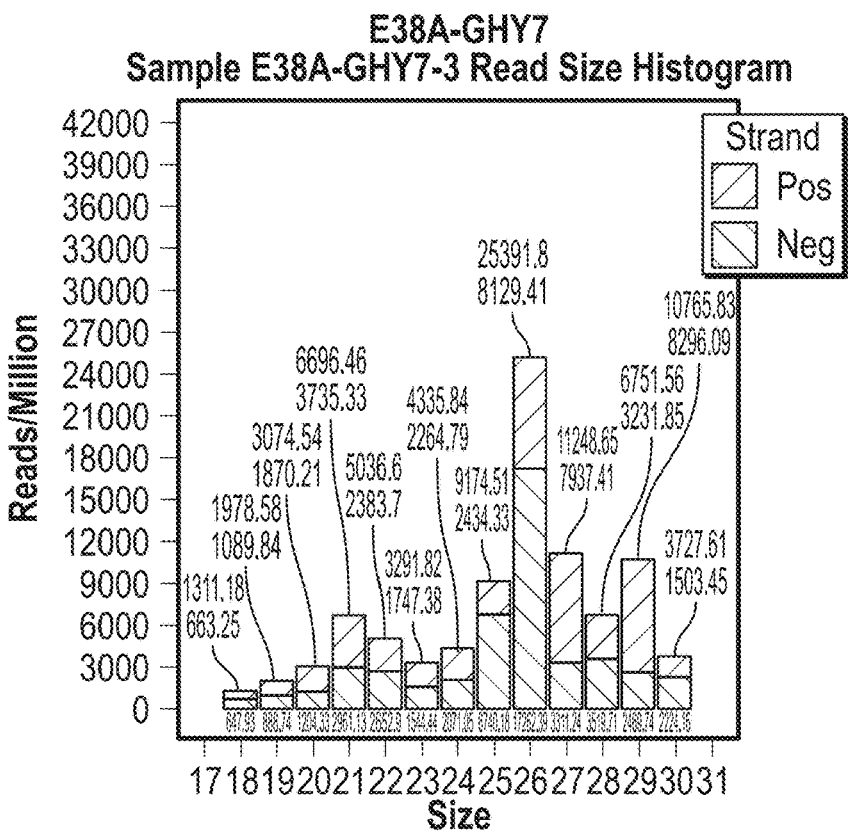
D
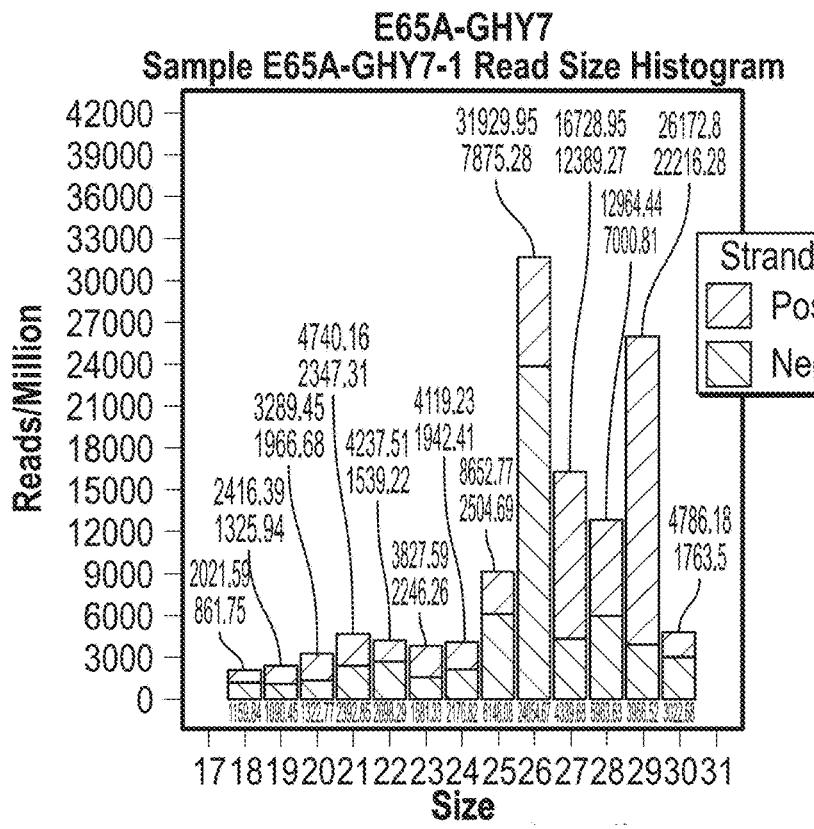
FIG. 24C-D

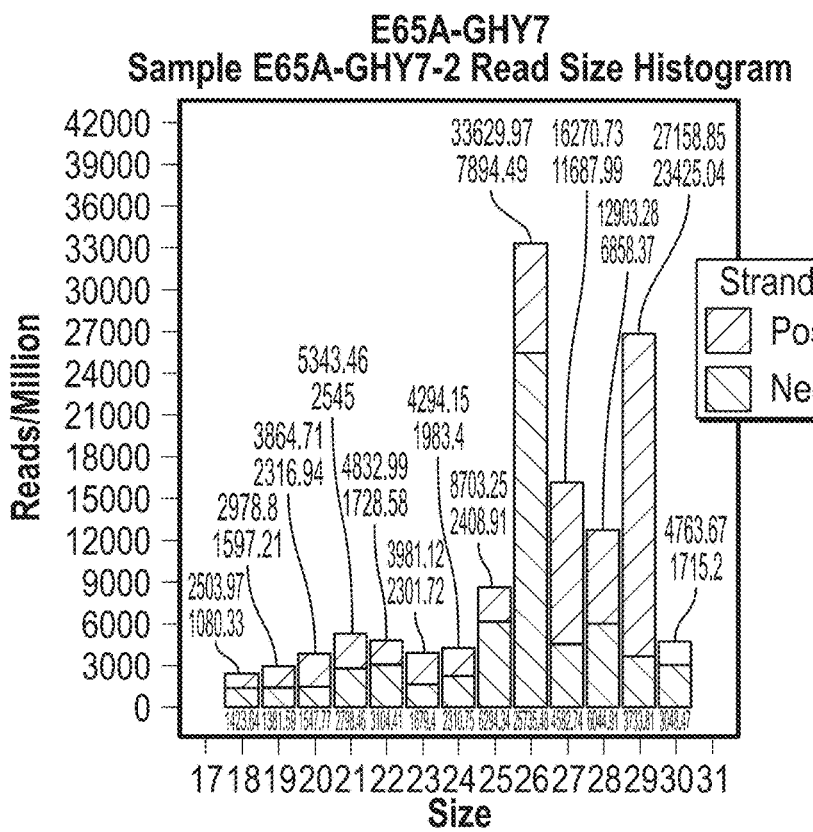
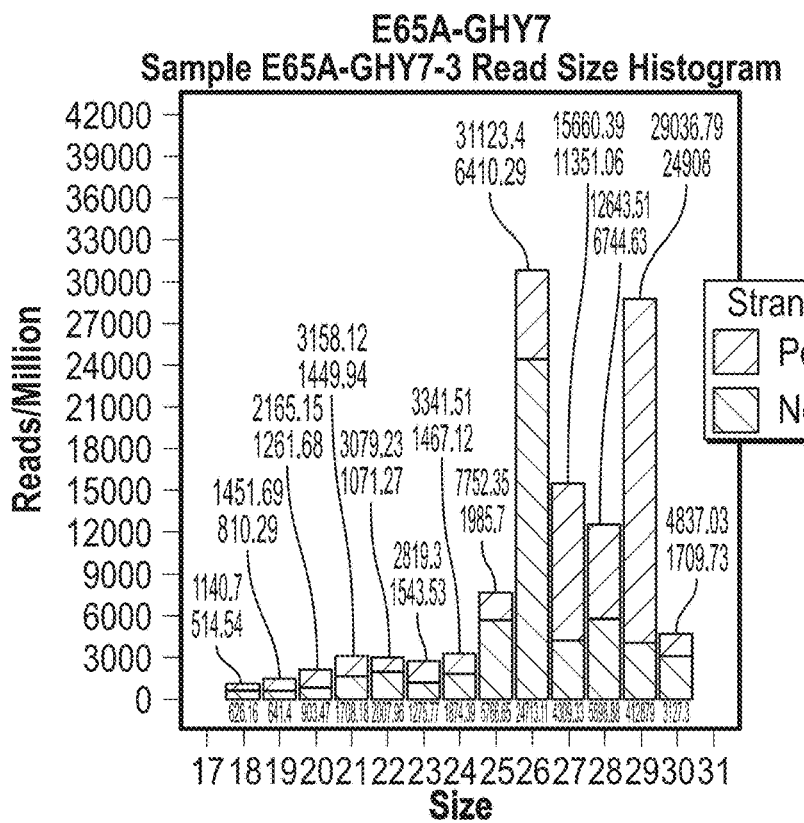
FIG. 24E-F

G
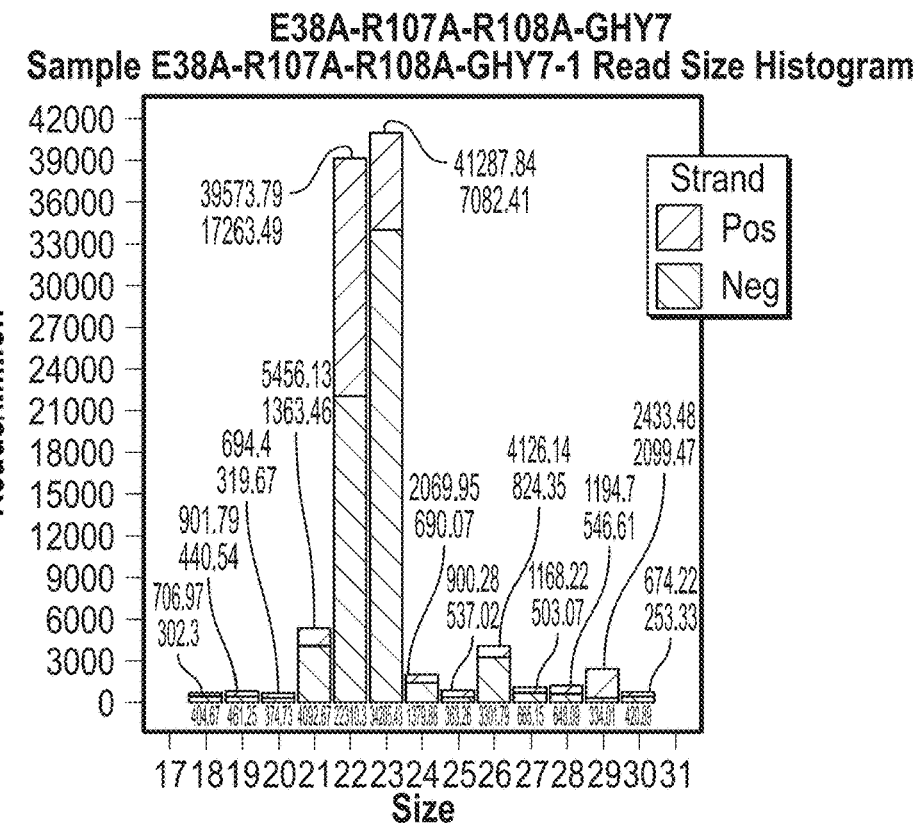
H
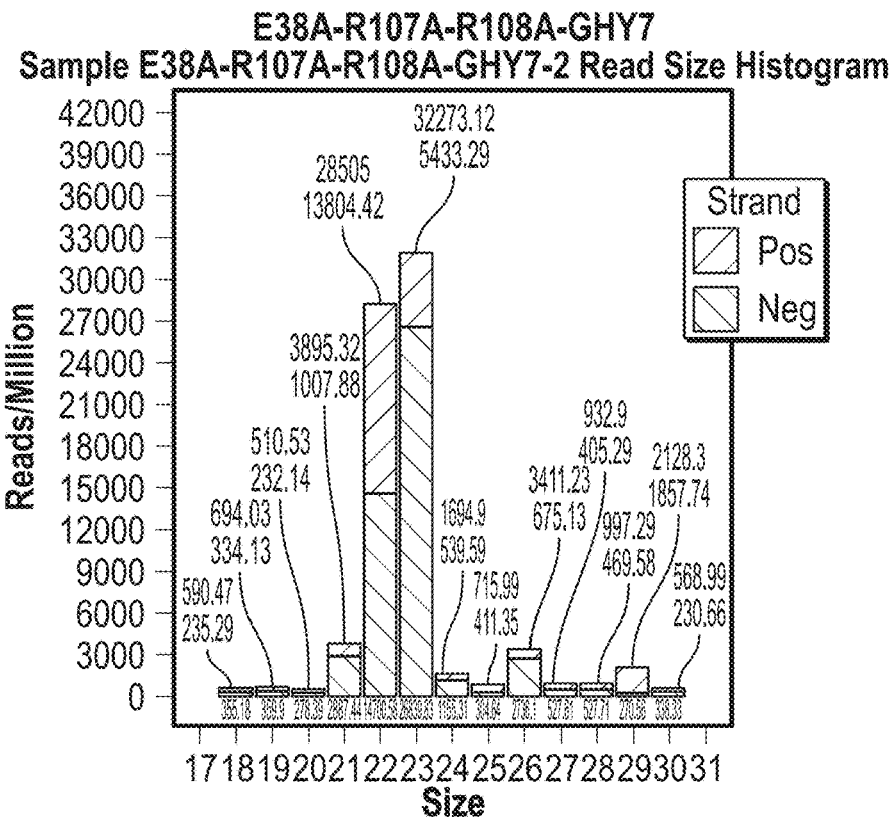
FIG. 24G-H

J
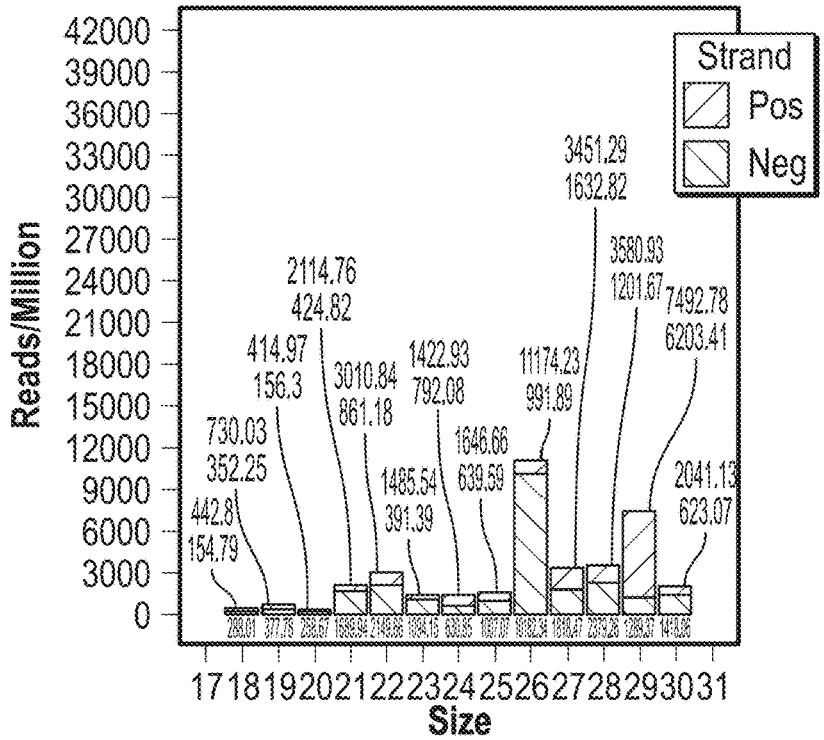
K
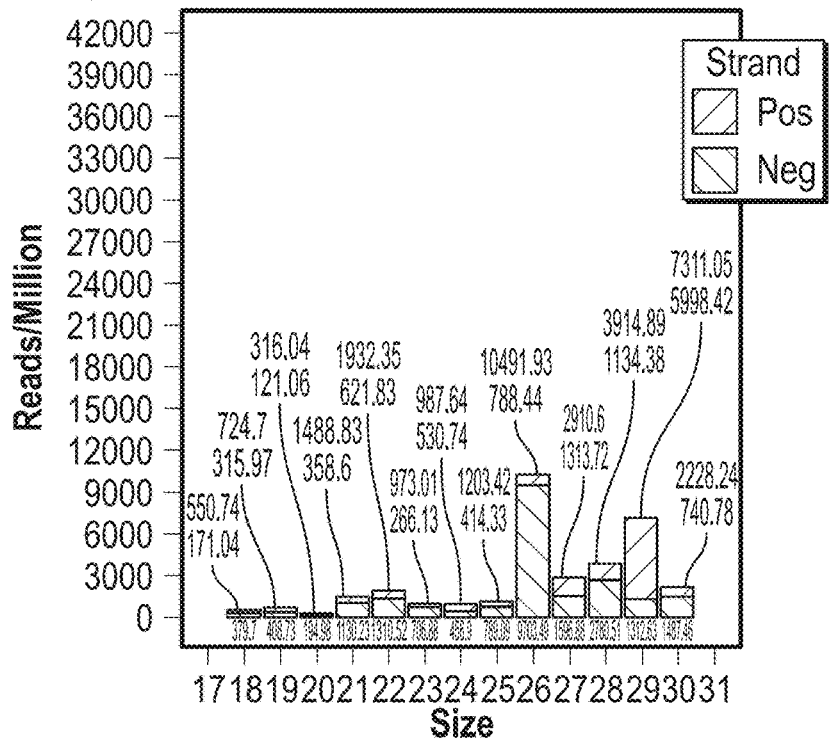
FIG. 24J-K

L
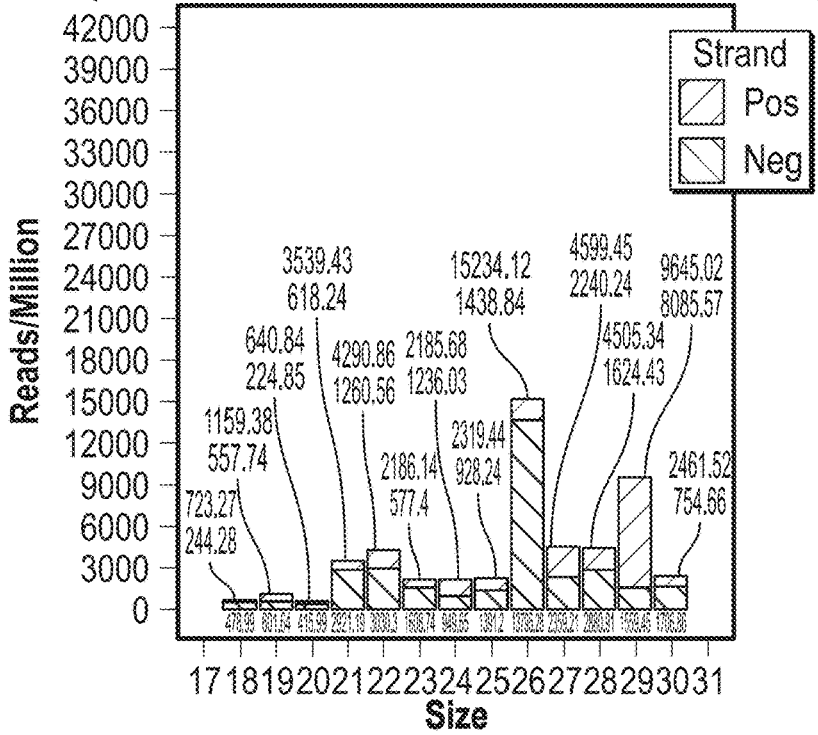
M
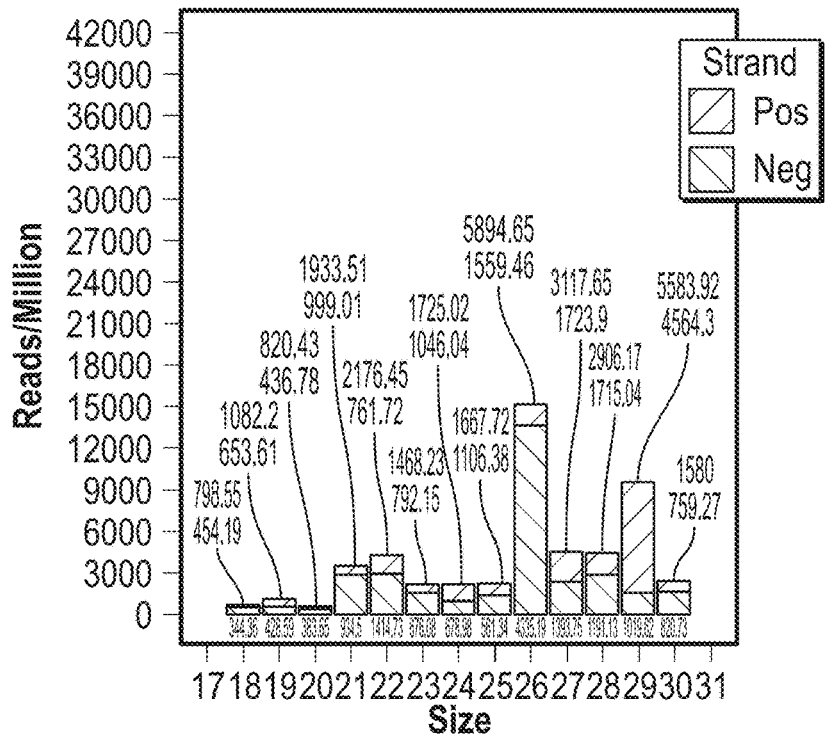
FIG. 24L-M

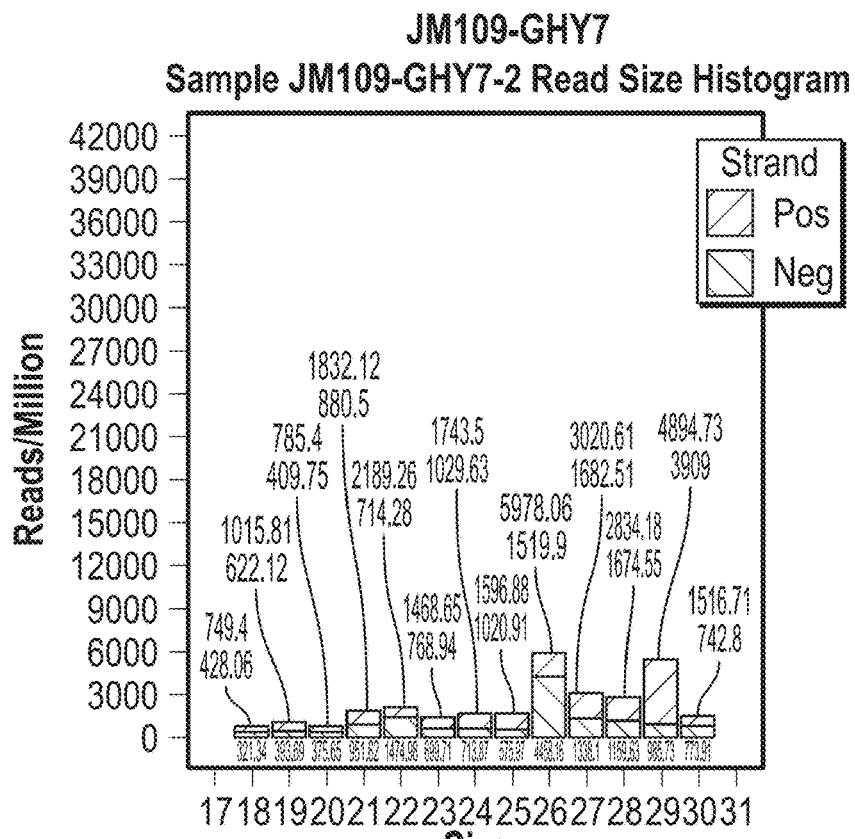
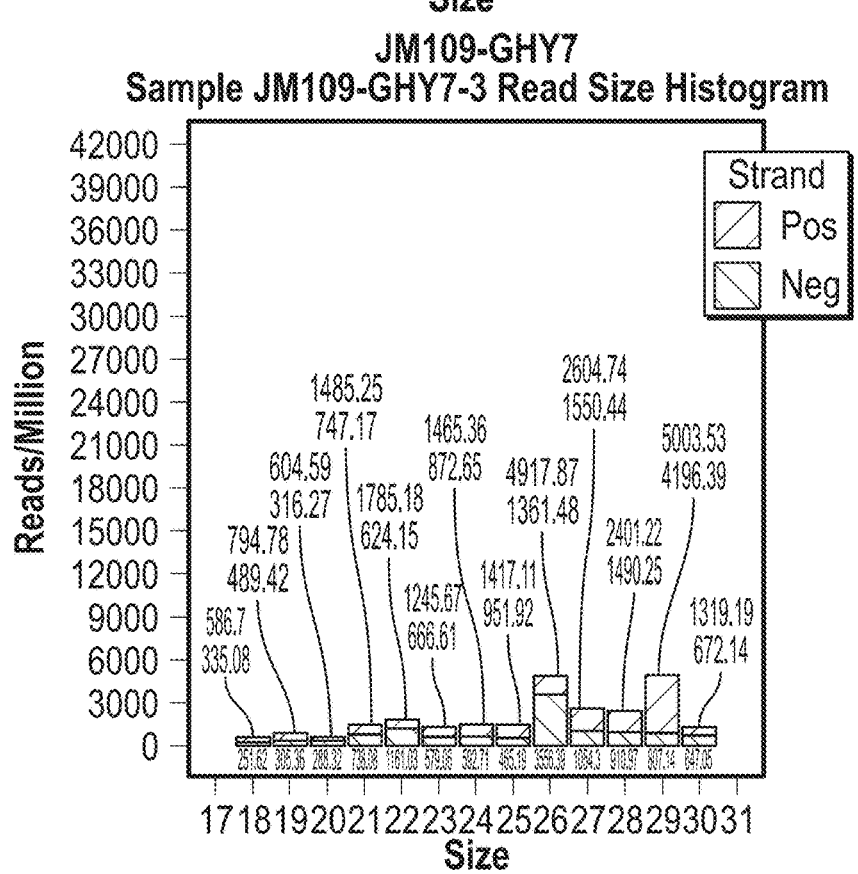
FIG. 24N-O

P
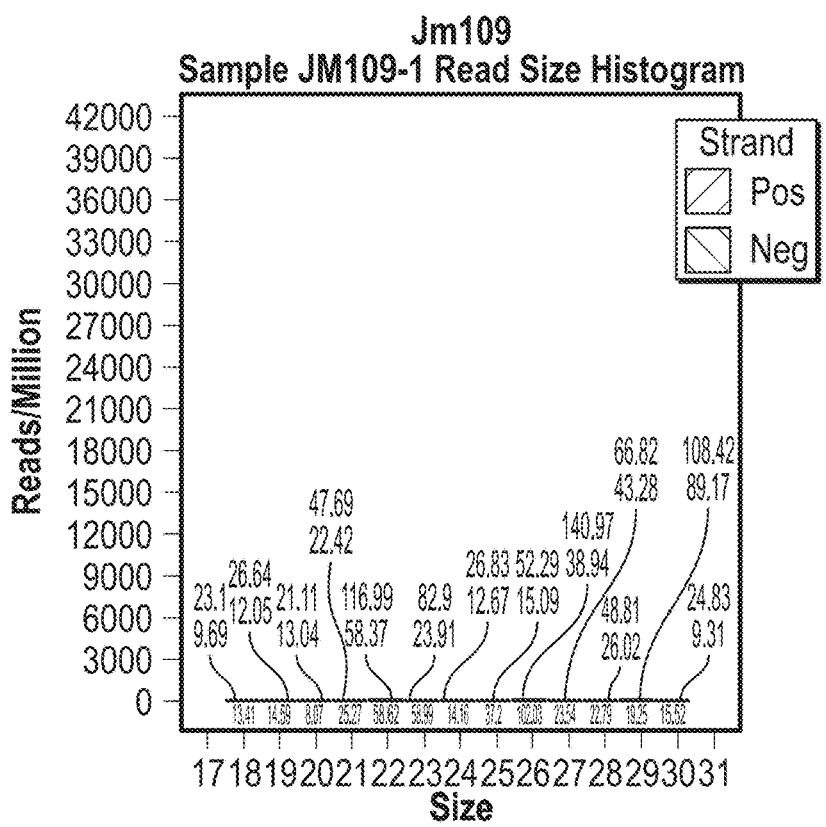
Q
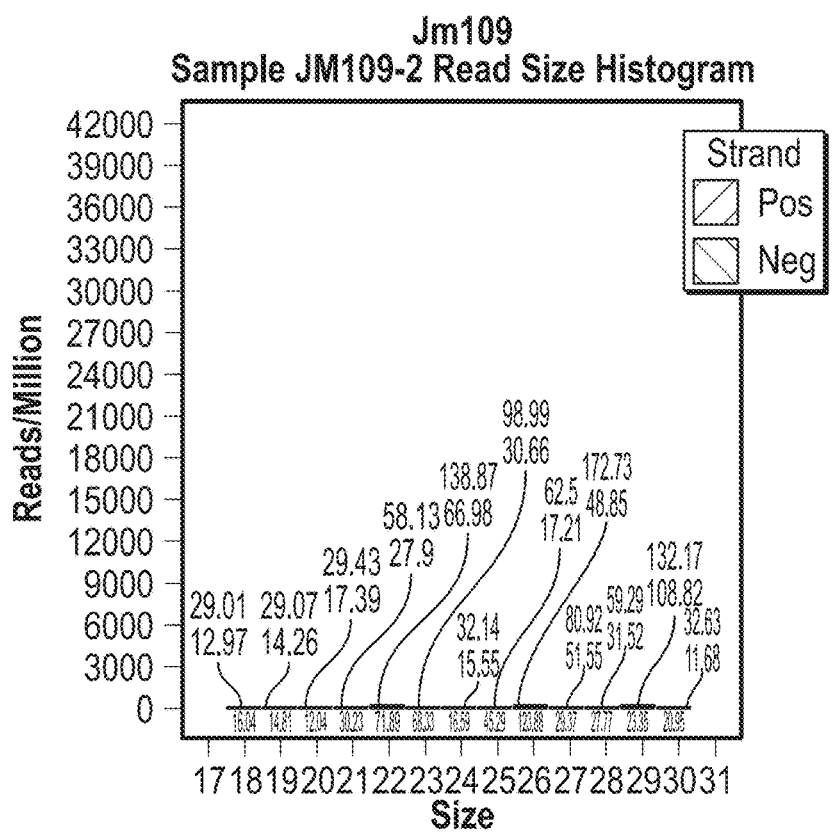
FIG. 24P-Q

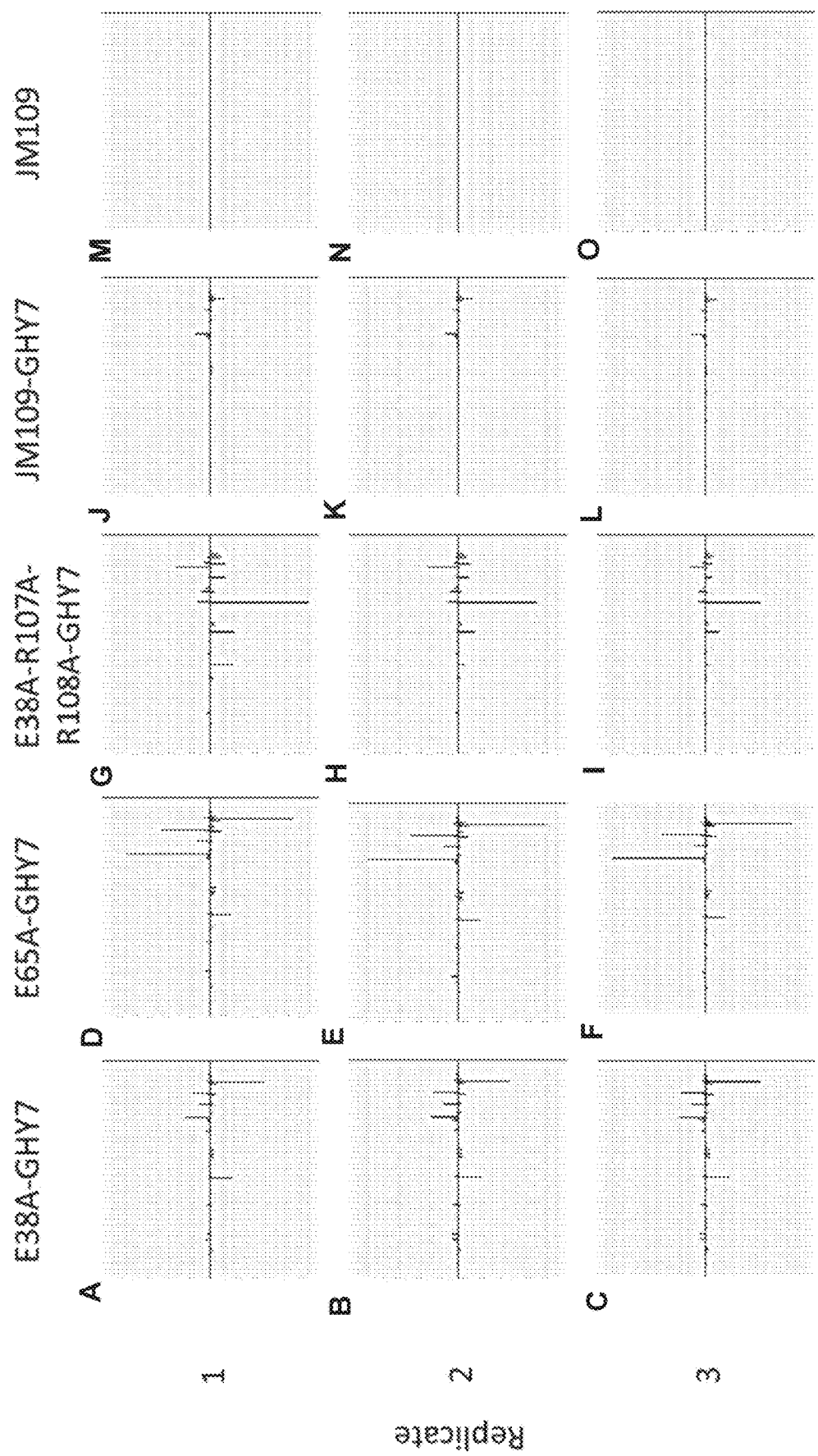
FIG. 25A-O

SEQUENCE LISTING

<160> NUMBER OF SEQ ID NOS: 121

<210> SEQ ID NO 1
<211> LENGTH: 681
<212> TYPE: DNA
<213> ORGANISM: E. coli

<400> SEQUENCE: 1

```
atgaacccca tcgtaattaa tcggcttcaa cggaagctgg gctacacttt taatcatcag      60
gaactgttgc agcaggcatt aactcatcgt agtgccagca gtaaacataa cgagcgttta     120 gaattttag gcgactctat tctgagctac gttatcgcca atgcgcttta tcaccgtttc     180
cctcgtgtgg atgaaggcga tatgagccgg atgcgcgcca cgctggtccg tggcaatacg     240
ctggcggaac tggcgcgcga atttgagtta ggcgagtgct tacgtttagg gccaggtgaa     300
cttaaaagcg gtggatttcg tcgtgagtca attctcgccg acaccgtcga agcattaatt     360
ggtggcgtat tcctcgacag tgatattcaa accgtcgaga aattaatcct caactggtat     420
caaactcgtt tggacgaaat tagcccaggc gataaacaaa aagatccgaa aacgcgcttg     480
caagaatatt tgcagggtcg ccatctgccg ctgccgactt atctggtagt ccaggtacgt     540
ggcgaagcgc acgatcagga atttactatc cactgccagg tcagcggcct gagtgaaccg     600
gtggttggca caggttcaag ccgtcgtaag gctgagcagg ctgccgccga acaggcgttg     660
aaaaaactgg agctggaatg a                                               681
```

<210> SEQ ID NO 2
<211> LENGTH: 226
<212> TYPE: PRT
<213> ORGANISM: E. coli

<400> SEQUENCE: 2

```
Met Asn Pro Ile Val Ile Asn Arg Leu Gln Arg Lys Leu Gly Tyr Thr
1               5                   10                  15

Phe Asn His Gln Glu Leu Leu Gln Gln Ala Leu Thr His Arg Ser Ala
            20                  25                  30

Ser Ser Lys His Asn Glu Arg Leu Glu Phe Leu Gly Asp Ser Ile Leu
        35                  40                  45

Ser Tyr Val Ile Ala Asn Ala Leu Tyr His Arg Phe Pro Arg Val Asp
    50                  55                  60

Glu Gly Asp Met Ser Arg Met Arg Ala Thr Leu Val Arg Gly Asn Thr
65                  70                  75                  80

Leu Ala Glu Leu Ala Arg Glu Phe Glu Leu Gly Glu Cys Leu Arg Leu
                85                  90                  95
```

Gly Pro Gly Glu Leu Lys Ser Gly Gly Phe Arg Arg Glu Ser Ile Leu
            100                 105                 110

Ala Asp Thr Val Glu Ala Leu Ile Gly Gly Val Phe Leu Asp Ser Asp
        115                 120                 125

Ile Gln Thr Val Glu Lys Leu Ile Leu Asn Trp Tyr Gln Thr Arg Leu
    130                 135                 140

Asp Glu Ile Ser Pro Gly Asp Lys Gln Lys Asp Pro Lys Thr Arg Leu
145                 150                 155                 160

Gln Glu Tyr Leu Gln Gly Arg His Leu Pro Leu Pro Thr Tyr Leu Val
                165                 170                 175

Val Gln Val Arg Gly Glu Ala His Asp Gln Glu Phe Thr Ile His Cys
            180                 185                 190

Gln Val Ser Gly Leu Ser Glu Pro Val Val Gly Thr Gly Ser Ser Arg
        195                 200                 205

Arg Lys Ala Glu Gln Ala Ala Ala Glu Gln Ala Leu Lys Lys Leu Glu
    210                 215                 220

Leu Glu
225

<210> SEQ ID NO 3
<211> LENGTH: 681
<212> TYPE: DNA
<213> ORGANISM: E. coli

<400> SEQUENCE: 3

```
atgaacccca tcgtaattaa tcggcttcaa cggaagctgg gctacacttt taatcatcag      60
gaactgttgc agcaggcatt aactcatcgt agtgccagca gtaaacacaa tgcccgcttg     120
gaatttttag cgactctata tctgagctac gttatcgcca atgcgcttta tcaccgtttc     180
cctcgtgtgg atgaaggcga tatgagccgg atgcgcgcca cgctggtccg tggcaatacg     240
ctggcggaac tggcgcgcga atttgagtta ggcgagtgct tacgtttagg gccaggtgaa     300
cttaaaagcg gtggatttcg tcgtgagtca attctcgccg acaccgtcga agcattaatt     360
ggtggcgtat tcctcgacag tgatattcaa accgtcgaga attaatcct caactggtat     420 caaactcgtt tggacgaaat tagcccaggc gataaacaaa agatccgaa acgcgcttg     480 caagaatatt tgcagggtcg ccatctgccg ctgccgactt atctggtagt ccaggtacgt     540
ggcgaagcgc acgatcagga atttactatc cactgccagg tcagcggcct gagtgaaccg     600
gtggttggca caggttcaag ccgtcgtaag gctgagcagg ctgccgccga acaggcgttg     660
aaaaaactgg agctggaatg a                                              681
```

<210> SEQ ID NO 4
<211> LENGTH: 226
<212> TYPE: PRT
<213> ORGANISM: E. coli

<400> SEQUENCE: 4

Met Asn Pro Ile Val Ile Asn Arg Leu Gln Arg Lys Leu Gly Tyr Thr
1               5                   10                  15

Phe Asn His Gln Glu Leu Leu Gln Gln Ala Leu Thr His Arg Ser Ala
            20                  25                  30

Ser Ser Lys His Asn Ala Arg Leu Glu Phe Leu Gly Asp Ser Ile Leu
        35                  40                  45

Ser Tyr Val Ile Ala Asn Ala Leu Tyr His Arg Phe Pro Arg Val Asp
    50                  55                  60

```
Glu Gly Asp Met Ser Arg Met Arg Ala Thr Leu Val Arg Gly Asn Thr
 65                  70                  75                  80

Leu Ala Glu Leu Ala Arg Glu Phe Glu Leu Gly Glu Cys Leu Arg Leu
                 85                  90                  95

Gly Pro Gly Glu Leu Lys Ser Gly Gly Phe Arg Arg Glu Ser Ile Leu
            100                 105                 110

Ala Asp Thr Val Glu Ala Leu Ile Gly Gly Val Phe Leu Asp Ser Asp
            115                 120                 125

Ile Gln Thr Val Glu Lys Leu Ile Leu Asn Trp Tyr Gln Thr Arg Leu
        130                 135                 140

Asp Glu Ile Ser Pro Gly Asp Lys Gln Lys Asp Pro Lys Thr Arg Leu
145                 150                 155                 160

Gln Glu Tyr Leu Gln Gly Arg His Leu Pro Leu Pro Thr Tyr Leu Val
                165                 170                 175

Val Gln Val Arg Gly Glu Ala His Asp Gln Glu Phe Thr Ile His Cys
            180                 185                 190

Gln Val Ser Gly Leu Ser Glu Pro Val Val Gly Thr Gly Ser Ser Arg
        195                 200                 205

Arg Lys Ala Glu Gln Ala Ala Ala Glu Gln Ala Leu Lys Lys Leu Glu
210                 215                 220

Leu Glu
225
```

<210> SEQ ID NO 5
<211> LENGTH: 681
<212> TYPE: DNA
<213> ORGANISM: E. coli

<400> SEQUENCE: 5

```
atgaacccca tcgtaattaa tcggcttcaa cggaagctgg gctacacttt taatcatcag      60
gaactgttgc agcaggcatt aactcatcgt agtgccagca gtaaacataa cgagcgttta     120 gaattttag gcgactctat tctgagctac gttatcgcca atgcgcttta tcaccgtttc      180
ccccgcgtcg acgccggcga tatgagccgg atgcgcgcca cgctggtccg tggcaatacg     240
ctggcggaac tggcgcgcga atttgagtta ggcgagtgct acgtttagg gccaggtgaa      300 cttaaaagcg gtggatttcg tcgtgagtca attctcgccg acaccgtcga agcattaatt     360
ggtggcgtat tcctcgacag tgatattcaa accgtcgaga attaatcct caactggtat     420 caaactcgtt tggacgaaat tagcccaggc gataaacaaa aagatccgaa acgcgcttg      480 caagaatatt tgcagggtcg ccatctgccg ctgccgactt atctggtagt ccaggtacgt     540
ggcgaagcgc acgatcagga atttactatc cactgccagg tcagcggcct gagtgaaccg     600
gtggttggca caggttcaag ccgtcgtaag gctgagcagg ctgccgccga acaggcgttg     660
aaaaaactgg agctggaatg a                                               681
```

<210> SEQ ID NO 6
<211> LENGTH: 226
<212> TYPE: PRT
<213> ORGANISM: E. coli

<400> SEQUENCE: 6

```
Met Asn Pro Ile Val Ile Asn Arg Leu Gln Arg Lys Leu Gly Tyr Thr
  1               5                  10                  15

Phe Asn His Gln Glu Leu Leu Gln Gln Ala Leu Thr His Arg Ser Ala
                 20                  25                  30
```

```
Ser Ser Lys His Asn Glu Arg Leu Glu Phe Leu Gly Asp Ser Ile Leu
        35                  40                  45

Ser Tyr Val Ile Ala Asn Ala Leu Tyr His Arg Phe Pro Arg Val Asp
 50                  55                  60

Ala Gly Asp Met Ser Arg Met Arg Ala Thr Leu Val Arg Gly Asn Thr
 65                  70                  75                  80

Leu Ala Glu Leu Ala Arg Glu Phe Gly Leu Gly Glu Cys Leu Arg Leu
                85                  90                  95

Gly Pro Gly Glu Leu Lys Ser Gly Phe Arg Arg Glu Ser Ile Leu
                100                 105                 110

Ala Asp Thr Val Glu Ala Leu Ile Gly Gly Val Phe Leu Asp Ser Asp
                115                 120                 125

Ile Gln Thr Val Glu Lys Leu Ile Leu Asn Trp Tyr Gln Thr Arg Leu
                130                 135                 140

Asp Glu Ile Ser Pro Gly Asp Lys Gln Lys Asp Pro Lys Thr Arg Leu
145                 150                 155                 160

Gln Glu Tyr Leu Gln Gly Arg His Leu Pro Leu Pro Thr Tyr Leu Val
                165                 170                 175

Val Gln Val Arg Gly Glu Ala His Asp Gln Glu Phe Thr Ile His Cys
                180                 185                 190

Gln Val Ser Gly Leu Ser Glu Pro Val Val Gly Thr Gly Ser Ser Arg
                195                 200                 205

Arg Lys Ala Glu Gln Ala Ala Glu Gln Ala Leu Lys Lys Leu Glu
                210                 215                 220

Leu Glu
225

<210> SEQ ID NO 7
<211> LENGTH: 681
<212> TYPE: DNA
<213> ORGANISM: E. coli

<400> SEQUENCE: 7
atgaacccca tcgtaattaa tcggcttcaa cggaagctgg gctacacttt taatcatcag      60
gaactgttgc agcaggcatt aactcatcgt agtgccagca gtaaacacaa tgcccgcttg     120 gaattttag  cgactctat  tctgagctac gttatcgcca  atgcgcttta tcaccgtttc     180
cctcgtgtgg atgaaggcga tatgagccgg atgcgcgcca cgctggtccg tggcaatacg     240
ctggcggaac tggcgcgcga atttgagtta ggcgagtgct tacgtttagg gccaggtgaa     300
cttaaaagcg gtggatttgc cgccgagtca attctcgccg acaccgtcga agcattaatt     360
ggtggcgtat tcctcgacag tgatattcaa accgtcgaga attaatcct  caactggtat     420 caaactcgtt tggacgaaat tagcccaggc gataaacaaa aagatccgaa acgcgcttg     480 caagaatatt tgcagggtcg ccatctgccg ctgccgactt atctggtagt ccaggtacgt     540
ggcgaagcgc acgatcagga atttactatc cactgccagg tcagcggcct gagtgaaccg     600
gtggttggca caggttcaag ccgtcgtaag gctgagcagg ctgccgccga acaggcgttg     660
aaaaaactgg agctggaatg a                                               681

<210> SEQ ID NO 8
<211> LENGTH: 226
<212> TYPE: PRT
<213> ORGANISM: E. coli

<400> SEQUENCE: 8
```

```
Met Asn Pro Ile Val Ile Asn Arg Leu Gln Arg Lys Leu Gly Tyr Thr
1               5                   10                  15
Phe Asn His Gln Glu Leu Leu Gln Gln Ala Leu Thr His Arg Ser Ala
            20                  25                  30
Ser Ser Lys His Asn Ala Arg Leu Glu Phe Leu Gly Asp Ser Ile Leu
        35                  40                  45
Ser Tyr Val Ile Ala Asn Ala Leu Tyr His Arg Phe Pro Arg Val Asp
    50                  55                  60
Glu Gly Asp Met Ser Arg Met Arg Ala Thr Leu Val Arg Gly Asn Thr
65                  70                  75                  80
Leu Ala Glu Leu Ala Arg Glu Phe Glu Leu Gly Glu Cys Leu Arg Leu
                85                  90                  95
Gly Pro Gly Glu Leu Lys Ser Gly Gly Phe Ala Ala Glu Ser Ile Leu
            100                 105                 110
Ala Asp Thr Val Glu Ala Leu Ile Gly Gly Val Phe Leu Asp Ser Asp
        115                 120                 125
Ile Gln Thr Val Glu Lys Leu Ile Leu Asn Trp Tyr Gln Thr Arg Leu
    130                 135                 140
Asp Glu Ile Ser Pro Gly Asp Lys Gln Lys Asp Pro Lys Thr Arg Leu
145                 150                 155                 160
Gln Glu Tyr Leu Gln Gly Arg His Leu Pro Leu Pro Thr Tyr Leu Val
                165                 170                 175
Val Gln Val Arg Gly Glu Ala His Asp Gln Glu Phe Thr Ile His Cys
            180                 185                 190
Gln Val Ser Gly Leu Ser Glu Pro Val Val Gly Thr Gly Ser Ser Arg
        195                 200                 205
Arg Lys Ala Glu Gln Ala Ala Ala Glu Gln Ala Leu Lys Lys Leu Glu
    210                 215                 220
Leu Glu
225
```

<210> SEQ ID NO 9
<211> LENGTH: 681
<212> TYPE: DNA
<213> ORGANISM: Enterobacteriaceae Ag001

<400> SEQUENCE: 9

| | | | | | | |
|---|---|---|---|---|---|---|
| atgaatccca | tcgtaataaa | taggctgcag | cgtaagctgg | gctacacttt | tcaacatcag | 60 |
| gatctgttgc | aacaggcatt | aacccatcgg | agtgccagca | gcaagcataa | tgcccgcttg | 120 |
| gagttttttgg | gtgactccat | tctcagttat | gtcatcgcga | atgcgctgta | tcatcgtttt | 180 |
| cctcgcgtag | atgaaggcga | catgagccgc | atgcgtgcga | cgctggtgcg | cggcaatacg | 240 |
| ctggcggaaa | tcgcccgcga | gttcgaactg | ggtgagtgtc | tgcgtcttgg | gccgggtgaa | 300 |
| ctgaaaagtg | gcggtttccg | tcgcgagtcg | attcttgctg | ataccgtgga | agcgttgatc | 360 |
| ggtggcgtct | tcctcgacag | cgacattcag | aacgttgagc | gtttgattct | ctcgtggtat | 420 |
| cagacccgtc | tcgacgaaat | cagtccaggc | gacaagcaaa | aagatccgaa | aacgcgtctg | 480 |
| caggagtacc | tgcagggtcg | ccatctgccg | ctgccgtcgt | atctggtggt | gcaggtgcgt | 540 |
| ggtgaagcgc | acgatcaaga | atttaccatt | cactgtcagg | tgagtggcct | gcctgagcct | 600 |
| gtcgtaggga | cgggctcaag | ccgccgtaaa | gcggaacagg | ctgcggctga | gcaggcactg | 660 |
| aaaaagctgg | agctggaatg | a | | | | 681 |

<210> SEQ ID NO 10

-continued

<211> LENGTH: 226
<212> TYPE: PRT
<213> ORGANISM: Enterobacteriaceae Ag001

<400> SEQUENCE: 10

Met Asn Pro Ile Val Ile Asn Arg Leu Gln Arg Lys Leu Gly Tyr Thr
1               5                   10                  15

Phe Gln His Gln Asp Leu Leu Gln Gln Ala Leu Thr His Arg Ser Ala
            20                  25                  30

Ser Ser Lys His Asn Ala Arg Leu Glu Phe Leu Gly Asp Ser Ile Leu
        35                  40                  45

Ser Tyr Val Ile Ala Asn Ala Leu Tyr His Arg Phe Pro Arg Val Asp
    50                  55                  60

Glu Gly Asp Met Ser Arg Met Arg Ala Thr Leu Val Arg Gly Asn Thr
65                  70                  75                  80

Leu Ala Glu Ile Ala Arg Glu Phe Glu Leu Gly Glu Cys Leu Arg Leu
                85                  90                  95

Gly Pro Gly Glu Leu Lys Ser Gly Gly Phe Arg Arg Glu Ser Ile Leu
            100                 105                 110

Ala Asp Thr Val Glu Ala Leu Ile Gly Gly Val Phe Leu Asp Ser Asp
        115                 120                 125

Ile Gln Asn Val Glu Arg Leu Ile Leu Ser Trp Tyr Gln Thr Arg Leu
    130                 135                 140

Asp Glu Ile Ser Pro Gly Asp Lys Gln Lys Asp Pro Lys Thr Arg Leu
145                 150                 155                 160

Gln Glu Tyr Leu Gln Gly Arg His Leu Pro Leu Pro Ser Tyr Leu Val
                165                 170                 175

Val Gln Val Arg Gly Glu Ala His Asp Gln Glu Phe Thr Ile His Cys
            180                 185                 190

Gln Val Ser Gly Leu Pro Glu Pro Val Val Gly Thr Gly Ser Ser Arg
        195                 200                 205

Arg Lys Ala Glu Gln Ala Ala Glu Gln Ala Leu Lys Lys Leu Glu
    210                 215                 220

Leu Glu
225

<210> SEQ ID NO 11
<211> LENGTH: 681
<212> TYPE: DNA
<213> ORGANISM: Enterobacteriaceae Ag001

<400> SEQUENCE: 11
atgaatccca tcgtaataaa taggctgcag cgtaagctgg gctacacttt tcaacatcag      60
gatctgttgc aacaggcatt aacccatcgg agtgccagca gcaagcataa tgcccgcttg     120 gagttttttgg gtgactccat tctcagttat gtcatcgcga atgcgctgta tcatcgtttt     180
cctcgcgtag atgaaggcga catgagccgc atgcgtgcga cgctggtgcg cggcaatacg     240
ctggcggaaa tcgcccgcga gttcgaactg ggtgagtgtc tgcgtcttgg ccgggtgaa      300 ctgaaaagtg gcggtttcgc cgccgagtcg attcttgctg ataccgtgga agcgttgatc     360
ggtggcgtct tcctcgacag cgacattcag aacgttgagc gtttgattct ctcgtggtat     420
cagacccgtc tcgacgaaat cagtccaggc gacaagcaaa agatccgaa acgcgtctg      480 caggagtacc tgcagggtcg ccatctgccg ctgccgtcgt atctggtggt gcaggtgcgt    540
ggtgaagcgc acgatcaaga atttaccatt cactgtcagg tgagtggcct gcctgagcct    600

```
gtcgtaggga cgggctcaag ccgccgtaaa gcggaacagg ctgcggctga gcaggcactg      660
aaaaagctgg agctggaatg a                                                681
```

```
<210> SEQ ID NO 12
<211> LENGTH: 226
<212> TYPE: PRT
<213> ORGANISM: Enterobacteriaceae Ag001

<400> SEQUENCE: 12
```

```
Met Asn Pro Ile Val Ile Asn Arg Leu Gln Arg Lys Leu Gly Tyr Thr
1               5                   10                  15

Phe Gln His Gln Asp Leu Leu Gln Gln Ala Leu Thr His Arg Ser Ala
            20                  25                  30

Ser Ser Lys His Asn Ala Arg Leu Glu Phe Leu Gly Asp Ser Ile Leu
        35                  40                  45

Ser Tyr Val Ile Ala Asn Ala Leu Tyr His Arg Phe Pro Arg Val Asp
    50                  55                  60

Glu Gly Asp Met Ser Arg Met Arg Ala Thr Leu Val Arg Gly Asn Thr
65                  70                  75                  80

Leu Ala Glu Ile Ala Arg Glu Phe Glu Leu Gly Glu Cys Leu Arg Leu
                85                  90                  95

Gly Pro Gly Glu Leu Lys Ser Gly Gly Phe Ala Ala Glu Ser Ile Leu
            100                 105                 110

Ala Asp Thr Val Glu Ala Leu Ile Gly Gly Val Phe Leu Asp Ser Asp
        115                 120                 125

Ile Gln Asn Val Glu Arg Leu Ile Leu Ser Trp Tyr Gln Thr Arg Leu
    130                 135                 140

Asp Glu Ile Ser Pro Gly Asp Lys Gln Lys Asp Pro Lys Thr Arg Leu
145                 150                 155                 160

Gln Glu Tyr Leu Gln Gly Arg His Leu Pro Leu Pro Ser Tyr Leu Val
                165                 170                 175

Val Gln Val Arg Gly Glu Ala His Asp Gln Glu Phe Thr Ile His Cys
            180                 185                 190

Gln Val Ser Gly Leu Pro Glu Pro Val Val Gly Thr Gly Ser Ser Arg
        195                 200                 205

Arg Lys Ala Glu Gln Ala Ala Glu Gln Ala Leu Lys Lys Leu Glu
    210                 215                 220

Leu Glu
225
```

```
<210> SEQ ID NO 13
<211> LENGTH: 681
<212> TYPE: DNA
<213> ORGANISM: Enterobacter Ae003

<400> SEQUENCE: 13
```

```
atgaacccca tcgtaattaa tcggcttcaa cggaagctgg gctacacttt tcatcatcag      60
gagttgttgc aacaggcatt aacccaccgc agtgccagca gcaagcacaa cgcccgcctg     120 gagttttag gcgactctat tttaagtttc gtgattgcga atgcgcttta tcatcgtttc     180
ccgcgcgtgg atgaaggtga tatgagccgc atgcgtgcca cgctggttcg ggtaacaccc     240
cttgcggaaa tcgcgcgcga atttgaactg gcgaatgtc tgcgtcttgg gccgggtgaa     300
ctgaaaagcg gcggcttccg tcgtgaatct attcttgccg atacggtcga agcattaatt     360
ggtggtgtgt tcctggacag cgatatccag accgtcgaaa agctgatcct gaactggtat     420
```

| | |
|---|---|
| cagacccgtc tggacgaaat cagcccgggc gataaacaaa aagatcccaa aacgcgtctg | 480 |
| caggaatatt tgcagggccg tcatctgccg ctgccatctt atctggtggt gcaggttcgt | 540 |
| ggcgaagcgc acgatcagga atttaccatc cattgccagg tcagtggcct gagtgaaccg | 600 |
| gtggtgggca caggttcaag ccgtcgtaag gctgaacagg ctgccgccga acaggcgtta | 660 |
| aaaatgctgg agctggaatg a | 681 |

<210> SEQ ID NO 14
<211> LENGTH: 226
<212> TYPE: PRT
<213> ORGANISM: Enterobacter Ae003

<400> SEQUENCE: 14

Met Asn Pro Ile Val Ile Asn Arg Leu Gln Arg Lys Leu Gly Tyr Thr
1               5                   10                  15

Phe His His Gln Glu Leu Leu Gln Gln Ala Leu Thr His Arg Ser Ala
            20                  25                  30

Ser Ser Lys His Asn Ala Arg Leu Glu Phe Leu Gly Asp Ser Ile Leu
        35                  40                  45

Ser Phe Val Ile Ala Asn Ala Leu Tyr His Arg Phe Pro Arg Val Asp
    50                  55                  60

Glu Gly Asp Met Ser Arg Met Arg Ala Thr Leu Val Arg Gly Asn Thr
65                  70                  75                  80

Leu Ala Glu Ile Ala Arg Glu Phe Glu Leu Gly Glu Cys Leu Arg Leu
                85                  90                  95

Gly Pro Gly Glu Leu Lys Ser Gly Gly Phe Arg Arg Glu Ser Ile Leu
            100                 105                 110

Ala Asp Thr Val Glu Ala Leu Ile Gly Gly Val Phe Leu Asp Ser Asp
        115                 120                 125

Ile Gln Thr Val Glu Lys Leu Ile Leu Asn Trp Tyr Gln Thr Arg Leu
    130                 135                 140

Asp Glu Ile Ser Pro Gly Asp Lys Gln Lys Asp Pro Lys Thr Arg Leu
145                 150                 155                 160

Gln Glu Tyr Leu Gln Gly Arg His Leu Pro Leu Pro Ser Tyr Leu Val
                165                 170                 175

Val Gln Val Arg Gly Glu Ala His Asp Gln Glu Phe Thr Ile His Cys
            180                 185                 190

Gln Val Ser Gly Leu Ser Glu Pro Val Val Gly Thr Gly Ser Ser Arg
        195                 200                 205

Arg Lys Ala Glu Gln Ala Ala Ala Glu Gln Ala Leu Lys Met Leu Glu
    210                 215                 220

Leu Glu
225

<210> SEQ ID NO 15
<211> LENGTH: 681
<212> TYPE: DNA
<213> ORGANISM: Enterobacter Ae003

<400> SEQUENCE: 15

| | |
|---|---|
| atgaacccca tcgtaattaa tcggcttcaa cggaagctgg gctacacttt tcatcatcag | 60 |
| gagttgttgc aacaggcatt aacccaccgc agtgccagca gcaagcacaa cgcccgcctg | 120 |
| gagtttttag cgactctat tttaagtttc gtgattgcga atgcgcttta tcatcgtttc | 180 |
| ccgcgcgtgg atgaaggtga tatgagccgc atgcgtgcca cgctggttcg gggtaacacc | 240 |

```
cttgcggaaa tcgcgcgcga atttgaactg ggcgaatgtc tgcgtcttgg gccgggtgaa      300
ctgaaaagcg gcggcttcgc cgccgaatct attcttgccg atacggtcga agcattaatt      360
ggtggtgtgt tcctggacag cgatatccag accgtcgaaa agctgatcct gaactggtat      420
cagacccgtc tggacgaaat cagcccgggc gataaacaaa aagatcccaa aacgcgtctg      480
caggaatatt tgcagggccg tcatctgccg ctgccatctt atctggtggt gcaggttcgt      540
ggcgaagcgc acgatcagga atttaccatc cattgccagg tcagtggcct gagtgaaccg      600
gtggtgggca caggttcaag ccgtcgtaag gctgaacagg ctgccgccga acaggcgtta      660
aaaatgctgg agctggaatg a                                                681
```

<210> SEQ ID NO 16
<211> LENGTH: 226
<212> TYPE: PRT
<213> ORGANISM: Enterobacter Ae003

<400> SEQUENCE: 16

```
Met Asn Pro Ile Val Ile Asn Arg Leu Gln Arg Lys Leu Gly Tyr Thr
1               5                   10                  15

Phe His His Gln Glu Leu Leu Gln Gln Ala Leu Thr His Arg Ser Ala
            20                  25                  30

Ser Ser Lys His Asn Ala Arg Leu Glu Phe Leu Gly Asp Ser Ile Leu
        35                  40                  45

Ser Phe Val Ile Ala Asn Ala Leu Tyr His Arg Phe Pro Arg Val Asp
    50                  55                  60

Glu Gly Asp Met Ser Arg Met Arg Ala Thr Leu Val Arg Gly Asn Thr
65                  70                  75                  80

Leu Ala Glu Ile Ala Arg Glu Phe Glu Leu Gly Glu Cys Leu Arg Leu
                85                  90                  95

Gly Pro Gly Glu Leu Lys Ser Gly Gly Phe Ala Ala Glu Ser Ile Leu
            100                 105                 110

Ala Asp Thr Val Glu Ala Leu Ile Gly Gly Val Phe Leu Asp Ser Asp
        115                 120                 125

Ile Gln Thr Val Glu Lys Leu Ile Leu Asn Trp Tyr Gln Thr Arg Leu
    130                 135                 140

Asp Glu Ile Ser Pro Gly Asp Lys Gln Lys Asp Pro Lys Thr Arg Leu
145                 150                 155                 160

Gln Glu Tyr Leu Gln Gly Arg His Leu Pro Leu Pro Ser Tyr Leu Val
                165                 170                 175

Val Gln Val Arg Gly Glu Ala His Asp Gln Glu Phe Thr Ile His Cys
            180                 185                 190

Gln Val Ser Gly Leu Ser Glu Pro Val Val Gly Thr Gly Ser Ser Arg
        195                 200                 205

Arg Lys Ala Glu Gln Ala Ala Ala Glu Gln Ala Leu Lys Met Leu Glu
    210                 215                 220

Leu Glu
225
```

<210> SEQ ID NO 17
<211> LENGTH: 226
<212> TYPE: PRT
<213> ORGANISM: E. coli

<400> SEQUENCE: 17

```
Met Asn Pro Ile Val Ile Asn Arg Leu Gln Arg Lys Leu Gly Tyr Thr
1               5                   10                  15
```

```
Phe Asn His Gln Glu Leu Leu Gln Gln Ala Leu Thr His Arg Ser Ala
         20                  25                  30
Ser Ser Lys His Asn Ala Arg Leu Glu Phe Leu Gly Asp Ser Ile Leu
         35                  40                  45
Ser Tyr Val Ile Ala Asn Ala Leu Tyr His Arg Phe Pro Arg Val Asp
 50                  55                  60
Ala Gly Asp Met Ser Arg Met Arg Ala Thr Leu Val Arg Gly Asn Thr
 65                  70                  75                  80
Leu Ala Glu Leu Ala Arg Glu Phe Glu Leu Gly Glu Cys Leu Arg Leu
                 85                  90                  95
Gly Pro Gly Glu Leu Lys Ser Gly Phe Arg Arg Glu Ser Ile Leu
                100                 105                 110
Ala Asp Thr Val Glu Ala Leu Ile Gly Gly Val Phe Leu Asp Ser Asp
             115                 120                 125
Ile Gln Thr Val Glu Lys Leu Ile Leu Asn Trp Tyr Gln Thr Arg Leu
        130                 135                 140
Asp Glu Ile Ser Pro Gly Asp Lys Gln Lys Asp Pro Lys Thr Arg Leu
145                 150                 155                 160
Gln Glu Tyr Leu Gln Gly Arg His Leu Pro Leu Pro Thr Tyr Leu Val
                165                 170                 175
Val Gln Val Arg Gly Glu Ala His Asp Gln Glu Phe Thr Ile His Cys
             180                 185                 190
Gln Val Ser Gly Leu Ser Glu Pro Val Val Gly Thr Gly Ser Ser Arg
        195                 200                 205
Arg Lys Ala Glu Gln Ala Ala Glu Gln Ala Leu Lys Lys Leu Glu
    210                 215                 220
Leu Glu
225

<210> SEQ ID NO 18
<211> LENGTH: 1166
<212> TYPE: DNA
<213> ORGANISM: Enterobacteria

<400> SEQUENCE: 18
aactaacgac atcccctgtc gttgtgtata gaatattccc ccgaagttta aggttggccc    60
tgcaagggtg ccacggcaca cgaaaccgcg ttggttttct caggtcggtt tcgtgtgctg   120
cattttgac gcattcattt attggtatcg catgaacccc atcgtaatta atcggcttca    180
acggaagctg ggctacactt ttcatcatca ggagttgttg caacaggcat taacccaccg   240
cagtgccagc agcaaacata tgagcgtct cgagttttta ggcgactcta ttttaagttt    300
cgtgattgcg aatgcgcttt atcatcgttt cccgcgcgtg gatgaaggtg atatgagccg   360
catgcgtgcc acgctggttc ggggtaacac ccttgcggaa atcgcgcgcg aatttgaact   420
gggcgaatgt ctgcgtcttg gccgggtga actgaaaagc ggcggcttcc gtcgtgaatc    480
tattcttgcc gatacggtcg aagcattaat tggtggtgtg ttcctggaca gcgatatcca   540
gaccgtcgaa aagctgatcc tgaactggta tcagacccgt ctggacgaaa tcagcccggg   600
cgataaacaa aaagatccca aaacgcgtct gcaggaatat ttgcagggcc gtcatctgcc   660
gctgccatct tatctggtgg tgcaggttcg tggcgaagcg cacgatcagg aatttaccat   720
ccattgccag gtcagtggcc tgagtgaacc ggtggtgggc acaggttcaa gccgtcgtaa   780
ggctgaacag gctgccgccg aacaggcgtt aaaaatgctg gagctggaat gagcgaagaa   840
```

```
aagacctatt gcggatttat tgccatcgtc ggacgtccga acgtcggcaa atccaccctg     900
ttgaataatc tgcttgggca gaagatttct atcacctcgc gtaaggctca gaccacgcgt     960
caccgcatcg tcggtatcca tactgaaggc gcgtatcagg cgatctacgt cgataccccg    1020
ggcctgcaca tggaagagaa gcgtgccatc aaccgtctga tgaacaaggc ggcgagcagc    1080
tcgattggcg acgtggagct ggtgattttc gttgtggaag cacccgctg gacgcctgac     1140 gacgagatgg tgctgaacaa gctgcg                                         1166

<210> SEQ ID NO 19
<211> LENGTH: 1166
<212> TYPE: DNA
<213> ORGANISM: Enterobacteria

<400> SEQUENCE: 19
aactaacgac atccctgtc gttgtgtata gaatattccc ccgaagttta aggttggccc       60
tgcaagggtg ccacggcaca cgaaaccgcg ttggttttct caggtcggtt tcgtgtgctg     120 cattttgac gcattcattt attggtatcg catgaacccc atcgtaatta atcggcttca      180
acggaagctg ggctacactt ttcatcatca ggagttgttg caacaggcat taacccaccg    240
cagtgccagc agcaaacata tgagcgtct cgagttttta ggcgactcta ttttaagttt     300
cgtgattgcg aatgcgcttt atcatcgttt cccgcgcgtg gatgaaggtg atatgagccg    360
catgcgtgcc acgctggttc ggggtaatac ccttgcggaa atcgcgcgcg aatttgagct    420
gggcgaatgt ctgcgtcttg gccgggtga actgaaaagc ggcggcttcc gtcgtgaatc    480
tattcttgcc gatacggtcg aagcattaat tggtggtgtg ttcctggaca gcgatatcca    540
gaccgtcgaa aagctgatcc tgaactggta tcagacccgt ctggacgaaa tcagcccggg    600
cgataaacaa aaagatccca aaacgcgtct gcaggaatat ttgcagggcc gtcatctgcc    660
gctgccatct tatctggtgg tgcaggttcg tggcgaagcg cacgatcagg aatttaccat    720
ccattgccag gtcagtggcc tgagtgaacc ggtggtgggc acaggttcaa gccgtcgtaa    780
ggctgaacag gctgccgccg aacaggcgtt aaaaatgctg gagctggaat gagcgaagaa    840
aagacctatt gcggatttat tgccatcgtc ggacgtccga acgtcggcaa atccaccctg    900
ttgaataatc tgcttgggca gaagatttct atcacctcgc gtaaggcgca gaccacgcgt    960
caccgcatcg tcggtatcca tactgaaggc gcgtatcagg cgatctacgt cgatacaccg   1020
ggcctgcaca tggaagagaa gcgtgccatc aaccgtctga tgaacaaggc ggcgagcagc   1080
tcaattggcg acgtggagct ggtgattttc gttgtggaag cacccgctg gacgccggac    1140 gacgagatgg tgctgaacaa gctgcg                                        1166

<210> SEQ ID NO 20
<211> LENGTH: 1172
<212> TYPE: DNA
<213> ORGANISM: Enterobacteria

<400> SEQUENCE: 20
aactaacgac atccctgtc gttgtgtata gaatattccc gcctttaaag attggctccc       60
gaaagggagc cacggcacac gaaacagcgt tggtttcctt ttttcaggtc tgttccgtgt    120
gctgaatagt tgacgcattc attaattttg gtatcgcatg aatcccatcg taataaatag    180
gctgcagcgt aagctgggct acactttca acatcaggat ctgttgcaac aggcattaac    240
ccatcggagt gccagcagca aacacaacga gcgtcttgag ttttgggtg actccattct    300 cagttatgtc atcgcgaatg cgctgtatca tcgttttcct cgcgtagatg aaggcgacat    360
```

```
gagccgcatg cgtgcgacgc tggtgcgcgg caatacgctg gcggaaatcg cccgcgagtt    420
cgaactgggt gagtgtctgc gtcttgggcc gggtgaactg aaaagtggcg gtttccgtcg    480
cgagtcgatt cttgctgata ccgtggaagc gttgatcggt ggcgtcttcc tcgacagcga    540
cattcagaac gttgagcgtt tgattctctc gtggtatcag acccgtctcg acgaaatcag    600
tccaggcgac aagcaaaaag atccgaaaac gcgtctgcag gagtacctgc agggtcgcca    660
tctgccgctg ccgtcgtatc tggtggtgca ggtgcgtggt gaagcgcacg atcaagaatt    720
taccattcac tgtcaggtga gtggcctgcc tgagcctgtc gtagggacgg gctcaagccg    780
ccgtaaagcg aacaggctg cggctgagca ggcactgaaa aagctggagc tggaatgagc    840
gaagaaaaaa cgtattgcgg cttcgcggcc attgttggtc gcccgaacgt cggcaaatcc    900
acgctgctga atcagctgct gggcaaaaaa gtttccatta cctcgcgtaa ggcgcaaacc    960
acgcgccacc gcatcatggg catccatacc gaagggccat atcaggcgat ttacgtcgat   1020 accccgggc tgcacatgga agaaaaacgc gccattaacc gcctgatgaa ccgcgcggca   1080
agcagctcca tcggtgacgt tgagctggtt atcttcgtgg ttgaaggcac ccgctggacg   1140
ccggatgatg aaatggtgct gaacaagctg cg                                 1172
```

<210> SEQ ID NO 21
<211> LENGTH: 226
<212> TYPE: PRT
<213> ORGANISM: Enterobacteria

<400> SEQUENCE: 21

```
Met Asn Pro Ile Val Ile Asn Arg Leu Gln Arg Lys Leu Gly Tyr Thr
1               5                   10                  15

Phe Gln His Gln Asp Leu Leu Gln Gln Ala Leu Thr His Arg Ser Ala
            20                  25                  30

Ser Ser Lys His Asn Glu Arg Leu Glu Phe Leu Gly Asp Ser Ile Leu
        35                  40                  45

Ser Tyr Val Ile Ala Asn Ala Leu Tyr His Arg Phe Pro Arg Val Asp
    50                  55                  60

Glu Gly Asp Met Ser Arg Met Arg Ala Thr Leu Val Arg Gly Asn Thr
65                  70                  75                  80

Leu Ala Glu Ile Ala Arg Glu Phe Glu Leu Gly Glu Cys Leu Arg Leu
                85                  90                  95

Gly Pro Gly Glu Leu Lys Ser Gly Gly Phe Arg Arg Glu Ser Ile Leu
            100                 105                 110

Ala Asp Thr Val Glu Ala Leu Ile Gly Gly Val Phe Leu Asp Ser Asp
        115                 120                 125

Ile Gln Asn Val Glu Arg Leu Ile Leu Ser Trp Tyr Gln Thr Arg Leu
    130                 135                 140

Asp Glu Ile Ser Pro Gly Asp Lys Gln Lys Asp Pro Lys Thr Arg Leu
145                 150                 155                 160

Gln Glu Tyr Leu Gln Gly Arg His Leu Pro Leu Pro Ser Tyr Leu Val
                165                 170                 175

Val Gln Val Arg Gly Glu Ala His Asp Gln Glu Phe Thr Ile His Cys
            180                 185                 190

Gln Val Ser Gly Leu Pro Glu Pro Val Val Gly Thr Gly Ser Ser Arg
        195                 200                 205

Arg Lys Ala Glu Gln Ala Ala Ala Glu Gln Ala Leu Lys Lys Leu Glu
    210                 215                 220
```

Leu Glu
225

<210> SEQ ID NO 22
<211> LENGTH: 226
<212> TYPE: PRT
<213> ORGANISM: Enterobacteria

<400> SEQUENCE: 22

Met Asn Pro Ile Val Ile Asn Arg Leu Gln Arg Lys Leu Gly Tyr Thr
1               5                   10                  15

Phe His His Gln Glu Leu Leu Gln Gln Ala Leu Thr His Arg Ser Ala
            20                  25                  30

Ser Ser Lys His Asn Glu Arg Leu Glu Phe Leu Gly Asp Ser Ile Leu
        35                  40                  45

Ser Phe Val Ile Ala Asn Ala Leu Tyr His Arg Phe Pro Arg Val Asp
    50                  55                  60

Glu Gly Asp Met Ser Arg Met Arg Ala Thr Leu Val Arg Gly Asn Thr
65                  70                  75                  80

Leu Ala Glu Ile Ala Arg Glu Phe Glu Leu Gly Glu Cys Leu Arg Leu
                85                  90                  95

Gly Pro Gly Glu Leu Lys Ser Gly Gly Phe Arg Arg Glu Ser Ile Leu
            100                 105                 110

Ala Asp Thr Val Glu Ala Leu Ile Gly Gly Val Phe Leu Asp Ser Asp
        115                 120                 125

Ile Gln Thr Val Glu Lys Leu Ile Leu Asn Trp Tyr Gln Thr Arg Leu
    130                 135                 140

Asp Glu Ile Ser Pro Gly Asp Lys Gln Lys Asp Pro Lys Thr Arg Leu
145                 150                 155                 160

Gln Glu Tyr Leu Gln Gly Arg His Leu Pro Leu Pro Ser Tyr Leu Val
                165                 170                 175

Val Gln Val Arg Gly Glu Ala His Asp Gln Glu Phe Thr Ile His Cys
            180                 185                 190

Gln Val Ser Gly Leu Ser Glu Pro Val Val Gly Thr Gly Ser Ser Arg
        195                 200                 205

Arg Lys Ala Glu Gln Ala Ala Ala Glu Gln Ala Leu Lys Met Leu Glu
    210                 215                 220

Leu Glu
225

<210> SEQ ID NO 23
<211> LENGTH: 684
<212> TYPE: DNA
<213> ORGANISM: Verrucomicrobia

<400> SEQUENCE: 23
atgaatccgc tcgaagaccg catcggttac aagttccgca acgcgctgtt gctggaagaa      60
gcgctcacgc atcccagtgt gaggcacgag cgcctggagt ttttgggcga tgcggtcctg     120
cagctcgtga tgacggaaca cctgttcggg cattttaaga agaagccga agggacgctg     180 acgaaactgc gctcgcggct tgtttcgcgg gaggccctcg ccgttcatgc ggcgacgctc     240
gaactgggac gctatctggc cgtcggccgc ggtgaggacg cgagcggcgg tcgcgaacgc     300
aattcgacgc tcgccgacgc tttcgaggcg ctcgtcggag cgatctatct cgatagcgat     360
ctggccacgt gcgtcgcctt tatcctggat caggcagcgg gcgatctggc gcaactcgtc     420
gacgaaccga ccgatatcaa cccgaagggt cacctgcagg aattgctcca ggcgatttcg     480

```
cccccgcagcc cggtttacga agtgatttcg cagaccgggc cggagcacga aaagacgttt    540
gtgattcgcg cggtttggga gggcatcacg ctcggggagg gaaccgggcg aagcaagaaa    600
caggcggaaa cggccgccgc cgaggaggcg atgcggcaaa gcggtggga acggaaaag     660 acgtcgaccg caccttctcg gtag                                           684
```

<210> SEQ ID NO 24
<211> LENGTH: 227
<212> TYPE: PRT
<213> ORGANISM: Verrucomicrobia

<400> SEQUENCE: 24

```
Met Asn Pro Leu Glu Asp Arg Ile Gly Tyr Lys Phe Arg Asn Ala Leu
1               5                   10                  15

Leu Leu Glu Glu Ala Leu Thr His Pro Ser Val Arg His Glu Arg Leu
            20                  25                  30

Glu Phe Leu Gly Asp Ala Val Leu Gln Leu Val Met Thr Glu His Leu
        35                  40                  45

Phe Gly His Phe Lys Lys Glu Ala Glu Gly Thr Leu Thr Lys Leu Arg
    50                  55                  60

Ser Arg Leu Val Ser Arg Glu Ala Leu Ala Val His Ala Ala Thr Leu
65                  70                  75                  80

Glu Leu Gly Arg Tyr Leu Ala Val Gly Arg Gly Glu Asp Ala Ser Gly
                85                  90                  95

Gly Arg Glu Arg Asn Ser Thr Leu Ala Asp Ala Phe Glu Ala Leu Val
            100                 105                 110

Gly Ala Ile Tyr Leu Asp Ser Asp Leu Ala Thr Val Arg Arg Phe Ile
        115                 120                 125

Leu Asp Gln Ala Ala Gly Asp Leu Ala Gln Leu Val Asp Glu Pro Thr
    130                 135                 140

Asp Ile Asn Pro Lys Gly His Leu Gln Glu Leu Leu Gln Ala Ile Ser
145                 150                 155                 160

Pro Arg Ser Pro Val Tyr Glu Val Ile Ser Gln Thr Gly Pro Glu His
                165                 170                 175

Glu Lys Thr Phe Val Ile Arg Ala Val Trp Glu Gly Ile Thr Leu Gly
            180                 185                 190

Glu Gly Thr Gly Arg Ser Lys Lys Gln Ala Glu Thr Ala Ala Ala Glu
        195                 200                 205

Glu Ala Met Arg Gln Lys Arg Trp Glu Thr Glu Lys Thr Ser Thr Ala
    210                 215                 220

Pro Ser Arg
225
```

<210> SEQ ID NO 25
<211> LENGTH: 681
<212> TYPE: DNA
<213> ORGANISM: E. coli

<400> SEQUENCE: 25

```
atgaacccca tcgtaattaa tcggcttcaa cggaagctgg gctacacttt taatcatcag    60
gaactgttgc agcaggcatt aactcatcgt agtgccagca gtaaacataa cgagcgttta   120 gaattttag cgactctat tctgagctac gttatcgcca atgcgcttta tcaccgtttc   180
cctcgtgtgg atgaaggcga tatgagccgg atgcgcgcca cgctggtccg tggcaatacg   240
ctggcggaac tggcgcgcga atttgagtta ggcgagtgct acgtttagg gccaggtgaa    300
```

```
cttaaaagcg gtggatttcg tcgtgagtca attctcgccg acaccgtgaa ggctttcatc        360
ggtggcgtat tcctcgacag tgatattcaa accgtcgaga aattaatcct caactggtat        420
caaactcgtt tggacgaaat tagcccaggc gataaacaaa aagatccgaa aacgcgcttg        480
caagaatatt tgcagggtcg ccatctgccg ctgccgactt atctggtagt ccaggtacgt        540
ggcgaagcgc acgatcagga atttactatc cactgccagg tcagcggcct gagtgaaccg        600
gtggttggca caggttcaag ccgtcgtaag gctgagcagg ctgccgccga acaggcgttg        660
aaaaaactgg agctggaatg a                                                  681
```

```
<210> SEQ ID NO 26
<211> LENGTH: 226
<212> TYPE: PRT
<213> ORGANISM: E. coli

<400> SEQUENCE: 26
```

Met Asn Pro Ile Val Ile Asn Arg Leu Gln Arg Lys Leu Gly Tyr Thr
1               5                   10                  15

Phe Asn His Gln Glu Leu Leu Gln Gln Ala Leu Thr His Arg Ser Ala
            20                  25                  30

Ser Ser Lys His Asn Glu Arg Leu Glu Phe Leu Gly Asp Ser Ile Leu
        35                  40                  45

Ser Tyr Val Ile Ala Asn Ala Leu Tyr His Arg Phe Pro Arg Val Asp
    50                  55                  60

Glu Gly Asp Met Ser Arg Met Arg Ala Thr Leu Val Arg Gly Asn Thr
65                  70                  75                  80

Leu Ala Glu Leu Ala Arg Glu Phe Glu Leu Gly Glu Cys Leu Arg Leu
                85                  90                  95

Gly Pro Gly Glu Leu Lys Ser Gly Gly Phe Arg Arg Glu Ser Ile Leu
            100                 105                 110

Ala Asp Thr Val Lys Ala Phe Ile Gly Gly Val Phe Leu Asp Ser Asp
        115                 120                 125

Ile Gln Thr Val Glu Lys Leu Ile Leu Asn Trp Tyr Gln Thr Arg Leu
    130                 135                 140

Asp Glu Ile Ser Pro Gly Asp Lys Gln Lys Asp Pro Lys Thr Arg Leu
145                 150                 155                 160

Gln Glu Tyr Leu Gln Gly Arg His Leu Pro Leu Pro Thr Tyr Leu Val
                165                 170                 175

Val Gln Val Arg Gly Glu Ala His Asp Gln Glu Phe Thr Ile His Cys
            180                 185                 190

Gln Val Ser Gly Leu Ser Glu Pro Val Val Gly Thr Gly Ser Ser Arg
        195                 200                 205

Arg Lys Ala Glu Gln Ala Ala Ala Glu Gln Ala Leu Lys Lys Leu Glu
    210                 215                 220

Leu Glu
225

```
<210> SEQ ID NO 27
<211> LENGTH: 681
<212> TYPE: DNA
<213> ORGANISM: E. coli

<400> SEQUENCE: 27
atgaacccca tcgtaattaa tcggcttcaa cggaagctgg gctacacttt taatcatcag        60
gaactgttgc agcaggcatt aactcatcgt agtgccagca gtaaacataa cgagcgttta       120
```

```
gaattttag cgactctat tctgagctac gttatcgcca atgcgcttta tcaccgtttc    180
cctcgtgtgg atgaaggcga tatgagccgg atgcgcgcca cgctggtccg tggcaatacg    240
ctggcggaac tggcgcgcga atttgagtta ggcgagtgct acgtttaggg ccaggtgaa    300 cttaaaagcg gtggatttcg tcgtgagtca attctcgccg acaccgtgaa ggctttgatc    360
ggtggcgtat tcctcgacag tgatattcaa accgtcgaga attaatcct caactggtat    420 caaactcgtt tggacgaaat tagcccaggc gataaacaaa aagatccgaa aacgcgcttg    480
caagaatatt tgcagggtcg ccatctgccg ctgccgactt atctggtagt ccaggtacgt    540
ggcgaagcgc acgatcagga atttactatc cactgccagg tcagcggcct gagtgaaccg    600
gtggttggca caggttcaag ccgtcgtaag gctgagcagg ctgccgccga acaggcgttg    660
aaaaaactgg agctggaatg a                                              681
```

<210> SEQ ID NO 28
<211> LENGTH: 226
<212> TYPE: PRT
<213> ORGANISM: E. coli

<400> SEQUENCE: 28

```
Met Asn Pro Ile Val Ile Asn Arg Leu Gln Arg Lys Leu Gly Tyr Thr
1               5                   10                  15

Phe Asn His Gln Glu Leu Leu Gln Gln Ala Leu Thr His Arg Ser Ala
            20                  25                  30

Ser Ser Lys His Asn Glu Arg Leu Glu Phe Leu Gly Asp Ser Ile Leu
        35                  40                  45

Ser Tyr Val Ile Ala Asn Ala Leu Tyr His Arg Phe Pro Arg Val Asp
    50                  55                  60

Glu Gly Asp Met Ser Arg Met Arg Ala Thr Leu Val Arg Gly Asn Thr
65                  70                  75                  80

Leu Ala Glu Leu Ala Arg Glu Phe Glu Leu Gly Glu Cys Leu Arg Leu
                85                  90                  95

Gly Pro Gly Glu Leu Lys Ser Gly Gly Phe Arg Arg Glu Ser Ile Leu
            100                 105                 110

Ala Asp Thr Val Lys Ala Leu Ile Gly Gly Val Phe Leu Asp Ser Asp
        115                 120                 125

Ile Gln Thr Val Glu Lys Leu Ile Leu Asn Trp Tyr Gln Thr Arg Leu
    130                 135                 140

Asp Glu Ile Ser Pro Gly Asp Lys Gln Lys Asp Pro Lys Thr Arg Leu
145                 150                 155                 160

Gln Glu Tyr Leu Gln Gly Arg His Leu Pro Leu Pro Thr Tyr Leu Val
                165                 170                 175

Val Gln Val Arg Gly Glu Ala His Asp Gln Glu Phe Thr Ile His Cys
            180                 185                 190

Gln Val Ser Gly Leu Ser Glu Pro Val Val Gly Thr Gly Ser Ser Arg
        195                 200                 205

Arg Lys Ala Glu Gln Ala Ala Ala Glu Gln Ala Leu Lys Lys Leu Glu
    210                 215                 220

Leu Glu
225
```

<210> SEQ ID NO 29
<211> LENGTH: 681
<212> TYPE: DNA
<213> ORGANISM: E. coli

<400> SEQUENCE: 29

```
atgaatccca tcgtgatcaa ccgttttgcag cgtaaattgg gttacacttt taatcaccaa    60
gaattgctgc agcaggcatt gacccaccgc tccgcttcgt ctaaacacaa cgcccgtctg   120
gaattttag gagattcgat cctgtcttac gtgatcgcca atgcactgta tcaccgcttt   180
ccccgcgtgg atgaaggaga tatgagccgt atgcgtgcga cacttgtgcg cggaaatacc   240
ctggcagaac tggcgcgcga gttcgaactg ggagagtgct acgccttgg tcccggtgag   300
ctgaagtccg ggggctttcg tcgtgagtct atccttgctg atacggttga agctttaatc   360
ggggggtgtat ttttagactc agacatccaa acagtggaaa agcttatctt gaactggtac   420
caaacccgtt tagatgagat cagcccgggg gacaaacaaa aggacccaaa gacacgtttg   480
caggagtacc ttcaagggcg tcacctgccc ttgccaacat acttagtagt ccaggtacgt   540
ggagaagcac acgatcagga gttcaccatt cactgtcaag ttagtgggtt atccgaacct   600
gtagtgggga cgggctcctc acgtcgcaaa gcggaacaag ctgcggctga acaggcattg   660
aaaaaattgg agcttgagta a                                             681
```

<210> SEQ ID NO 30
<211> LENGTH: 226
<212> TYPE: PRT
<213> ORGANISM: E. coli

<400> SEQUENCE: 30

```
Met Asn Pro Ile Val Ile Asn Arg Leu Gln Arg Lys Leu Gly Tyr Thr
1               5                   10                  15
Phe Asn His Gln Glu Leu Leu Gln Gln Ala Leu Thr His Arg Ser Ala
            20                  25                  30
Ser Ser Lys His Asn Ala Arg Leu Glu Phe Leu Gly Asp Ser Ile Leu
        35                  40                  45
Ser Tyr Val Ile Ala Asn Ala Leu Tyr His Arg Phe Pro Arg Val Asp
    50                  55                  60
Glu Gly Asp Met Ser Arg Met Arg Ala Thr Leu Val Arg Gly Asn Thr
65                  70                  75                  80
Leu Ala Glu Leu Ala Arg Glu Phe Glu Leu Gly Glu Cys Leu Arg Leu
                85                  90                  95
Gly Pro Gly Glu Leu Lys Ser Gly Gly Phe Arg Arg Glu Ser Ile Leu
            100                 105                 110
Ala Asp Thr Val Glu Ala Leu Ile Gly Gly Val Phe Leu Asp Ser Asp
        115                 120                 125
Ile Gln Thr Val Glu Lys Leu Ile Leu Asn Trp Tyr Gln Thr Arg Leu
    130                 135                 140
Asp Glu Ile Ser Pro Gly Asp Lys Gln Lys Asp Pro Lys Thr Arg Leu
145                 150                 155                 160
Gln Glu Tyr Leu Gln Gly Arg His Leu Pro Leu Pro Thr Tyr Leu Val
                165                 170                 175
Val Gln Val Arg Gly Glu Ala His Asp Gln Glu Phe Thr Ile His Cys
            180                 185                 190
Gln Val Ser Gly Leu Ser Glu Pro Val Val Gly Thr Gly Ser Ser Arg
        195                 200                 205
Arg Lys Ala Glu Gln Ala Ala Ala Glu Gln Ala Leu Lys Lys Leu Glu
    210                 215                 220
Leu Glu
225
```

<210> SEQ ID NO 31
<211> LENGTH: 681
<212> TYPE: DNA
<213> ORGANISM: Enterobacteriaceae

<400> SEQUENCE: 31

```
atgaatccca tcgtaataaa taggctgcag cgtaagctgg gctacacttt tcaacatcag      60
gatctgttgc aacaggcatt aacccatcgg agtgccagca gcaagcataa tgcccgcttg     120
gagttttggg gtgactccat tctcagttat gtcatcgcga atgcgctgta tcatcgtttt     180
cctcgcgtag atgaaggcga catgagccgc atgcgtgcga cgctggtgcg cggcaatacg     240
ctggcggaaa tcgcctgcga gttcgaactg ggtgagtgtc tgcgtcttgg ccgggtgaa      300
ctgaaaagtg gcggtttcgc cgccgagtcg attcttgctg ataccgtgga agcgttgatc     360
ggtggcgtct tcctcgacag cgacattcag aacgttgagc gtttgattct ctcgtggtat     420
cagacccgtc tcgacgaaat cagtccaggc gacaagcaaa aagatccgaa acgcgtctg      480
caggagtacc tgcagggtcg ccatctgccg ctgccgtcgt atctggtggt gcaggtgcgt     540
ggtgaagcgc acgatcaaga atttaccatt cactgtcagg tgagtggcct gcctgagcct     600
gtcgtaggga cgggctcaag ccgccgtaaa gcggaacagg ctgcggctga gcaggcactg     660
aaaaagctgg agctggaatg a                                               681
```

<210> SEQ ID NO 32
<211> LENGTH: 226
<212> TYPE: PRT
<213> ORGANISM: Enterobacteriaceae

<400> SEQUENCE: 32

Met Asn Pro Ile Val Ile Asn Arg Leu Gln Arg Lys Leu Gly Tyr Thr
1               5                   10                  15

Phe Gln His Gln Asp Leu Leu Gln Gln Ala Leu Thr His Arg Ser Ala
            20                  25                  30

Ser Ser Lys His Asn Ala Arg Leu Glu Phe Leu Gly Asp Ser Ile Leu
        35                  40                  45

Ser Tyr Val Ile Ala Asn Ala Leu Tyr His Arg Phe Pro Arg Val Asp
    50                  55                  60

Glu Gly Asp Met Ser Arg Met Arg Ala Thr Leu Val Arg Gly Asn Thr
65                  70                  75                  80

Leu Ala Glu Ile Ala Cys Glu Phe Glu Leu Gly Glu Cys Leu Arg Leu
                85                  90                  95

Gly Pro Gly Glu Leu Lys Ser Gly Gly Phe Ala Ala Glu Ser Ile Leu
            100                 105                 110

Ala Asp Thr Val Glu Ala Leu Ile Gly Gly Val Phe Leu Asp Ser Asp
        115                 120                 125

Ile Gln Asn Val Glu Arg Leu Ile Leu Ser Trp Tyr Gln Thr Arg Leu
    130                 135                 140

Asp Glu Ile Ser Pro Gly Asp Lys Gln Lys Asp Pro Lys Thr Arg Leu
145                 150                 155                 160

Gln Glu Tyr Leu Gln Gly Arg His Leu Pro Leu Pro Ser Tyr Leu Val
                165                 170                 175

Val Gln Val Arg Gly Glu Ala His Asp Gln Glu Phe Thr Ile His Cys
            180                 185                 190

Gln Val Ser Gly Leu Pro Glu Pro Val Val Gly Thr Gly Ser Ser Arg
        195                 200                 205

Arg Lys Ala Glu Gln Ala Ala Ala Glu Gln Ala Leu Lys Lys Leu Glu
            210                 215                 220

Leu Glu
225

<210> SEQ ID NO 33
<211> LENGTH: 681
<212> TYPE: DNA
<213> ORGANISM: E. coli

<400> SEQUENCE: 33
atgaacccca tcgtaattaa tcggcttcaa cggaagctgg gctacacttt taatcatcag        60
gaactgttgc agcaggcatt aactcatcgt agtgccagca gtaaacataa cgagcgttta       120 gaattttag gcgactctat tctgagctac gttatcgcca atgcgcttta tcaccgtttc       180
cctcgtgtgg atgaaggcga tatgagccgg atgcgcgcca cgctggtccg tggcaatacg       240
ctggcggaac tggcgcgcga atttgagtta ggcgagtgct acgtttagg gccaggtgaa       300 cttaaaagcg gtggatttcg tcgtgagtca attctcgccg acacggtgca ggctttgatc       360
ggtggcgtat tcctcgacag tgatattcaa accgtcgaga aattaatcct caactggtat       420
caaactcgtt tggacgaaat tagcccaggc gataaacaaa aagatccgaa aacgcgcttg       480
caagaatatt tgcagggtcg ccatctgccg ctgccgactt atctggtagt ccaggtacgt       540
ggcgaagcgc acgatcagga atttactatc cactgccagg tcagcggcct gagtgaaccg       600
gtggttggca caggttcaag ccgtcgtaag gctgagcagg ctgccgccga acaggcgttg       660
aaaaaactgg agctggaatg a                                                681

<210> SEQ ID NO 34
<211> LENGTH: 226
<212> TYPE: PRT
<213> ORGANISM: E. coli

<400> SEQUENCE: 34

Met Asn Pro Ile Val Ile Asn Arg Leu Gln Arg Lys Leu Gly Tyr Thr
1               5                   10                  15

Phe Asn His Gln Glu Leu Leu Gln Gln Ala Leu Thr His Arg Ser Ala
                20                  25                  30

Ser Ser Lys His Asn Glu Arg Leu Glu Phe Leu Gly Asp Ser Ile Leu
            35                  40                  45

Ser Tyr Val Ile Ala Asn Ala Leu Tyr His Arg Phe Pro Arg Val Asp
        50                  55                  60

Glu Gly Asp Met Ser Arg Met Arg Ala Thr Leu Val Arg Gly Asn Thr
65                  70                  75                  80

Leu Ala Glu Leu Ala Arg Glu Phe Glu Leu Gly Glu Cys Leu Arg Leu
                85                  90                  95

Gly Pro Gly Glu Leu Lys Ser Gly Gly Phe Arg Arg Glu Ser Ile Leu
            100                 105                 110

Ala Asp Thr Val Gln Ala Leu Ile Gly Gly Val Phe Leu Asp Ser Asp
        115                 120                 125

Ile Gln Thr Val Glu Lys Leu Ile Leu Asn Trp Tyr Gln Thr Arg Leu
    130                 135                 140

Asp Glu Ile Ser Pro Gly Asp Lys Gln Lys Asp Pro Lys Thr Arg Leu
145                 150                 155                 160

Gln Glu Tyr Leu Gln Gly Arg His Leu Pro Leu Pro Thr Tyr Leu Val
                165                 170                 175

```
Val Gln Val Arg Gly Glu Ala His Asp Gln Glu Phe Thr Ile His Cys
            180                 185                 190

Gln Val Ser Gly Leu Ser Glu Pro Val Val Gly Thr Gly Ser Ser Arg
        195                 200                 205

Arg Lys Ala Glu Gln Ala Ala Ala Glu Gln Ala Leu Lys Lys Leu Glu
    210                 215                 220

Leu Glu
225

<210> SEQ ID NO 35
<211> LENGTH: 681
<212> TYPE: DNA
<213> ORGANISM: E. coli

<400> SEQUENCE: 35
atgaacccca tcgtaattaa tcggcttcaa cggaagctgg gctacacttt taatcatcag      60
gaactgttgc agcaggcatt aactcatcgt agtgccagca gtaaacataa cgagcgttta     120 gaattttag gcgactctat tctgagctac gttatcgcca atgcgcttta tcaccgtttc     180
cctcgtgtgg atgaaggcga tatgagccgg atgcgcgcca cgctggtccg tggcaatacg     240
ctggcggaac tggcgcgcga atttgagtta ggcgagtgct acgtttagg gccaggtgaa      300 cttaaaagcg gtggatttcg tcgtgagtca attctcgccg acacggtgga cgctttgatc     360
ggtggcgtat tcctcgacag tgatattcaa accgtcgaga attaatcct caactggtat      420 caaactcgtt tggacgaaat tagcccaggc gataaacaaa aagatccgaa acgcgcttg      480 caagaatatt tgcagggtcg ccatctgccg ctgccgactt atctggtagt ccaggtacgt     540
ggcgaagcgc acgatcagga atttactatc cactgccagg tcagcggcct gagtgaaccg     600
gtggttggca caggttcaag ccgtcgtaag gctgagcagg ctgccgccga acaggcgttg     660
aaaaaactgg agctggaatg a                                                681

<210> SEQ ID NO 36
<211> LENGTH: 226
<212> TYPE: PRT
<213> ORGANISM: E. coli

<400> SEQUENCE: 36

Met Asn Pro Ile Val Ile Asn Arg Leu Gln Arg Lys Leu Gly Tyr Thr
1               5                   10                  15

Phe Asn His Gln Glu Leu Leu Gln Gln Ala Leu Thr His Arg Ser Ala
            20                  25                  30

Ser Ser Lys His Asn Glu Arg Leu Glu Phe Leu Gly Asp Ser Ile Leu
        35                  40                  45

Ser Tyr Val Ile Ala Asn Ala Leu Tyr His Arg Phe Pro Arg Val Asp
    50                  55                  60

Glu Gly Asp Met Ser Arg Met Arg Ala Thr Leu Val Arg Gly Asn Thr
65                  70                  75                  80

Leu Ala Glu Leu Ala Arg Glu Phe Glu Leu Gly Glu Cys Leu Arg Leu
                85                  90                  95

Gly Pro Gly Glu Leu Lys Ser Gly Gly Phe Arg Arg Glu Ser Ile Leu
            100                 105                 110

Ala Asp Thr Val Asp Ala Leu Ile Gly Gly Val Phe Leu Asp Ser Asp
        115                 120                 125

Ile Gln Thr Val Glu Lys Leu Ile Leu Asn Trp Tyr Gln Thr Arg Leu
    130                 135                 140
```

Asp Glu Ile Ser Pro Gly Asp Lys Gln Lys Asp Pro Lys Thr Arg Leu
145                 150                 155                 160

Gln Glu Tyr Leu Gln Gly Arg His Leu Pro Leu Pro Thr Tyr Leu Val
            165                 170                 175

Val Gln Val Arg Gly Glu Ala His Asp Gln Glu Phe Thr Ile His Cys
        180                 185                 190

Gln Val Ser Gly Leu Ser Glu Pro Val Val Gly Thr Gly Ser Ser Arg
    195                 200                 205

Arg Lys Ala Glu Gln Ala Ala Glu Gln Ala Leu Lys Lys Leu Glu
    210                 215                 220

Leu Glu
225

<210> SEQ ID NO 37
<211> LENGTH: 681
<212> TYPE: DNA
<213> ORGANISM: E. coli

<400> SEQUENCE: 37
atgaacccca tcgtaattaa tcggcttcaa cggaagctgg gctacacttt taatcatcag      60
gaactgttgc agcaggcatt aactcatcgt agtgccagca gtaaacataa cgagcgttta     120
gaatttttag cgactctat tctgagctac gttatcgcca atgcgcttta tcaccgtttc     180
cctcgtgtgg atgaaggcga tatgagccgg atgcgcgcca cgctggtccg tggcaatacg     240
ctggcggaac tggcgcgcga atttgagtta ggcgagtgct tacgtttagg gccaggtgaa     300
cttaaaagcg gtggatttcg tcgtgagtca attctcgccg acaccgtcga agcattaatt     360
ggtggcgtat cctcgacag tgatattcaa accgtcgaga attaatcct caactggtat     420 caaactcgtt tggacgaaat tagcccaggc gacaagccca aggacccgaa aacgcgcttg     480
caagaatatt tgcagggtcg ccatctgccg ctgccgactt atctggtagt ccaggtacgt     540
ggcgaagcgc acgatcagga atttactatc cactgccagg tcagcggcct gagtgaaccg     600
gtggttggca caggttcaag ccgtcgtaag gctgagcagg ctgccgccga acaggcgttg     660
aaaaaactgg agctggaatg a                                               681

<210> SEQ ID NO 38
<211> LENGTH: 226
<212> TYPE: PRT
<213> ORGANISM: E. coli

<400> SEQUENCE: 38

Met Asn Pro Ile Val Ile Asn Arg Leu Gln Arg Lys Leu Gly Tyr Thr
1               5                   10                  15

Phe Asn His Gln Glu Leu Leu Gln Gln Ala Leu Thr His Arg Ser Ala
            20                  25                  30

Ser Ser Lys His Asn Glu Arg Leu Glu Phe Leu Gly Asp Ser Ile Leu
        35                  40                  45

Ser Tyr Val Ile Ala Asn Ala Leu Tyr His Arg Phe Pro Arg Val Asp
    50                  55                  60

Glu Gly Asp Met Ser Arg Met Arg Ala Thr Leu Val Arg Gly Asn Thr
65                  70                  75                  80

Leu Ala Glu Leu Ala Arg Glu Phe Glu Leu Gly Glu Cys Leu Arg Leu
                85                  90                  95

Gly Pro Gly Glu Leu Lys Ser Gly Gly Phe Arg Arg Glu Ser Ile Leu
            100                 105                 110

```
Ala Asp Thr Val Glu Ala Leu Ile Gly Gly Val Phe Leu Asp Ser Asp
        115                 120                 125

Ile Gln Thr Val Glu Lys Leu Ile Leu Asn Trp Tyr Gln Thr Arg Leu
    130                 135                 140

Asp Glu Ile Ser Pro Gly Asp Lys Pro Lys Asp Pro Lys Thr Arg Leu
145                 150                 155                 160

Gln Glu Tyr Leu Gln Gly Arg His Leu Pro Leu Pro Thr Tyr Leu Val
                165                 170                 175

Val Gln Val Arg Gly Glu Ala His Asp Gln Glu Phe Thr Ile His Cys
                180                 185                 190

Gln Val Ser Gly Leu Ser Glu Pro Val Val Gly Thr Gly Ser Ser Arg
                195                 200                 205

Arg Lys Ala Glu Gln Ala Ala Ala Glu Gln Ala Leu Lys Lys Leu Glu
                210                 215                 220

Leu Glu
225
```

<210> SEQ ID NO 39
<211> LENGTH: 681
<212> TYPE: DNA
<213> ORGANISM: E. coli

<400> SEQUENCE: 39

```
atgaacccca tcgtaattaa tcggcttcaa cggaagctgg gctacacttt taatcatcag    60
gaactgttgc agcaggcatt aactcatcgt agtgccagca gtaaacataa cgagcgttta   120
gaatttttag cgactctat tctgagctac gttatcgcca atgcgcttta tcaccgtttc   180
cctcgtgtgg atgaaggcga tatgagccgg atgcgcgcca cgctggtccg tggcaatacg   240
ctggcggaac tggcgcgcga atttgagtta ggcgagtgct acgtttaggc gccaggtgaa   300
cttaaaagcg gtggatttcg tcgtgagtca attctcgccg acaccgtcga agcattaatt   360
ggtggcgtat tcctcgacag tgatattcaa accgtcgaga attaatcct caactggtat   420
caaactcgtt tggacgaaat tagcccaggc gacaagcaga aggagcccaa acgcgcttg   480
caagaatatt tgcagggtcg ccatctgccg ctgccgactt atctggtagt ccaggtacgt   540
ggcgaagcgc acgatcagga atttactatc cactgccagg tcagcggcct gagtgaaccg   600
gtggttggca caggttcaag ccgtcgtaag gctgagcagg ctgccgccga acaggcgttg   660
aaaaaactgg agctggaatg a                                              681
```

<210> SEQ ID NO 40
<211> LENGTH: 226
<212> TYPE: PRT
<213> ORGANISM: E. coli

<400> SEQUENCE: 40

```
Met Asn Pro Ile Val Ile Asn Arg Leu Gln Arg Lys Leu Gly Tyr Thr
1               5                   10                  15

Phe Asn His Gln Glu Leu Leu Gln Gln Ala Leu Thr His Arg Ser Ala
                20                  25                  30

Ser Ser Lys His Asn Glu Arg Leu Glu Phe Leu Gly Asp Ser Ile Leu
            35                  40                  45

Ser Tyr Val Ile Ala Asn Ala Leu Tyr His Arg Phe Pro Arg Val Asp
        50                  55                  60

Glu Gly Asp Met Ser Arg Met Arg Ala Thr Leu Val Arg Gly Asn Thr
65                  70                  75                  80
```

```
Leu Ala Glu Leu Ala Arg Glu Phe Glu Leu Gly Glu Cys Leu Arg Leu
                85                  90                  95

Gly Pro Gly Glu Leu Lys Ser Gly Gly Phe Arg Arg Glu Ser Ile Leu
            100                 105                 110

Ala Asp Thr Val Glu Ala Leu Ile Gly Val Phe Leu Asp Ser Asp
        115                 120                 125

Ile Gln Thr Val Glu Lys Leu Ile Leu Asn Trp Tyr Gln Thr Arg Leu
    130                 135                 140

Asp Glu Ile Ser Pro Gly Asp Lys Gln Lys Glu Pro Lys Thr Arg Leu
145                 150                 155                 160

Gln Glu Tyr Leu Gln Gly Arg His Leu Pro Leu Pro Thr Tyr Leu Val
                165                 170                 175

Val Gln Val Arg Gly Glu Ala His Asp Gln Glu Phe Thr Ile His Cys
            180                 185                 190

Gln Val Ser Gly Leu Ser Glu Pro Val Val Gly Thr Gly Ser Ser Arg
        195                 200                 205

Arg Lys Ala Glu Gln Ala Ala Ala Glu Gln Ala Leu Lys Lys Leu Glu
    210                 215                 220

Leu Glu
225

<210> SEQ ID NO 41
<211> LENGTH: 678
<212> TYPE: DNA
<213> ORGANISM: E. coli

<400> SEQUENCE: 41
atgaacccca tcgtaattaa tcggcttcaa cggaagctgg gctacacttt taatcatcag      60
gaactgttgc agcaggcatt aactcatcgt agtgccagta acacaatgc ccgcttggaa     120 tttttaggcg actctattct gagctacgtt atcgccaatg cgctttatca ccgtttccct     180
cgtgtggatg aaggcgatat gagccggatg cgcgccacgc tggtccgtgg caatacgctg     240
gcggaactgg cgcgcgaatt tgagttaggc gagtgcttac gtttagggcc aggtgaactt     300
aaaagcggtg gatttgccgc cgagtcaatt ctcgccgaca ccgtcgaagc attaattggt     360
ggcgtattcc tcgacagtga tattcaaacc gtcgagaaat taatcctcaa ctggtatcaa     420
actcgtttgg acgaaattag cccaggcgat aaacaaaaag atccgaaaac cgcgcttcaa     480
gaatatttgc agggtcgcca tctgccgctg ccgacttatc tggtagtcca ggtacgtggc     540
gaagcgcacg atcaggaatt tactatccac tgccaggtca gcggcctgag tgaaccggtg     600
gttggcacag gttcaagccg tcgtaaggct gagcaggctg ccgccgaaca ggcgttgaaa     660
aaactggagc tggaatga                                                    678

<210> SEQ ID NO 42
<211> LENGTH: 225
<212> TYPE: PRT
<213> ORGANISM: E. coli

<400> SEQUENCE: 42

Met Asn Pro Ile Val Ile Asn Arg Leu Gln Arg Lys Leu Gly Tyr Thr
1               5                   10                  15

Phe Asn His Gln Glu Leu Leu Gln Gln Ala Leu Thr His Arg Ser Ala
            20                  25                  30

Ser Lys His Asn Ala Arg Leu Glu Phe Leu Gly Asp Ser Ile Leu Ser
        35                  40                  45
```

-continued

Tyr Val Ile Ala Asn Ala Leu Tyr His Arg Phe Pro Arg Val Asp Glu
          50                  55                  60

Gly Asp Met Ser Arg Met Arg Ala Thr Leu Val Arg Gly Asn Thr Leu
65                  70                  75                  80

Ala Glu Leu Ala Arg Glu Phe Glu Leu Gly Glu Cys Leu Arg Leu Gly
                85                  90                  95

Pro Gly Glu Leu Lys Ser Gly Gly Phe Ala Ala Glu Ser Ile Leu Ala
            100                 105                 110

Asp Thr Val Glu Ala Leu Ile Gly Gly Val Phe Leu Asp Ser Asp Ile
        115                 120                 125

Gln Thr Val Glu Lys Leu Ile Leu Asn Trp Tyr Gln Thr Arg Leu Asp
    130                 135                 140

Glu Ile Ser Pro Gly Asp Lys Gln Lys Asp Pro Lys Thr Arg Leu Gln
145                 150                 155                 160

Glu Tyr Leu Gln Gly Arg His Leu Pro Leu Pro Thr Tyr Leu Val Val
                165                 170                 175

Gln Val Arg Gly Glu Ala His Asp Gln Glu Phe Thr Ile His Cys Gln
            180                 185                 190

Val Ser Gly Leu Ser Glu Pro Val Val Gly Thr Gly Ser Ser Arg Arg
        195                 200                 205

Lys Ala Glu Gln Ala Ala Ala Glu Gln Ala Leu Lys Lys Leu Glu Leu
    210                 215                 220

Glu
225

<210> SEQ ID NO 43
<211> LENGTH: 678
<212> TYPE: DNA
<213> ORGANISM: E. coli

<400> SEQUENCE: 43
atgaacccca tcgtaattaa tcggcttcaa cggaagctgg gctacacttt taatcatcag      60
gaactgttgc agcaggcatt aactcatcgt agtgccgcca acacaatgc ccgcttggaa     120 tttttaggcg actctattct gagctacgtt atcgccaatg cgctttatca ccgtttccct    180
cgtgtggatg aaggcgatat gagccggatg cgcgccacgc tggtccgtgg caatacgctg    240
gcggaactgg cgcgcgaatt tgagttaggc gagtgcttac gtttagggcc aggtgaactt    300
aaaagcggtg gatttgccgc cgagtcaatt ctcgccgaca ccgtcgaagc attaattggt    360
ggcgtattcc tcgacagtga tattcaaacc gtcgagaaat aatcctcaa ctggtatcaa     420 actcgtttgg acgaaattag cccaggcgat aaacaaaaag atccgaaaac gcgcttgcaa    480
gaatatttgc agggtcgcca tctgccgctg ccgacttatc tggtagtcca ggtacgtggc    540
gaagcgcacg atcaggaatt tactatccac tgccaggtca gcggcctgag tgaaccggtg    600
gttggcacag gttcaagccg tcgtaaggct gagcaggctg ccgccgaaca ggcgttgaaa    660
aaactggagc tggaatga                                                  678

<210> SEQ ID NO 44
<211> LENGTH: 225
<212> TYPE: PRT
<213> ORGANISM: E. coli

<400> SEQUENCE: 44

Met Asn Pro Ile Val Ile Asn Arg Leu Gln Arg Lys Leu Gly Tyr Thr
1               5                   10                  15

| Phe | Asn | His | Gln | Glu | Leu | Leu | Gln | Gln | Ala | Leu | Thr | His | Arg | Ser | Ala |
|---|---|---|---|---|---|---|---|---|---|---|---|---|---|---|---|
| | | | 20 | | | | 25 | | | | 30 | | | | |

Ala Lys His Asn Ala Arg Leu Glu Phe Leu Gly Asp Ser Ile Leu Ser
        35                  40                  45

Tyr Val Ile Ala Asn Ala Leu Tyr His Arg Phe Pro Arg Val Asp Glu
 50                  55                  60

Gly Asp Met Ser Arg Met Arg Ala Thr Leu Val Arg Gly Asn Thr Leu
65                  70                  75                  80

Ala Glu Leu Ala Arg Glu Phe Glu Leu Gly Glu Cys Leu Arg Leu Gly
                85                  90                  95

Pro Gly Glu Leu Lys Ser Gly Gly Phe Ala Ala Glu Ser Ile Leu Ala
            100                 105                 110

Asp Thr Val Glu Ala Leu Ile Gly Gly Val Phe Leu Asp Ser Asp Ile
            115                 120                 125

Gln Thr Val Glu Lys Leu Ile Leu Asn Trp Tyr Gln Thr Arg Leu Asp
        130                 135                 140

Glu Ile Ser Pro Gly Asp Lys Gln Lys Asp Pro Lys Thr Arg Leu Gln
145                 150                 155                 160

Glu Tyr Leu Gln Gly Arg His Leu Pro Leu Pro Thr Tyr Leu Val Val
                165                 170                 175

Gln Val Arg Gly Glu Ala His Asp Gln Glu Phe Thr Ile His Cys Gln
            180                 185                 190

Val Ser Gly Leu Ser Glu Pro Val Val Gly Thr Gly Ser Ser Arg Arg
            195                 200                 205

Lys Ala Glu Gln Ala Ala Ala Glu Gln Ala Leu Lys Lys Leu Glu Leu
        210                 215                 220

Glu
225

<210> SEQ ID NO 45
<211> LENGTH: 672
<212> TYPE: DNA
<213> ORGANISM: E. coli

<400> SEQUENCE: 45

```
atgaacccca tcgtaattaa tcggcttcaa cggaagctgg gctacacttt taatcatcag      60
gaactgttgc agcaggcatt aactcatcgt agtaaacaca tgcccgcttg gaattttta     120
ggcgactcta ttctgagcta cgttatcgcc aatgcgcttt atcaccgttt ccctcgtgtg    180
gatgaaggcg atatgagccg gatgcgcgcc acgctggtcc gtggcaatac gctggcggaa    240
ctggcgcgcg aatttgagtt aggcgagtgc ttacgtttag gccaggtga  acttaaaagc    300
ggtggatttg tcgtgagtc aattctcgcc gacaccgtcg aagcattaat tggtggcgta    360
ttcctcgaca gtgatattca aaccgtcgag aaattaatcc tcaactggta tcaaactcgt    420
ttggacgaaa ttagcccagg cgataaacaa aaagatccga aaacgcgctt gcaagaatat    480
ttgcagggtc gccatctgcc gctgccgact tatctggtag tccaggtacg tggcgaagcg    540
cacgatcagg aatttactat ccactgccag gtcagcggcc tgagtgaacc ggtggttggc    600
acaggttcaa gccgtcgtaa ggctgagcag gctgccgccg aacaggcgtt gaaaaaactg    660
gagctggaat ga                                                        672
```

<210> SEQ ID NO 46
<211> LENGTH: 223
<212> TYPE: PRT

<213> ORGANISM: E. coli

<400> SEQUENCE: 46

| | | | | | | | | | | | | | | |
|---|---|---|---|---|---|---|---|---|---|---|---|---|---|---|
| Met | Asn | Pro | Ile | Val | Ile | Asn | Arg | Leu | Gln | Arg | Lys | Leu | Gly | Tyr | Thr |
| 1 | | | | 5 | | | | | 10 | | | | | 15 | |

Phe Asn His Gln Glu Leu Leu Gln Gln Ala Leu Thr His Arg Ser Lys
          20                  25                  30

His Asn Ala Arg Leu Glu Phe Leu Gly Asp Ser Ile Leu Ser Tyr Val
              35                  40                  45

Ile Ala Asn Ala Leu Tyr His Arg Phe Pro Arg Val Asp Glu Gly Asp
 50                  55                  60

Met Ser Arg Met Arg Ala Thr Leu Val Arg Gly Asn Thr Leu Ala Glu
 65                  70                  75                  80

Leu Ala Arg Glu Phe Glu Leu Gly Glu Cys Leu Arg Leu Gly Pro Gly
                 85                  90                  95

Glu Leu Lys Ser Gly Gly Phe Arg Arg Glu Ser Ile Leu Ala Asp Thr
             100                 105                 110

Val Glu Ala Leu Ile Gly Gly Val Phe Leu Asp Ser Asp Ile Gln Thr
         115                 120                 125

Val Glu Lys Leu Ile Leu Asn Trp Tyr Gln Thr Arg Leu Asp Glu Ile
 130                 135                 140

Ser Pro Gly Asp Lys Gln Lys Asp Pro Lys Thr Arg Leu Gln Glu Tyr
145                 150                 155                 160

Leu Gln Gly Arg His Leu Pro Leu Pro Thr Tyr Leu Val Val Gln Val
                 165                 170                 175

Arg Gly Glu Ala His Asp Gln Glu Phe Thr Ile His Cys Gln Val Ser
             180                 185                 190

Gly Leu Ser Glu Pro Val Val Gly Thr Gly Ser Ser Arg Arg Lys Ala
         195                 200                 205

Glu Gln Ala Ala Ala Glu Gln Ala Leu Lys Lys Leu Glu Leu Glu
     210                 215                 220

<210> SEQ ID NO 47
<211> LENGTH: 672
<212> TYPE: DNA
<213> ORGANISM: E. coli

<400> SEQUENCE: 47

```
atgaacccca tcgtaattaa tcggcttcaa cggaagctgg gctacacttt taatcatcag    60
gaactgttgc agcaggcatt aactcatcgt agtgtacaca atgcccgctt ggaattttta   120
ggcgactcta ttctgagcta cgttatcgcc aatgcgcttt atcaccgttt ccctcgtgtg   180
gatgaaggcg atatgagccg gatgcgcgcc acgctggtcc gtggcaatac gctggcggaa   240
ctggcgcgcg aatttgagtt aggcgagtgc ttacgtttag gccaggtgaa cttaaaagc    300 ggtggatttc gtcgtgagtc aattctcgcc gacaccgtcg aagcattaat tggtggcgta   360
ttcctcgaca gtgatattca aaccgtcgag aaattaatcc tcaactggta tcaaactcgt   420
ttggacgaaa ttagcccagg cgataaacaa aaagatccga aaacgcgctt gcaagaatat   480
ttgcagggtc gccatctgcc gctgccgact tatctggtag tccaggtacg tggcgaagcg   540
cacgatcagg aatttactat ccactgccag gtcagcggcc tgagtgaacc ggtggttggc   600
acaggttcaa gccgtcgtaa ggctgagcag gctgccgccg aacaggcgtt gaaaaaactg   660
gagctggaat ga                                                       672
```

<210> SEQ ID NO 48
<211> LENGTH: 223
<212> TYPE: PRT
<213> ORGANISM: E. coli

<400> SEQUENCE: 48

| | | | | | | | | | | | | | | | |
|---|---|---|---|---|---|---|---|---|---|---|---|---|---|---|---|
| Met | Asn | Pro | Ile | Val | Ile | Asn | Arg | Leu | Gln | Arg | Lys | Leu | Gly | Tyr | Thr |
| 1 | | | | 5 | | | | | 10 | | | | | 15 | |
| Phe | Asn | His | Gln | Glu | Leu | Leu | Gln | Gln | Ala | Leu | Thr | His | Arg | Ser | Val |
| | | | 20 | | | | | 25 | | | | | 30 | | |
| His | Asn | Ala | Arg | Leu | Glu | Phe | Leu | Gly | Asp | Ser | Ile | Leu | Ser | Tyr | Val |
| | | | 35 | | | | | 40 | | | | | 45 | | |
| Ile | Ala | Asn | Ala | Leu | Tyr | His | Arg | Phe | Pro | Arg | Val | Asp | Glu | Gly | Asp |
| | 50 | | | | | 55 | | | | | 60 | | | | |
| Met | Ser | Arg | Met | Arg | Ala | Thr | Leu | Val | Arg | Gly | Asn | Thr | Leu | Ala | Glu |
| 65 | | | | | 70 | | | | | 75 | | | | | 80 |
| Leu | Ala | Arg | Glu | Phe | Glu | Leu | Gly | Glu | Cys | Leu | Arg | Leu | Gly | Pro | Gly |
| | | | | 85 | | | | | 90 | | | | | 95 | |
| Glu | Leu | Lys | Ser | Gly | Gly | Phe | Arg | Arg | Glu | Ser | Ile | Leu | Ala | Asp | Thr |
| | | | 100 | | | | | 105 | | | | | 110 | | |
| Val | Glu | Ala | Leu | Ile | Gly | Gly | Val | Phe | Leu | Asp | Ser | Asp | Ile | Gln | Thr |
| | | | 115 | | | | | 120 | | | | | 125 | | |
| Val | Glu | Lys | Leu | Ile | Leu | Asn | Trp | Tyr | Gln | Thr | Arg | Leu | Asp | Glu | Ile |
| | 130 | | | | | 135 | | | | | 140 | | | | |
| Ser | Pro | Gly | Asp | Lys | Gln | Lys | Asp | Pro | Lys | Thr | Arg | Leu | Gln | Glu | Tyr |
| 145 | | | | | 150 | | | | | 155 | | | | | 160 |
| Leu | Gln | Gly | Arg | His | Leu | Pro | Leu | Pro | Thr | Tyr | Leu | Val | Val | Gln | Val |
| | | | | 165 | | | | | 170 | | | | | 175 | |
| Arg | Gly | Glu | Ala | His | Asp | Gln | Glu | Phe | Thr | Ile | His | Cys | Gln | Val | Ser |
| | | | 180 | | | | | 185 | | | | | 190 | | |
| Gly | Leu | Ser | Glu | Pro | Val | Val | Gly | Thr | Gly | Ser | Ser | Arg | Arg | Lys | Ala |
| | | | 195 | | | | | 200 | | | | | 205 | | |
| Glu | Gln | Ala | Ala | Ala | Glu | Gln | Ala | Leu | Lys | Lys | Leu | Glu | Leu | Glu | |
| | 210 | | | | | 215 | | | | | 220 | | | | |

<210> SEQ ID NO 49
<211> LENGTH: 672
<212> TYPE: DNA
<213> ORGANISM: E. coli

<400> SEQUENCE: 49

| | | | | |
|---|---|---|---|---|
| atgaacccca | tcgtaattaa | tcggcttcaa | cggaagctgg | gctacacttt taatcatcag | 60 |
| gaactgttgc | agcaggcatt | aactcatcgt | agtgcccaca | atgcccgctt ggaattttta | 120 |
| ggcgactcta | ttctgagcta | cgttatcgcc | aatgcgcttt | atcaccgttt ccctcgtgtg | 180 |
| gatgaaggcg | atatgagccg | gatgcgcgcc | acgctggtcc | gtggcaatac gctggcggaa | 240 |
| ctggcgcgcg | aatttgagtt | aggcgagtgc | ttacgtttag | gccaggtgaa cttaaaagc | 300 |
| ggtggatttc | gtcgtgagtc | aattctcgcc | gacaccgtcg | aagcattaat tggtggcgta | 360 |
| ttcctcgaca | gtgatattca | aaccgtcgag | aaattaatcc | tcaactggta tcaaactcgt | 420 |
| ttggacgaaa | ttagcccagg | cgataaacaa | aaagatccga | aacgcgcttg caagaatat | 480 |
| ttgcagggtc | gccatctgcc | gctgccgact | tatctggtag | tccaggtacg tggcgaagcg | 540 |
| cacgatcagg | aatttactat | ccactgccag | gtcagcggcc | tgagtgaacc ggtggttggc | 600 |
| acaggttcaa | gccgtcgtaa | ggctgagcag | gctgccgccg | aacaggcgtt gaaaaaactg | 660 |

```
gagctggaat ga                                                    672
```

<210> SEQ ID NO 50
<211> LENGTH: 223
<212> TYPE: PRT
<213> ORGANISM: E. coli

<400> SEQUENCE: 50

```
Met Asn Pro Ile Val Ile Asn Arg Leu Gln Arg Lys Leu Gly Tyr Thr
1               5                   10                  15

Phe Asn His Gln Glu Leu Leu Gln Gln Ala Leu Thr His Arg Ser Ala
            20                  25                  30

His Asn Ala Arg Leu Glu Phe Leu Gly Asp Ser Ile Leu Ser Tyr Val
        35                  40                  45

Ile Ala Asn Ala Leu Tyr His Arg Phe Pro Arg Val Asp Glu Gly Asp
    50                  55                  60

Met Ser Arg Met Arg Ala Thr Leu Val Arg Gly Asn Thr Leu Ala Glu
65                  70                  75                  80

Leu Ala Arg Glu Phe Glu Leu Gly Glu Cys Leu Arg Leu Gly Pro Gly
                85                  90                  95

Glu Leu Lys Ser Gly Gly Phe Arg Arg Glu Ser Ile Leu Ala Asp Thr
            100                 105                 110

Val Glu Ala Leu Ile Gly Gly Val Phe Leu Asp Ser Asp Ile Gln Thr
        115                 120                 125

Val Glu Lys Leu Ile Leu Asn Trp Tyr Gln Thr Arg Leu Asp Glu Ile
    130                 135                 140

Ser Pro Gly Asp Lys Gln Lys Asp Pro Lys Thr Arg Leu Gln Glu Tyr
145                 150                 155                 160

Leu Gln Gly Arg His Leu Pro Leu Pro Thr Tyr Leu Val Val Gln Val
                165                 170                 175

Arg Gly Glu Ala His Asp Gln Glu Phe Thr Ile His Cys Gln Val Ser
            180                 185                 190

Gly Leu Ser Glu Pro Val Val Gly Thr Gly Ser Ser Arg Arg Lys Ala
        195                 200                 205

Glu Gln Ala Ala Ala Glu Gln Ala Leu Lys Lys Leu Glu Leu Glu
    210                 215                 220
```

<210> SEQ ID NO 51
<211> LENGTH: 684
<212> TYPE: DNA
<213> ORGANISM: Verrucomicrobia

<400> SEQUENCE: 51

```
atgaatccgc tcgaagaccg catcggttac aagttccgca acgcgctgtt gctggaagaa    60
gcgctcacgc atcccagtgt gaggcacgcg cgcctggagt ttttgggcga tgcggtcctg   120
cagctcgtga tgacggaaca cctgttcggg cattttaaga agaagccga agggacgctg    180 acgaaactgc gctcgcggct tgtttcgcgg gaggccctcg ccgttcatgc ggcgacgctc    240
gaactgggac gctatctggc cgtcggccgc ggtgaggacg cgagcggcgg tcgcgaacgc    300
aattcgacgc tcgccgacgc tttcgaggcg ctcgtcggag cgatctatct cgatagcgat    360
ctggccacgg tgcgtcgctt tatcctggat caggcagcgg gcgatctggc gcaactcgtc    420
gacgaaccga ccgatatcaa cccgaagggt cacctgcagg aattgctcca ggcgatttcg    480
ccccgcagcc cggtttacga agtgatttcg cagaccgggc cggagcacga aaagacgttt    540
gtgattcgcg cggtttggga gggcatcacg ctcggggagg gaaccgggcg aagcaagaaa    600
```

```
caggcggaaa cggccgccgc cgaggaggcg atgcggcaaa agcggtggga aacggaaaag    660
acgtcgaccg caccttctcg gtag                                          684
```

<210> SEQ ID NO 52
<211> LENGTH: 227
<212> TYPE: PRT
<213> ORGANISM: Verrucomicrobia

<400> SEQUENCE: 52

```
Met Asn Pro Leu Glu Asp Arg Ile Gly Tyr Lys Phe Arg Asn Ala Leu
1               5                   10                  15

Leu Leu Glu Glu Ala Leu Thr His Pro Ser Val Arg His Ala Arg Leu
            20                  25                  30

Glu Phe Leu Gly Asp Ala Val Leu Gln Leu Val Met Thr Glu His Leu
        35                  40                  45

Phe Gly His Phe Lys Lys Glu Ala Gly Thr Leu Thr Lys Leu Arg
    50                  55                  60

Ser Arg Leu Val Ser Arg Glu Ala Leu Ala Val His Ala Ala Thr Leu
65                  70                  75                  80

Glu Leu Gly Arg Tyr Leu Ala Val Gly Arg Gly Glu Asp Ala Ser Gly
                85                  90                  95

Gly Arg Glu Arg Asn Ser Thr Leu Ala Asp Ala Phe Glu Ala Leu Val
            100                 105                 110

Gly Ala Ile Tyr Leu Asp Ser Asp Leu Ala Thr Val Arg Arg Phe Ile
        115                 120                 125

Leu Asp Gln Ala Ala Gly Asp Leu Ala Gln Leu Val Asp Glu Pro Thr
    130                 135                 140

Asp Ile Asn Pro Lys Gly His Leu Gln Glu Leu Leu Gln Ala Ile Ser
145                 150                 155                 160

Pro Arg Ser Pro Val Tyr Glu Val Ile Ser Gln Thr Gly Pro Glu His
                165                 170                 175

Glu Lys Thr Phe Val Ile Arg Ala Val Trp Glu Gly Ile Thr Leu Gly
            180                 185                 190

Glu Gly Thr Gly Arg Ser Lys Lys Gln Ala Glu Thr Ala Ala Ala Glu
        195                 200                 205

Glu Ala Met Arg Gln Lys Arg Trp Glu Thr Glu Lys Thr Ser Thr Ala
    210                 215                 220

Pro Ser Arg
225
```

<210> SEQ ID NO 53
<211> LENGTH: 684
<212> TYPE: DNA
<213> ORGANISM: Verrucomicrobia

<400> SEQUENCE: 53

```
atgaatcctt tagaagaccg tattgggtat aagtttcgta atgctttact gctggaagaa    60
gctttgaccc acccatctgt gcgccacgct cgtttggagt tcttgggaga cgcggtgtta   120
caattagtaa tgacagaaca cctgttcggg cactttaaga agaagctgaa gggactttta   180
acgaaacttc gtagccgttt ggtttcccgc gaggctctgg ctgtccacgc tgccactttg   240
gaacttggac gttatttggc tgtgggccgt ggcgaggacg catccggcgg acgtgagcgt   300
aactcaacgt tagcggacgc cttcgaggct ctggtgggcg cgattatct tgattcagac   360 ctggcaaccg ttcgtcgctt tattcttgat caggctgcag gggatttggc acagttggta   420
```

```
gatgaaccga ccgatattaa ccctaaaggt catttacagg aacttttgca ggctatctcc    480
cctcgttccc cagtatatga agttatctct caaactggtc cagaacacga aaagacattc    540
gtaatccgcg cagtatggga gggtatcact ttaggggagg gaacgggacg cagtaaaaaa    600
caagctgaga cggcagctgc tgaggaagct atgcgccaaa agcgttggga gacggagaaa    660
acttccacgg ccccttcccg ttaa                                           684

<210> SEQ ID NO 54
<211> LENGTH: 227
<212> TYPE: PRT
<213> ORGANISM: Verrucomicrobia

<400> SEQUENCE: 54

Met Asn Pro Leu Glu Asp Arg Ile Gly Tyr Lys Phe Arg Asn Ala Leu
1               5                   10                  15

Leu Leu Glu Glu Ala Leu Thr His Pro Ser Val Arg His Ala Arg Leu
            20                  25                  30

Glu Phe Leu Gly Asp Ala Val Leu Gln Leu Val Met Thr Glu His Leu
        35                  40                  45

Phe Gly His Phe Lys Lys Glu Ala Glu Gly Thr Leu Thr Lys Leu Arg
    50                  55                  60

Ser Arg Leu Val Ser Arg Glu Ala Leu Ala Val His Ala Ala Thr Leu
65                  70                  75                  80

Glu Leu Gly Arg Tyr Leu Ala Val Gly Arg Gly Glu Asp Ala Ser Gly
                85                  90                  95

Gly Arg Glu Arg Asn Ser Thr Leu Ala Asp Ala Phe Glu Ala Leu Val
            100                 105                 110

Gly Ala Ile Tyr Leu Asp Ser Asp Leu Ala Thr Val Arg Arg Phe Ile
        115                 120                 125

Leu Asp Gln Ala Ala Gly Asp Leu Ala Gln Leu Val Asp Glu Pro Thr
    130                 135                 140

Asp Ile Asn Pro Lys Gly His Leu Gln Glu Leu Leu Gln Ala Ile Ser
145                 150                 155                 160

Pro Arg Ser Pro Val Tyr Glu Val Ile Ser Gln Thr Gly Pro Glu His
                165                 170                 175

Glu Lys Thr Phe Val Ile Arg Ala Val Trp Glu Gly Ile Thr Leu Gly
            180                 185                 190

Glu Gly Thr Gly Arg Ser Lys Lys Gln Ala Glu Thr Ala Ala Ala Glu
        195                 200                 205

Glu Ala Met Arg Gln Lys Arg Trp Glu Thr Glu Lys Thr Ser Thr Ala
    210                 215                 220

Pro Ser Arg
225

<210> SEQ ID NO 55
<211> LENGTH: 738
<212> TYPE: DNA
<213> ORGANISM: B. cereus

<400> SEQUENCE: 55
atgccgtacc gaaaatatag agaaaaaaaa tacgaaacaa aatatcgtga agcatttaaa     60
gtgtttcaag aaaagatagg tattacgttt acagatgaaa aattattgat tcaagcattt    120
acgcattcat cgtatgtgaa tgagcatcga aaaaaaccgc atgaagacaa cgcccgcctc    180
gaatttcttg gagatgcagt attggaactt actgtatcgc agtatctgtt tcaaaaatat    240
```

-continued

```
ccgacaatga gcgaaggaga gttaacaaaa ctacgtgcag ctattgtatg tgagccatct    300
cttgttcgtt ttgcgaacga attgtcattt ggtagccttg ttttattagg aaaaggtgaa    360
gaaatgacag gtggacgtga acgaccagct ttattagcgg atgtctttga agcgtttatt    420
ggtgcccttt atcttgatca agggttagaa acagtttggg aattcttaaa agaaattgta    480
tatccgaaaa ttaatgaggg tgcttttttct catgtgatgg attataagag tcagttacaa    540
gaattgattc agcgtgatgg tagtggcaat gttgagtatc aaattttgca agaaaaagga    600
ccagctcaca atcgagaatt tgtgtcacgt gttacgttaa ataacgtagc tttaggtctt    660
ggtagtggta agtcgaaaaa agaagcagag caacaagctg ctgcagaagc attgaaaaaa    720
ttaaaagaac aactataa                                                   738
```

<210> SEQ ID NO 56
<211> LENGTH: 245
<212> TYPE: PRT
<213> ORGANISM: B. cereus

<400> SEQUENCE: 56

```
Met Pro Tyr Arg Lys Tyr Arg Glu Lys Lys Tyr Glu Thr Lys Tyr Arg
1               5                   10                  15

Glu Ala Phe Lys Val Phe Gln Glu Lys Ile Gly Ile Thr Phe Thr Asp
            20                  25                  30

Glu Lys Leu Le

<213> ORGANISM: B. cereus

<400> SEQUENCE: 57

```
atgtcaaaac actcacatta taaagataaa aaaaagttct ataaaaaagt agaacaattt     60
aaagagtttc aagaacggat ttcggttcac tttcaaaatg aaaagctttt gtatcaagca    120
tttacacatt catcttatgt gaatgagcat cggaaaaagc cgtatgagga caacgctaga    180
cttgaatttt taggtgacgc tgttttggaa ctgacgatct ccagattctt atttgccaaa    240
tacccggcta tgagtgaagg agatttgacg aaattgagag ccgcaattgt ttgcgaaccg    300
tctctcgttt cattggctca cgagctgtca ttcggcgatc ttgtcctgtt gggtaaaggc    360
gaggaaatga caggcggaag aaagcgtcct gctctattgg cggatgtttt tgaggcattt    420
atcggagcct tgtaccttga ccaaggatta gagccggtcg aaagtttctt aaaagtttat    480
gtgttcccta aaattaacga tggtgctttt tctcatgtga tggatttcaa aagccagctg    540
caggaatacg tgcagcggga cggcaaaggc tctctggagt ataaaatctc caacgaaaaa    600
ggacctgcgc acaaccgtga atttgaagcc atcgtatctc taaaaggtga accactcgga    660
gtcggaaacg gccgttcaaa gaaagaagcc gaacagcacg ctgctcagga agctttagct    720
aaattgcaaa aacaccatac gaaacaataa                                     750
```

<210> SEQ ID NO 58
<211> LENGTH: 249
<212> TYPE: PRT
<213> ORGANISM: B. subtilis

<400> SEQUENCE: 58

```
Met Ser Lys His Ser His Tyr Lys Asp Lys Lys Lys Phe Tyr Lys Lys
1               5                   10                  15

Val Glu Gln Phe Lys Glu Phe Gln Glu Arg Ile Ser Val His Phe Gln
            20                  25                  30

Asn Glu Lys Leu Leu Tyr Gln Ala Phe Thr His Ser Ser Tyr Val Asn
        35                  40                  45

Glu His Arg Lys Lys Pro Tyr Glu Asp Asn Ala Arg Leu Glu Phe Leu
    50                  55                  60

Gly Asp Ala Val Leu Glu Leu Thr Ile Ser Arg Phe Leu Phe Ala Lys
65                  70                  75                  80

Tyr Pro Ala Met Ser Glu Gly Asp Leu Thr Lys Leu Arg Ala Ala Ile
                85                  90                  95

Val Cys Glu Pro Ser Leu Val Ser Leu Ala His Glu Leu Ser Phe Gly
            100                 105                 110

Asp Leu Val Leu Leu Gly Lys Gly Glu Glu Met Thr Gly Gly Arg Lys
        115                 120                 125

Arg Pro Ala Leu Leu Ala Asp Val Phe Glu Ala Phe Ile Gly Ala Leu
    130                 135                 140

Tyr Leu Asp Gln Gly Leu Glu Pro Val Glu Ser Phe Leu Lys Val Tyr
145                 150                 155                 160

Val Phe Pro Lys Ile Asn Asp Gly Ala Phe Ser His Val Met Asp Phe
                165                 170                 175

Lys Ser Gln Leu Gln Glu Tyr Val Gln Arg Asp Gly Lys Gly Ser Leu
            180                 185                 190

Glu Tyr Lys Ile Ser Asn Glu Lys Gly Pro Ala His Asn Arg Glu Phe
        195                 200                 205

Glu Ala Ile Val Ser Leu Lys Gly Glu Pro Leu Gly Val Gly Asn Gly
    210                 215                 220

Arg Ser Lys Lys Glu Ala Glu Gln His Ala Ala Gln Glu Ala Leu Ala
225                 230                 235                 240

Lys Leu Gln Lys His His Thr Lys Gln
                245

<210> SEQ ID NO 59
<211> LENGTH: 738
<212> TYPE: DNA
<213> ORGANISM: B. cere

-continued

```
            Tyr Pro Lys Ile Asn Glu Gly Ala Phe Ser His Val Met Asp Tyr Lys
                            165                 170                 175

Ser Gln Leu Gln Glu Leu Ile Gln Arg Asp Gly Ser Gly Asn Val Glu
                        180                 185                 190

Tyr Gln Ile Leu Gln Glu Lys Gly Pro Ala His Asn Arg Glu Phe Val
                    195                 200                 205

Ser Arg Val Thr Leu Asn Asn Val Ala Leu Gly Leu Gly Ser Gly Lys
                210                 215                 220

Ser Lys Lys Glu Ala Glu Gln Gln Ala Ala Glu Ala Leu Lys Lys
            225                 230                 235                 240

Leu Lys Glu Gln Leu
                        245

<210> SEQ ID NO 61
<211> LENGTH: 45
<212> TYPE: DNA
<213> ORGANISM: Artificial Sequence
<220> FEATURE:
<223> OTHER INFORMATION: Ecoli-tetsac - trunc

<400> SEQUENCE: 61
gaactgttgc agcaggcatt aactcatcgt agtgccagca gtaaa              45

<210> SEQ ID NO 62
<211> LENGTH: 79
<212> TYPE: DNA
<213> ORGANISM: Artificial Sequence
<220> FEATURE:
<223> OTHER INFORMATION: Ecoli-tetsac

<400> SEQUENCE: 62
gaactgttgc agcaggcatt aactcatcgt agtgccagca gtaaacataa cgagtcctaa    60
tttttgttga cactctatc                                                 79

<210> SEQ ID NO 63
<211> LENGTH: 76
<212> TYPE: DNA
<213> ORGANISM: Artificial Sequence
<220> FEATURE:
<223> OTHER INFORMATION: Ecoli-tet-sacB38R1

<400> SEQUENCE: 63
cgcattggcg ataacgtagc tcagaataga gtcgcctaaa aattctaaac gatcaaaggg    60
aaaactgtcc atatgc                                                    76

<210> SEQ ID NO 64
<211> LENGTH: 75
<212> TYPE: DNA
<213> ORGANISM: Artificial Sequence
<220> FEATURE:
<223> OTHER INFORMATION: Ecoli-oligo-E38A

<400> SEQUENCE: 64
gtagctcaga atagagtcgc ctaaaaattc gaagcgggca ttgtgtttac tgctggcact    60
acgatgagtt aatgc                                                     75

<210> SEQ ID NO 65
<211> LENGTH: 21
<212> TYPE: DNA
<213> ORGANISM: Artificial Sequence
<220> FEATURE:
<223> OTHER INFORMATION: Ecoli-E38A-1F
```

<400> SEQUENCE: 65
agtaaacaca atgcccgctt c                                            21

<210> SEQ ID NO 66
<211> LENGTH: 18
<212> TYPE: DNA
<213> ORGANISM: Artificial Sequence
<220> FEATURE:
<223> OTHER INFORMATION: Ecoli-E38A-1R

<400> SEQUENCE: 66
atgcttcgac ggtgtcgg                                                18

<210> SEQ ID NO 67
<211> LENGTH: 76
<212> TYPE: DNA
<213> ORGANISM: Artificial Sequence
<220> FEATURE:
<223> OTHER INFORMATION: Ecoli-tet-sacB117F1

<400> SEQUENCE: 67
cttaaaagcg gtggatttcg tcgtgagtca attctcgccg acaccgtcga atcctaattt   60
ttgttgacac tctatc                                                  76

<210> SEQ ID NO 68
<211> LENGTH: 79
<212> TYPE: DNA
<213> ORGANISM: Artificial Sequence
<220> FEATURE:
<223> OTHER INFORMATION: Ecoli-tet-sacB117R1

<400> SEQUENCE: 68
taatttctcg acggtttgaa tatcactgtc gaggaatacg ccaccaatta atgcatcaaa   60
gggaaaactg tccatatgc                                               79

<210> SEQ ID NO 69
<211> LENGTH: 75
<212> TYPE: DNA
<213> ORGANISM: Artificial Sequence
<220> FEATURE:
<223> OTHER INFORMATION: Ecoli-oligo-E117K

<400> SEQUENCE: 69
ttgaatatca ctgtcgagga atacgccacc gatgaaagcc ttcacggtgt cggcgagaat   60
tgactcacga cgaaa                                                   75

<210> SEQ ID NO 70
<211> LENGTH: 21
<212> TYPE: DNA
<213> ORGANISM: Artificial Sequence
<220> FEATURE:
<223> OTHER INFORMATION: Ecoli-E117K-1F

<400> SEQUENCE: 70
gacaccgtga aggctttcat c                                            21

<210> SEQ ID NO 71
<211> LENGTH: 17
<212> TYPE: DNA
<213> ORGANISM: Artificial Sequence
<220> FEATURE:
<223> OTHER INFORMATION: Ecoli-E117K-1R

<400> SEQUENCE: 71
ttcaacgcct gttcggc                                              17

<210> SEQ ID NO 72
<211> LENGTH: 75
<212> TYPE: DNA
<213> ORGANISM: Artificial Sequence
<220> FEATURE:
<223> OTHER INFORMATION: Ecoli-oligo-E38A-F2

<400> SEQUENCE: 72
gtagctcaga atagagtcgc ctaaaaattc caagcgggca ttgtgtttac tgctggcact    60
acgatgagtt aatgc                                                75

<210> SEQ ID NO 73
<211> LENGTH: 21
<212> TYPE: DNA
<213> ORGANISM: Artificial Sequence
<220> FEATURE:
<223> OTHER INFORMATION: Ecoli-E38A-2F

<400> SEQUENCE: 73
agtaaacaca atgcccgctt g                                         21

<210> SEQ ID NO 74
<211> LENGTH: 75
<212> TYPE: DNA
<213> ORGANISM: Artificial Sequence
<220> FEATURE:
<223> OTHER INFORMATION: Ecoli-oligo-E117K-F2

<400> SEQUENCE: 74
ttgaatatca ctgtcgagga atacgccacc gatcaaagcc ttcacggtgt cggcgagaat    60
tgactcacga cgaaa                                                75

<210> SEQ ID NO 75
<211> LENGTH: 21
<212> TYPE: DNA
<213> ORGANISM: Artificial Sequence
<220> FEATURE:
<223> OTHER INFORMATION: Ecoli-E117K-2F

<400> SEQUENCE: 75
gacaccgtga aggctttgat c                                         21

<210> SEQ ID NO 76
<211> LENGTH: 76
<212> TYPE: DNA
<213> ORGANISM: Artificial Sequence
<220> FEATURE:
<223> OTHER INFORMATION: Ecoli-tet-sacB-E65F1

<400> SEQUENCE: 76
agctacgtta tcgccaatgc gctttatcac cgtttccctc gtgtggatga atcctaattt    60
ttgttgacac tctatc                                               76

<210> SEQ ID NO 77
<211> LENGTH: 76
<212> TYPE: DNA
<213> ORGANISM: Artificial Sequence
<220> FEATURE:
<223> OTHER INFORMATION: Ecoli-tet-sacB-E65R1

<400> SEQUENCE: 77

```
cgccagcgta ttgccacgga ccagcgtggc gcgcatccgg ctcatatcgc catcaaaggg    60
aaaactgtcc atatgc                                                    76
```

<210> SEQ ID NO 78
<211> LENGTH: 75
<212> TYPE: DNA
<213> ORGANISM: Artificial Sequence
<220> FEATURE:
<223> OTHER INFORMATION: Ecoli-oligo-E65A-F1

<400> SEQUENCE: 78

```
cagcgtggcg cgcatccggc tcatatcgcc ggcgtcgacg cggggaaac ggtgataaag    60 cgcattggcg ataac                                                     75
```

<210> SEQ ID NO 79
<211> LENGTH: 18
<212> TYPE: DNA
<213> ORGANISM: Artificial Sequence
<220> FEATURE:
<223> OTHER INFORMATION: Ecoli-E65A-1F

<400> SEQUENCE: 79

```
tttcccccgc gtcgacgc                                                  18
```

<210> SEQ ID NO 80
<211> LENGTH: 20
<212> TYPE: DNA
<213> ORGANISM: Artificial Sequence
<220> FEATURE:
<223> OTHER INFORMATION: JD-5

<400> SEQUENCE: 80

```
accggtaaac tgaaactgca                                                20
```

<210> SEQ ID NO 81
<211> LENGTH: 21
<212> TYPE: DNA
<213> ORGANISM: Artificial Sequence
<220> FEATURE:
<223> OTHER INFORMATION: Tet-sacB-JD-R1

<400> SEQUENCE: 81

```
tggcaagact ggcatgataa g                                              21
```

<210> SEQ ID NO 82
<211> LENGTH: 19
<212> TYPE: DNA
<213> ORGANISM: Artificial Sequence
<220> FEATURE:
<223> OTHER INFORMATION: JD-3

<400> SEQUENCE: 82

```
tggagatttt ctgccccag                                                 19
```

<210> SEQ ID NO 83
<211> LENGTH: 21
<212> TYPE: RNA
<213> ORGANISM: Artificial Sequence
<220> FEATURE:
<223> OTHER INFORMATION: TMVU1-MP-F6-RNA21

<400> SEQUENCE: 83

```
caguucaagg ucguucccaa u                                              21
```

<210> SEQ ID NO 84
<211> LENGTH: 23
<212> TYPE: RNA
<213> ORGANISM: Artificial Sequence
<220> FEATURE:
<223> OTHER INFORMATION: TMVU1-MP-F7-RNA23

<400> SEQUENCE: 84
ugaagauguc agcgguuuc ugu                                              23

<210> SEQ ID NO 85
<211> LENGTH: 25
<212> TYPE: RNA
<213> ORGANISM: Artificial Sequence
<220> FEATURE:
<223> OTHER INFORMATION: TMVU1-MP-R6-RNA25

<400> SEQUENCE: 85
ccagacguuu uucaucgcgu ccugg                                           25

<210> SEQ ID NO 86
<211> LENGTH: 27
<212> TYPE: RNA
<213> ORGANISM: Artificial Sequence
<220> FEATURE:
<223> OTHER INFORMATION: TMVU1-MP-R7-RNA27

<400> SEQUENCE: 86
acgacuucuu cuguaaguuc caugggc                                         27

<210> SEQ ID NO 87
<211> LENGTH: 29
<212> TYPE: RNA
<213> ORGANISM: Artificial Sequence
<220> FEATURE:
<223> OTHER INFORMATION: TMVU1-MP-F6-RNA29

<400> SEQUENCE: 87
caguucaagg ucguucccaa uuaugcuau                                       29

<210> SEQ ID NO 88
<211> LENGTH: 47
<212> TYPE: DNA
<213> ORGANISM: Artificial Sequence
<220> FEATURE:
<223> OTHER INFORMATION: Pveg-F1

<400> SEQUENCE: 88
atcacgaggc cctttcgtct tcaagggagt tctgagaatt ggtatgc                   47

<210> SEQ ID NO 89
<211> LENGTH: 36
<212> TYPE: DNA
<213> ORGANISM: Artificial Sequence
<220> FEATURE:
<223> OTHER INFORMATION: Pveg-R1

<400> SEQUENCE: 89
acacctcctt tactacattt attgtacaac acgagc                               36

<210> SEQ ID NO 90
<211> LENGTH: 53
<212> TYPE: DNA
<213> ORGANISM: Artificial Sequence
<220> FEATURE:
<223> OTHER INFORMATION: Pveg-F2

<400> SEQUENCE: 90
atcacgaggc cctttcgtct tcaagaagct tggagttctg agaattggta tgc       53

<210> SEQ ID NO 91
<211> LENGTH: 67
<212> TYPE: DNA
<213> ORGANISM: Artificial Sequence
<220> FEATURE:
<223> OTHER INFORMATION: Pveg-R2

<400> SEQUENCE: 91
acgcgatccc cgggtaccga gctcgctcga gacacctcct ttactacatt tattgtacaa       60
cacgagc       67

<210> SEQ ID NO 92
<211> LENGTH: 47
<212> TYPE: DNA
<213> ORGANISM: Artificial Sequence
<220> FEATURE:
<223> OTHER INFORMATION: Bc-E58A-F1

<400> SEQUENCE: 92
acaataaatg tagtaaagga ggtgtatgcc gtaccgaaaa tatagag       47

<210> SEQ ID NO 93
<211> LENGTH: 33
<212> TYPE: DNA
<213> ORGANISM: Artificial Sequence
<220> FEATURE:
<223> OTHER INFORMATION: Bc-E58A-R1

<400> SEQUENCE: 93
gaggcgggcg ttgtcttcat gcggtttttt tcg       33

<210> SEQ ID NO 94
<211> LENGTH: 49
<212> TYPE: DNA
<213> ORGANISM: Artificial Sequence
<220> FEATURE:
<223> OTHER INFORMATION: Bc-E58A-F2

<400> SEQUENCE: 94
accgcatgaa gacaacgccc gcctcgaatt tcttggagat gcagtattg       49

<210> SEQ ID NO 95
<211> LENGTH: 54
<212> TYPE: DNA
<213> ORGANISM: Artificial Sequence
<220> FEATURE:
<223> OTHER INFORMATION: Bc-E58A-R2

<400> SEQUENCE: 95
acgcgatccc cgggtaccga gctcgttata gttgttcttt taattttttc aatg       54

<210> SEQ ID NO 96
<211> LENGTH: 36
<212> TYPE: DNA
<213> ORGANISM: Artificial Sequence
<220> FEATURE:
<223> OTHER INFORMATION: Bc-E137K-R1

<400> SEQUENCE: 96
gatgaaggcc ttgaagacat ccgctaataa agctgg       36

<210> SEQ ID NO 97
<211> LENGTH: 47
<212> TYPE: DNA
<213> ORGANISM: Artificial Sequence
<220> FEATURE:
<223> OTHER INFORMATION: Bc-E137K-F1

<400> SEQUENCE: 97
agcggatgtc ttcaaggcct tcatcggtgc cctttatctt gatcaag        47

<210> SEQ ID NO 98
<211> LENGTH: 47
<212> TYPE: DNA
<213> ORGANISM: Artificial Sequence
<220> FEATURE:
<223> OTHER INFORMATION: pAD-E58A-F1

<400> SEQUENCE: 98
caataaatgt agtaaaggag gtgtcatgcc gtaccgaaaa tatagag        47

<210> SEQ ID NO 99
<211> LENGTH: 54
<212> TYPE: DNA
<213> ORGANISM: Artificial Sequence
<220> FEATURE:
<223> OTHER INFORMATION: pAD-E58A

<400> SEQUENCE: 99
gcgagctcgg tacccgggga tcgcgttata gttgttcttt aattttttc aatg        54

<210> SEQ ID NO 100
<211> LENGTH: 21
<212> TYPE: DNA
<213> ORGANISM: Artificial Sequence
<220> FEATURE:
<223> OTHER INFORMATION: Eco-F1

<400> SEQUENCE: 100
acgaggccct tcgtcttca a        21

<210> SEQ ID NO 101
<211> LENGTH: 19
<212> TYPE: DNA
<213> ORGANISM: Artificial Sequence
<220> FEATURE:
<223> OTHER INFORMATION: SglyA-R1

<400> SEQUENCE: 101
catgttcgct tgtgcacca        19

<210> SEQ ID NO 102
<211> LENGTH: 22
<212> TYPE: DNA
<213> ORGANISM: Artificial Sequence
<220> FEATURE:
<223> OTHER INFORMATION: Ae-JD-5

<400> SEQUENCE: 102
aactaacgac atcccctgtc gt        22

<210> SEQ ID NO 103
<211> LENGTH: 20
<212> TYPE: DNA
<213> ORGANISM: Artificial Sequence
<220> FEATURE:
<223> OTHER INFORMATION: Ae-JD-3

<400> SEQUENCE: 103
cgcagcttgt tcagcaccat                                              20

<210> SEQ ID NO 104
<211> LENGTH: 45
<212> TYPE: DNA
<213> ORGANISM: Artificial Sequence
<220> FEATURE:
<223> OTHER INFORMATION: TMVMP-probe1s

<400> SEQUENCE: 104
tctcggatct tactacacag cagctgcaaa gaaaagattt cagtt                  45

<210> SEQ ID NO 105
<211> LENGTH: 45
<212> TYPE: DNA
<213> ORGANISM: Artificial Sequence
<220> FEATURE:
<223> OTHER INFORMATION: TMVMP-probe2as

<400> SEQUENCE: 105
tcctgggtgg ttatagcata attgggaacg accttgaact gaaat                  45

<210> SEQ ID NO 106
<211> LENGTH: 45
<212> TYPE: DNA
<213> ORGANISM: Artificial Sequence
<220> FEATURE:
<223> OTHER INFORMATION: TMVMP-probe3s

<400> SEQUENCE: 106
cacccaggac gcgatgaaaa acgtctggca agttttagtt aatat                  45

<210> SEQ ID NO 107
<211> LENGTH: 45
<212> TYPE: DNA
<213> ORGANISM: Artificial Sequence
<220> FEATURE:
<223> OTHER INFORMATION: TMVMP-probe4as

<400> SEQUENCE: 107
agcggacaga aacccgctga catcttcaca tttctaatat taact                  45

<210> SEQ ID NO 108
<211> LENGTH: 45
<212> TYPE: DNA
<213> ORGANISM: Artificial Sequence
<220> FEATURE:
<223> OTHER INFORMATION: TMVMP-probe5s

<400> SEQUENCE: 108
ctgtccgctt tctctggagt ttgtgtcggt gtgtattgtt tatag                  45

<210> SEQ ID NO 109
<211> LENGTH: 45
<212> TYPE: DNA
<213> ORGANISM: Artificial Sequence
<220> FEATURE:
<223> OTHER INFORMATION: TMVMP-probe6as

<400> SEQUENCE: 109
ccctccgtct ctcacgtttg taatcttctc tctcaaacct aattt                  45

<210> SEQ ID NO 110

```
<211> LENGTH: 45
<212> TYPE: DNA
<213> ORGANISM: Artificial Sequence
<220> FEATURE:
<223> OTHER INFORMATION: TMVMP-probe8as

<400> SEQUENCE: 110
ctttgcaagc ctgatcgaca tagggacatc ttccatgaac tcatc             45

<210> SEQ ID NO 111
<211> LENGTH: 45
<212> TYPE: DNA
<213> ORGANISM: Artificial Sequence
<220> FEATURE:
<223> OTHER INFORMATION: TMVMP-probe9s

<400> SEQUENCE: 111
gtttcgatct cgaaccggaa aaagagtga tgtccgcaaa gggaa              45

<210> SEQ ID NO 112
<211> LENGTH: 21
<212> TYPE: DNA
<213> ORGANISM: Artificial Sequence
<220> FEATURE:
<223> OTHER INFORMATION: TMVU1-MP-F6-21

<400> SEQUENCE: 112
cagttcaagg tcgttcccaa t                                       21

<210> SEQ ID NO 113
<211> LENGTH: 21
<212> TYPE: DNA
<213> ORGANISM: Artificial Sequence
<220> FEATURE:
<223> OTHER INFORMATION: TMVU1-MP-R6-21

<400> SEQUENCE: 113
gtttttcatc gcgtcctggg t                                       21

<210> SEQ ID NO 114
<211> LENGTH: 21
<212> TYPE: DNA
<213> ORGANISM: Artificial Sequence
<220> FEATURE:
<223> OTHER INFORMATION: TMVU1-MP-F7-21

<400> SEQUENCE: 114
aagatgtcag cgggtttctg t                                       21

<210> SEQ ID NO 115
<211> LENGTH: 21
<212> TYPE: DNA
<213> ORGANISM: Artificial Sequence
<220> FEATURE:
<223> OTHER INFORMATION: TMVU1-MP-R7-21

<400> SEQUENCE: 115
cttcttctgt aagttccatg g                                       21

<210> SEQ ID NO 116
<211> LENGTH: 21
<212> TYPE: DNA
<213> ORGANISM: Artificial Sequence
<220> FEATURE:
<223> OTHER INFORMATION: TMVU1-MP-F7-21

<400> SEQUENCE: 116
```
aagatgtcag cgggtttctg t                          21

<210> SEQ ID NO 117
<211> LENGTH: 21
<212> TYPE: DNA
<213> ORGANISM: Artificial Sequence
<220> FEATURE:
<223> OTHER INFORMATION: TMVU1-MP-R7-21

<400> SEQUENCE: 117
cttcttctgt aagttccatg g                          21

<210> SEQ ID NO 118
<211> LENGTH: 20
<212> TYPE: DNA
<213> ORGANISM: Artificial Sequence
<220> FEATURE:
<223> OTHER INFORMATION: TMVU1-MP-F4

<400> SEQUENCE: 118
ccaggacgcg atgaaaaacg                            20

<210> SEQ ID NO 119
<211> LENGTH: 20
<212> TYPE: DNA
<213> ORGANISM: Artificial Sequence
<220> FEATURE:
<223> OTHER INFORMATION: TMVU1-MP-R4

<400> SEQUENCE: 119
ggacagaaac ccgctgacat                            20

<210> SEQ ID NO 120
<211> LENGTH: 21
<212> TYPE: DNA
<213> ORGANISM: Artificial Sequence
<220> FEATURE:
<223> OTHER INFORMATION: Ec-16SrRNA-F1

<400> SEQUENCE: 120
gaatgccacg gtgaatacgt t                          21

<210> SEQ ID NO 121
<211> LENGTH: 19
<212> TYPE: DNA
<213> ORGANISM: Artificial Sequence
<220> FEATURE:
<223> OTHER INFORMATION: Ec-16SrRNA-R1

<400> SEQUENCE: 121
acccactccc atggtgtga                             19

SYSTEMS, METHODS AND COMPOSITION OF USING RNASE III MUTANTS TO PRODUCE SRNA TO CONTROL HOST PATHOGEN INFECTION

This application claims the benefit of and priority to U.S. Provisional Patent Application No. 62/651,143, filed Mar. 31, 2018, which is incorporated herein by reference in its entirety.

SEQUENCE LISTING

The instant application contains a Sequence Listing which has been submitted electronically in ASCII format and is hereby incorporated by reference in its entirety.

TECHNICAL FIELD

The field of the present invention relates generally to bacterial ribonuclease mutations, in particular point mutations in ribonuclease III, and their uses in the production of bacterial small RNA (sRNA).

BACKGROUND

RNA interference (RNAi) is the process by which double-stranded RNA (dsRNA) triggers the cleavage of mRNAs containing homologous sequences (reviewed in reference 5). The RNAi pathway appears to be an ancient evolutionary invention that has been retained in species as divergent as plants, worms, and mammals. While the details of this process are still being worked out, key components of the RNAi pathway have been identified, and a model for their action has begun to take shape. Long duplex RNA species are cleaved by the protein Dicer into small (~21- to 23-nucleotide [nt]) interfering double-stranded RNAs (siRNAs), which serve as the recognition cue to target homologous mRNA cleavage. In addition to fully duplex RNAs, small hairpin RNAs (shRNAs) generated experimentally can also serve as a substrate for the Dicer cleavage reaction to generate ~22-nt siRNA products.

In addition to their roles in mRNA cleavage, components of the RNAi pathway also function in other biological processes. For example, certain endogenously encoded imperfect hairpin RNAs, called microRNAs (miRNAs), can be processed by Dicer from their ~75-nt precursor (pre-miRNA) and the resulting short products (miRNAs) can be incorporated into RISC. In this context, these short RNAs recognize imperfect homologies in the 3' untranslated region (UTR) of target mRNAs, resulting in an impairment of translation. RNAi has been shown effective in silencing gene expression in a broad variety of species, including plants, with wide ranging implications for cancer, inherited disease, infectious disease in plants and animals. Studies have also shown in a variety of organisms that dsRNA or their siRNA derivatives can be used to arrest, retard or even prevent a variety of pathogens, most notably viral diseases. However, to combat RNAi-mediated immunity by host organisms, certain viruses encode viral suppressors of RNA silencing (VSRs) that target RNA and protein components in the RNAi machinery, such as DICER. Moreover, the ability to generate a scalable dsRNA production system is limited as the DICER-mediated system is not present in prokaryotic systems such as bacteria. As a result, the production of dsRNA for therapeutic or other industrial applications is hampered by the need to either directly chemically synthesize the dsRNA, or use eukaryotic-based production systems—which are expensive and largely inefficient production platforms. As a result, there is a need for a DICER-independent mechanism to initiate an RNAi pathway response. As shown below, the present inventors have developed systems, methods and compositions to initiate a DICER-independent mechanism to initiate an RNAi pathway response through targeted mutations in bacterial Ribonuclease III enzymes.

Ribonuclease III ("RNase III") represents a highly conserved family of double-strand-specific endoribonucleases that are important for RNA processing and post-transcriptional gene regulation in both prokaryotes and eukaryotes. The family can be divided into three classes. Class 1 is the simplest in structure, having a single ribonuclease domain and a dsRNA-binding domain, and is the best characterized. Its members are found in eubacteria, archaebacteria, and yeast. Class 2 members have two ribonuclease domains and a single dsRNA-binding domain. These are found in eukaryotes, with Drosha being a typical example. Class 3, also known as the Dicer family of enzymes, are the largest and typically contain two ribonuclease domains, a dsRNA-binding domain, a DEAD box helicase domain, and a PAZ domain. RNase III helps regulate gene expression by degrading and processing mRNA. RNase III specifically cleaves double-stranded RNA (dsRNA), creating 5'-phosphate and 3'-hydroxyl termini with a two-nucleotide overhang. For example, in *Escherichia coli*, RNase III, encoded by the rnc gene, consists of a ribonuclease domain (amino acid residues 21-149) and a dsRNA-binding domain (residues 155-209). *E. coli* RNase III functions as a homodimer in which two ribonuclease domains form a single processing center, and each domain contributes to the cleavage of one RNA strand of the duplex substrate.

For example, *E. coli* RNase III residue E38 has been shown to be involved in protein dimerization. Its mutant can process dsRNA into a discrete sized sRNA at the primary site and also remain bound to the dsRNA product, thereby protecting it from further digestion. Significantly, this dsRNA product is similar in size to the product generated by Dicer. As such, an RNase III having an E38A mutation can generate short dsRNA fragments suitable for RNA interference experiments. Further, RNase III amino acid E65 has been shown to be involved in substrate recognition and scissile-bond selection, while D45, D114, and D117 chelate the $Mn^{2+}$ ion. Residues E41, D45, D114, and E117 have been shown to carry out the hydrolysis of the scissile bond. Studies of RNase III mutants have further shown that two transgenic maize lines that constitutively expressed rnc70 (RNC70, E117K mutant, binding but not cleaving dsRNAs) were more resistant to Maize rough dwarf virus infection.

Based on the forging, it is evident there exists a need to incorporate specific combinations of RNase III mutations that may be stably integrated, and/or expressed in a cell that may be susceptible to infection by viral and other pathogens, to facilitate an enhanced RNA interference response.

SUMMARY OF THE INVENTION(S)

One aim of the current invention includes systems, methods and compositions for the generation of sRNA molecules using RNase III mutants. In one preferred embodiment, invention includes systems, methods and compositions for the generation of sRNA molecules using RNase III mutants to control a host pathogen. Another aim of the current invention includes systems, methods and compositions for the generation of sRNA molecules using RNase III mutants in vivo. Another aim of the current invention includes systems, methods and compositions for the generation of sRNA molecules using RNase III mutants in vitro.

Another aim of the current invention includes systems, methods and compositions for the generation of sRNA molecules using RNase III mutants to produce a DICER-independent RNAi response in a host.

One aim of the current invention includes systems, methods and compositions for the high-level generation of sRNA molecules using RNase III mutants that have enhanced catalytic activity.

One aim of the current invention includes systems, methods and compositions for the high-level generation of sRNA molecules using RNase III mutants having enhanced stabilization of RNase III cutting patterns leading to more consistent dsRNA cutting and increases percentages of discrete sized sRNA in a heterologous mixture of digested sRNAs.

Another aim of the current invention includes the generation of a series of single/multiple amino acids mutants in an RNase III N-terminal catalytic domain to produce discrete-sized sRNAs, which have the potential to serve as triggers of RNA silencing. In certain embodiments, RNase III from the family Enterobacteriaceae, such as *E. coli* and *Enterobacter* as well as Bacillaceae among others, may be engineered to include one or more point mutations that improve catalytic efficiency of dsRNA cutting, as well as the production of discrete-sized sRNAs.

Another aim of the current invention may include the expression of one or more RNase III mutants described herein in a select bacterium that may trigger RNA interference (RNAi) pathway response. In this embodiment, for example a heterologous dsRNA directed preferably to an essential gene of a select host pathogen, may be co-expressed with one or more of the RNase III mutants described herein. In this embodiment, one or more of the RNase III mutants may generate discrete-sized sRNAs that may induce an RNAi pathway response, preferably in the host.

Another aim of the current invention may include the expression of one or more RNase III mutants described herein in a select bacterium that may trigger RNA interference (RNAi) pathway response in a plant. In this embodiment, for example a heterologous dsRNA directed preferably to an essential gene of a select host pathogen, may be co-expressed with one or more of the RNase III mutants described herein. In this embodiment, one or more of the RNase III mutants may generate discrete-sized sRNAs that may induce an RNAi pathway response, preferably in the plant host.

Another aim of the current invention may include the expression of one or more RNase III mutants described herein in a select bacterium that may trigger RNA interference (RNAi) pathway response in an animal host. In this embodiment, for example a heterologous dsRNA directed preferably to an essential gene of a select host pathogen, may be co-expressed with one or more of the RNase III mutants described herein. In this embodiment, one or more of the RNase III mutants may generate discrete-sized sRNAs that may induce an RNAi pathway response, preferably in the animal host.

Another aim of the current invention may include the trans-kingdom delivery of sRNA molecules to a host through expression of one or more RNase III mutants described herein in a select symbiotic bacterium that may trigger RNA interference (RNAi) pathway response in a plant. In this embodiment, for example a heterologous dsRNA directed preferably to an essential gene of a select host pathogen, may be co-expressed with one or more of the RNase III mutants described herein in a bacterium that is a natural symbiont with the plant host. In a preferred embodiment, this natural symbiont may include one or more endophytic bacteria. In this embodiment, one or more of the RNase III mutants may generate discrete-sized sRNAs that may induce an RNAi pathway response, preferably in the plant host.

Another aim of the current invention may include the trans-kingdom delivery of sRNA molecules to a host through expression of one or more RNase III mutants described herein in a symbiotic or endosymbiotic bacterium that may trigger RNA interference (RNAi) pathway response in an animal host. In this embodiment, for example a heterologous dsRNA directed preferably to an essential gene of a select host pathogen, may be co-expressed with one or more of the RNase III mutants described herein in a bacterium that is a natural symbiont with the plant host. In a preferred embodiment, this natural symbiont may include one or more symbiotic or endosymbiotic bacteria, and preferably an enteric bacteria. In this embodiment, one or more of the RNase III mutants may generate discrete-sized sRNAs that may induce an RNAi pathway response, preferably in the animal host.

Another aim of the current invention may include the expression of one or more RNase III mutants described herein in a select bacterium that may produce discrete-sized sRNAs, which may trigger an RNAi pathway response. In this embodiment, for example dsRNA from a select pathogen, and preferably an essential gene of a select host pathogen may be co-expressed with one or more of the RNase III mutants described herein. In this embodiment, one or more of the RNase III mutants may generate discrete-sized sRNAs that may induce an RNAi pathway response, preferably in the host.

Another aim of the current invention may include the expression of one or more RNase III mutants described herein in a select bacterium that may produce discrete-sized sRNAs, which may trigger a prophylactic RNAi pathway response. In this embodiment, for example dsRNA from a select pathogen, and preferably an essential gene of a select host pathogen may be co-expressed with one or more of the RNase III mutants described herein. In this embodiment, one or more of the RNase III mutants may generate discrete-sized sRNAs that may induce a prophylactic RNAi pathway response, preferably in the host, that may protect the host from infection by the select pathogen.

Another aim of the current invention may include the expression of one or more RNase III mutants described herein in a select bacterium that may produce discrete-sized sRNAs, which may trigger a DICER-independent RNAi pathway response. In this embodiment, for example dsRNA from a select pathogen, and preferably an essential gene of a select host pathogen may be co-expressed with one or more of the RNase III mutants described herein. In this embodiment, one or more of the RNase III mutants may generate discrete-sized sRNAs that may induce an RNAi pathway response, preferably in the host, that is independent of the action of a DICER enzyme that may be inhibited by certain viral pathogens.

Another aim of the current invention may include the expression of one or more RNase III mutants described herein in a select bacterium that may exhibit enhanced catalytic activity and thereby produce higher amounts of sRNA compared to wild-type or other RNase III mutants previously described in the art.

Another aim of the current invention may include the expression of one or more RNase III mutants described herein in a select bacterium that may exhibit enhanced stabilization of RNase III cutting patterns leading to more consistent dsRNA cutting and thereby produce sRNA having greater homogeneity, such that the sRNA's produced exhibit a greater consistency of size compared to wild-type or other RNase III mutants previously described in the art.

Another aim of the current invention may include the expression of one or more RNase III mutants described herein in a select bacterium that may generate discreet sized sRNA molecules. In one preferred embodiment, such discrete sized sRNA may be 26-29 nt, and/or 22-23. In one preferred embodiment, such discrete sized sRNA may be greater than 26-29 nt, and/or 22-23. In one preferred embodiment, such discrete sized sRNA may be less than 26-29 nt, and/or 22-23. In one preferred embodiment, such sRNA molecules generated by one or more RNase III mutants described herein may exhibit greater diffusion in the host due to improved fixed-flow diffusion.

Another aim of the current invention may include systems, methods and compositions for the high-level production of sRNA molecules. In one preferred embodiment, bacteria may be genetically modified to heterologously express one or more of the RNase III mutants described herein. In a preferred embodiment, the genetically modified bacteria may further co-express a target dsRNA molecule, preferably directed to an essential gene of a pathogen, pest or herbivore. These genetically modified bacteria may be grown in a fermenter, or other industrial production system. The target dsRNA molecule may be converted into sRNA molecules of a discrete size and isolated. In another embodiment such sRNA molecules may be generated as described above and then further isolated, while in other embodiments, the bacterium containing the sRNA molecules may be isolated. Another aim of the invention may include compositions that include a quantity of sRNA molecules or bacteria that contain sRNA molecules. Such compositions may include compositions that may be administered and/or applied to a host, such as a plant or animal host. Examples may include pharmaceutical compositions, topical compositions, encapsulated compositions, gel compositions, spray compositions and the like. Another aim of the invention may include the use of such sRNA molecules compositions to treat and/or prevent a pathogen caused disease condition in a host. Another aim of the invention may include the use of such sRNA molecules compositions to treat, prevent or kill a pest that may consume a host, preferably a plant host.

Another aim of the invention may include a polynucleotide encoding one or more RNase III mutants as described herein. Another aim of the invention may include a polynucleotide encoding one or more RNase III mutants as described herein operably linked to a promoter. Another aim of the invention may include a polynucleotide encoding one or more RNase III mutants as described herein as an expression cassette. Another aim of the invention may include a polynucleotide encoding one or more RNase III mutants as described herein as a vector that may be used to transform a bacteria or other organism.

Another aim of the invention may include a polynucleotide encoding one or more RNase III mutants as described herein and a polynucleotide encoding one or more dsRNAs directed to an essential gene in a host pathogen. Another aim of the invention may include a polynucleotide encoding one or more RNase III mutants as described herein and a polynucleotide encoding one or more dsRNAs directed to an essential gene in a host pathogen wherein each sequence is operably linked to a promoter. Another aim of the invention may include a polynucleotide encoding one or more RNase III mutants as described herein and a polynucleotide encoding one or more dsRNAs directed to an essential gene in a host pathogen as an expression cassette. Another aim of the invention may include a polynucleotide encoding one or more RNase III mutants as described herein and a polynucleotide encoding one or more dsRNAs directed to an essential gene in a host pathogen as a vector that may be used to transform a bacteria or other organism. Another aim of the invention may include the stable transformation and expression of one or more RNase III mutants as described herein.

Another aim of the current invention includes systems and methods of genetically modifying a target organism, such as a target bacterium, to express a polypeptide of one or more RNase III mutants as described herein.

Another aim of the current invention includes systems and methods of genetically modifying a target organism, such as a target bacterium, to co-express a polypeptide of one or more RNase III mutants as described herein and a polypeptide encoding one or more dsRNAs directed to an essential gene in a host pathogen Another aim of the current invention includes systems and methods of genetically modifying a target organism, such as a target bacterium, to express a polypeptide of one or more RNase III mutants as described herein.

Another aim of the invention may include a polypeptide encoding one or more RNase III mutants as described herein.

Another aim of the current invention includes systems and methods of genetically modifying a target organism, such as a bacterium, to express a polypeptide encoding one or more RNase III mutants as described herein.

Another aim of the current invention includes systems and methods of genetically modifying a target organism, such as a bacterium, to express a polypeptide encoding one or more RNase III mutants as described herein, and co-express a dsRNA directed to an essential gene in a host pathogen.

Another aim of the current invention includes the generation of a series of single/multiple amino acids mutants in an RNase III N-terminal catalytic domain to produce discrete-sized sRNAs, which have the potential to serve as triggers of RNA silencing. In certain embodiments, RNase III from the family Enterobacteriaceae, such as Enterobacteriaceae and *Enterobacter* as well as other bacteria families, such as Bacillaceae among others, may be engineered to include one or more point mutations that improve catalytic efficiency of dsRNA cutting, as well as the production of discrete-sized sRNAs.

Another aim of the invention may include the generation of a series of single/multiple amino acids mutants in an RNase III, wherein the RNase III is a bacterial RNase III. Another aim of the invention may include the generation of a series of single/multiple amino acids mutants in an RNase III from *E. coli*. In one embodiment, an RNase III from *E. coli* may be according to polynucleotide sequence SEQ ID NO. 1, and/or amino acid sequence SEQ ID NO. 2.

Another aim of the invention may include the generation of a series of single/multiple amino acids mutants in an RNase III from Enterobacteriaceae. Another aim of the invention may include the generation of a series of single/multiple amino acids mutants in an RNase III from *Enterobacter*. Another aim of the invention may include the generation of a series of single/multiple amino acids mutants in an RNase III, wherein the RNase III is a homolog of at an RNase III described herein. Another aim of the invention may include the generation of a series of single/multiple amino acids mutants in an RNase III, wherein the RNase III is an ortholog of an RNase III described herein.

Another aim of the current invention may include the generation of an E38A RNase III mutant. Another aim of the current invention may include the generation of an E38A RNase III mutant that is integrated into the bacterial chromosome. Another aim of the current invention may include the transformation and/or expression of an E38A RNase III mutant in bacteria. Another aim of the current invention may include the transformation and/or expression of an E38A RNase III mutant in bacteria that is symbiotic or endosymbiotic with a target host. Another aim of the current invention may include the transformation and/or expression of a an E38A RNase III mutant in bacteria that is symbiotic or endosymbiotic with a target host, wherein the RNase III mutant generates sRNA that are delivered to the target host and induce an RNAi pathway response. Another aim of the current invention may include the co-expression in a bacterium of an E38A RNase III mutant and a dsRNA directed to an essential pathogen gene in a target host.

Another aim of the current invention may include the generation of an E65A RNase III mutant. Another aim of the current invention may include the transformation and/or expression of an E65A RNase III mutant in bacteria. Another aim of the current invention may include the transformation and/or expression of an E65A RNase III mutant in bacteria that is symbiotic or endosymbiotic with a target host. Another aim of the current invention may include the transformation and/or expression of a an E65A RNase III mutant in bacteria that is symbiotic or endosymbiotic with a target host, wherein the RNase III mutant generates sRNA that are delivered to the target host and induce an RNAi pathway response. Another aim of the current invention may include the co-expression in a bacterium of an E65A RNase III mutant and a dsRNA directed to an essential pathogen gene in a target host.

Another aim of the current invention may include the generation of an E38A-E65A RNase III mutant. Another aim of the current invention may include the transformation and/or expression of an E38A-E65A RNase III mutant in bacteria. Another aim of the current invention may include the transformation and/or expression of an E38A-E65A RNase III mutant in bacteria that is symbiotic or endosymbiotic with a target host. Another aim of the current invention may include the transformation and/or expression of a an E38A-E65A RNase III mutant in bacteria that is symbiotic or endosymbiotic with a target host, wherein the RNase III mutant generates sRNA that are delivered to the target host and induce an RNAi pathway response. Another aim of the current invention may include the co-expression in a bacterium of an E38A-E65A RNase III mutant and a dsRNA directed to an essential pathogen gene in a target host.

Another aim of the current invention may include the generation of an E38A-R107A-R108A RNase III mutant. Another aim of the current invention may include the transformation and/or expression of an E38A-R107A-R108A RNase III mutant in a bacterium. Another aim of the current invention may include the transformation and/or expression of an E38A-R107A-R108A RNase III mutant in bacteria that is symbiotic or endosymbiotic with a target host. Another aim of the current invention may include the transformation and/or expression of a an E38A-R107A-R108A RNase III mutant in bacteria that is symbiotic or endosymbiotic with a target host, wherein the RNase III mutant generates sRNA that are delivered to the target host and induce an RNAi pathway response. Another aim of the current invention may include the co-expression in a bacterium of an E38A-R107A-R108A RNase III mutant and a dsRNA directed to an essential pathogen gene in a target host.

Another aim of the current invention may include the generation of an E38A RNase III mutant having a size preference for the generation of 26 and 29 nt sRNAs. Another aim of the current invention may include the generation of an E38A RNase III mutant having improved catalytic efficiency. Another aim of the current invention may include the generation of an E38A RNase III mutant according to SEQ ID NOs. 3-4, 13-14, and 9-10.

Another aim of the current invention may include the generation of an E65A RNase III mutant having a size preference for the generation of 26 and 29 nt sRNAs. Another aim of the current invention may include the generation of an E65A RNase III mutant having improved catalytic efficiency. Another aim of the current invention may include the generation of an E65A RNase III mutant according to SEQ ID NO. 5-6.

Another aim of the current invention may include the generation of an E38A-E65A RNase III mutant having a size preference for the generation of 26 and 29 nt sRNAs. Another aim of the current invention may include the generation of an E38A-E65A RNase III mutant having improved catalytic efficiency. Another aim of the current invention may include the generation of an E65A RNase III mutant according to SEQ ID NO. 17.

Another aim of the current invention may include the generation of an E38A-R107A-R108A RNase III mutant having a size preference for the generation of 22 and 23 nt sRNAs. In certain other embodiment, the current invention may include the generation of an E38A-R107A-R108A RNase III mutant having a size preference for the generation of 22 and 23 nt sRNAs in an RNase III from Enterobacteriaceae, for example according to SEQ ID NOs. 7-8, In certain other embodiment, the current invention may include the generation of an E38A-R107A-R108A RNase III mutant having a size preference for the generation of 22 and 23 nt sRNAs in an RNase III from *Enterobacter*, for example according to SEQ ID NOs. 11-12, and 15-16, as well as other bacteria families, such as Bacillaceae among others. In certain other embodiment, the current invention may include the generation of an E38A-R107A-R108A RNase III mutant from a homolog of an RNase III identified herein.

Another aim of the current invention may include the generation of an E38A-R107A-R108A RNase III mutant having improved catalytic efficiency and enhanced dsRNA cutting specificity for 22 and 23 nt sRNAs. Another aim of the current invention may include the generation of an E65A RNase III mutant according to SEQ ID NO. 7-8, 11-12, and 15-16.

Another aim of the current invention may include the generation of one or more RNase III mutants that may be expressed in bacteria and generate sRNA that may be further isolated. In one preferred embodiment, the current invention may include the generation of RNase III mutants that may be expressed in bacteria and generate sRNA according to SEQ ID NOs. 3-17, or 37-40, and 55-58.

Another aim of the current invention may include the generation of one or more RNase III mutants that may be expressed in bacteria configured to deliver sRNA to a host. In one preferred embodiment, the current invention may include the generation of RNase III mutants according to SEQ ID NOs. 3-17, or 37-40, and 55-58 that may be expressed in bacteria configured to deliver sRNA to a host and initiate a DICER-independent RNAi pathway response.

Another aim of the current invention may include the generation of one or more RNase III mutants according to SEQ ID NOs. 3-17, or 37-40, and 55-58 that may be co-expressed with a dsRNA directed to an essential pathogen gene, preferably a symbiotic and/or endosymbiotic bacteria to the host. In this embodiment, the RNase III mutants that may generate sRNA from the co-expressed dsRNA and to deliver the sRNA to a host initiating an RNAi pathway response.

Another aim of the current invention may include the generation of one or more RNase III mutants according to SEQ ID NOs. 3-17, or 37-40, and 55-58 that may be co-expressed with a dsRNA directed to an essential pest gene, preferably a symbiotic and/or endosymbiotic bacteria to the host. In this embodiment, the RNase III mutants that may generate sRNA from the co-expressed dsRNA and to deliver the sRNA to a host initiating an RNAi pathway response in pest consuming the host, preferably a plant.

Another aim of the current invention may include the generation of one or more RNase III mutants according to SEQ ID NOs. 37-40, and 55-58 that may be co-expressed with a dsRNA directed to an essential pathogen gene, preferably a symbiotic and/or endosymbiotic bacteria to the host. In this embodiment, the RNase III mutants that may generate sRNA from the co-expressed dsRNA and to deliver the sRNA to a host initiating an RNAi pathway response, preferably in a plant or animal.

Another aim of the current invention may include the generation of one or more RNase III mutants that may exhibit differential cutting of dsRNA compared to a wildtype RNase III.

Another aim of the current invention may include the generation of an Q153P RNase III mutants wherein the RNase III mutants generate dsRNA, and may further exhibit differential cutting of dsRNA compared to a wildtype RNase III Another aim of the current invention may include the generation of an D115E RNase III mutants wherein the RNase III mutants generate dsRNA, and may further exhibit differential cutting of dsRNA compared to a wildtype RNase III Another aim of the current invention may include the generation of an E58A RNase III mutants wherein the RNase III mutants generate dsRNA, and may further exhibit differential cutting of dsRNA compared to a wildtype RNase III Another aim of the current invention may include the generation of an E59A RNase III mutants wherein the RNase III mutants generate dsRNA, and may further exhibit differential cutting of dsRNA compared to a wildtype RNase III Another aim of the current invention may include the generation of an E117K RNase III mutant that may bind to, but not cut dsRNA.

Another aim of the current invention may include the generation of one or more RNase III mutants according to SEQ ID NOs. 37-40, 55-58, wherein the RNase III mutants generate dsRNA, and may further exhibit differential cutting of dsRNA compared to a wildtype RNase III.

Another aim of the current invention may include the generation of one or more RNase III mutants according to SEQ ID NOs. 27-28, wherein the RNase III mutants bind to, but does not generate sRNA.

Additional aims of the invention may include one or more of the following embodiments:

Base Composition

1. A genetically modified cell expressing a heterologous polynucleotide sequence operably linked to a promoter sequence encoding an RNase III mutant configured for enhanced generation of small RNA (sRNA) from catalytic cutting of double stranded RNA (dsRNA), wherein said RNase III mutant exhibits at least one of the following enhanced characteristics compared to a wild type RNase III:
   enhanced stabilization of dsRNA cutting patterns;
   enhanced catalytic efficiency of dsRNA cutting; and
   enhanced specificity for one or more discrete dsRNA cutting size preferences.

2. The genetically modified bacteria of embodiment 1 wherein said genetically modified cell is selected from the group consisting of: a genetically modified prokaryotic cell, and a genetically modified eukaryotic cell.

3. The genetically modified cell of embodiment 2 wherein said genetically modified prokaryotic cell comprises a genetically modified bacteria.

4. The genetically modified cell of embodiment 3 wherein said genetically modified bacteria comprises a genetically modified bacteria that is symbiotic and/or endosymbiotic with a target host.

5. The genetically modified cell of embodiment 4 wherein said target host is selected from the group consisting of: a plant host, and an animal host.

6. The genetically modified cell of embodiment 5 wherein said RNase III mutant comprises at least one of the following:
   an E38A RNase III mutant, wherein a glutamic acid is replaced with an alanine at residue 38, or a homologous RNase III mutant thereof;
   an E65A RNase III mutant, wherein a glutamic acid is replaced with an alanine at residue 65, or a homologous RNase III mutant thereof;
   an RNase III E38A-E65A mutant, wherein a glutamic acid is replaced with an alanine at residue 38, and a glutamic acid is replaced with an alanine at residue 65, or a homologous RNase III mutant thereof; and
   an E38A-R107A-R108A RNase III mutant, wherein a glutamic acid is replaced with an alanine at residue 38 and an arginine is replaced with an alanine at residue 107, and an arginine is replaced with an alanine at residue 108, or a homologous RNase III mutant thereof.

7. The genetically modified cell of embodiment 1 wherein said heterologous polynucleotide sequence operably linked to a promoter sequence encoding an RNase III mutant comprises at least one of the following:
   a heterologous polynucleotide sequence operably linked to a promoter sequence encoding an E38A RNase III mutant according SEQ ID NO. 3;
   a heterologous polynucleotide sequence operably linked to a promoter sequence encoding an E38A RNase III mutant according SEQ ID NOs. 9, and 13;
   a heterologous polynucleotide sequence operably linked to a promoter sequence encoding an E38A RNase III mutant according SEQ ID NO. 13;
   a heterologous polynucleotide sequence operably linked to a promoter sequence encoding an E65A RNase III mutant according to SEQ ID NO. 5;
   a heterologous polynucleotide sequence operably linked to a promoter sequence encoding an E38A-E65A RNase III mutant polynucleotide sequence encoding a the amino acid sequence according to SEQ ID NO. 17;
   a heterologous polynucleotide sequence operably linked to a promoter sequence encoding an E38A-R107A-R108A RNase III mutant according to SEQ ID NO. 7;
   a heterologous polynucleotide sequence operably linked to a promoter sequence encoding an E38A-R107A-R108A RNase III mutant according to SEQ ID NO. 11; and a heterologous polynucleotide sequence operably linked to a promoter sequence encoding an E38A-R107A-R108A RNase III mutant according to SEQ ID NO. 15.

8. The genetically modified cell of embodiment 1 wherein said heterologous polynucleotide sequence operably linked to a promoter sequence encoding an RNase III mutant comprises at least one of the following:

a heterologous polynucleotide sequence operably linked to a promoter sequence encoding an E38A RNase III mutant polypeptide according to SEQ ID NO. 4;

a heterologous polynucleotide sequence operably linked to a promoter sequence encoding an E38A RNase III mutant polypeptide according to SEQ ID NO. 10;

a heterologous polynucleotide sequence operably linked to a promoter sequence encoding an E38A RNase III mutant polypeptide according to SEQ ID NO. 14;

a heterologous polynucleotide sequence operably linked to a promoter sequence encoding an E65A RNase III mutant polypeptide according to SEQ ID NO. 6;

a heterologous polynucleotide sequence operably linked to a promoter sequence encoding an E38A-E65A RNase III mutant polypeptide according to SEQ ID NO. 17;

a heterologous polynucleotide sequence operably linked to a promoter sequence encoding an E38A-R107A-R108A RNase III mutant polypeptide according to SEQ ID NO. 8;

a heterologous polynucleotide sequence operably linked to a promoter sequence encoding an E38A-R107A-R108A RNase III mutant polypeptide according to SEQ ID NO. 12; and a heterologous polynucleotide sequence operably linked to a promoter sequence encoding an E38A-R107A-R108A RNase III mutant polypeptide according to SEQ ID NO. 16.

9. The genetically modified cell of embodiments 6, 7, and 8 wherein the E38A-R107A-R108A RNase III mutant exhibits discrete dsRNA cutting size preferences of 22, and 23 nucleotides (nt).

10. The genetically modified cell of embodiment 1 wherein said RNase III mutant was derived from an RNase III selected from the group consisting of: an RNase III from an Enterobacteriaceae, an RNase III from an *E. coli*, an RNase III from an *Enterobacter*, an RNase III from an Bacillaceae, an RNase III from a *Bacillus*, an RNase III from a *B. subtilis*, an RNase III from a *B. cereus*, an RNase III from an *S. enterica*, an RNase III from a *P. aeruginosa*, an RNase III from a *C. burnetii*, an RNase III from a *R. capsulatus*, an RNase III from am *S. coelicolor*, an RNase III from a *C. jejuni*, an RNase III from an *H. pylori*, an RNase III from an *S. aureus*; and an RNase III from an *L. lactis*.

11. The genetically modified cell of embodiments 6, 7, and 8 wherein said genetically modified bacteria further co-expresses a heterologous polynucleotide sequence operably linked to a promoter sequence encoding a dsRNA.

12. The genetically modified cell of embodiment 11 wherein said co-expressed dsRNA comprises a dsRNA directed to a an essential pathogen gene.

13. The genetically modified cell of embodiment 12 wherein said essential pathogen gene comprises an essential viral pathogen gene.

14. The genetically modified cell of embodiment 6 wherein said genetically modified bacteria is introduced to a target host and wherein said sRNA initiates an RNA interference (RNAi) response pathway in a target host.

15. The genetically modified cell of embodiment 14 wherein said genetically modified bacteria is introduced to a target host comprises genetically modified bacteria is applied to a target host plant topically.

16. The genetically modified cell of embodiment 15 wherein said genetically modified bacteria is introduced to a target host comprises genetically modified bacteria is introduced to a target host animal through a feed.

17. The genetically modified cell of embodiment 6 wherein said genetically modified bacteria is grown in an fermenter.

18. The genetically modified cell of embodiment 17 wherein said sRNAs produced by said genetically modified bacteria are isolated.

19. The genetically modified cell of embodiment 17 wherein said isolated sRNAs produced by said genetically modified bacteria are introduced to a target host and wherein said sRNA initiates an RNAi response pathway in said target host.

20. A composition comprising: an E38A-R107A-R108A RNase III mutant, wherein a glutamic acid is replaced with an alanine at residue 38 and an arginine is replaced with an alanine at residue 107, and an arginine is replaced with an alanine at residue 108, or a homologous RNase III mutant thereof.

21. The composition of embodiment 20 wherein said E38A-R107A-R108A RNase III mutant exhibits:
a discrete dsRNA cutting size preferences of 22, and 23 nucleotides (nt);
enhanced stabilization of dsRNA cutting patterns; and
enhanced catalytic efficiency of dsRNA cutting.

22. A composition comprising: a heterologous polynucleotide sequence operably linked to a promoter sequence encoding an E38A-R107A-R108A RNase III mutant according to SEQ ID NO. 7.

23. The composition of embodiment 22 wherein said E38A-R107A-R108A RNase III mutant exhibits:
a discrete dsRNA cutting size preferences of 22, and 23 nucleotides (nt);
enhanced stabilization of dsRNA cutting patterns; and
enhanced catalytic efficiency of dsRNA cutting.

24. A composition comprising: a heterologous polynucleotide sequence operably linked to a promoter sequence encoding an E38A-R107A-R108A RNase III mutant according to SEQ ID NO. 11.

25. The composition of embodiment 24 wherein said E38A-R107A-R108A RNase III mutant exhibits:
a discrete dsRNA cutting size preferences of 22, and 23 nucleotides (nt);
enhanced stabilization of dsRNA cutting patterns; and
enhanced catalytic efficiency of dsRNA cutting.

26. A composition comprising: a heterologous polynucleotide sequence operably linked to a promoter sequence encoding an E38A-R107A-R108A RNase III mutant according to SEQ ID NO. 15.

27. The composition of embodiment 26 wherein said E38A-R107A-R108A RNase III mutant exhibits:
a discrete dsRNA cutting size preferences of 22, and 23 nucleotides (nt);
enhanced stabilization of dsRNA cutting patterns; and
enhanced catalytic efficiency of dsRNA cutting.

28. A composition comprising: a heterologous polynucleotide sequence operably linked to a promoter sequence encoding an E38A-R107A-R108A RNase III mutant polypeptide according to SEQ ID NO. 8.

29. The composition of embodiment 28 wherein said E38A-R107A-R108A RNase III mutant exhibits:
a discrete dsRNA cutting size preferences of 22, and 23 nucleotides (nt);

enhanced stabilization of dsRNA cutting patterns; and
enhanced catalytic efficiency of dsRNA cutting.

30. A composition comprising: a heterologous polynucleotide sequence operably linked to a promoter sequence encoding an E38A-R107A-R108A RNase III mutant polypeptide according to SEQ ID NO. 12.

31. The composition of embodiment 30 wherein said E38A-R107A-R108A RNase III mutant exhibits:
a discrete dsRNA cutting size preferences of 22, and 23 nucleotides (nt);
enhanced stabilization of dsRNA cutting patterns; and
enhanced catalytic efficiency of dsRNA cutting.

32. A composition comprising: a heterologous polynucleotide sequence operably linked to a promoter sequence encoding an E38A-R107A-R108A RNase III mutant polypeptide according to SEQ ID NO. 16.

33. The composition of embodiment 32 wherein said E38A-R107A-R108A RNase III mutant exhibits:
a discrete dsRNA cutting size preferences of 22, and 23 nucleotides (nt);
enhanced stabilization of dsRNA cutting patterns; and
enhanced catalytic efficiency of dsRNA cutting.

34. A composition comprising: a heterologous polynucleotide sequence operably linked to a promoter sequence encoding an E38A-R107A-R108A RNase III mutant polypeptide according to SEQ ID NO. 8.

35. The composition of embodiment 34 wherein said E38A-R107A-R108A RNase III mutant exhibits:
a discrete dsRNA cutting size preferences of 22, and 23 nucleotides (nt);
enhanced stabilization of dsRNA cutting patterns; and
enhanced catalytic efficiency of dsRNA cutting.

36. A composition comprising: a heterologous polynucleotide sequence operably linked to a promoter sequence encoding an E38A-R107A-R108A RNase III mutant polypeptide according to SEQ ID NO. 12.

37. The composition of embodiment 36 wherein said E38A-R107A-R108A RNase III mutant exhibits:
a discrete dsRNA cutting size preferences of 22, and 23 nucleotides (nt);
enhanced stabilization of dsRNA cutting patterns; and
enhanced catalytic efficiency of dsRNA cutting.

37. A composition comprising: a heterologous polynucleotide sequence operably linked to a promoter sequence encoding an E38A-R107A-R108A RNase III mutant polypeptide according to SEQ ID NO. 16.

38. A composition comprising: an E38A RNase III mutant, wherein a glutamic acid is replaced with an alanine at residue 38, or a homologous RNase III mutant thereof.

39. A composition comprising: an E65A RNase III mutant, wherein a glutamic acid is replaced with an alanine at residue 65, or a homologous RNase III mutant thereof.

40. A composition comprising: an RNase III E38A-E65A mutant, wherein a glutamic acid is replaced with an alanine at residue 38 and a glutamic acid is replaced with an alanine at residue 65, or a homologous RNase III mutant thereof.

41. A composition comprising: an RNase III E58A mutant, wherein a glutamic acid is replaced with an alanine at residue 58, or a homologous RNase III mutant thereof.

42. A composition comprising: an RNase III E59A mutant, wherein an aspartic acid is replaced with an alanine at residue 59, or a homologous RNase III mutant thereof.

43. A composition comprising: an RNase III Q153P mutant, wherein a glutamine is replaced with a proline at residue, or a homologous RNase III mutant thereof.

44. A composition comprising: an RNase III D115E mutant, wherein a glutamic acid is replaced with a lysine at residue, or a homologous RNase III mutant thereof.

45. A composition comprising: an RNase III E115K mutant, wherein a glutamic acid is replaced with a lysine at residue, or a homologous RNase III mutant thereof.

46. A composition comprising: a heterologous polynucleotide sequence operably linked to a promoter sequence encoding an E38A RNase III mutant according SEQ ID NO. 3.

47. A composition comprising: a heterologous polynucleotide sequence operably linked to a promoter sequence encoding an E38A RNase III mutant according SEQ ID NOs. 9 and 13.

48. A composition comprising: a heterologous polynucleotide sequence operably linked to a promoter sequence encoding an E38A RNase III mutant according SEQ ID NO. 13.

49. A composition comprising: a heterologous polynucleotide sequence operably linked to a promoter sequence encoding an E65A RNase III mutant according to SEQ ID NO. 5.

50. A composition comprising: a heterologous polynucleotide sequence operably linked to a promoter sequence encoding an E38A-E65A RNase III mutant polynucleotide sequence encoding the amino acid sequence according to SEQ ID NO. 17.

51. A composition comprising: a heterologous polynucleotide sequence operably linked to a promoter sequence encoding an RNase III E58A mutant according to SEQ ID NO. 24.

52. A composition comprising: a heterologous polynucleotide sequence operably linked to a promoter sequence encoding an RNase III E59A mutant according to SEQ ID NO. 26.

53. A composition comprising: a heterologous polynucleotide sequence operably linked to a promoter sequence encoding an E38A RNase III mutant polypeptide according to SEQ ID NO. 4.

54. A composition comprising: a heterologous polynucleotide sequence operably linked to a promoter sequence encoding an E38A RNase III mutant polypeptide according to SEQ ID NO. 10.

55. A composition comprising: a heterologous polynucleotide sequence operably linked to a promoter sequence encoding an E38A RNase III mutant polypeptide according to SEQ ID NO. 14.

56. A composition comprising: a heterologous polynucleotide sequence operably linked to a promoter sequence encoding an E65A RNase III mutant polypeptide according to SEQ ID NO. 6.

57. A composition comprising: a heterologous polynucleotide sequence operably linked to a promoter sequence encoding an E38A-E65A RNase III mutant polypeptide according to SEQ ID NO. 17.

58. A composition comprising: a heterologous polynucleotide sequence operably linked to a promoter sequence encoding an RNase III E58A mutant polypeptide according to SEQ ID NO. 25.

59. A composition comprising: a heterologous polynucleotide sequence operably linked to a promoter sequence encoding an RNase III E59A mutant polypeptide according to SEQ ID NO. 27.

60. A method of generating sRNA comprising the steps of:
genetically modifying a cell to express one or more heterologous polynucleotide sequences operably linked to at least one promotor encoding:

an RNase III mutant configured to generate small RNA (sRNA) from catalytic cutting of double stranded RNA (dsRNA);
a dsRNA directed to an essential pathogen gene;
growing the genetically modified cell in a culture;
catalytic cutting the dsRNA by the RNase III mutant to form a population of sRNAs to
generate a plurality of sRNA of a discrete size; and
isolating said genetically modified cell or isolating said sRNAs of a discrete size.

61. The method of embodiment 60 wherein said genetically modified cell comprises a genetically modified cell is selected from the group consisting of: a genetically modified prokaryotic cell, and a genetically modified eukaryotic cell.

62. The method of embodiment 61 wherein said genetically modified prokaryotic cell comprises a genetically modified bacteria.

63. The method of embodiment 62 wherein said genetically modified bacteria comprise a genetically modified bacteria that is symbiotic and/or endosymbiotic with a target host.

64. The method of embodiment 62 wherein said step of growing the genetically modified cell in a culture comprises the step of growing the genetically modified cell in a fermenter.

65. The method of embodiment 60 wherein said RNase III mutant comprises at least one of the following:
an E38A RNase III mutant, wherein a glutamic acid is replaced with an alanine at residue 38, or a homologous RNase III mutant thereof;
an E65A RNase III mutant, wherein a glutamic acid is replaced with an alanine at residue 65, or a homologous RNase III mutant thereof;
an RNase III E38A-E65A mutant, wherein a glutamic acid is replaced with an alanine at residue 38, and a glutamic acid is replaced with an alanine at residue 65, or a homologous RNase III mutant thereof; and
an E38A-R107A-R108A RNase III mutant, wherein a glutamic acid is replaced with an alanine at residue 38 and an arginine is replaced with an alanine at residue 107, and an arginine is replaced with an alanine at residue 108, or a homologous RNase III mutant thereof.

66. The method of embodiment 60 wherein said heterologous polynucleotide sequence operably linked to a promoter sequence encoding an RNase III mutant comprises at least one of the following:
a heterologous polynucleotide sequence operably linked to a promoter sequence encoding an E38A RNase III mutant according SEQ ID NO. 3;
a heterologous polynucleotide sequence operably linked to a promoter sequence encoding an E38A RNase III mutant according SEQ ID NO. 9 and 13;
a heterologous polynucleotide sequence operably linked to a promoter sequence encoding an E38A RNase III mutant according SEQ ID NO. 13;
a heterologous polynucleotide sequence operably linked to a promoter sequence encoding an E65A RNase III mutant according to SEQ ID NO. 5;
a heterologous polynucleotide sequence operably linked to a promoter sequence encoding an E38A-E65A RNase III mutant polynucleotide sequence encoding the amino acid sequence according to SEQ ID NO. 17;
a heterologous polynucleotide sequence operably linked to a promoter sequence encoding an E38A-R107A-R108A RNase III mutant according to SEQ ID NO. 7;
a heterologous polynucleotide sequence operably linked to a promoter sequence encoding an E38A-R107A-R108A RNase III mutant according to SEQ ID NO. 11; and
a heterologous polynucleotide sequence operably linked to a promoter sequence encoding an E38A-R107A-R108A RNase III mutant according to SEQ ID NO. 15.

67. The method of embodiment 60 wherein said heterologous polynucleotide sequence operably linked to a promoter sequence encoding an RNase III mutant comprises at least one of the following:
a heterologous polynucleotide sequence operably linked to a promoter sequence encoding an E38A RNase III mutant polypeptide according to SEQ ID NO. 4;
a heterologous polynucleotide sequence operably linked to a promoter sequence encoding an E38A RNase III mutant polypeptide according to SEQ ID NO. 10;
a heterologous polynucleotide sequence operably linked to a promoter sequence encoding an E38A RNase III mutant polypeptide according to SEQ ID NO. 14;
a heterologous polynucleotide sequence operably linked to a promoter sequence encoding an E65A RNase III mutant polypeptide according to SEQ ID NO. 6;
a heterologous polynucleotide sequence operably linked to a promoter sequence encoding an E38A-E65A RNase III mutant polypeptide according to SEQ ID NO. 17;
a heterologous polynucleotide sequence operably linked to a promoter sequence encoding an E38A-R107A-R108A RNase III mutant polypeptide according to SEQ ID NO. 8;
a heterologous polynucleotide sequence operably linked to a promoter sequence encoding an E38A-R107A-R108A RNase III mutant polypeptide according to SEQ ID NO. 12; and
a heterologous polynucleotide sequence operably linked to a promoter sequence encoding an E38A-R107A-R108A RNase III mutant polypeptide according to SEQ ID NO. 16.

68. The method of embodiments 65, 66, and 67 wherein said E38A-R107A-R108A RNase III mutant exhibits discrete dsRNA cutting size preferences of 22, and 23 nucleotides (nt).

69. The method of embodiment 60 wherein said RNase III mutant configured to generate small RNA (sRNA) from catalytic cutting of double stranded RNA (dsRNA) exhibits at least one of the following enhanced characteristics compared to a wild type RNase III:
enhanced stabilization of dsRNA cutting patterns;
enhanced catalytic efficiency of dsRNA cutting; and
enhanced specificity for one or more discrete dsRNA cutting size preferences.

70. The method of embodiment 62 wherein said RNase III mutant was derived from an RNase III selected from the group consisting of: an RNase III from an Enterobacteriaceae, an RNase III from an *E. coli*, an RNase III from an *Enterobacter*, an RNase III from an Bacillaceae, an RNase III from a *Bacillus*, an RNase III from a *B. subtilis*, an RNase III from a *B. cereus*, an RNase III from an *S. enterica*, an RNase III from a *P. aeruginosa*, an RNase III from a *C. burnetii*, an RNase III from a *R. capsulatus*, an RNase III from am *S. coelicolor*, an RNase III from a *C. jejuni*, an RNase III from an *H. pylori*, an RNase III from an *S. aureus*; and an RNase III from an *L. lactis*.

80. The method of embodiment 60 wherein said isolated cells are introduced to a target host and wherein said sRNA initiates an RNAi response pathway in said target host.

81. The method of embodiment 60 wherein said isolated sRNAs are introduced to a target host and wherein said sRNA initiates an RNAi response pathway in said target host.

82. The method of embodiment 60 wherein said essential pathogen gene is an essential viral pathogen gene.

83. A method of initiating a DICER independent RNA interference (RNAi) response pathway in a target host comprising the steps of:
genetically modifying a cell that lacks a DICER enzyme to express one or more heterologous polynucleotide sequences operably linked to at least one promotor encoding:
an RNase III mutant configured to catalytic cut double stranded RNA (dsRNA) in the absence of a DICER enzyme; and
a dsRNA directed to an essential pathogen gene;
introducing the genetically modified cell to a target host;
catalytic cutting the expressed dsRNA by the RNase III mutant to form a population of small RNAs (sRNAs) capable of initiating a DICER-independent RNAi response pathway; and
allowing said sRNAs to diffuse from the cell to the target host and initiate a DICER-independent RNAi response pathway directed to said essential in said target host; and
downregulating said essential pathogen gene through said a DICER-independent RNAi response pathway.

84. The method of embodiment 83 wherein said genetically modified cell comprises a genetically modified cell is selected from the group consisting of: a genetically modified prokaryotic cell, and a genetically modified eukaryotic cell.

85. The method of embodiment 84 wherein said genetically modified prokaryotic cell comprises a genetically modified bacteria.

86. The method of embodiment 85 wherein said genetically modified bacteria comprise a genetically modified bacteria that is symbiotic and/or endosymbiotic with said target host.

87. The method of embodiment 85 wherein said target host is selected from the group consisting of: a plant target host, and an animal target host.

88. The method of embodiment 83 wherein said RNase III mutant comprises at least one of the following:
an E38A RNase III mutant, wherein a glutamic acid is replaced with an alanine at residue 38, or a homologous RNase III mutant thereof;
an E65A RNase III mutant, wherein a glutamic acid is replaced with an alanine at residue 65, or a homologous RNase III mutant thereof;
an RNase III E38A-E65A mutant, wherein a glutamic acid is replaced with an alanine at residue 38, and a glutamic acid is replaced with an alanine at residue 65, or a homologous RNase III mutant thereof; and
an E38A-R107A-R108A RNase III mutant, wherein a glutamic acid is replaced with an alanine at residue 38 and an arginine is replaced with an alanine at residue 107, and an arginine is replaced with an alanine at residue 108, or a homologous RNase III mutant thereof.

89. The method of embodiment 83 wherein said heterologous polynucleotide sequence operably linked to a promoter sequence encoding an RNase III mutant comprises at least one of the following:
a heterologous polynucleotide sequence operably linked to a promoter sequence encoding an E38A RNase III mutant according SEQ ID NO. 3;
a heterologous polynucleotide sequence operably linked to a promoter sequence encoding an E38A RNase III mutant according SEQ ID NO. 9 and 13;
a heterologous polynucleotide sequence operably linked to a promoter sequence encoding an E38A RNase III mutant according SEQ ID NO. 13;
a heterologous polynucleotide sequence operably linked to a promoter sequence encoding an E65A RNase III mutant according to SEQ ID NO. 5;
a heterologous polynucleotide sequence operably linked to a promoter sequence encoding an E38A-E65A RNase III mutant polynucleotide sequence encoding the amino acid sequence according to SEQ ID NO. 17; and
a heterologous polynucleotide sequence operably linked to a promoter sequence encoding an E38A-R107A-R108A RNase III mutant according to SEQ ID NO. 7;
a heterologous polynucleotide sequence operably linked to a promoter sequence encoding an E38A-R107A-R108A RNase III mutant according to SEQ ID NO. 11; and
a heterologous polynucleotide sequence operably linked to a promoter sequence encoding an E38A-R107A-R108A RNase III mutant according to SEQ ID NO. 15.

90. The method of embodiment 84 wherein said heterologous polynucleotide sequence operably linked to a promoter sequence encoding an RNase III mutant comprises at least one of the following:
a heterologous polynucleotide sequence operably linked to a promoter sequence encoding an E38A RNase III mutant polypeptide according to SEQ ID NO. 4;
a heterologous polynucleotide sequence operably linked to a promoter sequence encoding an E38A RNase III mutant polypeptide according to SEQ ID NO. 10;
a heterologous polynucleotide sequence operably linked to a promoter sequence encoding an E38A RNase III mutant polypeptide according to SEQ ID NO. 14;
a heterologous polynucleotide sequence operably linked to a promoter sequence encoding an E65A RNase III mutant polypeptide according to SEQ ID NO. 6;
a heterologous polynucleotide sequence operably linked to a promoter sequence encoding an E38A-E65A RNase III mutant polypeptide according to SEQ ID NO. 17;
a heterologous polynucleotide sequence operably linked to a promoter sequence encoding an E38A-R107A-R108A RNase III mutant polypeptide according to SEQ ID NO. 8;
a heterologous polynucleotide sequence operably linked to a promoter sequence encoding an E38A-R107A-R108A RNase III mutant polypeptide according to SEQ ID NO. 12; and
a heterologous polynucleotide sequence operably linked to a promoter sequence encoding an E38A-R107A-R108A RNase III mutant polypeptide according to SEQ ID NO. 16.

91. The method of embodiments 88, 89, and 90 wherein said E38A-R107A-R108A RNase III mutant exhibits discrete dsRNA cutting size preferences of 22, and 23 nucleotides (nt).

92. The method of embodiment 83 wherein said RNase III mutant configured to generate small RNA (sRNA) from catalytic cutting of double stranded RNA (dsRNA) exhibits at least one of the following enhanced characteristics compared to a wild type RNase III:

enhanced stabilization of dsRNA cutting patterns;
enhanced catalytic efficiency of dsRNA cutting; and
enhanced specificity for one or more discrete dsRNA cutting size preferences.

93. The method of embodiment 85 wherein said RNase III mutant was derived from an RNase III selected from the group consisting of: an RNase III from an Enterobacteriaceae, an RNase III from an *E. coli*, an RNase III from an *Enterobacter*, an RNase III from an Bacillaceae, an RNase III from a *Bacillus*, an RNase III from a *B. subtilis*, an RNase III from a *B. cereus*, an RNase III from an *S. enterica*, an RNase III from a *P. aeruginosa*, an RNase III from a *C. burnetii*, an RNase III from a *R. capsulatus*, an RNase III from am *S. coelicolor*, an RNase III from a *C. jejuni*, an RNase III from an *H. pylori*, an RNase III from an *S. aureus*; and an RNase III from an *L. lactis*.

94. The method of embodiment 83 wherein said essential pathogen gene is an essential viral pathogen gene.

Further scope of the applicability of the presently disclosed embodiments will become apparent from the detailed description and drawing(s) provided below. However, it should be understood that the detailed description and specific examples, while indicating preferred embodiments of this disclosure, are given by way of illustration only since various changes and modifications within the spirit and scope of these embodiments will become apparent to those skilled in the art from this detailed description.

BRIEF DESCRIPTION OF THE FIGURES

The above and other aspects, features, and advantages of the present disclosure will be better understood from the following detailed descriptions taken in conjunction with the accompanying figures, all of which are given by way of illustration only, and are not limiting the presently disclosed embodiments, in which.

Lanes 10-11: The total small RNAs extracted from HT115-E38A-R107A-R108A.

Figure 15:
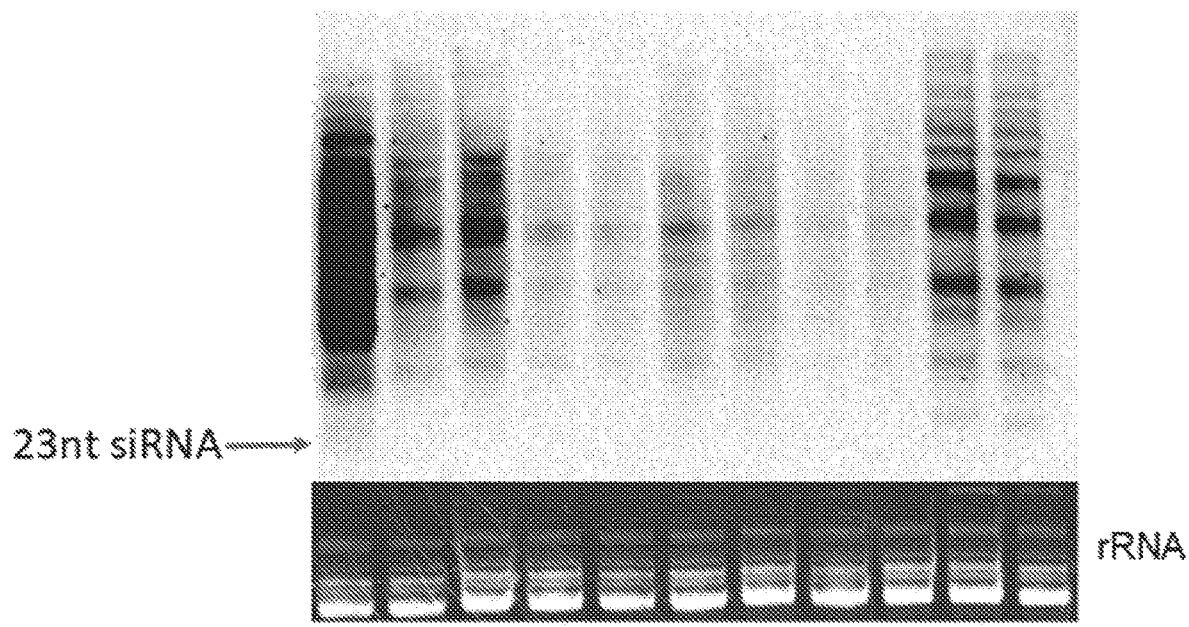

FIG. 15: Northern blot revealing small interfering RNA molecules of 23 nucleotides (upper panel). GelGreen® Nucleic Acid-stained rRNA served as loading controls in the gel prior to RNA transfer (lower panel). 6 μg total small RNA was loaded per well. Lane 1: The siRNA extracted from E38A-L40F mutant containing pAD-WRKY-GHY7 plasmid (TMV movement protein hpRNA), positive control; Lanes 2-3: The siRNA extracted from predicted mutant HT115-E38A-ΔSA; Lanes 4-5: The siRNA extracted from predicted mutant HT115-E38A-ΔSASS; Lanes 6-7: The siRNA extracted from predicted mutant HT115-E38A-ΔSA-ΔGPG; Lanes 8-9: The siRNA extracted from predicted mutant HT115-E38A-ΔSASS-ΔGPG; Lanes 10-11: The siRNA extracted from predicted mutant HT115-E38A R107E-R108E.

Figure 16:
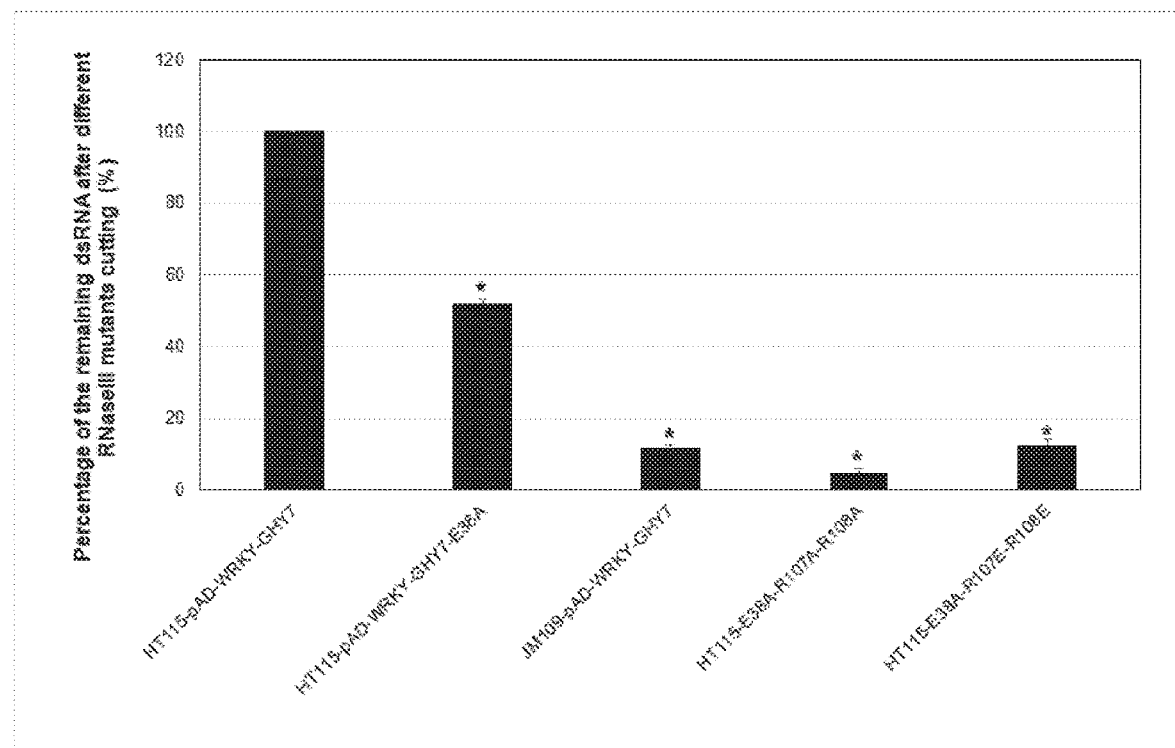

FIG. 16: qRT-PCR of dsRNA cleavage from different E. coli RNase III mutants. * indicates P<0.05. HT115-pAD-WRKY-GHY7: HT115 strain containing pAD-WRKY-GHY7 plasmid (tetracycline and chloramphenicol resistance), and it cannot digest dsRNA; HT115-pAD-WRKY-GHY7-E38A: HT115 strain containing pAD-WRKY-GHY7-E38A plasmid (tetracycline and chloramphenicol resistance), and E38A RNaseIII mutant can digest dsRNA into 26-29 bp small RNA; this strain can convert almost half of dsRNA into small RNAs compared to HT115-pAD-WRKY-GHY7, which cannot digest the dsRNA molecules; JM109-pAD-WRKY-GHY7: JM109 (DE3) RNaseIII E38A mutant containing pAD-WRKY-GHY7 plasmid (chloramphenicol resistance), it can cleave dsRNA into 26-29 bp small RNA; this strain can convert almost 85% dsRNA into small RNAs compared to HT115-pAD-WRKY-GHY7. HT115-E38A-R107A-R108A: HT115 strain containing pAD-WRKY-GHY7-E38A-R107A-R108A plasmid (tetracycline and chloramphenicol resistance), and it can effectively cleave dsRNA into 22-23 bp small RNA; it can convert almost 95% dsRNA into small RNAs compared to HT115-pAD-WRKY-GHY7; HT115-E38A-R107E-R108E: HT115 strain containing pAD-WRKY-GHY7-E38A-R107E-R108E plasmid (tetracycline and chloramphenicol resistance), and it can cleave dsRNA into 26-29 bp small RNA and can convert almost 80% dsRNA into small RNA compared to HT115-pAD-WRKY-GHY7-E38A.

Figure 17:
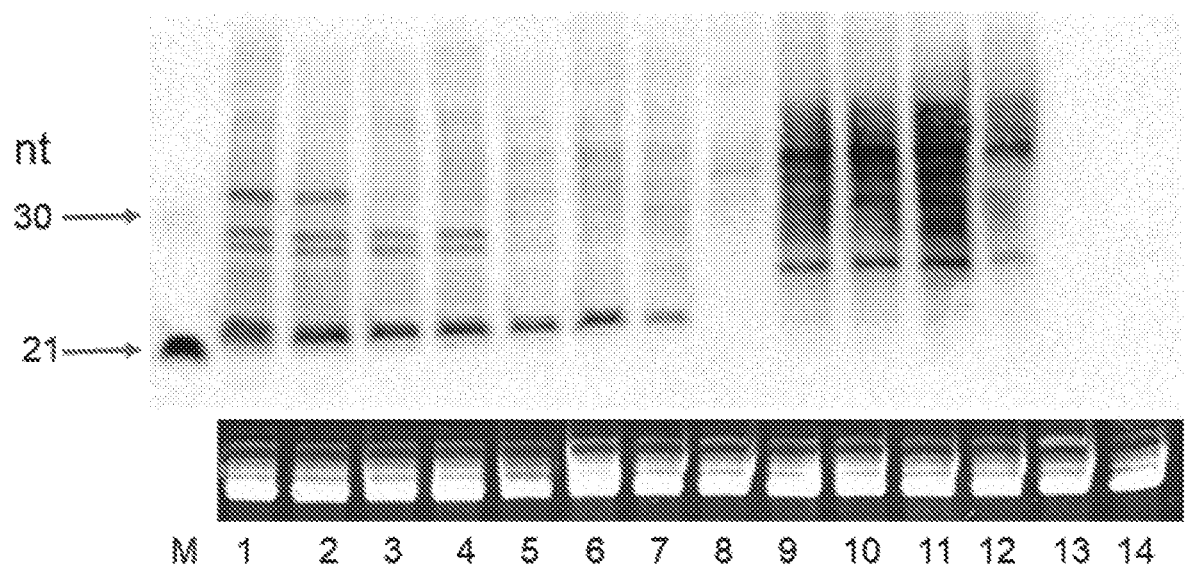

FIG. 17: Northern blot revealing small interfering RNA molecules of 23 nucleotides (upper panel). GelGreen® Nucleic Acid-stained RNA indicated the RNA bands in the gel prior to RNA transfer. 12 μg total small RNA was loaded per well. 18 nM TMV movement protein gene-specific DNA primers (21 nt) mixed with dsRNA Ladder (NEB) was used to indicate 21 nt. Lanes 1-2: The total siRNAs extracted from HT115-E38A (RNase III mutant, code optimization with E. coli K12 strain), positive control; Lanes 3-4: The total siRNAs extracted from HT115-Ae003-E38A, and this is to check if Enterobacteria RNase III E38A mutant shows similar dsRNA cleavage like E. coli strains; Lanes 5-6: The total siRNAs extracted from HT115-Ag001-E38A-R107A-R108A, and this is to check if this mutant shows similar dsRNA cleavage like E. coli E38A-R107A-R108A mutant; Lane 7: The total siRNAs extracted from HT115-Ag001-E38A-R86C-R107A-R108A, and this is to check if this mutant shows similar dsRNA cleavage like *E. coli* E38A-R107A-R108A mutant; Lane 8: The total siRNAs extracted from HT115-ver-E30A, the Verrucomicrobia bacterium E30A RNase III mutant, dsRNA cleavage is supposed to be similar to *E. coli* E38A mutant; Lanes 9-10: The total siRNA extracted from predicted mutant HT115-E38A-ΔS33-ΔS34-ΔK35; Lanes 11-12: The total siRNA extracted from predicted mutant HT115-E38A-ΔA32-ΔS33-ΔS34-K35; Lane 13: The total siRNA extracted from wide-type bacterial strain JM109 (DE3), negative control; Lane 14: The total siRNA extracted from RNase III mutant HT115 (DE3), negative control.

Figure 18:
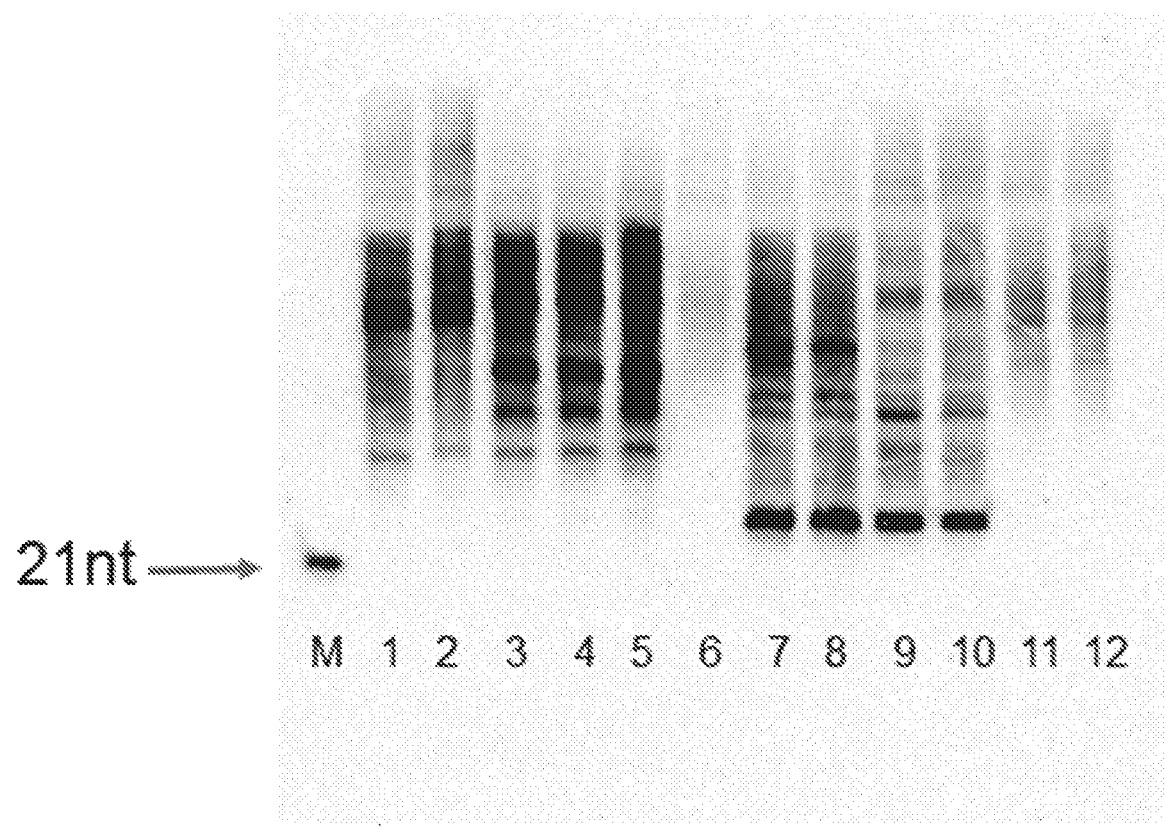

FIG. 18: Northern blot revealing small interfering RNA molecules of 22-23 nucleotides. 12 μg total small RNA was loaded per well. 6 nM TMV movement protein gene-specific DNA primers (21nt) mixed with dsRNA Ladder (NEB) was used to indicate 21 nt. Lanes 1-2: The total siRNAs extracted from predicted mutant HT115-Ec-E38A-ΔA32-ΔS33-ΔS34; Lanes 3-4: The total siRNAs extracted from predicted mutant HT115-Ec-E38A-ΔS33-R107A-R108A; Lanes 5-6: The total siRNAs extracted from predicted mutant HT115-Ec-E38A-S33A-ΔS34-R107A-R108A; Lanes 7-8: The total siRNA extracted from Ag001-E38A and this mutant produced 26-29 nt siRNA; this is to check if this mutant shows similar dsRNA cleavage like *E. coli* Ec-E38A mutant; Lanes 9-10: The total siRNAs extracted from HT115-Ae003-E38A-R107A-R108A, and this mutant produced 22-23 nt siRNA; this is to check if this mutant shows similar dsRNA cleavage like *E. coli*-E38A-R107A-R108A mutant; Lanes 11-12: The total siRNAs extracted from HT115-ver-E30A-K12opt, the Verrucomicrobia bacterium E30A RNase III mutant with code optimization.

Figure 19:

FIG. 19: Homology model of WT *E. coli* RNase III dimer (green and blue cartoons) based on a crystal structure of WT *A. aeolicus* RNase III (light green and cyan cartoons). Bound dsRNA is shown in the center as orange cartoons. Note the high structural overlap of the *E. coli* model with the *A. aeolicus* structure, particularly at secondary structural elements (α-helices and β-sheets). For clarity, bound magnesium ions are not shown.

Figure 20:
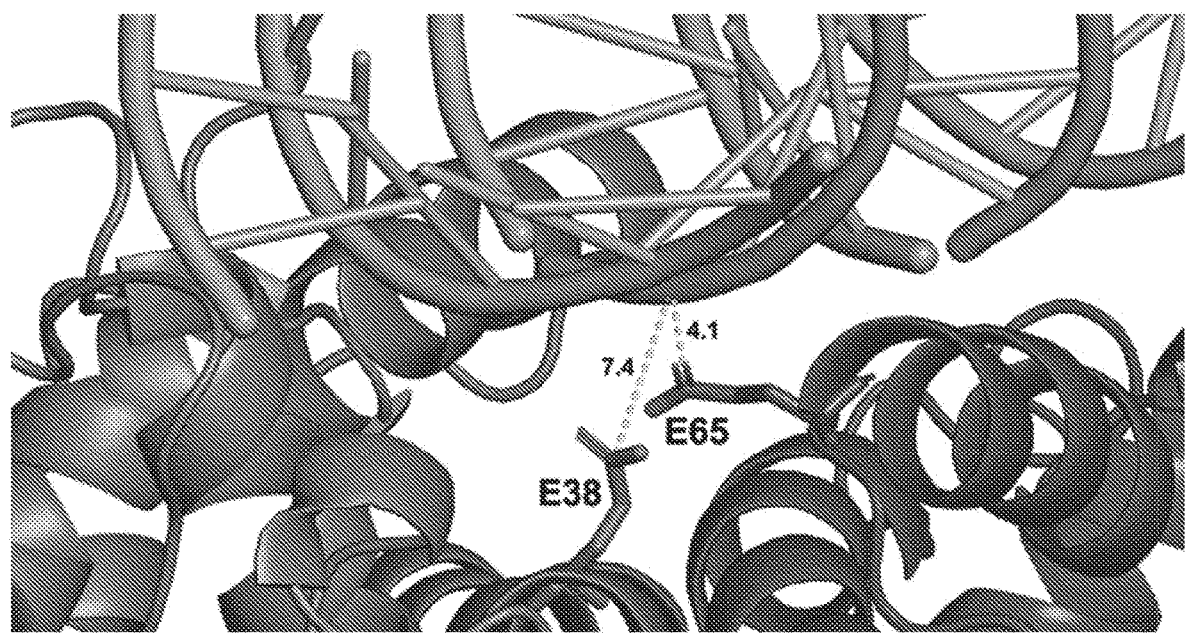

FIG. 20: Close-up of binding interface in the homology model of WT *E. coli* RNase III dimer (green and blue cartoons). Bound dsRNA is shown as orange cartoons. E38 from one monomer and E65 from the other monomer are shown as sticks. The carboxyl groups of both anionic side chains are pointing towards the negatively-charged backbone of the bound dsRNA, which can lead to electrostatic repulsions at the binding interface. Yellow dashed lines give the distance (in Ångstroms) between each side chain and the dsRNA backbone. Note that the E65 side chain is positioned closer to the dsRNA backbone. For clarity, bound magnesium ions are not shown.

Figure 21:
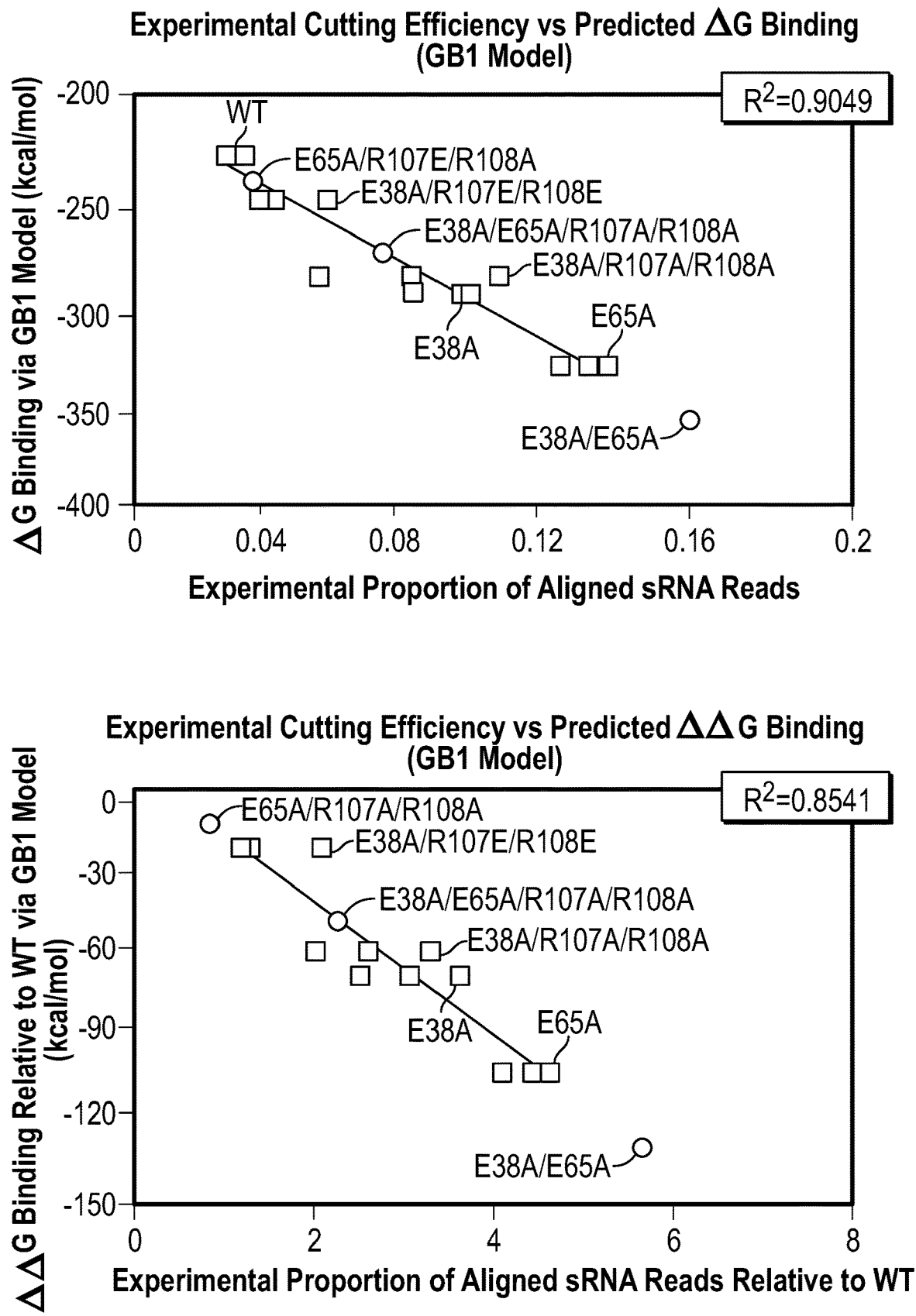

FIG. 21A-B: Correlation between predicted dsRNA-binding free energy of *E. coli* RNase III and its cutting efficiency (based on experimental measurements of the proportion of aligned sRNA reads). The left plot (A) shows the correlation using non-relative values on both axes (y-axis here gives ΔG binding), while the right plot (B) gives the corresponding correlation when both axes are taken relative to WT values (y-axis here gives ΔΔG binding relative to WT). Blue squares represent data points for individual experimental measurements (see Table 1); the point mutations for these data points are given to the right in black text. A trend line was calculated for these data points in both plots, with the $R^2$ of the linear fit given at the lower-left of each plot. Note the high linear correlation observed in both plots. Orange diamonds represent predictions for particular RNase III mutants that are still being tested; the point mutations for these constructs are given to the right in red text.

Figure 22:
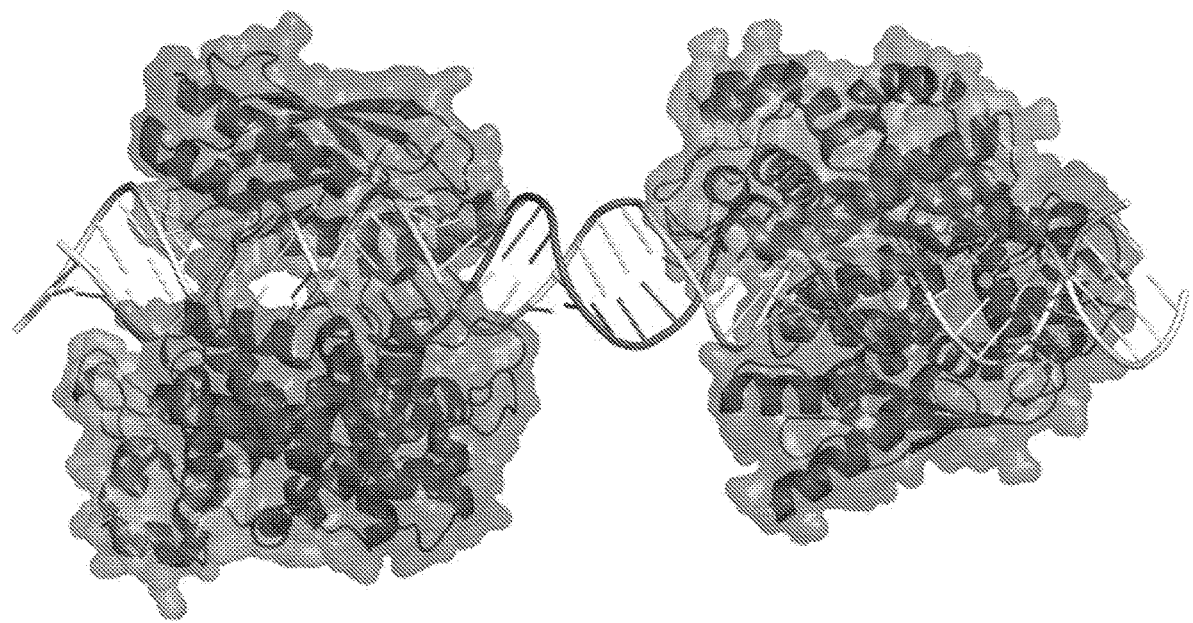

FIG. 22: Structural model of two *E. coli* WT RNase III dimers (green and blue cartoons) separated by 26 nt along a dsRNA target. Note that at this separation, both dimers are not showing steric clashes with each other, as indicated by the absence of any overlaps between their van der Waals (i.e., molecular) surfaces. Yellow and red RNA strands represent the 26-nt long dsRNA cleavage product, while white RNA strands denote the rest of the dsRNA target. For clarity, bound magnesium ions are not shown.

Figure 23:
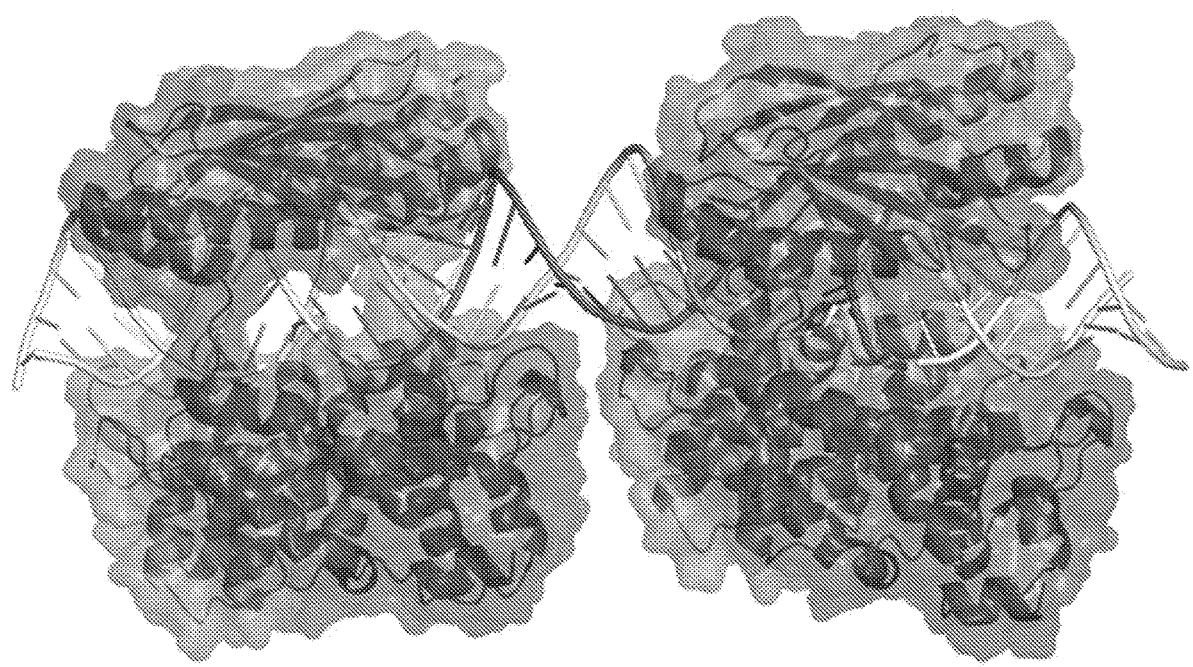

FIG. 23: Structural model of two *E. coli* E38A/R107A/R108A mutant RNase III dimers (green and blue cartoons) separated by 22 nt along a dsRNA target. Note that at this separation, both dimers are not showing steric clashes with each other, as indicated by the absence of any overlaps between their van der Waals (i.e., molecular) surfaces. Yellow and red RNA strands represent the 22-nt long dsRNA cleavage product, while white RNA strands denote the rest of the dsRNA target. For clarity, bound magnesium ions are not shown.

Figure 24I:
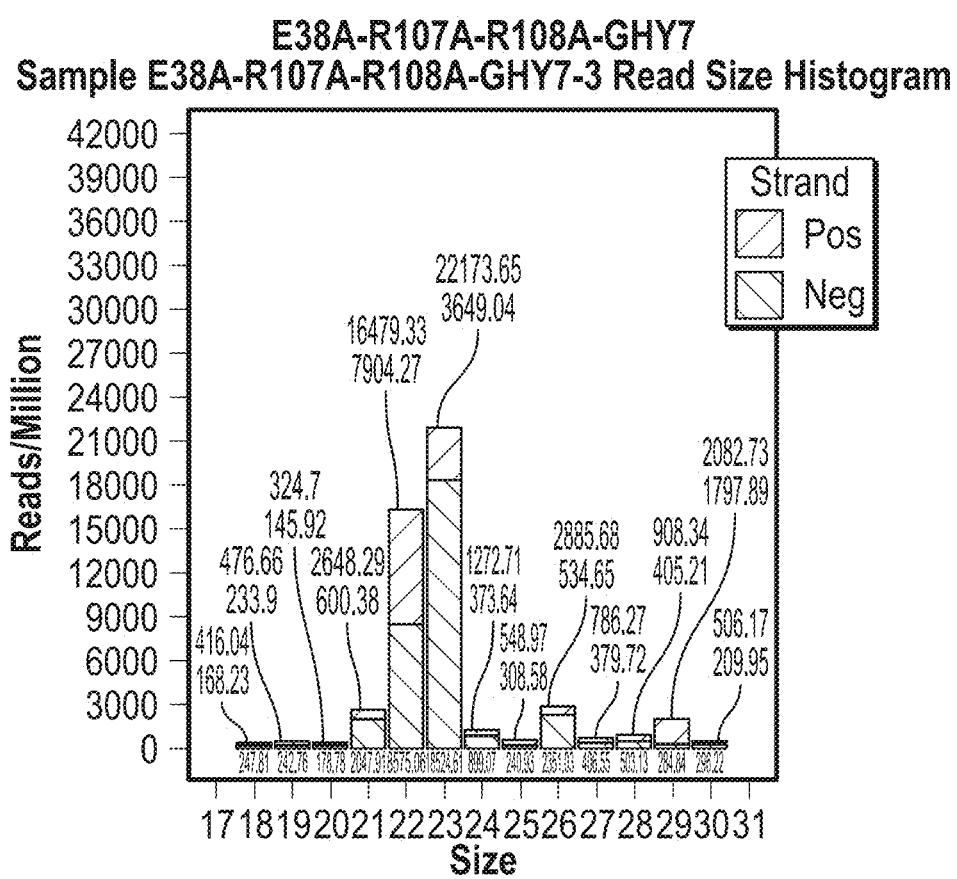
Figure 24R:
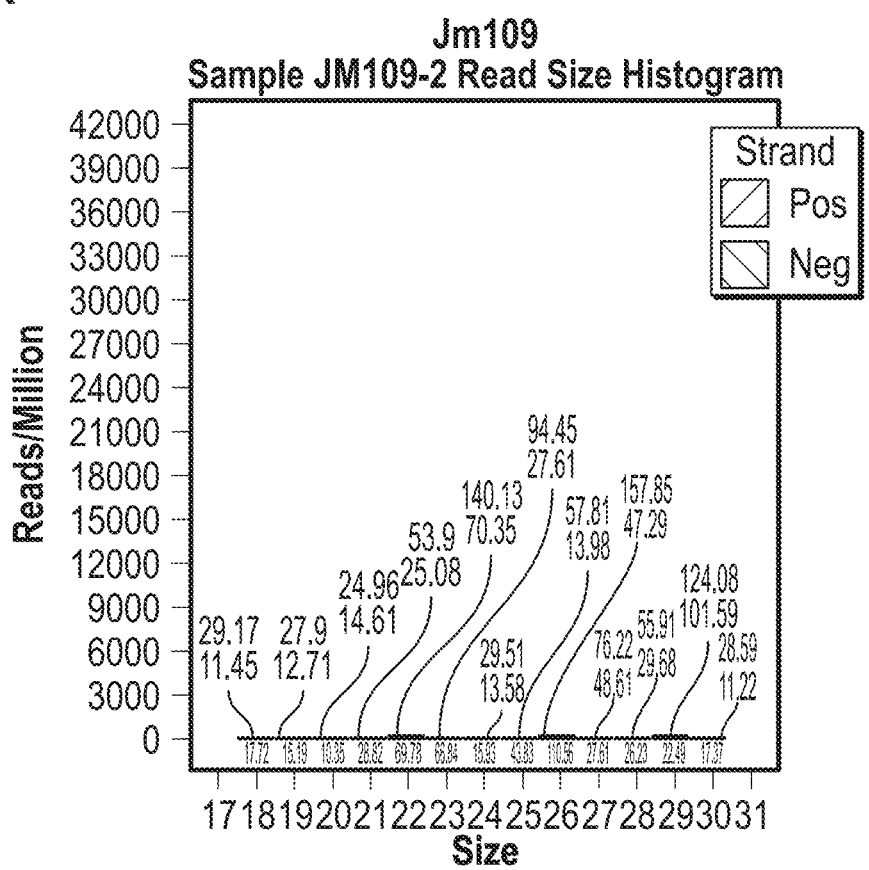

FIG. 24A-S: Size distributions of sRNA 18nt-30nt (Fixed Y) for multiple RNase III mutants.

FIG. 25A-O: Coverage mapping to GHY7 construct of sRNA 18nt-30nt.

Figure 26:
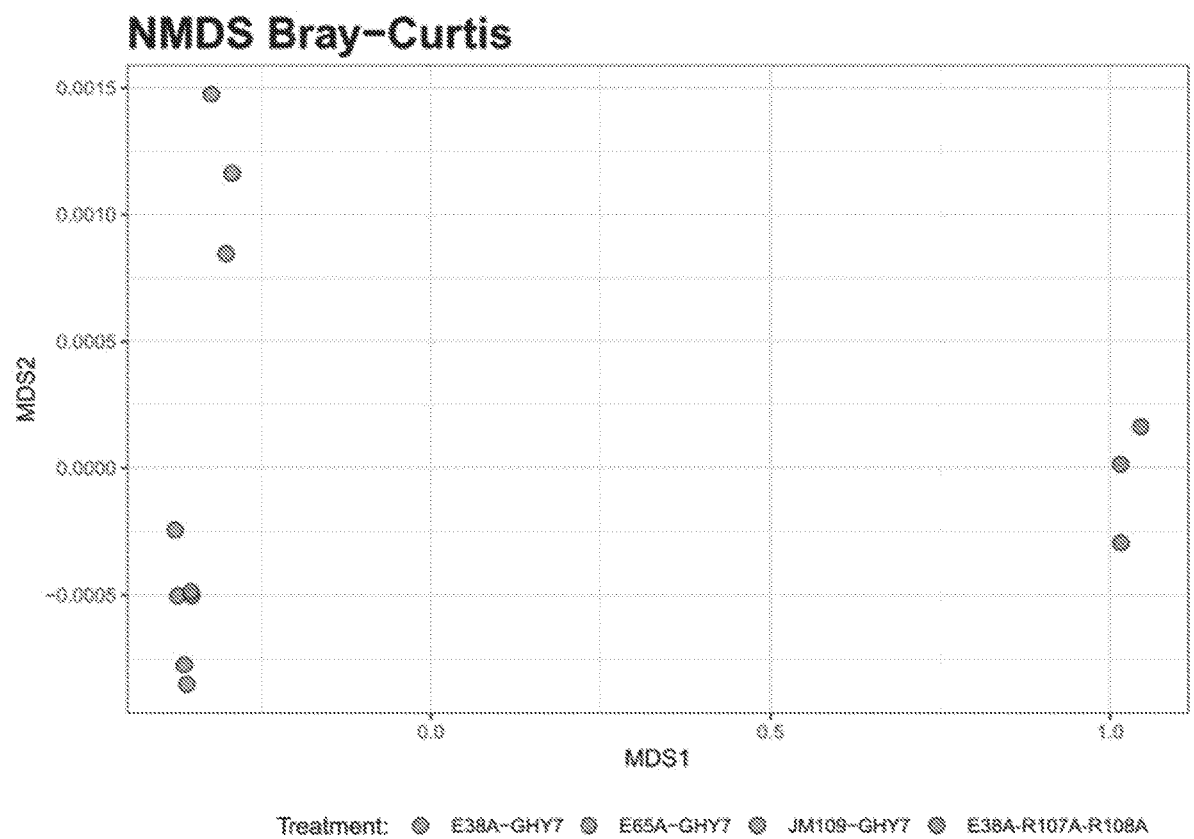

FIG. 26: Unconstrained ordination of sRNA populations in each sample.

Figure 27:
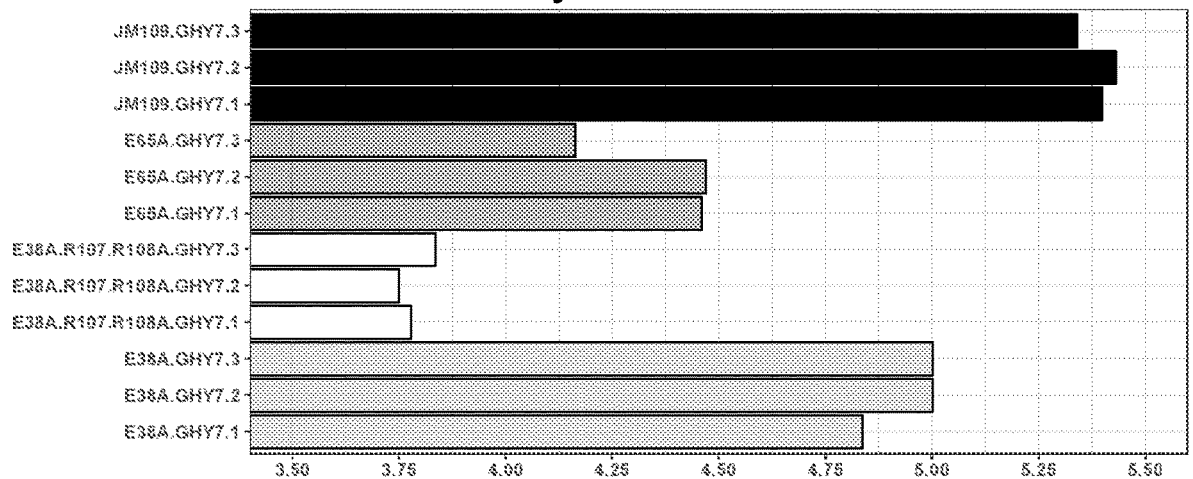

FIG. 27: Shannon Diversity index scores of sRNA populations.

Figure 28:
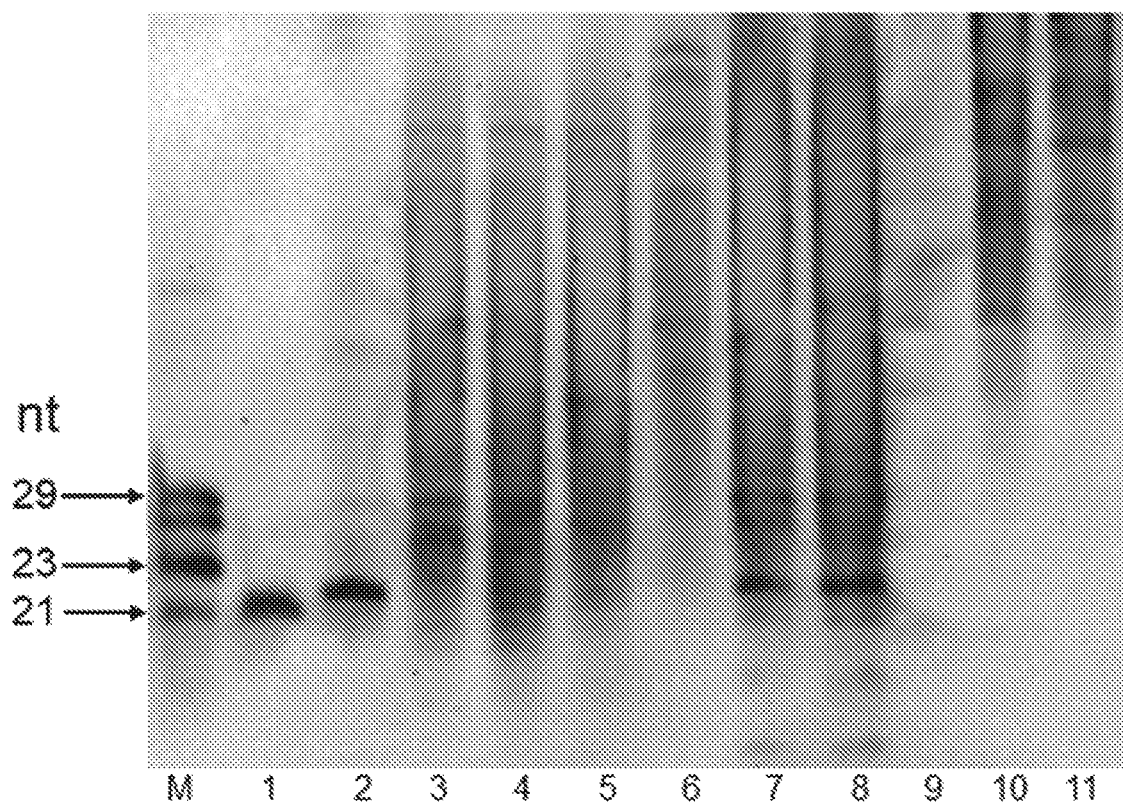

FIG. 28: Northern blot revealing small RNA nucleotides. 6 μg total small RNA was loaded per well. Lanes M: TMV movement protein gene specific single-stranded RNA marker and it consists of five ssRNA: 21, 23, 25, 27 and 29 bases. Lane 1: TMV movement protein gene specific single-stranded RNA marker, 21 base; Lane 2: The total small RNAs extracted from HT115-E38A-R107A-R108A, and 5 ug loaded; Lane 3: The total small RNAs extracted from HT115-Bc-E58A; Lane 4: The total small RNAs extracted from HT115-Bs-E59A; Lane 5: The total small RNAs extracted from HT115-Ec-E117D; Lane 6: The total small RNAs extracted from HT115-Ec-E117Q; Lane 7: The total small RNAs extracted from HT115-Ec-Q153P; Lane 8: The total small RNAs extracted from HT115-Ec-D155E; Lane 9: The total small RNAs extracted from HT115-Bc-E138K; Lane 10: The total small RNAs extracted from *E. coli* mutant E117K containing pAD-WRKY-GHY7 plasmid; Lane 10: The total small RNAs extracted from *E. coli* mutant E117K-L119F containing pAD-WRKY-GHY7 plasmid.

MODE(S) FOR CARRYING OUT THE INVENTION(S)

The following detailed description is provided to aid those skilled in the art in practicing the various embodiments of the present disclosure, including all the methods, uses, compositions, etc., described herein. Even so, the following detailed description should not be construed to unduly limit the present disclosure, as modifications and variations in the embodiments herein discussed may be made by those of ordinary skill in the art without departing from the spirit or scope of the present discoveries. The present disclosure is explained in greater detail below. This disclosure is not intended to be a detailed catalog of all the different ways in which embodiments of this disclosure can be implemented, or all the features that can be added to the instant embodiments. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure, which variations and additions do not depart from the scope of the instant disclosure. Hence, the following specification is intended to illustrate some particular embodiments of the disclosure, and not to exhaustively specify all permutations, combinations, and variations thereof.

As shown in the figures, in one embodiment, mutations in an RNase III protein identified herein may result in the stabilization of RNase III cutting patterns leading to more consistent dsRNA cutting. As used herein, the term consistent dsRNA cutting, generally refer to the RNase III mutant protein's ability to produce relatively more sRNA products of a specific size and less relative undesirable sRNA of off-target sizes. This may be demonstrated by effectively narrowing the distribution of sRNA in the population around a specific peak as generally demonstrated in FIG. 24A-S and Table 7. The present inventors have demonstrated that this "consistent dsRNA cutting" effect also results in a more consistent cutting profile of sRNA by not stochastically shifting the cutting "ladder" of the protein with each cut as would be expected to occur in a wider sRNA size distribution such as that from the wild-type RNase III or DICER. The ultimate result of these factors is more predictable cutting and sequence-based end products in a final heterologous sRNA population measurable as a decrease in population diversity.

In another embodiment, the present inventors demonstrate that the current literature potentially misinterprets E38A as a mutant RNase III that cuts a preferred 23 nt pattern. Xiao et al. originally characterized dsRNA cutting by the E38A mutant to prefer producing 23nt sRNA (Xiao et al. 2009). This finding was based on northern analysis techniques lack enough resolution to call fragment sizes accurately to the specific base pair (Doran et al. 1999). Modern sequencing technologies can vastly improve size evaluation by looking at the actual sequence of sRNA reads to get an accurate length.

The present inventors performed high throughput sRNA sequencing using the Illumina Hi-Seq platform as outlined in sRNA Analysis methods. As shown in FIG. 24A-S, the present inventors identified that E38A's preferred cutting length is actually 26 nt. The size distribution of E38A is actually highly similar to that of the wild-type with a peak at 26 nt. However, wildtype has another peak at 29 nt not see as prevalently in E38A.

As further demonstrated in FIG. 25A-O, the preferred cutting locations along the exemplary sRNA from Tobacco mosaic virus (TMV) GHY7 dsRNA sequence are also very similar to those of the wildtype (JM109). Populations of sRNA in E38A and wildtype did not differ significantly in pairwise analysis (via DMRT). However, E38A did differ significantly in terms of relative abundance of sRNA in the 18-30 nt range when compared to wildtype (DMRT, stat=2.19, p=0.014). These findings demonstrate that E38A, rather than primarily making discrete cuts at 23 nt, instead acts as a catalytic efficiency mutant producing approximately 3× more sRNA than wildtype as shown in Table 5. As also demonstrated in FIG. 20, the mutation E38A is changing a strongly negative residue to a hydrophobic one which may increases the binding affinity with dsRNA. As further shown in FIG. 21A-B, estimation of binding free energies using the MM-GBSA computational technique indeed shows that mutation E38A causes the RNase III dimer to bind more stably to dsRNA (compared to WT).

As generally shown in FIG. 22, structural modeling of two E. coli WT RNase III dimers on a dsRNA target indicate that with a separation of 26 nt, both RNase III are separated far enough to not cause steric clashes and thus to not interfere with each other. Structural models also show no steric clashes between both RNase III dimers when separated by 23 nt.

The present inventors further demonstrate that a new RNase III mutant, E65A, is more catalytically efficient than both E38A and wildtype RNase III. Generally referring to FIG. 20, the E38 and E65 residues of RNase III are adjacent in a dimer formation of RNase III protein monomers bound to dsRNA. The empirical data show that the E65A is significantly more efficient at producing sRNA than JM109 wildtype (DMRT, stat=3.3, p<0.01) and E38A (KW, stat=3.9, p=0.049). As shown in Table 5 below, the RNase III E65A mutant is approximately 4.4× more catalytically efficient than the wildtype and approximately 1.5× more efficient than E38A. The increase in catalytic efficiency may be due to a similar mechanism as dsRNA binding affinity enhancement seen in RNase III mutant E38A. As shown in FIG. 20, the E65 side chain is positioned closer to the dsRNA backbone (compared to the E38-dsRNA distance), and so the mutation E65A may decrease the electrostatic repulsion forces at the binding interface more than the E38A mutation. As shown in FIG. 21A-B, estimation of binding free energies using the MM-GBSA computational technique indeed shows that mutation E65A causes the RNase III dimer to bind more stably to dsRNA compared to both E38A and WT.

In another embodiment, the present inventors demonstrate that a novel RNase III mutant E38A-R107A-R108A possesses increased catalytic efficiency and differential discrete cutting when compared to wildtype (JM109). The present inventors performed sRNA analysis using methods outlined herein. The RNase III mutant E38A-R107A-R108A produced significantly different relative abundances of sRNA product than wildtype (KW, stat 3.86, p=0.049). As shown in Table 5, the increase was approximately 2.7× over wildtype (JM109). As further shown in Table 6, sRNA populations were significantly different between tested mutants and wildtypes in both PERMANOVA and ANOSIM tests. As shown in FIG. 26, NMDS analysis shows how divergent the sRNA populations are in the RNase III mutant E38A-R107A-R108A from other tested mutants and wildtype. One of the primary causes for this is the redistribution of sRNA products into what is almost exclusively 22 and 23 nt sRNA as demonstrated in FIG. 24A-S. Additionally, this represents a decrease in diversity of sRNA products, (see FIG. 27), or, a more homogenous mix of sized sRNA products of 22 and 23 nt. The RNase III mutant E38A-R107A-R108A ultimately results in fewer differentially sized products in higher quantity, desirable traits for RNAi technologies. Diversity of sRNA populations in the RNase III mutant E38A-R107A-R108A was significantly different from both E38A (DMRT, stat=2.04, p<0.0208) and the JM109 wildtype (DMRT, stat=3.06, p<0.01).

As further demonstrated in FIG. 21A-B, estimation of binding free energies using the MM-GBSA computational technique demonstrates that triple mutation E38A/R107A/R108A causes the RNase III dimer to bind more stably to dsRNA (compared to WT). As further demonstrated in FIG. 23, structural modeling of two E. coli E38A/R107A/R108A mutant RNase III dimers on a dsRNA target indicate that with a separation of 22 nt, both RNase III are separated far enough to not cause steric clashes and thus to not interfere with each other. This observation is further generally applicable for the slightly farther separation of 23 nt.

Further evidence of cutting changes in the RNase III mutant E38A-R107A-R108A can be shown in the cutting pattern or ladder along the GHY7 construct. As shown in FIG. 25A-O, peak regions or hot spots along the dsRNA construct, while similar in E38A, E65A, and JM109, are very different in E38A-R107A-R108A.

Another RNase III mutant, E28A-R107E-R108E was tested in the same manner as RNase III mutant E38A-R107A-R108A. It was able to cleave dsRNA per northern analyses. However, in RNA-seq analysis, it did not demonstrate significant efficiency or cutting pattern/size differentiation from the wildtype. In this RNase III E28A-R107E-R108E mutant, the two arginine to glutamic acid mutations are replacing electrostatic attractive forces with electrostatic repulsive forces to make dsRNA binding less stable. Indeed, as shown in FIG. 21A-B, estimation of binding free energies using the MM-GBSA computational technique shows that triple mutation E38A/R107E/R108E causes reduced stability of binding by RNase III dimer to dsRNA relative to both E38A and E38A/R107A/R108A RNase III.

In another embodiment, the present inventors demonstrate that RNase III mutant E38A-E65A is combinatorial regarding the catalytic effects of E38A and E65A. As demonstrated in FIG. 21A-B, estimation of binding free energies using the MM-GBSA computational technique predicts that mutation E38A/E65A causes the RNase III dimer to bind more stably to dsRNA (compared to E38A alone or E65A alone), although the contributions of the single mutations to increasing the binding free energy are not additive (i.e., predicted binding free energy for E38A/E65A is less than the sum of those for E38A alone and E65A alone). As a result, the E38A/E65A mutant may have high catalytic efficiency, with a preferred dsRNA cutting length of 26 nt.

The present inventors next tested if the quadruple RNase III mutant E38A-E65A-R107A-R108A combines the predicted enhanced catalytic efficiency of E38A-E65A with the observed preferred cutting length of 22-23 nt when R107A-R108A mutations were added to E38A. Surprisingly, estimation of binding free energies using the MM-GBSA computational technique predicts that quadruple RNase III mutant E38A-E65A-R107A-R108A causes the RNase III dimer to bind less stably to dsRNA (compared to E38A or triple RNase III mutant E38A-R107A-E108A) as shown in FIG. 21A-B. Thus, the quadruple mutant may also exhibit a preferred cutting length of 22-23 nt; it may be less efficient than RNase III mutant E38A-R107A-R108A as described above at performing this cleavage of dsRNA.

An additional test using independent MD simulations and analysis of RNase III mutant E65A-R107A-R108A shows that this tripe mutant is predicted to be comparable to WT in terms of predicted binding free energy to dsRNA (and less than those of E38A, E38A-R107A-R108A, and even E38A-R107E-R108E) (See FIG. 21A-B). It should also be noted that the predicted change in binding free energy between E38A-E65A and E38A-E65A-R107A-R108A is comparable to the change between RNase III mutants E65A and E65A-R107A-R108A (See e.g., FIG. 21A-B). As such, the present inventors demonstrate that unlike with E38A, there is more structural dialogue of R107A-R108A with E65A such that combination of these causes reduced binding free energy and thus reduced catalytic efficiency.

As noted above, RNAi silencing mechanisms are generally reliant on sRNAs sized 21-23nt (Martinez and Richard 2013, Zamore et al. 2000). As shown generally in FIG. 24A-S and Table 7, 21 nt sRNA production was relatively the same in RNase III mutants E38A and E38A-R107A-R108A, with both producing ~1.5× the amount the wildtype produces. However, RNase III mutant E38A-R107A-R108A produced ~6.5× more 22 nt sRNA than E38A alone and ~14× more than the wildtype. The present inventor further demonstrated that RNase III mutant E38A-R107A-R108A also produced ~10.5× more 23 nt sRNA than E38A and ~22.5× more 23 nt sRNA than wildtype.

Each of the aforementioned RNaseIII mutants may be generally be referred to as an "RNase III mutant," "mutant," or by its specific amino acid mutation designation i.e. residue and location.

One embodiment of the current invention includes systems, methods and compositions for the generation of sRNA molecules using RNase III mutants. In one preferred embodiment, invention includes systems, methods and compositions for the generation of sRNA molecules using RNase III mutants to control a host pathogen through the production and diffusion of sRNA molecules that may initiate an RNAi pathway response directed to a host pathogen. Another embodiment of the current invention includes systems, methods and compositions for the generation of sRNA molecules using RNase III mutants may be accomplished in vivo, in vitro, or ex vivo.

Another embodiment of the current invention includes systems, methods and compositions for the generation of sRNA molecules using RNase III mutants to produce a DICER-independent RNAi response in a host. In this embodiment, one or more of the RNase III mutants described herein may be introduced to a host through an in vivo, in vitro, or ex vivo mechanism. In a preferred embodiment, bacteria may be transformed to heterologously express one or more RNase III mutants according to sequences according to of SEQ ID NO. 3-17, or 37-40, and 55-58. Such RNase III mutants may be introduced to a dsRNA from a pathogen, or a dsRNA that is co-expressed in said bacteria that is directed to an essential pathogen gene. The RNase III mutants may produce enhanced levels of sRNA that may further be diffused into a host and initiate an RNAi response pathway which my inhibit expression of a pathogen essential gene.

A polynucleotide sequences encoding at least one RNase III mutant and/or a polynucleotide sequence encoding a dsRNA directed to an essential pathogen gene may be operable linked to a shared or distinct promoter. A polynucleotide sequences encoding at least one RNase III mutant and/or a polynucleotide sequence encoding a dsRNA directed to an essential pathogen gene may form an expression cassette. Further, a polynucleotide sequence encoding at least one RNase III mutant and/or a polynucleotide sequence encoding a dsRNA directed to an essential pathogen gene may form a vector that may transform a target bacteria. Methods of bacterial transformation being generally known by those of ordinary skill in the art.

Another embodiment of the current invention includes systems, methods and compositions for the high-level generation of sRNA molecules using RNase III mutants that have enhanced catalytic activity compared to a wild type RNase III enzyme. In a preferred embodiment, RNase III mutants having enhanced catalytic activity may include an RNase III mutant having at least one of the following mutations:

E38A (a glutamic acid replaced with an alanine at residue 38) according to SEQ ID NOs. 3-4;

E65A (a glutamic acid replaced with an alanine at residue 65) according to SEQ ID NOs. 5-6;

E38A-E65A (a glutamic acid replaced with an alanine at residue 38, and a glutamic acid replaced with an alanine at residue 65) according to SEQ ID NO. 17;

E38A-R107A-R108A (a glutamic acid replaced with an alanine at residue 38, and an arginine replaced with an alanine at residue 107, and an arginine replaced with an alanine at residue 108) according to SEQ ID NOs. 7-8.

Another embodiment of the current invention includes systems, methods and compositions for the high-level generation of sRNA molecules using RNase III mutants having enhanced stabilization of RNase III cutting patterns leading to more consistent dsRNA cutting, and increased percentages of discrete sized sRNA in a heterologous mixture of digested sRNAs compared to wildtype RNase III. In a preferred embodiment, RNase III mutants having enhanced catalytic activity may include the following RNase III mutant:

E38A (a glutamic acid replaced with an alanine at residue 38) according to SEQ ID NOs. 3-4, 9-10, and 13-14;

E65A (a glutamic acid replaced with an alanine at residue 65) according to SEQ ID NOs. 5-6;

E38A-E65A (a glutamic acid replaced with an alanine at residue 38, and a glutamic acid replaced with an alanine at residue 65) according to SEQ ID NO. 17;

E38A-R107A-R108A (a glutamic acid replaced with an alanine at residue 38, and an arginine replaced with an alanine at residue 107, and an arginine replaced with an alanine at residue 108) according to SEQ ID NOs. 7-8, 11-12, and 15-16.

Another embodiment of the current invention includes the generation of a series of single/multiple amino acids mutants in an RNase III N-terminal catalytic domain to produce discrete-sized sRNAs, which have the potential to serve as triggers of RNA silencing. In certain embodiments, RNase III from the family Enterobacteriaceae, such as *E. coli* and *Enterobacter*, as well as from the family Bacillaceae among others, may be engineered to include one or more point mutations that improve catalytic efficiency of dsRNA cutting, as well as the production of discrete-sized sRNAs. RNase III homologs from this another families are specifically contemplated herein. Examples of additional RNase III protein sequences may include *S. enterica* (Uniprot ID: E7V351), *P. aeruginosa* (Uniprot ID: B7UYX2), *C. burnetii* (Uniprot ID: P51837), *R. capsulatus* (Uniprot ID: Q52698), *S. coelicolor* (Uniprot ID: Q9ZBQ7), *C. jejuni* (NCBI Reference Sequence: YP_001001278), *H. pylori* (Uniprot ID: P56118), *S. aureus* (Uniprot ID: P66668) and *L. lactis* (Uniprot ID: Q9CHD0). (Such Uniprot sequences being understood by one of ordinary skill in the art and such sequences being further incorporated herein by reference)

Another embodiment of the current invention may include the expression of one or more RNase III mutants according to SEQ ID NOs. 3-17, or 37-40, and 55-58 in a select bacterium that may trigger RNA interference (RNAi) pathway response in an animal host. In this embodiment, for example a heterologous dsRNA directed preferably to an essential gene of a select host pathogen, may be co-expressed with one or more of the RNase III mutants described herein. In this embodiment, one or more of the RNase III mutants may generate discrete-sized sRNAs that may induce an RNAi pathway response, preferably in the animal host, and preferably in a symbiotic or endosymbiotic bacteria, such as symbiotic or endosymbiotic enteric bacteria. Exemplary animal, and in particular mammal hosts, and animal pathogens are provided in Tables 8-12, and elsewhere in the specification.

Another embodiment of the current invention may include the expression of one or more RNase III mutants according to SEQ ID NOs. 3-17, or 37-40, and 55-58 in a select bacterium that may trigger RNA interference (RNAi) pathway response in a plant. In this embodiment, for example a heterologous dsRNA directed preferably to an essential gene of a select host pathogen, may be co-expressed with one or more of the RNase III mutants described herein. In this embodiment, one or more of the RNase III mutants may generate discrete-sized sRNAs that may induce an RNAi pathway response, preferably in the plant host and preferably in a symbiotic or endosymbiotic bacteria, such as an endophytic bacteria. Exemplary plant hosts, and plant pathogens are provided in Tables 8-12, and elsewhere in the specification.

Another embodiment of the current invention may include the trans-kingdom delivery of sRNA molecules to a host through expression of one or more RNase III mutants according to SEQ ID NOs. 3-17, or 37-40, and 55-58 in a select symbiotic bacterium that may trigger RNA interference (RNAi) pathway response in a plant. In this embodiment, for example a heterologous dsRNA directed preferably to an essential gene of a select host pathogen, may be co-expressed with one or more of the RNase III mutants described herein in a bacterium that is a natural symbiont with the plant host. In a preferred embodiment, this natural symbiont may include one or more endophytic bacteria. In this embodiment, one or more of the RNase III mutants may generate discrete-sized sRNAs that may induce an RNAi pathway response, preferably in the plant host.

Another embodiment of the current invention may include the trans-kingdom delivery of sRNA molecules to a host through expression of one or more RNase III mutants according to SEQ ID NOs. 3-17, or 37-40, and 55-58 in a symbiotic or endosymbiotic bacterium that may trigger RNA interference (RNAi) pathway response in an animal host. In this embodiment, for example a heterologous dsRNA directed preferably to an essential gene of a select host pathogen, may be co-expressed with one or more of the RNase III mutants described herein in a bacterium that is a natural symbiont with the plant host. In a preferred embodiment, this natural symbiont may include one or more symbiotic or endosymbiotic bacteria, and preferably an enteric bacteria. In this embodiment, one or more of the RNase III mutants may generate discrete-sized sRNAs that may induce an RNAi pathway response, preferably in the animal host.

Another embodiment of the current invention may include the expression of one or more RNase III mutants according to SEQ ID NOs. 3-17, or 37-40, and 55-58 in a select bacterium that may produce discrete-sized sRNAs, which may trigger a prophylactic RNAi pathway response in a host. In this embodiment, for example dsRNA from a select pathogen, and preferably an essential gene of a select host pathogen may be co-expressed with one or more of the RNase III mutants described herein. In this embodiment, one or more of the RNase III mutants may generate discrete-sized sRNAs that may induce a prophylactic RNAi pathway response, preferably in the host, that may protect the host from infection by the select pathogen.

Another embodiment of the current invention may include the expression of one or more RNase III mutants in a select bacterium that may exhibit enhanced stabilization of RNase III cutting patterns leading to more consistent dsRNA cutting and thereby produce sRNA having greater homogeneity, such that the sRNA's produced exhibit a greater consistency of size compared to wild-type or other RNase III mutants previously described in the art.

Another embodiment of the current invention may include the expression of one or more RNase III mutants according to SEQ ID NOs. 3-17, or 37-40, and 55-58 in a select bacterium that may include a size preference for the production of discreet sized sRNA molecules. In one preferred embodiment, such discrete sized sRNA may be 26-29 nt, and/or 22-23. In one preferred embodiment, such sRNA molecules generated by one or more RNase III mutants described herein may exhibit greater homogeneity of nt size and diffusion in the host due to improved fixed-flow diffusion. With this increase diffusion, and more consistent sized sRNA molecules, a more effective and diffused RNAi response may be triggered in the host.

Another embodiment of the current invention may include the expression of one or more RNase III mutants described herein in a select bacterium that may exhibit enhanced catalytic activity and thereby produce higher amounts of sRNA compared to wild-type or other RNase III mutants previously described in the art, and exhibit enhanced stabilization of RNase III cutting patterns leading to more consistent dsRNA cutting. In a preferred embodiment, an RNase III mutant according to SEQ ID NOs. 7-8 may be expressed in a select bacterium that may demonstrate enhanced production of discreet sized sRNA molecules of 22 to 23 nt, as well as an enhanced catalytic rate of sRNA molecule production.

Another embodiment of the current invention may include systems, methods and compositions for the high-level production of sRNA molecules. In one preferred embodiment of the current invention may include systems, methods and compositions for the high-level production of sRNA molecules in a DICER-independent prokaryotic system. In this preferred embodiment, bacteria may be genetically modified to heterologously express one or more of the RNase III mutants, and preferably a RNase III mutant according to SEQ ID NO. 3-17, or 37-40, and 55-58 that may generate sRNA in a DICER-independent manner. The genetically modified bacteria may further co-express a target dsRNA molecule, preferably directed to an essential gene of a pathogen, pest or herbivore. These genetically modified bacteria may be grown in a fermenter, or other industrial production system known in the art. The target dsRNA molecule may be converted into sRNA molecules of a discrete size by a heterologously expressed RNase III mutant. These sRNA molecules may be generated as described above and then further isolated, while in other embodiments, the bacterium containing the sRNA molecules may be isolated or harvested for later use, such as application/administration to a plant or animal.

Another embodiment of the invention may include compositions that include a quantity of sRNA molecules or bacteria that contain sRNA molecules generated by an RNase III mutant, and preferably a RNase III mutant according to SEQ ID NO. 3-17, or 37-40, and 55-58. Such compositions may include compositions that may be administered and/or applied to a host, such as a plant or animal host. Examples may include pharmaceutical compositions, topical compositions, encapsulated compositions, gel compositions, spray compositions and the like. Another embodiment of the invention may include the use of such sRNA molecules compositions to treat and/or prevent a pathogen caused disease condition in a host. Another embodiment of the invention may include the use of such sRNA molecules compositions to treat, prevent or kill a pest that may consume a host, preferably a plant host.

Another embodiment of the invention may include a polynucleotide encoding one or more RNase III mutants according to SEQ ID NOs. 3, 5, 7, 9, 11, 13, and 15. Another embodiment of the invention may include a polynucleotide encoding one or more RNase III mutants according to SEQ ID NOs. 3, 5, 7, 9, 11, 13, and 15 further operably linked to a promoter. Another embodiment of the invention may include a polynucleotide encoding one or more RNase III mutants according to SEQ ID NOs. 3, 5, 7, 9, 11, 13, and 15 as an expression cassette. Another embodiment of the invention may include a polynucleotide encoding one or more RNase III mutants according to SEQ ID NOs. 3, 5, 7, 9, 11, 13, and 15 as a vector that may be used to transform a bacteria or other organism.

Another embodiment of the invention may include a polynucleotide encoding one or more RNase III mutants according to SEQ ID NOs. 3, 5, 7, 9, 11, 13, and 15, and a polynucleotide encoding one or more dsRNAs directed to an essential gene in a host pathogen as generally identified in Tables 8-12. Another embodiment of the invention may include a polynucleotide encoding one or more RNase III mutants according to SEQ ID NOs. 3, 5, 7, 9, 11, 13, and 15, and a polynucleotide encoding one or more dsRNAs directed to an essential gene in a host pathogen wherein each sequence is operably linked to a promoter. Another embodiment of the invention may include a polynucleotide encoding one or more RNase III mutants according to SEQ ID NOs. 3, 5, 7, 9, 11, 13, and 15, and a polynucleotide encoding one or more dsRNAs directed to an essential gene in a host pathogen as an expression cassette. Another embodiment of the invention may include a polynucleotide encoding one or more RNase III mutants according to SEQ ID NOs. 3, 5, 7, 9, 11, 13, and 15, and a polynucleotide encoding one or more dsRNAs directed to an essential gene in a host pathogen as a vector that may be used to transform a bacteria or other organism.

Another embodiment of the current invention includes systems and methods of genetically modifying a target organism, such as a target bacterium, to express a polypeptide of one or more RNase III mutants according to SEQ ID NOs. 4, 6, 8, 10, 12, 14, 16, and 17. Another embodiment of the current invention includes systems and methods of genetically modifying a target organism, such as a target bacterium, to co-express a polypeptide of one or more RNase III mutants according to SEQ ID NOs. 4, 6, 8, 10, 12, 14, 16, and 17 and a polypeptide encoding one or more dsRNAs directed to an essential gene in a host pathogen, for example as identified in Tables 8-12.

Another embodiment of the current invention includes systems and methods of genetically modifying a target organism, such as a target bacterium, to express a polypeptide of one or more RNase III mutants according to SEQ ID NOs. 4, 6, 8, 10, 12, 14, 16, and 17. Methods of transforming a bacteria are generally known by those of ordinary skill in the art.

Another embodiment of the invention may include an isolated polypeptide encoding one or more RNase III mutants according to SEQ ID NOs. 4, 6, 8, 10, 12, 14, 16, and 17. Another embodiment of the invention may include an isolated polynucleotide encoding one or more RNase III mutants according to SEQ ID NOs. according to SEQ ID NOs. 3, 5, 7, 9, 11, 13, and 15. In one prefer embodiment, a polynucleotide encoding one or more RNase III mutants according to SEQ ID NOs. according to SEQ ID NOs. 3, 5, 7, 9, 11, 13, and 15 may be isolated as part of a plasmid construct.

Another embodiment may include the stable transformation of a plant or bacteria with one or more RNase III mutants according to SEQ ID NOs. 3, 5, 7, 9, 11, 13, and 15.

Another embodiment may include the stable transformation of a plant or bacteria that expresses one or more RNase III mutants according to SEQ ID NOs. 4, 6, 8, 10, 12, 14, 16, and 17.

Another embodiment of the invention may include the generation of a series of single/multiple amino acids mutants in an RNase III, wherein the RNase III is a bacterial RNase III. Another embodiment of the invention may include the generation of a series of single/multiple amino acids mutants in an RNase III from *E. coli*, preferably according to SEQ ID NOs.3-8, and 17. In one embodiment, an RNase III from *E. coli* may be according to polynucleotide sequence SEQ ID NO. 1, and/or amino acid sequence SEQ ID NO. 2.

Another embodiment of the invention may include the generation of a series of single/multiple amino acids mutants in an RNase III from Enterobacteriaceae, preferably according to SEQ ID NOs. 9-12. Another embodiment of the invention may include the generation of a series of single/multiple amino acids mutants in an RNase III from *Enterobacter*, preferably according to SEQ ID NOs. 13-16. Another embodiment of the invention may include the generation of a series of single/multiple amino acids mutants in an RNase III, wherein the RNase III is a homolog of an RNase III described herein. Another embodiment of the invention may include the generation of a series of single/multiple amino acids mutants in an RNase III, wherein the RNase III is an ortholog of an RNase III described herein.

Another embodiment of the current invention may include the generation of an E38A RNase III mutant. Another embodiment of the current invention may include the transformation and/or expression of an E38A RNase III mutant in bacteria. Another embodiment of the current invention may include the transformation and/or expression of an E38A RNase III mutant in bacteria that is symbiotic or endosymbiotic with a target host. Another embodiment of the current invention may include the transformation and/or expression of a an E38A RNase III mutant in bacteria that is symbiotic or endosymbiotic with a target host, wherein the RNase III mutant generates sRNA that are delivered to the target host and induce an RNAi pathway response. Another embodiment of the current invention may include the co-expression in a bacterium of an E38A RNase III mutant and a dsRNA directed to an essential pathogen gene in a target host.

Another embodiment of the current invention may include the generation of an E65A RNase III mutant. Another embodiment of the current invention may include the transformation and/or expression of an E65A RNase III mutant in bacteria. Another embodiment of the current invention may include the transformation and/or expression of an E65A RNase III mutant in bacteria that is symbiotic or endosymbiotic with a target host. Another embodiment of the current invention may include the transformation and/or expression of a an E65A RNase III mutant in bacteria that is symbiotic or endosymbiotic with a target host, wherein the RNase III mutant generates sRNA that are delivered to the target host and induce an RNAi pathway response. Another embodiment of the current invention may include the co-expression in a bacterium of an E65A RNase III mutant and a dsRNA directed to an essential pathogen gene in a target host.

Another embodiment of the current invention may include the generation of an E38A-E65A RNase III mutant. Another embodiment of the current invention may include the transformation and/or expression of an E38A-E65A RNase III mutant in bacteria. Another embodiment of the current invention may include the transformation and/or expression of an E38A-E65A RNase III mutant in bacteria that is symbiotic or endosymbiotic with a target host. Another embodiment of the current invention may include the transformation and/or expression of a an E38A-E65A RNase III mutant in bacteria that is symbiotic or endosymbiotic with a target host, wherein the RNase III mutant generates sRNA that are delivered to the target host and induce an RNAi pathway response. Another embodiment of the current invention may include the co-expression in a bacterium of an E38A-E65A RNase III mutant and a dsRNA directed to an essential pathogen gene in a target host.

Another embodiment of the current invention may include the generation of an E38A-R107A-R108A RNase III mutant. Another embodiment of the current invention may include the transformation and/or expression of an E38A-R107A-R108A RNase III mutant in a bacteria. Another embodiment of the current invention may include the transformation and/or expression of an E38A-R107A-R108A RNase III mutant in bacteria that is symbiotic or endosymbiotic with a target host. Another embodiment of the current invention may include the transformation and/or expression of a an E38A-R107A-R108A RNase III mutant in bacteria that is symbiotic or endosymbiotic with a target host, wherein the RNase III mutant generates sRNA that are delivered to the target host and induce an RNAi pathway response. Another embodiment of the current invention may include the co-expression in a bacterium of an E38A-R107A-R108A RNase III mutant and a dsRNA directed to an essential pathogen gene in a target host.

Another embodiment of the current invention may include the generation of an E38A RNase III mutant having a size preference for the generation of 26 and 29 nt sRNAs. Another embodiment of the current invention may include the generation of an E38A RNase III mutant having improved catalytic efficiency. Another embodiment of the current invention may include the generation of an E38A RNase III mutant according to SEQ ID NOs. 3-4, 13-14, and 9-10.

Another embodiment of the current invention may include the generation of an E65A RNase III mutant having a size preference for the generation of 26 and 29 nt sRNAs. Another embodiment of the current invention may include the generation of an E65A RNase III mutant having improved catalytic efficiency. Another embodiment of the current invention may include the generation of an E65A RNase III mutant according to SEQ ID NO. 5-6.

Another embodiment of the current invention may include the generation of an E38A-E65A RNase III mutant having a size preference for the generation of 26 and 29 nt sRNAs. Another embodiment of the current invention may include the generation of an E38A-E65A RNase III mutant having improved catalytic efficiency. Another embodiment of the current invention may include the generation of an E65A RNase III mutant according to SEQ ID NO. 17.

Another embodiment of the current invention may include the generation of an E38A-R107A-R108A RNase III mutant having a size preference for the generation of 22 and 23 nt sRNAs. Another embodiment of the current invention may include the generation of an E38A-R107A-R108A RNase III mutant having improved catalytic efficiency and enhanced dsRNA cutting specificity for 22 and 23 nt sRNAs. Another embodiment of the current invention may include the generation of an E65A RNase III mutant according to SEQ ID NO. 7-8, 11-12, and 15-16.

Another embodiment of the current invention may include the generation of one or more RNase III mutants that may be expressed in bacteria and generate sRNA that may be further isolated. In one preferred embodiment, the current invention may include the generation of RNase III mutants that may be expressed in bacteria and generate sRNA according to SEQ ID NOs. 3-17, or 37-40, and 55-58.

Another embodiment of the current invention may include the generation of one or more RNase III mutants that may be expressed in bacteria configured to deliver sRNA to a host. In one preferred embodiment, the current invention may include the generation of RNase III mutants according to SEQ ID NOs. 3-17, or 37-40, and 55-58 that may be expressed in bacteria configured to deliver sRNA to a host and initiate a DICER-independent RNAi pathway response.

Another embodiment of the current invention may include the generation of one or more RNase III mutants according to SEQ ID NOs. 3-17, or 37-40, and 55-58 that may be co-expressed with a dsRNA directed to an essential pathogen gene, preferably a symbiotic and/or endosymbiotic bacteria to the host. In this embodiment, the RNase III mutants that may generate sRNA from the co-expressed dsRNA and to deliver the sRNA to a host initiating a RNAi pathway response.

Another embodiment of the current invention may include the generation of one or more RNase III mutants according to SEQ ID NOs. 3-17, or 37-40, and 55-58 that may be co-expressed with a dsRNA directed to an essential pest gene, preferably a symbiotic and/or endosymbiotic bacteria to the host. In this embodiment, the RNase III mutants that may generate sRNA from the co-expressed dsRNA and to deliver the sRNA to a host initiating a RNAi pathway response in pest consuming the host, preferably a plant.

In another embodiment, the present inventors may generate a RNase III mutant that is integrated into a bacterial chromosome. In a preferred embodiment, an RNAase III mutant may include, but not be limited to:

E38A (a glutamic acid replaced with an alanine at residue 38) according to SEQ ID NOs. 3-4, 9-10, and 13-14;

E65A (a glutamic acid replaced with an alanine at residue 65) according to SEQ ID NOs. 5-6;

E38A-E65A (a glutamic acid replaced with an alanine at residue 38, and a glutamic acid replaced with an alanine at residue 65) according to SEQ ID NO. 17;

E38A-R107A-R108A (a glutamic acid replaced with an alanine at residue 38, and an arginine replaced with an alanine at residue 107, and an arginine replaced with an alanine at residue 108) according to SEQ ID NOs. 7-8, 11-12, and 15-16.

In a preferred embodiment, an RNAase III mutant according to SEQ ID NOs. 3-17, or 37-40, and 55-58 may be integrated into a bacterial chromosome and expressed.

In further aspects, the present invention includes methods of administering a therapeutically effective amount of one or more genetically modified bacteria expressing a heterologous RNase III mutant and a dsRNA directed to an essential pathogen gene as generally described above.

The following definitions are provided to aid the reader in understanding the various aspects of the present disclosure. Unless defined otherwise, all technical and scientific terms used herein have the same meaning as commonly understood by those of ordinary skill in the art to which the disclosure pertains.

As used herein and in the appended claims, the singular forms "a", "an", and "the" include plural referents unless the context clearly dictates otherwise. Thus, for example, reference to "a plant" includes a plurality of such plants; reference to "a cell" includes one or more cells and equivalents thereof known to those skilled in the art, and so forth. Similarly, the word "or" is intended to include "and" unless the context clearly indicates otherwise. Hence "comprising A or B" means including A, or B, or A and B. Furthermore, the use of the term "including", as well as other related forms, such as "includes" and "included", is not limiting.

The term "about" as used herein is a flexible word with a meaning similar to "approximately" or "nearly". The term "about" indicates that exactitude is not claimed, but rather a contemplated variation. Thus, as used herein, the term "about" means within 1 or 2 standard deviations from the specifically recited value, or ±a range of up to 20%, up to 15%, up to 10%, up to 5%, or up to 4%, 3%, 2%, or 1% compared to the specifically recited value.

The term "comprising" as used in a claim herein is open-ended, and means that the claim must have all the features specifically recited therein, but that there is no bar on additional features that are not recited being present as well. The term "comprising" leaves the claim open for the inclusion of unspecified ingredients even in major amounts. The term "consisting essentially of" in a claim means that the invention necessarily includes the listed ingredients, and is open to unlisted ingredients that do not materially affect the basic and novel properties of the invention. A "consisting essentially of" claim occupies a middle ground between closed claims that are written in a closed "consisting of" format and fully open claims that are drafted in a "comprising' format". These terms can be used interchangeably herein if, and when, this may become necessary. Furthermore, the use of the term "including", as well as other related forms, such as "includes" and "included", is not limiting. Notably, where the specification or other parts of this application refer to a polynucleotide sequence, it may also refer to the corresponding protein sequence and vice verse.

The term "derived" means an RNase III that was mutated to generate an RNase III mutant. The term "fed" means introducing a bacteria expressing a RNase III mutant to an animal, for example directly, or through a feed infused with the bacteria or other cell.

"RNase III" refers to a naturally occurring enzyme or its recombinant form. The RNase III family of dsRNA-specific endonucleases is characterized by the presence of a highly conserved 9 amino acid stretch in their catalytic center known as the RNaseIII signature motif. Mutants and derivatives are included in the definition. The utility of bacterial RNase III described herein to achieve silencing in mammalian cells further supports the use of RNases from eukaryotes, prokaryotes viruses or archaea in the present embodiments based on the presence of common characteristic consensus sequences. The designations for the mutants are assigned by an amino acid position in a particular RNaseIII isolate. These amino acid positions may vary between RNase III enzymes from different sources. For example, E38 in *E. coli* corresponds to E37 in *Aquifex aeolicus*. The positions E38 in *E. coli* and E37 in *A. aeolicus* correspond to the first amino acid position of the consensus sequence described above and determined by aligning RNaseIII amino acid sequences from the public databases by their consensus sequences. Embodiments of the invention are not intended to be limited to the actual number designation. Preferred embodiments refer to relative position of the amino acid in the RNaseIII consensus sequence(s). In particular, the invention includes residues 38, 65, 107 and 108 and their corresponding residues across various homologous bacterial RNase III proteins, or homologs.

Mutations in the RNaseIII refer to any of point mutations, additions, deletions (though preferably not in the cleavage domain), and rearrangements (preferably in the domain linking regions). Mutations may be at a single site or at multiple sites in the RNaseIII protein. Mutations can be generated by standard techniques including random mutagenesis, targeted genetics and other methods know by those of ordinary skill in the art.

According to the present invention "sRNA" is small RNA, in particular RNA of a length of 200 nucleotides or less that is not translated into a protein. sRNA may be an RNA molecules digested by one or more of the RNase III mutants described herein. sRNA may include siRNA mRNA, or even dsRNA molecules that may be generated by or initiate an RNAi pathway response which may result in the downregulation of a target gene. "RNAi" refers to gene downregulation or inhibition that is induced by the introduction of a double-stranded RNA molecule.

In still other embodiments of the invention, inhibition of the expression of one or more pathogen gene products by RNAi may be obtained through a dsRNA-mediated RNAi action and/or a form of dsRNA known as a hairpin RNA (hpRNA) interference or intron-containing hairpin RNA (ihpRNA) interference. For hpRNA interference, the expression cassette is designed to express an RNA molecule that hybridizes with itself to form a hairpin structure that comprises a single-stranded loop region and a base-paired stem. The base-paired stem region comprises a sense sequence corresponding to all or part of the endogenous messenger RNA encoding the gene product whose expression is to be inhibited, in this case, a pathogen essential gene described herein, and an antisense sequence that is fully or partially complementary to the sense sequence. Alternatively, the base-paired stem region may correspond to a portion of a promoter sequence controlling expression of the gene encoding the target polypeptide to be inhibited. Thus, the base-paired stem region of the molecule generally determines the specificity of the RNA interference. HpRNA molecules are highly efficient at inhibiting the expression of endogenous genes, and the RNA interference they induce is inherited by subsequent generations of plants. See, for example, Chuang and Meyerowitz (2000) Proc. Natl. Acad. Sci. USA 97:4985-4990; Stoutjesdijk et al. (2002) Plant Physiol. 129:1723-1731; and Waterhouse and Helliwell (2003) Nat. Rev. Genet. 4:29-38. Methods for using hpRNA interference to inhibit or silence the expression of genes are described, for example, in Chuang and Meyerowitz (2000) Proc. Natl. Acad. Sci. USA 97:4985-4990; Stoutjesdijk et al. (2002) Plant Physiol. 129:1723-1731; Waterhouse and Helliwell (2003) Nat. Rev. Genet. 4:29-38; Pandolfini et al. BMC Biotechnology 3:7, and U.S. Patent Publication No. 20030175965; each of which is herein incorporated by reference. A transient assay for the efficiency of hpRNA constructs to silence gene expression in vivo has been described by Panstruga et al. (2003) Mol. Biol. Rep. 30:135-140, herein incorporated by reference.

For ihpRNA, the interfering molecules have the same general structure as for hpRNA, but the RNA molecule additionally comprises an intron that is capable of being spliced in the cell in which the ihpRNA is expressed. The use of an intron minimizes the size of the loop in the hairpin RNA molecule following splicing, and this increases the efficiency of interference. See, for example, Smith et al. (2000) Nature 407:319-320. In fact, Smith et al. show 100% suppression of endogenous gene expression using ihpRNA-mediated interference. Methods for using ihpRNA interference to inhibit the expression of endogenous plant genes are described, for example, in Smith et al. (2000) Nature 407: 319-320; Wesley et al. (2001) Plant J 27:581-590; Wang and Waterhouse (2001) Curr. Opin. Plant Biol. 5:146-150; Waterhouse and Helliwell (2003) Nat. Rev. Genet. 4:29-38; Helliwell and Waterhouse (2003) Methods 30:289-295, and U.S. Patent Publication No. 20030180945, each of which is herein incorporated by reference.

The term "gene" or "gene sequence" refers to a coding region operably joined to appropriate regulatory sequences capable of regulating the expression of the gene product (e.g., a polypeptide or a functional RNA) in some manner. A gene includes untranslated regulatory regions of DNA (e.g., promoters, enhancers, repressors, etc.) preceding (upstream) and following (down-stream) the coding region (open reading frame, ORF) as well as, where applicable, intervening sequences (i.e., introns) between individual coding regions (i.e., exons). The term "structural gene" as used herein is intended to mean a DNA sequence that is transcribed into mRNA which is then translated into a sequence of amino acids characteristic of a specific polypeptide.

As used herein, "inhibit, "inhibition," "suppress," "down-regulate" or "silencing" refers to partial or complete loss-of-function through targeted inhibition of gene expression in a cell and may also be referred to as "knock down," preferably through an RNAi pathway response. Depending on the circumstances and the biological problem to be addressed, it may be preferable to partially reduce gene expression. Alternatively, it might be desirable to reduce gene expression as much as possible. The extent of silencing may be determined by any method known in the art, some of which are summarized in International Publication No. WO 99/32619, incorporated herein by reference. As used herein, ""inhibit, "inhibition," "suppress," "downregulate" or "silencing" of the level or activity of an agent, such as, for example, a preRNA, mRNA, rRNA, tRNA, snoRNA, snRNA expressed by the target gene, and/or of the protein product encoded by it, means that the amount is reduced by 10% or more, for example, 20% or more, preferably 30% or more, more preferably 50% or more, even more preferably 70% or more, most preferably 80% or more, for example, 90%, relative to a cell or organism lacking a dsRNA molecule of the disclosure.

"Large double-stranded RNA" refers to any dsRNA or hairpin having a double-stranded region greater than about 40 base pairs (bp) for example, larger than 100 bp, or more, particularly larger than 300 bp. The sequence of a large dsRNA may represent one or more segments of one or more mRNAs or the entire mRNAs. The maximum size of the large dsRNA is not limited herein. The dsRNA may include modified bases where the modification may be to the phosphate sugar backbone or to the nucleotide. Such modifications may include a nitrogen or sulfur heteroatom or any other modification known in the art. The dsRNA may be made enzymatically, by recombinant techniques, and/or by chemical synthesis or using commercial kits such as MEGA-SCRIPT® (Ambion, Austin, Tex.) and methods known in the art. An embodiment of the invention utilizes HiScribe™ (New England Biolabs, Inc., Beverly, Mass.) for making large dsRNA. Other methods for making and storing large dsRNA are described in International Publication No. WO 99/32619. The double-stranded structure may be formed by a self-complementary RNA strand such as occurs for a hairpin or a micro RNA, or by annealing of two distinct complementary RNA strands.

As used herein a "wild type" means a cell or organism that does not contain the heterologous recombinant DNA that expressed a protein or element that imparts an enhanced trait as described herein.

"Expression" or "expressing" refers to production of a functional product, such as, the generation of an RNA transcript from an introduced construct, an endogenous DNA sequence, or a stably incorporated heterologous DNA sequence. A nucleotide encoding sequence may comprise intervening sequence (e.g., intrans) or may lack such intervening non-translated sequences (e.g., as in cDNA). Expressed genes include those that are transcribed into mRNA and then translated into protein and those that are transcribed into RNA but not translated (for example, siRNA, transfer RNA, and ribosomal RNA). The term may also refer to a polypeptide produced from an mRNA generated from any of the above DNA precursors. Thus, expression of a nucleic acid fragment, such as a gene or a promoter region of a gene, may refer to transcription of the nucleic acid fragment (e.g., transcription resulting in mRNA or other functional RNA) and/or translation of RNA into a precursor or mature protein (polypeptide), or both.

An "expression cassette or "expression vector" or "vector" refers to a nucleic acid construct, which when introduced into a host cell, results in transcription and/or translation of a RNA or polypeptide, respectively. More specifically, the term "vector" refers to some means by which DNA, RNA, a protein, or polypeptide can be introduced into a host. The polynucleotides, protein, and polypeptide which are to be introduced into a host can be therapeutic or prophylactic in nature; can encode or be an antigen; can be regulatory in nature, etc. There are various types of vectors including virus, plasmid, bacteriophages, cosmids, and bacteria. Again, more specifically, "expression vector" is nucleic acid capable of replicating in a selected host cell or organism. An expression vector can replicate as an autonomous structure, or alternatively can integrate, in whole or in part, into the host cell chromosomes or the nucleic acids of an organelle, or it is used as a shuttle for delivering foreign DNA to cells, and thus replicate along with the host cell genome. Thus, an expression vector are polynucleotides capable of replicating in a selected host cell, organelle, or organism, e.g., a plasmid, virus, artificial chromosome, nucleic acid fragment, and for which certain genes on the expression vector (including genes of interest) are transcribed and translated into a polypeptide or protein within the cell, organelle or organism; or any suitable construct known in the art, which comprises an "expression cassette." In contrast, as described in the examples herein, a "cassette" is a polynucleotide containing a section of an expression vector of this invention. The use of the cassettes assists in the assembly of the expression vectors. An expression vector is a replicon, such as plasmid, phage, virus, chimeric virus, or cosmid, and which contains the desired polynucleotide sequence operably linked to the expression control sequence(s). A polynucleotide sequence is operably linked to an expression control sequence(s) (e.g., a promoter and, optionally, an enhancer) when the expression control sequence controls and regulates the transcription and/or translation of that polynucleotide sequence.

The term "genome" encompasses not only chromosomal DNA found within the nucleus, but organelle DNA found within subcellular components (e.g., mitochondrial, plastid) of the cell. As used herein, the term "genome" refers to the nuclear genome unless indicated otherwise.

The term "heterologous" refers to a nucleic acid fragment or protein that is foreign to its surroundings. In the context of a nucleic acid fragment, this is typically accomplished by introducing such fragment, derived from one source, into a different host. Heterologous nucleic acid fragments, such as coding sequences that have been inserted into a host organism, are not normally found in the genetic complement of the host organism. As used herein, the term "heterologous" also refers to a nucleic acid fragment derived from the same organism, but which is located in a different, e.g., non-native, location within the genome of this organism. Thus, the organism can have more than the usual number of copy(ies) of such fragment located in its(their) normal position within the genome and in addition, in the case of plant cells, within different genomes within a cell, for example in the nuclear genome and within a plastid or mitochondrial genome as well. A nucleic acid fragment that is heterologous with respect to an organism into which it has been inserted or transferred is sometimes referred to as a "transgene."

"Host cell" means a cell which contains an expression vector and supports the replication and/or expression of that vector. The term "introduced" means providing a nucleic acid (e.g., an expression construct) or protein into a cell. "Introduced" includes reference to the incorporation of a nucleic acid into a eukaryotic or prokaryotic cell where the nucleic acid may be incorporated into the genome of the cell, and includes reference to the transient provision of a nucleic acid or protein to the cell. "Introduced" includes reference to stable or transient transformation methods, as well as sexually crossing. Thus, "introduced" in the context of inserting a nucleic acid fragment (e.g., a recombinant DNA construct/expression construct) into a cell, can mean "transfection" or "transformation" or "transduction", and includes reference to the incorporation of a nucleic acid fragment into a eukaryotic or prokaryotic cell where the nucleic acid fragment may be incorporated into the genome of the cell (e.g., chromosome, plasmid, plastid, or mitochondrial DNA), converted into an autonomous replicon, or transiently expressed (e.g., transfected mRNA).

As used herein, "nucleic acid" or "nucleotide sequence" means a polynucleotide (or oligonucleotide), including single or double-stranded polymers of deoxyribonucleotides or ribonucleotide bases, and unless otherwise indicated, encompasses naturally occurring and synthetic nucleotide analogues having the essential nature of natural nucleotides in that they hybridize to complementary single stranded nucleic acids in a manner similar to naturally occurring nucleotides. Nucleic acids may also include fragments and modified nucleotide sequences. Nucleic acids disclosed herein can either be naturally occurring, for example genomic nucleic acids, or isolated, purified, nongenomic nucleic acids, including synthetically produced nucleic acid sequences such as those made by solid phase chemical oligonucleotide synthesis, enzymatic synthesis, or by recombinant methods, including for example, cDNA, codon-optimized sequences for efficient expression in different transgenic plants reflecting the pattern of codon usage in such plants, nucleotide sequences that differ from the nucleotide sequences disclosed herein due to the degeneracy of the genetic code but that still encode the protein(s) of interest disclosed herein, nucleotide sequences encoding the presently disclosed protein(s) comprising conservative (or non-conservative) amino acid substitutions that do not adversely affect their normal activity, PCR-amplified nucleotide sequences, and other non-genomic forms of nucleotide sequences familiar to those of ordinary skill in the art.

"Nucleic acid construct" or "construct" refers to an isolated polynucleotide which can be introduced into a host cell, for example a plasmid. This construct may comprise any combination of deoxyribonucleotides, ribonucleotides, and/or modified nucleotides. This construct may comprise an expression cassette that can be introduced into and expressed in a host cell.

"Operably linked" refers to a functional arrangement of elements. A first nucleic acid sequence is operably linked with a second nucleic acid sequence when the first nucleic acid sequence is placed in a functional relationship with the second nucleic acid sequence. For instance, a promoter is operably linked to a coding sequence if the promoter effects the transcription or expression of the coding sequence. The control elements need not be contiguous with the coding sequence, so long as they function to direct the expression thereof. Thus, for example, intervening untranslated yet transcribed sequences can be present between a promoter and the coding sequence and the promoter can still be considered "operably linked" to the coding sequence.

The terms "peptide", "polypeptide", and "protein" are used to refer to polymers of amino acid residues. These terms are specifically intended to cover naturally occurring biomolecules, as well as those that are recombinantly or synthetically produced, for example by solid phase synthesis.

The term "promoter" or "regulatory element" refers to a region or nucleic acid sequence located upstream or downstream from the start of transcription and which is involved in recognition and binding of RNA polymerase and/or other proteins to initiate transcription of RNA. Promoters need not be of plant or algal origin. For example, promoters derived from plant viruses, such as the CaMV35S promoter, or from other organisms, can be used in variations of the embodiments discussed herein. Promoters useful in the present methods include, for example, constitutive, strong, weak, tissue-specific, cell-type specific, seed-specific, inducible, repressible, and developmentally regulated promoters. Examples of suitable promoters for gene suppressing cassettes include, but are not limited to, T7 promoter, bla promotor, U6 promoter, pol II promoter, E11 promoter, and CMV promoter and the like.

A "cell type-specific" promoter primarily drives expression in certain cell types in one or more organs. An "inducible" promoter may be a promoter which may be under environmental control or induced by a secondary molecule or compound Tissue-specific, tissue-preferred, cell type specific, and inducible promoters constitute the class of "non-constitutive" promoters. A "constitutive" promoter is a promoter which may be active under most environmental conditions or in most cell or tissue types.

As used herein, the term "transformation" or "genetically modified" refers to the transfer of one or more nucleic acid molecule(s) into a cell. A microorganism is "transformed" or "genetically modified" by a nucleic acid molecule transduced into the bacteria when the nucleic acid molecule becomes stably replicated by the bacteria. As used herein, the term "transformation" or "genetically modified" encompasses all techniques by which a nucleic acid molecule can be introduced into, such as a bacterium.

As used herein, a "genetically modified plant or "transgenic plant" is one whose genome has been altered by the incorporation of exogenous genetic material, e.g. by transformation as described herein. The term "transgenic plant" is used to refer to the plant produced from an original transformation event, or progeny from later generations or crosses of a transgenic plant so long as the progeny contains the exogenous genetic material in its genome. By "exogenous" is meant that a nucleic acid molecule, for example, a recombinant DNA, originates from outside the plant into which it is introduced. An exogenous nucleic acid molecule may comprise naturally or non-naturally occurring DNA, and may be derived from the same or a different plant species than that into which it is introduced.

"Stable transformation" is intended to mean that the nucleotide construct introduced into a host and integrates into the genome of the plant and is capable of being inherited by the progeny thereof. The nucleic acid molecule can be transiently expressed or non-stably maintained in a functional form in the cell for less than three months i.e. is transiently expressed.

The terms "plant" or "plants" that can be used in the present methods broadly include the classes of higher and lower plants amenable to transformation techniques, including angiosperms (monocotyledonous and dicotyledonous plants), gymnosperms, ferns, and unicellular and multicellular algae. The term "plant" also includes plants which have been modified by breeding, mutagenesis, or genetic engineering (transgenic and non-transgenic plants). It includes plants of a variety of ploidy levels, including aneuploid, polyploid, diploid, haploid, and hemizygous. The plant may be in any form including suspension cultures, embryos, meristematic regions, callus tissue, gametophytes, sporophytes, pollen, microspores, whole plants, shoot vegetative organs/structures (e.g. leaves, stems and tubers), roots, flowers and floral organs/structures, seed (including embryo, endosperm, and seed coat) and fruit, plant tissue (e.g. vascular tissue, ground tissue, and the like) and cells, and progeny of same.

The term "probiotic" refers to a microorganism, such as bacteria, that may colonize a host for a sufficient length of time to delver a therapeutic or effective amount of an interfering RNA molecule. A probiotic may include endosymbiotic bacteria, or naturally occurring flora that may permanently to temporarily colonize an animal, such as an aquatic organism. Probiotic organisms may also include algae, and fungi, such as yeast.

The invention encompasses isolated or substantially purified RNase III mutant polynucleotides or amino acid compositions. An "isolated" or "purified" RNase III mutant polynucleotide or protein, or biologically active portion thereof, is substantially or essentially free from components that normally accompany or interact with the RNase III mutant polynucleotide or protein as found in its naturally occurring environment. Thus, an isolated or purified polynucleotide or protein is substantially free of other cellular material, or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived.

A "variant," or "isoform," or "protein variant" is a member of a set of similar proteins that perform the same or similar biological roles. For example, fragments and variants of the disclosed RNase III polynucleotides and amino acid sequences encoded thereby are also encompassed by the present invention. By "fragment" is intended a portion of the polynucleotide or a portion of the amino acid sequence. For polynucleotides, a variant comprises a polynucleotide having deletions (i.e., truncations) at the 5' and/or 3' end; deletion and/or addition of one or more nucleotides at one or more internal sites in the native polynucleotide; and/or substitution of one or more nucleotides at one or more sites in the native polynucleotide. As used herein, a "native" or "wildtype" polynucleotide or polypeptide comprises a naturally occurring nucleotide sequence or amino acid sequence, respectively. Generally, variants of a particular RNase III disclosed herein will have at least about 75%, 80%, 85%, 90%, 91%, 92%, 93%, 94%, 95%, 96%, 97%, 98%, 99% or more sequence identity to that particular polynucleotide as determined by sequence alignment programs and parameters as described elsewhere herein.

The compositions disclosed herein also comprise synthetic oligonucleotides or nucleotide sequences encoding RNase III mutant sequences. A synthetic sequence is one that is produced or reproduced in a laboratory setting. While the nucleotide sequence may have an altered nucleotide sequence relative to the parent sequence, the synthetic sequence may be identical to the naturally occurring sequence. In both instances, however, the structure of the synthetic sequence is altered or different from that found in the sequence that is directly isolated from its natural setting.

As used herein, the phrase "host" refers to an organism, such as a plant or animal, carrying a disease-causing pathogen, an organism susceptible to a disease-causing pathogen, an organism population where members are carrying a disease-causing pathogen, or an organism population where members are susceptible to a disease-causing pathogen. These include hosts listed in tables 8-12, and elsewhere. In one embodiment a target host may be a aquatic organism, and preferably an organism grown in aquaculture. The term "aquaculture" as used herein includes the cultivation of aquatic organisms under controlled conditions. The term "aquatic organism" and/or "aquatic animal" as used herein include organisms grown in water, either fresh or saltwater. Aquatic organisms/animals includes vertebrates, invertebrates, arthropods, fish, mollusks, including, shrimp (e.g., penaeid shrimp, *Penaeus esculentu, Penaeus setiferus, Penaeus stylirostris, Penaeus occidentalis, Penaeus japonicus, Penaeus vannamei, Penaeus monodon, Penaeus chinensis, Penaeus aztecus, Penaeus duorarum, Penaeus indicus*, and *Penaeus merguiensis, Penaeus californiensis, Penaeus semisulcatus, Penaeus monodon*, brine shrimp, freshwater shrimp, etc), crabs, oysters, scallop, prawn clams, cartilaginous fish (e.g., sea bream, trout, bass, striped bass, tilapia, catfish, salmonids, carp, catfish, yellowtail, carp zebrafish, red drum, etc), crustaceans, among others. Shrimp include shrimp raised in aquaculture as well. Example pathogens affecting aquatic organisms may include white spot syndrome (WSS)

As used herein, "pathogen" refers to a disease causing agent. These include the pathogens included in tables 8-12, and elsewhere.

"Target" or "essential gene" refers to any gene or mRNA of interest. Indeed any of the genes previously identified by genetics or by sequencing may represent a target. Target genes or mRNA may include developmental genes and regulatory genes as well as metabolic or structural genes or genes encoding enzymes. The target gene may be expressed in those cells in which a phenotype is being investigated or in an organism in a manner that directly or indirectly impacts a phenotypic characteristic. The target gene may be endogenous or exogenous. An "essential gene," for example may be a gene necessary for survival, replication or pathogenicity in a pathogen. Such cells include any cell in the body of an adult or embryonic animal or plant including gamete or any isolated cell such as occurs in an immortal cell line or primary cell culture.

Moreover, the terms "enhance", "enhanced", "increase", "increased" or "improved" generally refer to a statistically significant increase, for example in a trait, phenotype or catalytic rate. For the avoidance of doubt, these terms generally refer to about a 5% increase in a given parameter or value, about a 10% increase, about a 15% increase, about a 20% increase, about a 25% increase, about a 30% increase, about a 35% increase, about a 40% increase, about a 45% increase, about a 50% increase, about a 55% increase, about a 60% increase, about a 65% increase, about 70% increase, about a 75% increase, about an 80% increase, about an 85% increase, about a 90% increase, about a 95% increase, about a 100% increase, or more over the control value. These terms also encompass ranges consisting of any lower indicated value to any higher indicated value, for example "from about 5% to about 50%", etc.

Unless otherwise stated, nucleic acid sequences in the text of this specification are given, when read from left to right, in the 5' to 3' direction. Nucleic acid sequences may be provided as DNA or as RNA, as specified; disclosure of one necessarily defines the other, as is known to one of ordinary skill in the art and is understood as included in embodiments where it would be appropriate. Nucleotides may be referred to by their commonly accepted single-letter codes. Unless otherwise indicated, amino acid sequences are written left to right in amino to carboxyl orientation, respectively. Amino acids may be referred to herein by either their commonly known three letter symbols or by the one-letter symbols as generally understood by those skilled in the relevant art.

Regarding disclosed ranges, the endpoints of all ranges directed to the same component or property are inclusive and independently combinable (e.g., ranges of "about 25%, or, more, about 5% to about 20 wt. %," is inclusive of the endpoints and all intermediate values of the ranges of "about 5% to about 25%," etc.). Numeric ranges recited with the specification are inclusive of the numbers defining the range and include each integer within the defined range.

Notably, all peptides disclosed in specifically encompass peptides having conservative amino acid substitutions. As used herein, "conservative amino acid substitutions" means the manifestation that certain amino acids can be substituted for other amino acids in a protein structure without appreciable loss of biochemical or biological activity. Since it is the interactive capacity and nature of a protein that defines that protein's biological functional activity, certain amino acid sequence substitutions can be made in a protein sequence, and, of course, the underlying DNA coding sequence, and nevertheless obtain a protein with like properties. Thus, various changes can be made in the amino acid sequences disclosed herein, or in the corresponding DNA sequences that encode these amino acid sequences, without appreciable loss of their biological utility or activity.

Examples of amino acid groups defined in this manner include: a "charged polar group," consisting of glutamic acid (Glu), aspartic acid (Asp), asparagine (Asn), glutamine (Gln), lysine (Lys), arginine (Arg) and histidine (His); an "aromatic, or cyclic group," consisting of proline (Pro), phenylalanine (Phe), tyrosine (Tyr) and tryptophan (Trp); and an "aliphatic group" consisting of glycine (Gly), alanine (Ala), valine (Val), leucine (Leu), isoleucine (Ile), methionine (Met), serine (Ser), threonine (Thr) and cysteine (Cys).

Within each group, subgroups can also be identified, for example, the group of charged polar amino acids can be sub-divided into the sub-groups consisting of the "positively-charged sub-group," consisting of Lys, Arg and His; the negatively-charged sub-group," consisting of Glu and Asp, and the "polar sub-group" consisting of Asn and Gln. The aromatic or cyclic group can be sub-divided into the sub-groups consisting of the "nitrogen ring sub-group," consisting of Pro, His and Trp; and the "phenyl sub-group" consisting of Phe and Tyr. The aliphatic group can be sub-divided into the sub-groups consisting of the "large aliphatic non-polar sub-group," consisting of Val, Leu and Ile; the "aliphatic slightly-polar sub-group," consisting of Met, Ser, Thr and Cys; and the "small-residue sub-group," consisting of Gly and Ala. Examples of conservative mutations include substitutions of amino acids within the subgroups above, for example, Lys for Arg and vice versa such that a positive charge can be maintained; Glu for Asp and vice versa such that a negative charge can be maintained; Ser for Thr such that a free —OH can be maintained; and Gln for Asn such that a free —NH2 can be maintained.

Proteins and peptides biologically functionally equivalent to the proteins and peptides disclosed herein include amino acid sequences containing conservative amino acid changes in the fundamental amino acid sequence. In such amino acid sequences, one or more amino acids in the fundamental sequence can be substituted, for example, with another amino acid(s), the charge and polarity of which is similar to that of the native amino acid, i.e., a conservative amino acid substitution, resulting in a silent change. It should be noted that there are a number of different classification systems in the art that have been developed to describe the interchangeability of amino acids for one another within peptides, polypeptides, and proteins. The following discussion is merely illustrative of some of these systems, and the present disclosure encompasses any of the "conservative" amino acid changes that would be apparent to one of ordinary skill in the art of peptide, polypeptide, and protein chemistry from any of these different systems. Unless otherwise indicated, a particular nucleic acid sequence also implicitly encompasses conservatively modified variants thereof (e.g., degenerate codon substitutions), the complementary (or complement) sequence, and the reverse complement sequence, as well as the sequence explicitly indicated. Specifically, degenerate codon substitutions may be achieved by generating sequences in which the third position of one or more selected (or all) codons is substituted with mixed-base and/or deoxyinosine residues (see e.g., Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)). Because of the degeneracy of nucleic acid codons, one can use various different polynucleotides to encode identical polypeptides. Table 13, infra, contains information about which nucleic acid codons encode which amino acids.

TABLE 13

Amino acid Nucleic acid codons

| Amino Acid | Nucleic Acid Codons |
|---|---|
| Ala/A | GCT, GCC, GCA, GCG |
| Arg/R | CGT, CGC, CGA, CGG, AGA, AGG |
| Asn/N | AAT, AAC |
| Asp/D | GAT, GAC |
| Cys/C | TGT, TGC |
| Gln/Q | CAA, CAG |
| Glu/E | GAA, GAG |
| Gly/G | GGT, GGC, GGA, GGG |
| His/H | CAT, CAC |
| Ile/I | ATT, ATC, ATA |
| Leu/L | TTA, TTG, CTT, CTC, CTA, CTG |
| Lys/K | AAA, AAG |
| Met/M | ATG |
| Phe/F | TTT, TTC |
| Pro/P | CCT, CCC, CCA, CCG |
| Ser/S | TCT, TCC, TCA, TCG, AGT, AGC |
| Thr/T | ACT, ACC, ACA, ACG |
| Trp/W | TGG |
| Tyr/Y | TAT, TAC |
| Val/V | GTT, GTC, GTA, GTG |

Any commercially or scientifically valuable plant is encompassed in accordance with some embodiments of the disclosure. Plants that are particularly useful in the methods of the disclosure, for example expression of, and/or application of sRNAs as described herein, include all plants which belong to the super family Viridiplantae, in particular monocotyledonous and dicotyledonous plants including a fodder or forage legume, ornamental plant, food crop, tree, or shrub selected from the list comprising *Acacia* spp., *Acer* spp., *Actinidia* spp., *Aesculus* spp., *Agathis australis*, *Albizia amara*, *Alsophila tricolor*, *Andropogon* spp., *Arachis* spp, *Areca catechu*, *Astelia fragrans*, *Astragalus cicer*, *Baikiaea plurijuga*, *Betula* spp., *Brassica* spp., *Bruguiera gymnorrhiza*, *Burkea africana*, *Butea frondosa*, *Cadaba farinosa*, *Calliandra* spp, *Camellia sinensis*, *Canna indica*, *Capsicum* spp., *Cassia* spp., *Centroema pubescens*, *Chacoomeles* spp., *Cinnamomum cassia*, *Coffea arabica*, *Colophospermum mopane*, *Coronillia varia*, *Cotoneaster serotina*, *Crataegus* spp., *Cucumis* spp., *Cupressus* spp., *Cyathea dealbata*, *Cydonia oblonga*, *Cryptomeria japonica*, *Cymbopogon* spp., *Cynthea dealbata*, *Cydonia oblonga*, *Dalbergia monetaria*, *Davallia divaricata*, *Desmodium* spp., *Dicksonia squarosa*, *Dibeteropogon amplectens*, *Dioclea* spp, *Dolichos* spp., *Dorycnium rectum*, *Echinochloa pyramidalis*, *Ehraffia* spp., *Eleusine coracana*, *Eragrestis* spp., *Erythrina* spp., *Eucalyptus* spp., *Euclea schimperi*, *Eulalia vi/losa*, *Pagopyrum* spp., *Feijoa sellowlana*, *Fragaria* spp., *Flemingia* spp, *Freycinetia banksli*, *Geranium thunbergii*, *GinAgo biloba*, *Glycine javanica*, *Gliricidia* spp, *Gossypium hirsutum*, *Grevillea* spp., *Guibourtia coleosperma*, *Hedysarum* spp., *Hemaffhia altissima*, *Heteropogon contoffus*, *Hordeum vulgare*, *Hyparrhenia rufa*, *Hypericum erectum*, *Hypeffhelia dissolute*, *Indigo incamata*, *Iris* spp., *Leptarrhena pyrolifolia*, *Lespediza* spp., *Lettuca* spp., *Leucaena leucocephala*, *Loudetia simplex*, *Lotonus bainesli*, *Lotus* spp., *Macrotyloma axillare*, *Malus* spp., *Manihot esculenta*, *Medicago saliva*, *Metasequoia glyptostroboides*, *Musa sapientum*, *Nicotianum* spp., *Onobrychis* spp., *Ornithopus* spp., *Oryza* spp., *Peltophorum africanum*, *Pennisetum* spp., *Persea gratissima*, *Petunia* spp., *Phaseolus* spp., *Phoenix canariensis*, *Phormium cookianum*, *Photinia* spp., *Picea glauca*, *Pinus* spp., *Pisum sativam*, *Podocarpus totara*, *Pogonarthria fleckii*, *Pogonaffhria squamosa*, *Populus* spp., *Prosopis cineraria*, *Pseudotsuga menziesii*, *Pterolobium stellatum*, *Pyrus communis*, *Quercus* spp., *Rhaphiolepis umbellata*, *Rhopalostylis sapida*, *Rhus natalensis*, *Ribes grossularia*, *Ribes* spp., *Robinia pseudoacacia*, *Rosa* spp., *Rubus* spp., *Salix* spp., *Schyzachyrium sanguineum*, *Sciadopitys vefficillata*, *Sequoia sempervirens*, *Sequoiadendron giganteum*, *Sorghum bicolor*, *Spinacia* spp., *Sporobolus fimbriatus*, *Stiburus alopecuroides*, *Stylosanthos humilis*, *Tadehagi* spp, *Taxodium distichum*, *Themeda triandra*, *Trifolium* spp., *Triticum* spp., *Tsuga heterophylla*, *Vaccinium* spp., *Vicia* spp., *Vitis vinifera*, *Watsonia pyramidata*, *Zantedeschia aethiopica*, *Zea mays*, amaranth, artichoke, asparagus, broccoli, Brussels sprouts, cabbage, canola, carrot, cauliflower, celery, collard greens, flax, kale, lentil, oilseed rape, okra, onion, potato, rice, soybean, straw, sugar beet, sugar cane, sunflower, tomato, squash tea, maize, wheat, barley, rye, oat, peanut, pea, lentil and alfalfa, cotton, rapeseed, canola, pepper, sunflower, tobacco, eggplant, *eucalyptus*, a tree, an ornamental plant, a perennial grass and a forage crop. Alternatively algae and other non-Viridiplantae can be used for the methods of the present disclosure.

According to some embodiments of the disclosure, the plant used by the method of the disclosure is a crop plant including, but not limited to, cotton, *Brassica* vegetables, oilseed rape, sesame, olive tree, palm oil, banana, wheat, corn or maize, barley, alfalfa, peanuts, sunflowers, rice, oats, sugarcane, soybean, turf grasses, barley, rye, *sorghum*, sugar cane, chicory, lettuce, tomato, zucchini, bell pepper, eggplant, cucumber, melon, watermelon, beans, hibiscus, okra, apple, rose, strawberry, chili, garlic, pea, lentil, canola, mums, *Arabidopsis*, broccoli, cabbage, beet, *quinoa*, spinach, squash, onion, leek, tobacco, potato, sugar beet, *papaya*, pineapple, mango, *Arabidopsis thaliana*, and also plants used in horticulture, floriculture or forestry, such as, but not limited to, poplar, fir, *eucalyptus*, pine, an ornamental plant, a perennial grass and a forage crop, coniferous plants, moss, algae, as well as other plants available on the internet at, for example, wwwdotnationmasterdotcom/encyclopedia/Plantae.

According to a specific embodiment, the plant is selected from the group consisting of corn, rice, wheat, tomato, cotton and *sorghum*. In certain embodiments, the plant is a corn plant. In certain embodiments, the plant is a rice plant. In certain embodiments, the plant is a wheat plant. In certain embodiments, the plant is a cotton plant. In certain embodiments, the plant is a *sorghum* plant.

The availability of sRNA fragments produced by one or more of the RNase III mutants provides a supply of a reagent or therapeutic agent and a novel therapeutic approach in which a desired knockdown effect can be achieved in a whole organism without the disadvantages of gene therapy. A gene derived from a pathogen can be targeted for inhibition. For example, the gene could cause immunosuppression of the host directly or be essential for replication of the pathogen, transmission of the pathogen or maintenance of the infection. The inhibitory RNA could be introduced in cells in vitro or ex vivo and then subsequently placed into an organism to effect therapy, or the organism could be directly treated by in vivo administration. A method of gene therapy can be envisioned. For example, cells at risk for infection by a pathogen or already infected cells, may be targeted for treatment by introduction of sRNA according to the invention. The target gene might be a pathogen or host gene responsible for entry of a pathogen into its host, drug metabolism by the pathogen or host, replication or integration of the pathogen's genome, establishment or spread of an infection in the host, or assembly of the next generation of pathogen. Methods of prophylaxis (i.e., prevention or decreased risk of infection), as well as reduction in the frequency or severity of symptoms associated with infection, can be envisioned.

In a further embodiment, a composition including a genetically modified bacteria configured to express one or more RNase III mutants that produce sRNA may be formulated as feed and/or a water dispersible granule or powder that may further be configured to be dispersed into the environment. In yet a further embodiment, the compositions of the present invention may also comprise a wettable powder, spray, emulsion, colloid, aqueous or organic solution, dust, pellet, or colloidal concentrate. Dry forms of the compositions may be formulated to dissolve immediately upon wetting, or alternatively, dissolve in a controlled-release, sustained-release, or other time-dependent manner. Alternatively or additionally, the composition may comprise an aqueous solution. Such aqueous solutions or suspensions may be provided as a concentrated stock solution which is diluted prior to application, or alternatively, as a diluted solution ready-to-apply. Such compositions may be formulated in a variety of ways. They may be employed as wettable powders, granules or dusts, by mixing with various inert materials, such as inorganic minerals (silicone or silicon derivatives, phyllosilicates, carbonates, sulfates, phosphates, and the like) or botanical materials (powdered corncobs, rice hulls, walnut shells, and the like). The formulations or compositions containing genetically modified bacteria may include spreader-sticker adjuvants, stabilizing agents, other pesticidal additives, or surfactants. Liquid formulations may be employed as foams, suspensions, emulsifiable concentrates, or the like. The ingredients may include Theological agents, surfactants, emulsifiers, dispersants, or polymers.

According to one embodiment, the composition is administered to the host by feeding. Feeding the host with the composition can be effected once, regularly, or semi-regularly over the span of hours, days, weeks, months or even years.

As mentioned, the sRNA of the invention may be administered as a naked sRNA. Alternatively, the sRNA of the invention may be conjugated to a carrier known to one of skill in the art, such as a transfection agent e.g. PEI or chitosan or a protein/lipid carrier or coupled to nanoparticles. The compositions may be formulated prior to administration in an appropriate means such as lyophilized, freeze-dried, microencapsulated, desiccated, or in an aqueous carrier, medium or suitable diluent, such as saline or other buffer. Suitable agricultural carriers can be solid, semi-solid or liquid and are well known in the art. Such compositions may be considered "agriculturally-acceptable carriers", which may covers all adjuvants, e.g., inert components, dispersants, surfactants, tackifiers, binders, etc. that are ordinarily used in pesticide formulation technology.

The invention now being generally described will be more readily understood by reference to the following examples, which are included merely for the purposes of illustration of certain aspects of the embodiments of the present invention. The examples are not intended to limit the invention, as one of skill in the art would recognize from the above teachings and the following examples that other techniques and methods can satisfy the claims and can be employed without departing from the scope of the claimed invention. Indeed, while this invention has been particularly shown and described with references to preferred embodiments thereof, it will be understood by those skilled in the art that various changes in form and details may be made therein without departing from the scope of the invention encompassed by the appended claims.

EXAMPLES

Example 1: RNase III Mutants Screening Procedures

The present inventors utilized a tetA-sacB counter selection method to screen several bacterial RNase III mutants constructed on the bacterial chromosome. Specifically, the present inventors utilizes tetA-sacB counter selection method to screen several *E. coli* RNase III mutants constructed on the bacterial chromosome.

Example 2: Construction of E38A-L40F and E117K-L119F RNase III Mutants

Figure 1A:
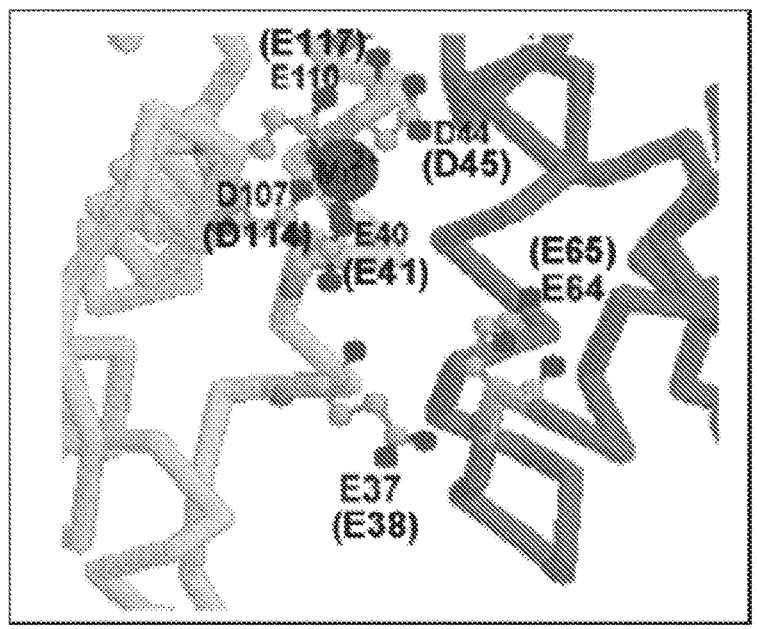
FIG. 1A: The catalytic centers of *E. coli* Ribonuclease III (RNase III).
Figure 1B:
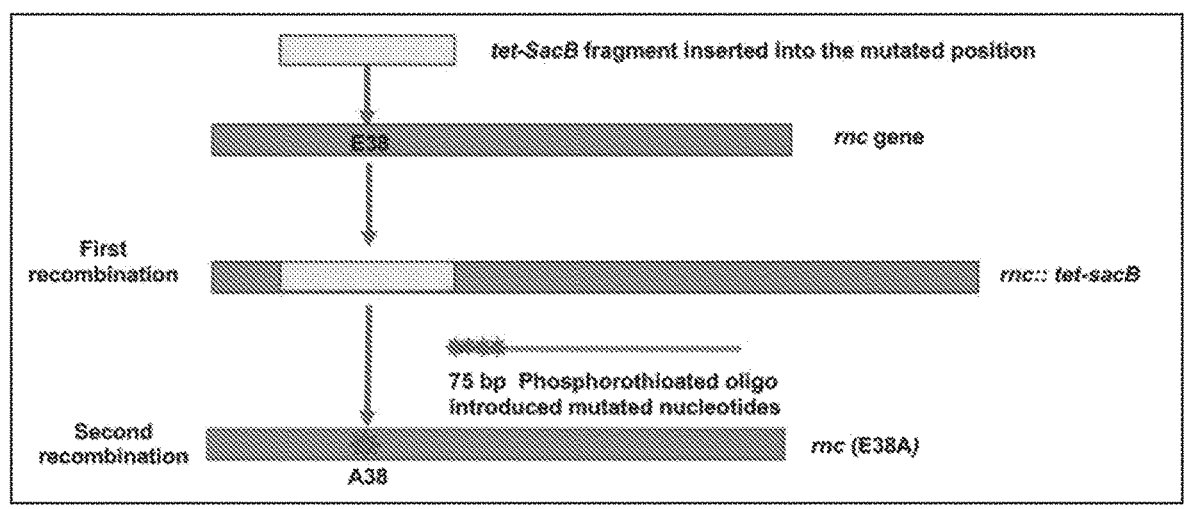
FIG. 1B: Homologous recombination to directly make bacterial RNase III point mutant (tet-sacB counter selection) in the bacterial chromosome.
Figure 2:
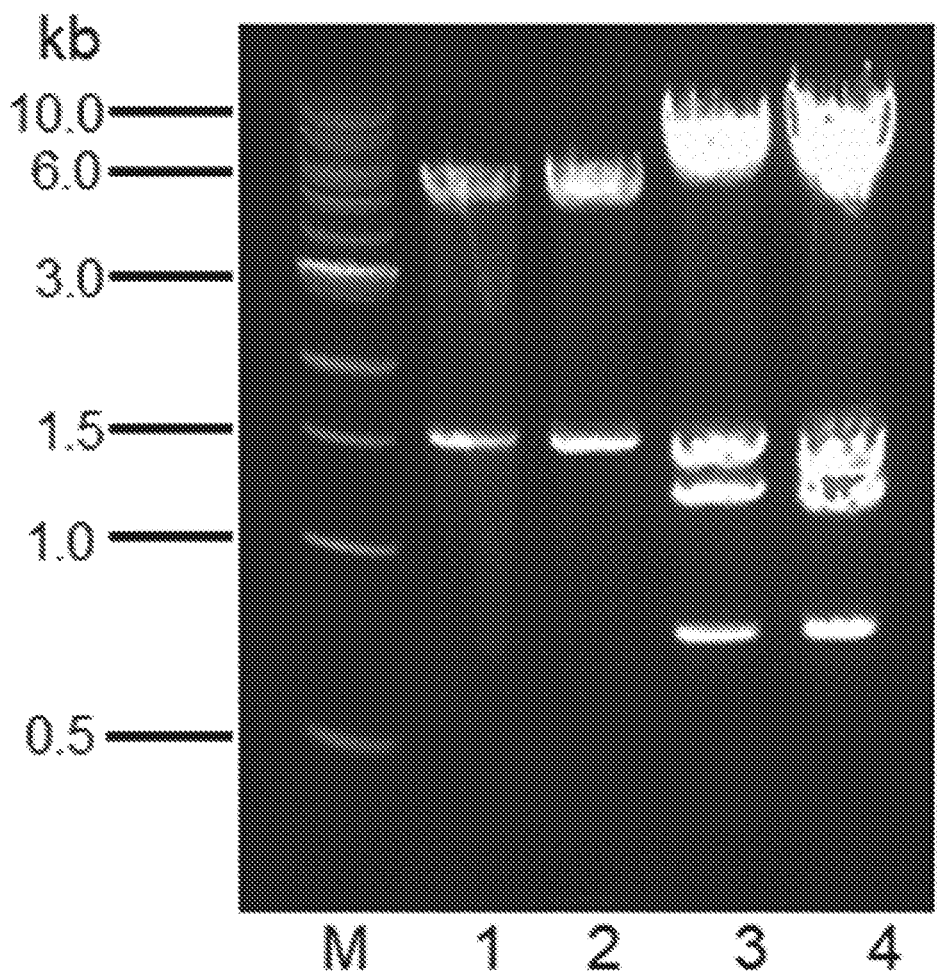
FIG. 2: The identification of pKD46 and pSIJ8 plasmids by digestion with EcoRI-HF® restriction enzyme. Lane M: 1 kb DNA ladder; lanes 1-2: pKD46 digested with EcoRI-HF® restriction enzyme, and the expected fragment sizes are ~4.8 kb and ~1.5 kb; lanes 3-4: pSIJ8 digested with EcoRI-HF® restriction enzyme, and the expected fragment sizes are ~0.8 kb, ~1.3 kb, ~1.5 kb, and ~6.0 kb.

In one embodiment, the present inventors demonstrated the use of a wild-type *Escherichia coli* JM109(DE3) strain to construct E38A-L40F and E117K-L119F mutants on the bacterial chromosome. JM109 (DE3) genotype: endA1, recA1, gyrA96, thi, hsdR17 (rk−, mk+), relA1, supE44, λ−, Δ(lac-proAB), [F', traD36, proAB, lacIqZΔM15], 1DE3. TetA-sacB counter selection method was used to construct the E38A-L40F and E117K-L119F mutants as shown in FIG. 1B. In this embodiment, the plasmid pKD46 or pSIJ8, as shown in FIG. 2, was transformed into JM109 (DE3) for Red recombination.

The present inventors initiated the following protocol: T-SACK strain was used as a template to clone tetA-sacB cassette (~3.5 kb targeting fragment) with primers Ecoli-tet-sacB38F1 and Ecoli-tet-sacB38R1, where each primer included over 50 bp homology arms as generally shown in Table 1). The JM109 (DE3) containing pKD46 (identified at cgsc2.biology.yale.edu/Strain.php?ID=68099), or pSIJ8 (identified at addgene.org/68122/), plasmid is grown overnight at 30° C. in LB with a final concentration of 100 μg/mL ampicillin to maintain the plasmid. The overnight culture is diluted 100-fold in SOB with a final concentration of 100 μg/mL ampicillin and is grown at 30° C. to $OD_{600}$~0.3. L-arabinose is then added with a final concentration of 10 mmol/L to induce another 2 hrs to express Red enzyme, and then is used to make electro-competent cells. About 1 μg of purified tetA-sacB PCR product mixes with 100 μL competent cell for electroporation. The electroporation condition is 0.1 cm cuvette, 1.8 kV, 200Ω, and 25 μF. After electroporation, the cells are transformed into 1 mL of SOC and grown for over 4 hrs with aeration before plating on the pre-warmed (37° C.) tetracycline plate (final concentration 10 μg/mL) and then incubated for one day.

Figure 3:
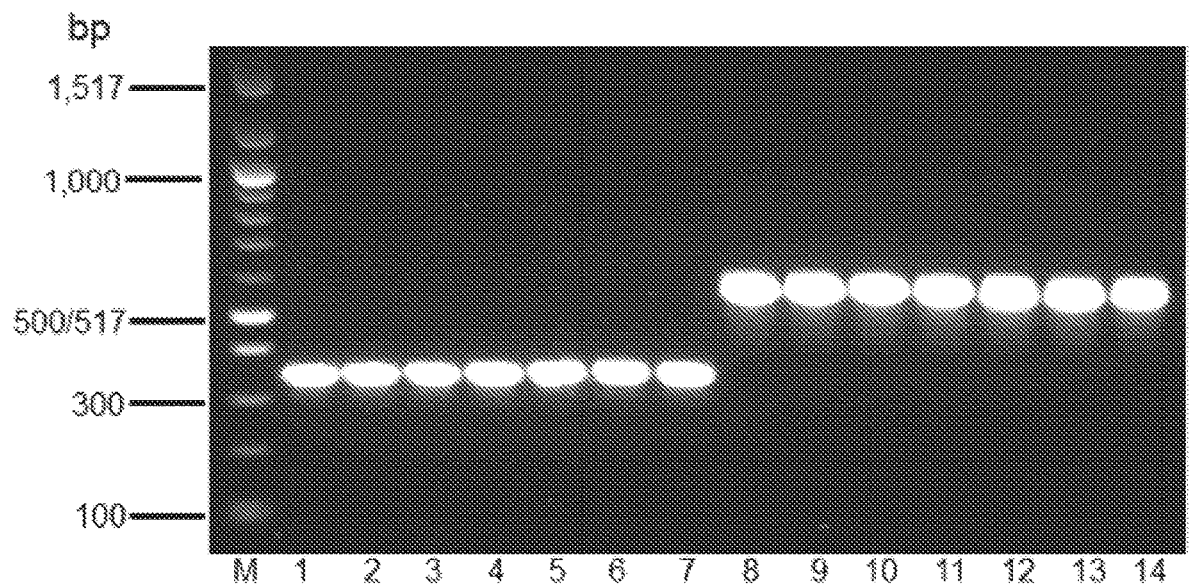
FIG. 3: PCR amplification of tetA-sacB cassette inserted into *E. coli* JM109 (DE3) RNase III E38 and E117K positions. Lane M: 100 bp DNA ladder; lanes 1-7: PCR amplification of tetA-sacB cassette inserted into *E. coli* JM109 (DE3) RNase III E38 position with primers JD-5 and Tet-sacB-JD-R1, and the expected fragment size is 368 bp; lanes 8-14: PCR amplification of tetA-sacB cassette inserted into *E. coli* JM109 (DE3) RNase III E117 position with primers JD-5 and Tet-sacB-JD-R1, and the expected fragment size is 605 bp.
Figure 4:
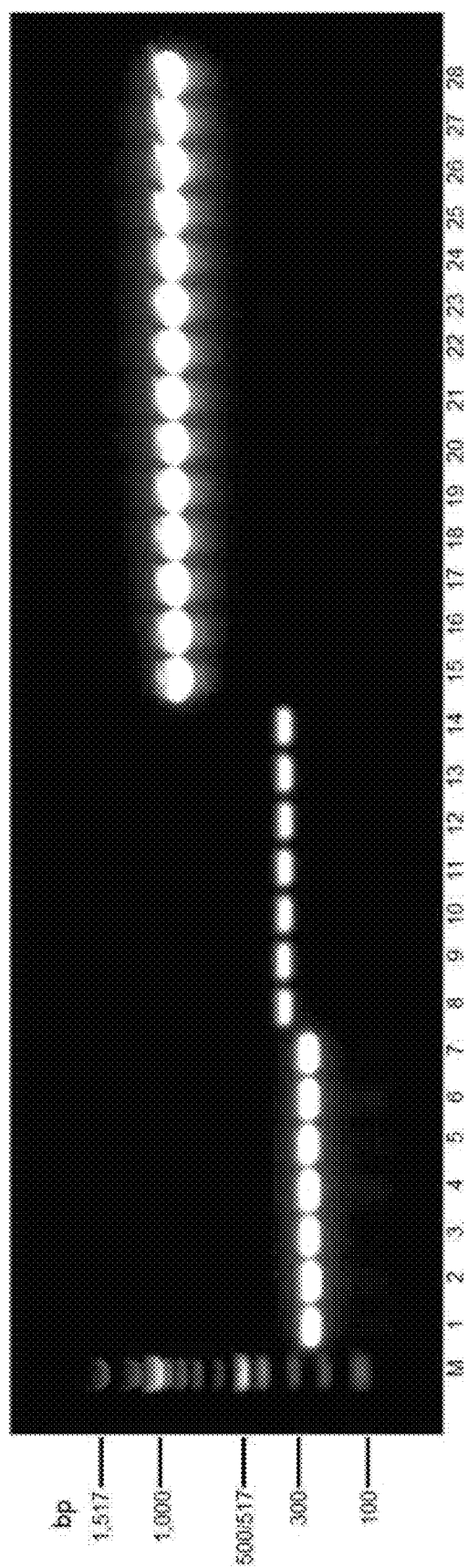
FIG. 4: Screening of E38A-L40F and E117K-L119F mutants. Lane M: 100 bp DNA ladder; lanes 1-7: PCR amplification of *E. coli* JM109 (DE3) RNase III E38A-L40F candidate mutants with primers Ecoli-E38A-1F and Ecoli-E38A-1R, and the expected fragment size is 256 bp; lanes 8-14: PCR amplification of *E. coli* JM109 (DE3) RNase III E117K-L119F candidate mutants with primers Ecoli-E117K-1F and Ecoli-E117K-1R, and the expected fragment size is 323 bp; lanes 15-21: PCR amplification of the same *E. coli* JM109 (DE3) RNase III E38A-L40F candidate mutants in lanes 1-7 with primers JD-5 and JD-3, and the expected fragment size is 879 bp; lanes 22-28: PCR amplification of the same *E. coli* JM109 (DE3) RNase III E117K-L119F candidate mutants in lanes 8-14 with primers JD-5 and JD-3, and the expected fragment size is 879 bp.

Notably, the <tetA-sacB> designation denotes the insertion of tetA-sacB gene by recombineering within the designated position. The E38<tetA-sacB> and E117<tetA-sacB> mutants were screening with by colony PCR with specific primers JD-5 and Tet-sacB-JD-R1 as shown in FIG. 3 and Table 1. The correct E38<tetA-sacB> and E117<tetA-sacB> mutants containing the recombination plasmid are grown overnight and are used to make electro-competent cell as generally described above. About 5 μL of 10 mmol/L Ecoli-oligo-E38A or Ecoli-oligo-E117K (See Table 1) is mixed with E38<tetA-sacB> or E117<tetA-sacB> competent cells, respectively, and then electroporation is performed under the same condition as described above. After electroporation, the cells are transferred to 1 mL of SOC at 30° C. and grown for over 5 hrs with aeration before plating on pre-warmed (37° C.) sacB agar plate and incubated for 2 days. The colony PCR with specific primer pairs Ecoli-E38A-1F and Ecoli-E38A-1R, and JD-5 and JD-3 generally identified in Table 1, are performed to screen the correct mutants E38A and E117K as shown in FIG. 4. The correct mutants were cultivated at 42° C. for overnight to eliminate pKD46 or pSIJ8 plasmid. All the mutants are confirmed by sequencing.

As generally shown in FIG. 1B, the present inventors demonstrated that the recombination plasmids pKD46 or pSIJ8 were transformed into *E. coli* JM109 (DE3) strain and positive colonies were confirmed by extraction the plasmid and the restriction digestion. As further shown in FIG. 3, the tetA-sacB cassette was inserted into *E. coli* RNase III E38 and E117 positions, respectively. The present inventors randomly picked up 7 individual colonies for colony PCR with identification primers JD-5 and Tet-sacB-JD-R, and the expected fragment sizes are 368 bp and 605 bp, respectively. As demonstrated in FIG. 5, the correct insertions of E38<tetA-sacB> or E117<tetA-sacB> were purified at least two times and then used for E38A and E117K mutant construction. Ecoli-oligo-E38A was used to construct E38A-L40F mutant; Ecoli-oligo-E117K was used to construct E117K-L119F mutant. PCR with primer pairs of Ecoli-E38A-1F and Ecoli-E38A-1R (the expected PCR size 256 bp), Ecoli-E117K-1F and Ecoli-E117K-1R (the expected PCR size 323 bp) were performed to screen the correct mutants.

Example 3: Construction of E38A and E117K RNase III Mutants

Figure 5:
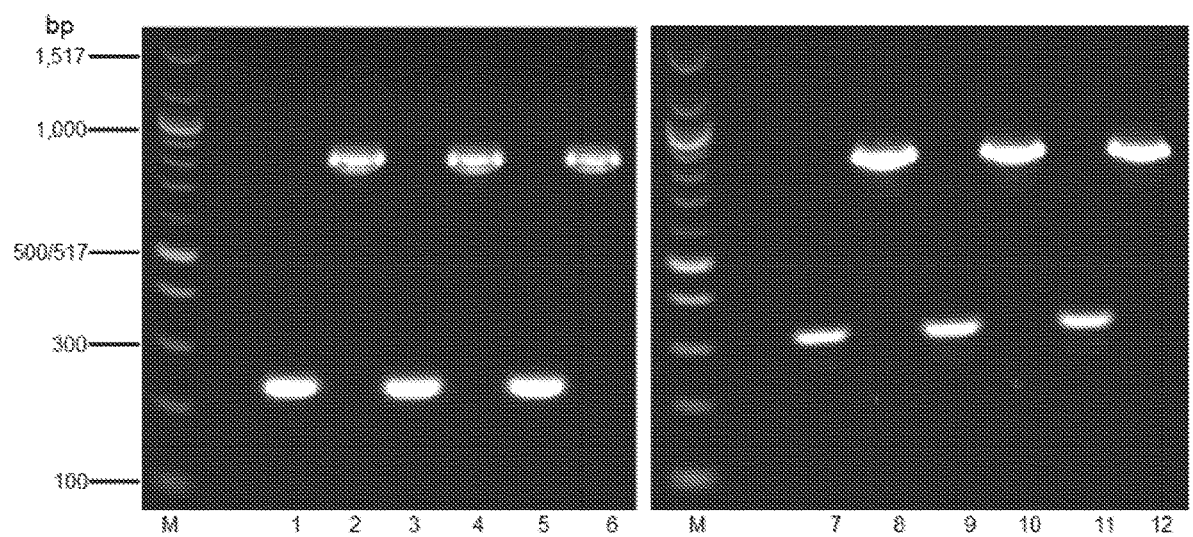
FIG. 5: Screening of E38A and E117K mutants. Lane M: 100 bp DNA ladder; lanes 1, 3, and 5: PCR amplification *E. coli* JM109 (DE3) RNase III E38A mutants with primers Ecoli-E38A-2F and Ecoli-E38A-1R, and the expected fragment size is 256 bp; lanes 2, 4, and 6: PCR amplification of the same possible *E. coli* JM109 (DE3) RNase III E38A-L40F mutants in lanes 1, 3, and 5 with primers JD-5 and JD-3, and the expected fragment size is 879 bp; lanes 7, 9, and 11: PCR amplification *E. coli* JM109 (DE3) RNase III E117K mutants with primers Ecoli-E117K-2F and Ecoli-E117K-1R, and the expected fragment size is 323 bp; lanes 8, 10, and 12: PCR amplification of the same possible *E. coli* JM109 (DE3) RNase III E117K mutants in lanes 7, 9, and 11 with primers JD-5 and JD-3, and the expected fragment size is 879 bp.

Similar to the example of the construction of the E38A-L40F mutants, as shown in FIG. 5 and Table 1, a E38A was constructed by the present inventors with Ecoli-oligo-E38A-F2 and then screened with identification primer pair Ecoli-E38A-2F and Ecoli-E38A-1R, and JD-5 and JD-3. As also shown in FIG. 5 and Table 1, an E117K mutant was also constructed with Ecoli-oligo-E117K-F2 and then screened with identification primer pair Ecoli-E117K-2F and Ecoli-E117K-1R, and JD-5 and JD-3.

Example 4: Construction of E65A RNase III Mutant

Figure 6:
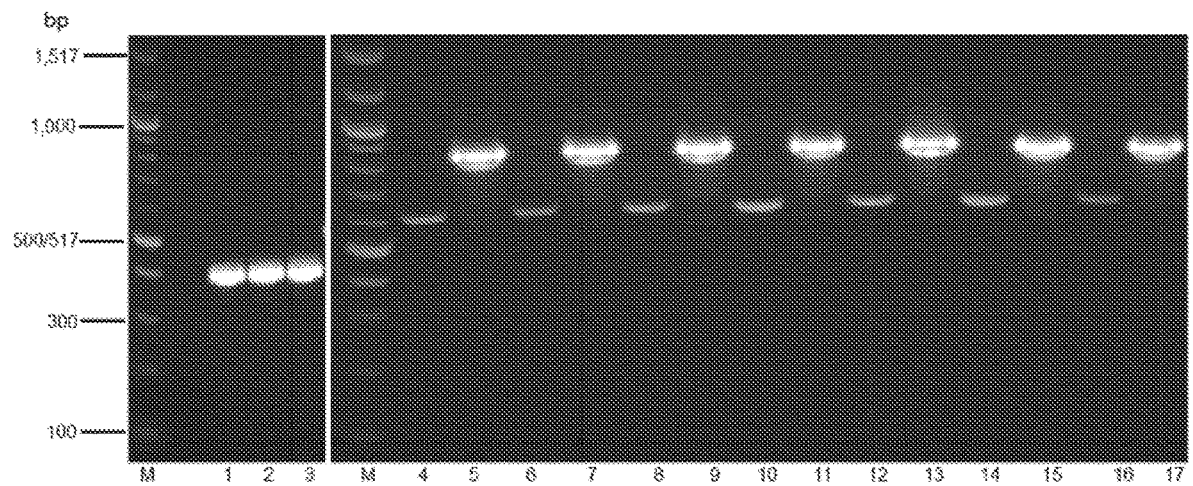
FIG. 6: Screening of E65A mutant. Lane M: 100 bp DNA ladder; lanes 1-3, PCR amplification of *E. coli* JM109 (DE3) RNase III E65<tetA-sacB> mutant with primers JD-5 and Tet-sacB-JD-R1, and the expected fragment size is 449 bp; lanes 4, 6, 8, 10, 12, 14, and 16: PCR amplification of *E. coli* JM109 (DE3) RNase III candidate E65A mutants with primers Ecoli-E65A-1F and JD-3, and the expected fragment size is 604 bp; lanes 5, 7, 9, 11, 13, 15, and 17: PCR amplification of the same *E. coli* JM109 (DE3) candidate RNase III 65A mutants in lanes 4, 6, 8, 10, 12, 14, and 16 with primers JD-5 and JD-3, and the expected fragment size is 879 bp.

Similar to example provided above related to the insertion of E38<tetA-sacB> into the bacterial chromosome, PCR was performed to clone tetA-sacB cassette with primer pair of Ecoli-tet-sacB-E65F1 and Ecoli-tet-sacB-E65R1. The tetA-sacB PCR fragments were used for homologous recombination to insert this cassette into *E. coli* JM109 (DE3) RNase III E65 position. The present inventors performed colony PCR was with primers JD-5 and Tet-sacB-JD-R, as identified in Table 1, to screen the correct insertion, and the expected fragment size is 449 bp (See FIG. 6). As again, shown in FIG. 6, Ecoli-oligo-E65A-F1 was used to construct the E65A mutant; primer pairs of Ecoli-E65A-1F and JD-3, JD-5 and JD-3 were used to screen the correct E65A candidate mutants.

Example 5: Construction of Bc-E58A and Bc-E137K RNase III Mutants

The present inventors demonstrated the construction of a *Bacillus cereus* 53522 E58A mutant, having three individual fragments: Pveg promoter fragment (primers Pveg-F1 and Pveg-R1 as shown in Table 2), Bc-E58A fragment I (primers Bc-E58A-F1 and Bc-E58A-R1 as shown in Table 2) and Bc-E58A (primers Bc-E58A-F2 and Bc-E58A-R2 as shown in Table 2). Fragment II was amplified by PCR using Q5® High-Fidelity DNA Polymerase. Each fragment was purified with QIAquick Gel Extraction Kit. Then the inventors assembled the three fragments with EcoRI-HF® digested pAD-WRKY-GHY7 plasmid to construct Bc-E58A mutant.

Figure 7:
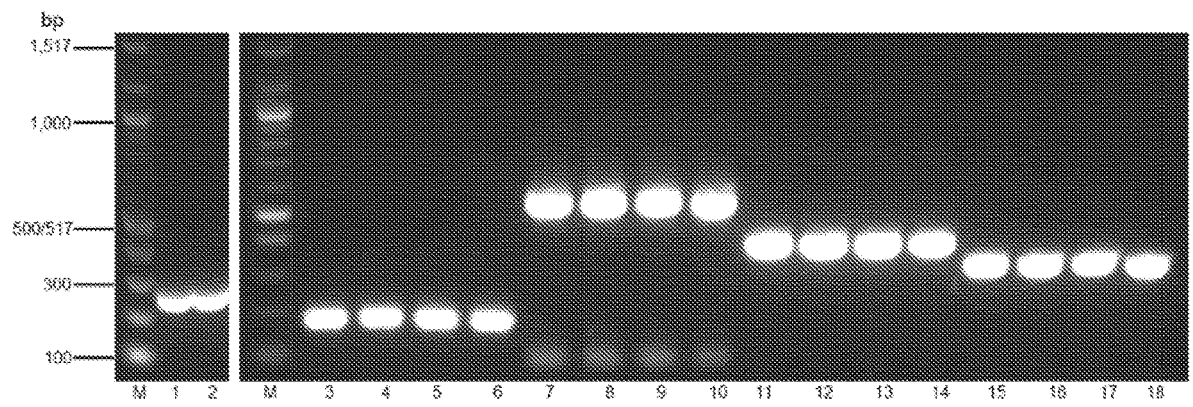
FIG. 7: Bc-E58A and Bc-E137K mutant construction. Lane M: 100 bp DNA ladder; lanes 1-2: PCR amplification using Pveg plasmid as template with primers Pveg-F1 and Pveg-R1, and the expected PCR size is 273 bp; lanes 3-6: PCR amplification using the genomic DNA of *B. cereus* 53522 as template with primers Bc-E58A-F1 and Bc-E58A-R1, and the expected PCR fragment size is 205 bp; lanes 7-10: PCR amplification using the genomic DNA of *B. cereus* 53522 as template with primers Bc-E58A-F2 and Bc-E58A-R2, and the expected PCR fragment size is 608 bp; lanes 11-14: PCR amplification using the genomic DNA of *B. cereus* 53522 as template with primers Bc-E58A-F1 and Bc-E137K-R1, and the expected PCR fragment size is 445 bp; lanes 15-18: PCR amplification using the genomic DNA of *B. cereus* 53522 as template with primers Bc-E137K-F1 and Bc-E58A-R2, and the expected PCR fragment size is 368 bp.

Similar to the construction of pAD-Bc-E58A, Bc-E137K fragment I (primers Bc-E58A-F1 and Bc-E137K-R1 as shown in Table 2) and Bc-E137K fragment II (primers Bc-E137K-F1 and Bc-E58A-R2 as shown in Table 2) are amplified by PCR using Q5® High-Fidelity DNA Polymerase, and then assembled with Pveg promoter fragment and EcoRI-HF® digested pAD-43-25 plasmid using NEBuilder® HiFi DNA Assembly Cloning Kit to construct Bc-E137K mutant as demonstrated in FIG. 7). The correct mutant was then amplified by primers pAD-E58A-F1 and pAD-E58A-R1 then ligated into XhoI digested pAD-WRKY-GHY7 plasmid, and the correct mutant is labelled as pAD-Bc-E137K.

Example 6: Construction of Additional Predicted RNase III Mutants

Figure 8:
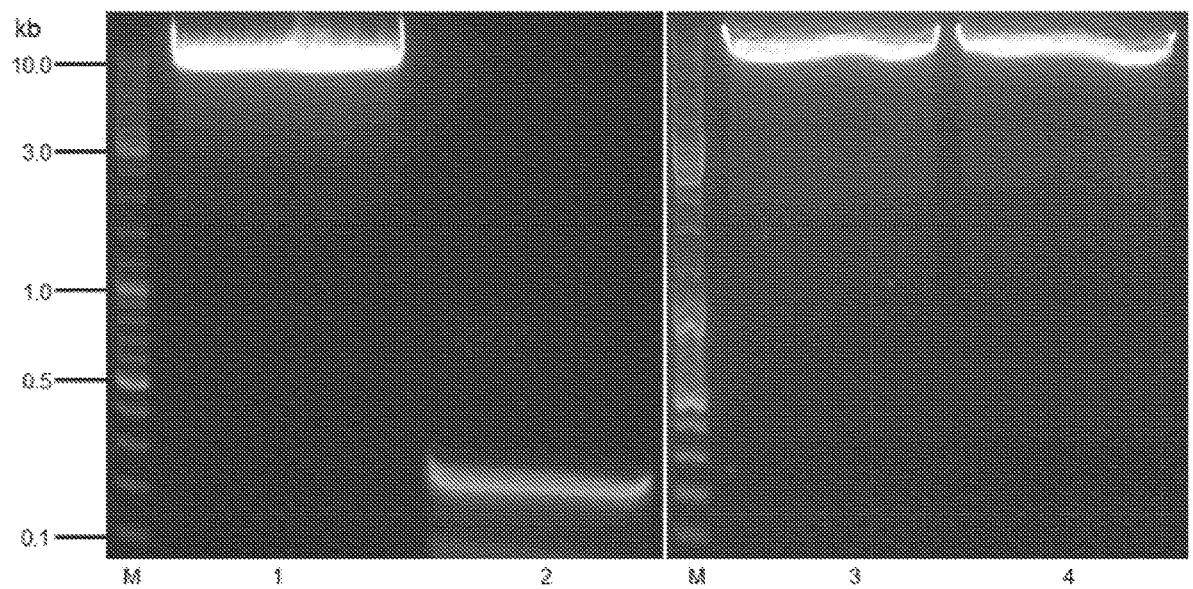
FIG. 8: Construction of the pAD-WRKY-GHY7-Pveg3 plasmid. Lane M: GeneRuler DNA Ladder Mix; lane 1: pAD-WRKY-GHY7 was digested with EcoRI-HF® restriction enzyme, and the expected fragment size is ~7.2 kb; lane 2: PCR amplification with primers Pveg-F2 and Pveg-R2 using Pveg plasmid as template, and the expected fragment size is 273 bp; lanes 3-4: pAD-WRKY-GHY7-Pveg3 plasmid was digested with XhoI and the expected fragment size is ~7.5 kb.
Figure 9:
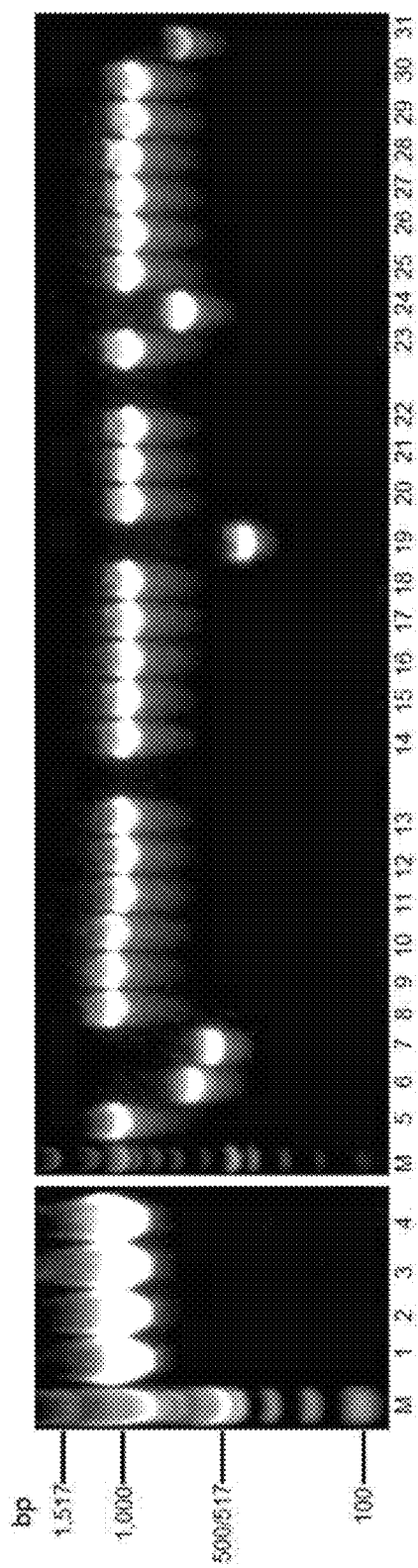
FIG. 9: PCR screening of the predicted RNase III mutants. Lane M: 100 bp DNA ladder; lanes 1-7: PCR amplification of HT115-Bs (*Bacillus subtilis*)-E59A mutants; lanes 8-10: PCR amplification of HT115-Bs-E138K mutants; lanes 11-13: PCR amplification of HT115-Ec-E38A-ΔSA mutants; lanes 14-16: PCR amplification of HT115-Ec-E38A-ΔSASS mutants; lanes 17-19: PCR amplification of HT115-Ec-E38A-ΔSA-ΔGPG mutants; lanes 20-21: PCR amplification of HT115-Ec-E38A-ΔSASS-ΔGPG mutants; lanes 23-25: PCR amplification of HT115-Ec-E38A-R107A-R108A mutants; lanes 26-28: PCR amplification of HT115-Ec-E38A-R107E-R108E mutants; lanes 29-30: PCR amplification of HT115-Ec-ΔSASS-ΔGPG mutants.

Using Pveg plasmid as the template, PCR was performed to clone the Pveg promoter fragment (primers Pveg-F2 and Pveg-R2 as identified in Table 2) containing the HindIII and XhoI restriction enzyme sites on each side with Pveg-F2 and Pveg-R2 primers. The purified Pveg promoter fragment was then ligated to EcoRI-HF® digested pAD-WRKY-GHY7, and the correct vector was labelled as pAD-WRKY-GHY7-Pveg3. The predicted RNase III mutant fragments were synthesized by a third party as would be readily identified by those of ordinary skill in the art. As shown in FIG. 8, each predicted RNase III mutant fragment was ligated to the XhoI digested pAD-WRKY-GHY7-Veg3 plasmid and followed by transformation into HT115 competent cell. The positive colonies were selected on LB plates containing tetracycline (final concentration 10 μg/mL) and chloramphenicol antibiotics (final concentration 12.5 μg/mL). Primers Eco-F1 and SglyA-R1, as identified in Table 2, were used to amplify the positive mutants, with the expected PCR size of ~1.0 kb as shown in FIG. 9. At least 2 plasmids were extracted for each predicted mutants and their sequences were independently confirmed.

Example 7: Construction of Additional Enterobacteria RNase III Mutants

Figure 10:
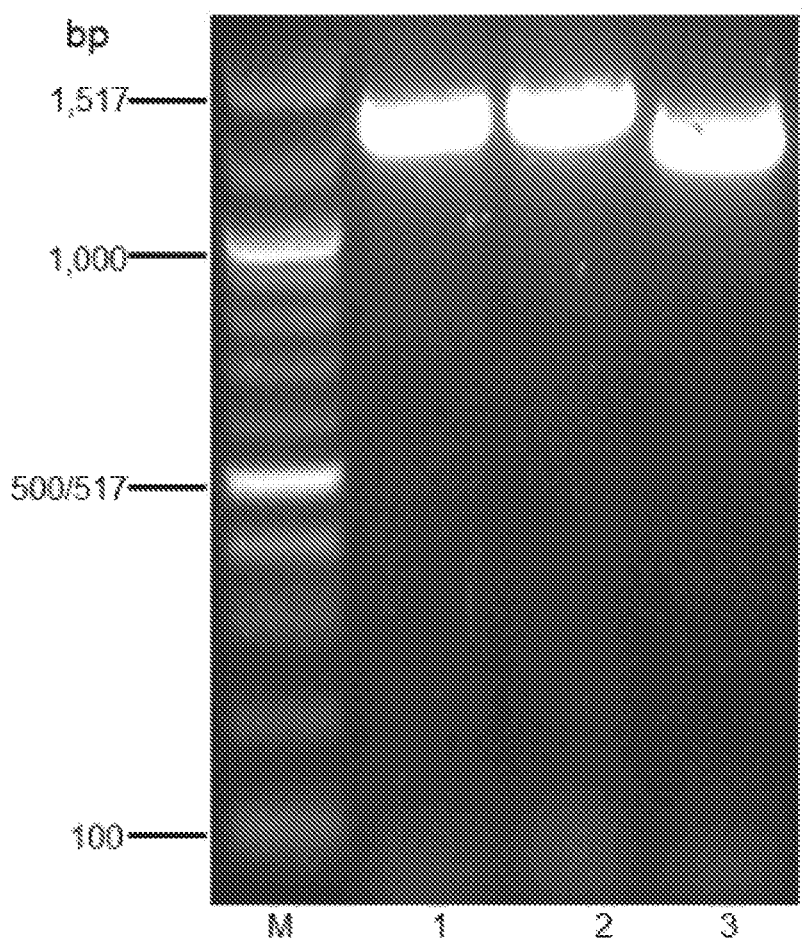
FIG. 10: The rnc gene of Enterobacteria Ae003, Ae073, and Ag001. Lane M: 100 bp DNA ladder; lane 1: PCR amplification of Ae003 with Ae-JD-5 and Ae-JD-3 primers, and the expected fragment size is ~1.2 kb; lane 2: PCR amplification of Ae073 with Ae-JD-5 and Ae-JD-3 primers, and the expected fragment size is ~1.2 kb; lane 3: PCR amplification of Ag001 with Ae-JD-5 and Ae-JD-3 primer identification, and the expected fragment size is ~1.2 kb.
Figure 11:
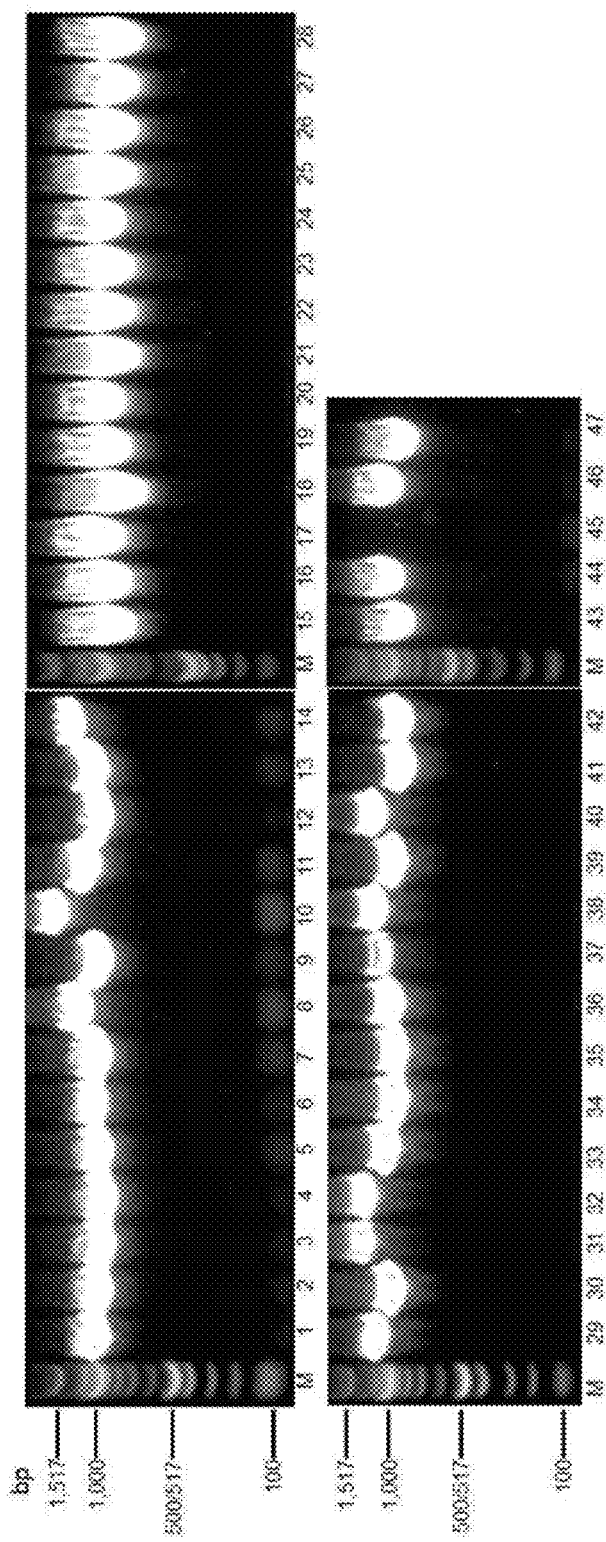
FIG. 11: PCR screening of the predicted RNase III mutants. Lane M: 100 bp DNA ladder; lanes 1-6: PCR amplification of HT115-Ae003-E38A mutants; lanes 7-14: PCR amplification of HT115-E38A-ΔS33-ΔS34-ΔK35 mutants; lanes 15-21: PCR amplification of HT115-Ag001-E38A-R107A-R108A mutant; lanes 22-28: PCR amplification of HT115-E30A mutant; lanes 29-35: PCR amplification of HT115-E38A-ΔA32-ΔS33-ΔS34-K35V mutants; lanes 36-42: PCR amplification of HT115-E38A-K12opt mutants; lanes 43-47: PCR amplification of HT115-E117D.
Figure 12:
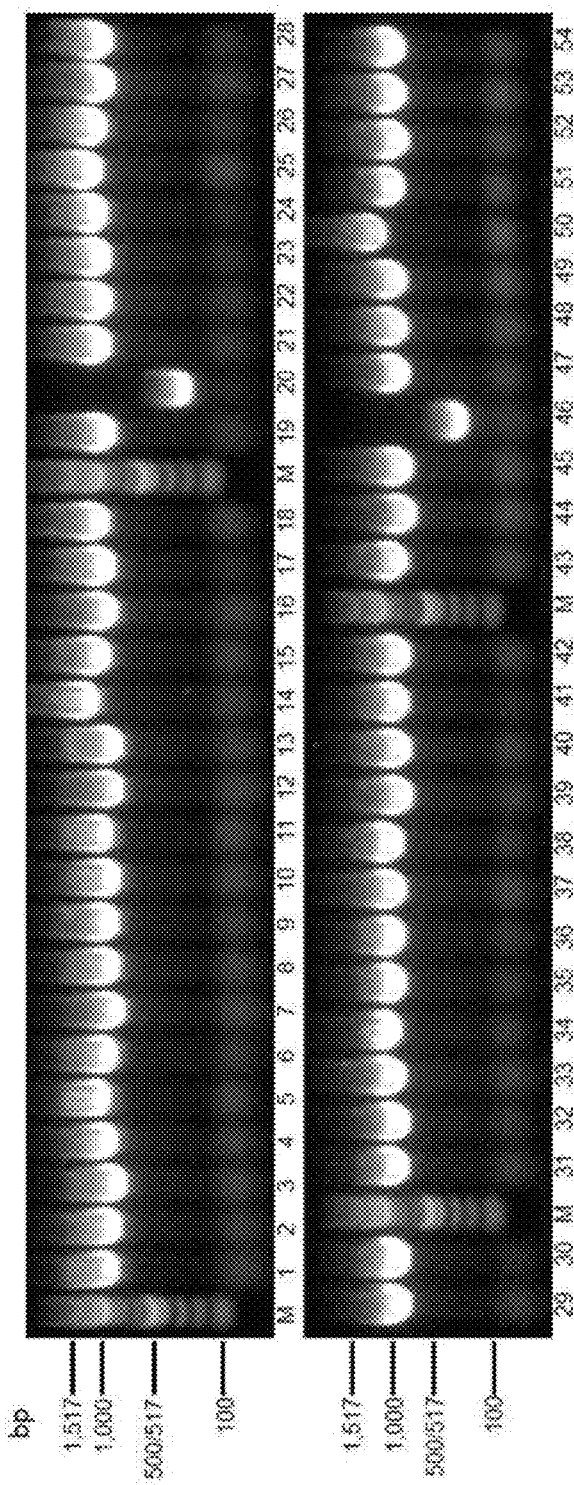
FIG. 12: PCR screening of the predicted RNase III mutants. Lane M: 100 bp DNA ladder; lanes 1-6: PCR amplification of HT115-E38A-ΔA32-ΔS33-ΔS34 mutants; lanes 7-12: PCR amplification of HT115-E38A-ΔS33-R107A-R108A mutants; lanes 13-18: PCR amplification of HT115-E38A-S33A-ΔS34-R107A-R108A mutants; lanes 19-24: PCR amplification of HT115-Ag001-E38A mutants; lanes 25-30: PCR amplification of HT115-Ae003-E38A-R107A-R108A mutants; lanes 31-36: PCR amplification of HT115-E30A-K12opt mutants; lanes 37-42: PCR amplification of HT115-E117Q mutants; lanes 43-48: PCR amplification of HT115-Q153P mutants; lanes 49-54: PCR amplification of HT115-D155E mutants.
Figure 13:
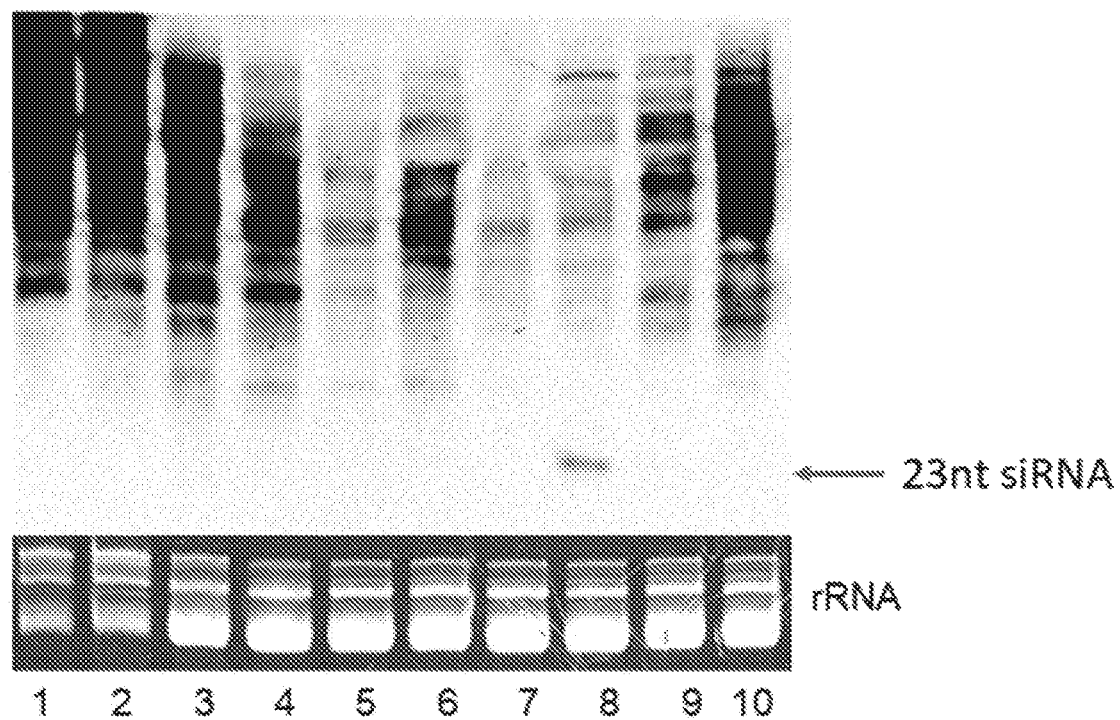
FIG. 13: Northern blot revealing small interfering RNA molecules of 23 nucleotides (upper panel). GelGreen® Nucleic Acid-stained rRNA served as loading controls in the gel prior to RNA transfer (lower panel). 6 μg total small RNA was loaded per well. Lane 1: The dsRNA extracted from HT115(DE3) (RNase III mutant) containing pAD-WRKY-GHY7 plasmid (TMV movement protein sRNA, and specifically a hpRNA), negative control; Lane 2: The dsRNA extracted from JM109 (wide-type E. coli) containing pAD-WRKY-GHY7 plasmid, negative control; Lane 3: The siRNA extracted from JM109 (wide-type E. coli) containing pAD-WRKY-GHY7 plasmid, negative control; Lane 4: The siRNA extracted from predicted mutant HT115-E38A-ΔSA; Lane 5: The siRNA extracted from predicted mutant HT115-E38A-ΔSASS; Lane 6: The siRNA extracted from predicted mutant HT115-E38A-ΔSA-ΔGPG; Lane 7: The siRNA extracted from predicted mutant HT115-E38A-ΔSASS-ΔGPG; Lane 8: The siRNA extracted from predicted mutant HT115-E38A-R107A-R108A; Lane 9: The siRNA extracted from predicted mutant HT115-E38A-R107E-R108E; Lane 9: The siRNA extracted from predicted mutant HT115-Ec-ΔSASS-ΔGPG.

To construct the Enterobacteria Ae003, and Ag001 RNase III mutants, the present inventors designed Ae-JD-5 and Ae-JD-3, as shown in Table 2, which have been configured to clone the complete rnc gene (encoding RNase III enzyme) of these three Enterobacteria strains as shown in FIG. 10. Based on the rnc gene sequences of Ae003 (SEQ ID NO. 18), Ae073 (SEQ ID NO. 19), and Ag001 (SEQ ID NO. 20), more RNase III mutants were designed by the present inventors. Primers Eco-F1 and SglyA-R1 as shown in Table 2, were used to amplify all the predicted RNase III mutants as shown in FIGS. 11 and 12, having an expected PCR size is ~1.0 kb. All RNase III mutants are generally summarized in Table 3. Notably, predicted RNase III mutants were synthesize by GenScript.

Example 8: Northern Blot Analyses of siRNA Production

Total siRNA extracted using the MiniVana microRNA kit according to the manufacturer's instruction and then run on a 15% polyacrylamide gel electrophoresis. Table 4 lists the probes used for Northern blot analysis. The DIG Oligonucleotide 3"-End Labeling Kit, 2nd generation was used to label the oligo fragments. TMVU1-MP-F6-21, TMVU1-MP-R6-21, TMVU1-MP-F7-21, and TMVU1-MP-R7-21, again as identified in Table 4, were used as DNA markers to indicate the 21nt siRNA. Norther blot analysis is demonstrated in FIGS. 13-15, and 17-18.

Example 9: qRT-PCR of dsRNA Cleavage Analysis

As demonstrated in FIG. 16, the present inventors performed qRT-PCR of dsRNA cleavage from different *E. coli* RNase III mutants. Specifically, in this embodiment, the present inventors demonstrated the following: HT115-pAD-WRKY-GHY7: HT115 strain containing pAD-WRKY-GHY7 plasmid (tetracycline and chloramphenicol resistance), and it cannot digest dsRNA.
HT115-pAD-WRKY-GHY7-E38A: HT115 strain containing pAD-WRKY-GHY7-E38A plasmid (tetracycline and chloramphenicol resistance), and E38A RNaseIII mutant can digest dsRNA into 26-29 bp small RNA; this strain can convert almost half of dsRNA into small RNAs compared to HT115-pAD-WRKY-GHY7, which cannot digest the dsRNA molecules. JM109-pAD-WRKY-GHY7: JM109 (DE3) RNaseIII E38A mutant containing pAD-WRKY GHY7 plasmid (chloramphenicol resistance), it can cleave dsRNA into 26-29 bp small RNA; this strain can convert almost 85% dsRNA into small RNAs compared to HT115-pAD-WRKY-GHY7. HT115-E38A-R107A-R108A: HT115 strain containing pAD-WRKY-GHY7-E38A-R107A-R108A plasmid (tetracycline and chloramphenicol resistance), and it can effectively cleave dsRNA into 22-23 bp small RNA; it can convert almost 95% dsRNA into small RNAs compared to HT115-pAD-WRKY-GHY7. HT115-E38A-R107E-R108E: HT115 strain containing pAD-WRKY-GHY7-E38A-R107E-R108E plasmid (tetracycline and chloramphenicol resistance), and it can cleave dsRNA into 26-29 bp small RNA and can convert almost 80% dsRNA into small RNA compared to HT115-pAD-WRKY-GHY7-E38A.

Example 10: siRNA Sequencing Analyses and Computational Estimation of Binding Free Energies Six samples (each three replicates, 18 in total) were sent to GENEWIZ (South Plainfield, N.J.) for sequencing. They consisted of: JM109 (wide-type *E. coli*), JM109-GHY7 (wide-type *E. coli* containing pAD-WRKY-GHY7 plasmid, targeting both TMV-GFP and movement protein gene), E38A-GHY7 (E38A mutant containing pAD-WRKY-GHY7 plasmid), E65A-GHY7 (E65A mutant containing pAD-WRKY-GHY7 plasmid), and E38A-R107A-R108A-GHY7 (E38A-R107A-R108A mutant containing pAD-WRKY-GHY7 plasmid), E38A-R107E-R108E (E38A-R107E-R108E containing pAD-WRKY-GHY7 plasmid).

Example 11: Methods of sRNA Analysis

Paired end Illumina sequencing data was received from GENEWIZ (South Plainfield, N.J.). Paired reads were first joined using the bbmerge script from BBMap. Adapters were removed and quality trimming was then performed using Trimmomatic 0.38 with end and sliding window quality trimming. Resulting reads were filtered to include only reads of size 18 nt through 30 nt. Filtered reads were then aligned to the GHY7 gene sequence using bowtie 1.2.2 allowing for 0 mismatches on "-best" parameter settings. Alignments were converted to bam format and indexed using samtools 1.7. To identify and count RNA features, each unique RNA sequence seen was designated as a "feature" and the collection was converted to GTF format using the GenomicAlignments 1.16.0 (and rtracklayer 1.40.6 packages in R. The number of copies of each feature in each sample was then used to build a feature counts table.

Further analyses on aligned read data were performed in R 3.5.1. Coverage plots were generated in R with the help of the Rsamtools 1.32.3 package. All other figures and plots were produced using the ggplot2 3.1.0 package. NMDS ordinations were built using the vegan package in R. Pairwise analyses including Kruskal-Wallis (KW) tests and MANOVA type analyses including PERMANOVA and ANOSIM were performed using the vegan package in R. MANOVA type analyses were performed using 1000 permutations. Post-hoc Dunn's (DMRT) tests were performed based on significant Kruskal-Wallis tests using the dunn.test 1.5.3 package in R.

Example 11: Methods for Estimation of Binding Free Energies Via Molecular Modeling and Simulations A homology model for WT *E. coli* RNase III was constructed using as template the crystal structure (PDB 2NUG)

of WT *Aquifex aeolicus* RNase III in complex with dsRNA (Modeller version 9.20 was used to generate five models of *E. coli* RNase III, from which the best homology model, as shown in FIG. 19, was chosen based on the lowest DOPE (Discrete Optimized Protein Energy) assessment score (Shen and Sali 2006). From this WT model, corresponding models for various mutant constructs (E38A, E65A, E38A/R107A/R108A, E38A/R107E/R108E, E38A/E65A, R107A/R108A, E65A/R107A/R108A, and E38A/E65A/R107A/R108A) were generated by introducing in silico point mutations with PyMOL version 2.3.

All-atom MD simulations in explicit solvent were then performed for each of the *E. coli* RNase III dimer models in complex with dsRNA (taken from PDB 2NUG) using the Amber ff99SB-ILDN force field. For each dsRNA-bound RNase III model, TIP3P water molecules were added to fill a rhombic dodecahedral box around the protein-RNA complex, with a minimum distance of 1.0 nm from any protein or RNA atom to any edge of the simulation box. Monovalent sodium and chloride ions were added to each system in order to neutralize the total charge and to reach a physiological ionic strength of 150 mM. Molecular dynamics (MD) simulations were then performed for each of these systems using the Amber MD engine version 16 that has been GPU-optimized for simulating explicit solvent systems. A cut-value of 8 Å was used for calculating short-range pairwise Coulomb and Lennard Jones interaction energies. Long-range electrostatics were calculated with the PME (Particle Mesh Ewald) method (Bonds containing hydrogen atoms were constrained using the SHAKE algorithm. A hydrogen mass repartitioning approach allowed the used of a 4-fs time step. Temperature was maintained at 310 K via Langevin dynamics with a collision frequency of 1.0 ps$^{-1}$, while isotropic pressure coupling was set at 1 bar using a Monte Carlo barostat with a relaxation time of 4.0 ps. Each system was energy minimized using steepest descent for 500 steps followed by conjugant gradient for 500 steps. This was followed by equilibration under NVT ensemble conditions at 310 K for 1 ns, and then by equilibration under NPT ensemble conditions at 1 bar and 310 K for 1 ns. All protein and RNA heavy atoms had position restraints of 5000 kcal/mol·Å$^2$ up to this point. These position restraints were removed for the production runs, which were performed for 250 ns per simulation.

To estimate absolute and relative (to WT) binding free energies for each *E. coli* RNase III model to dsRNA, the MM-GBSA (Molecular Mechanics—Generalized Born Surface Area) computational technique was employed via the MMPBSA.py tool. Changes in the conformational entropy were not considered here due to the high computational cost yet low predictive accuracy. The nonpolar portion of the desolvation energy was calculated using the LCPO (Linear Combinations of Pairwise Overlaps) method, with the surface tension and offset parameters set at the Amber-default values of 0.0072 and 0, respectively. The polar portion of the desolvation energy was computed and compared between five Generalized Born (GB) models and atomic radii parameters: i) GB1 with 'mbondi' radii, ii) GB2 with 'mbondi2' radii, iii) GB5 with 'mbondi2' radii, iv) GB7 with 'bondi' radii, and v) GB8 with 'mbondi3' radii. Prior to processing, all water molecules and monovalent ions were stripped from each frame from all simulation trajectories. The ionic strength was set at 150 mM in the GB calculations for each frame.

Tables

TABLE 1

Primers used for RNase III mutant construction.

| Primers | Sequences (5→3) | Purpose |
|---|---|---|
| Ecoli-tet-sacB38F1 | GAACTGTTGCAGCAGGCATTAACTCATCGTA GTGCCAGCAGTAAACATAACGAGTCCTAAT TTTTGTTGACACTCTATC (SEQ ID NO. 62) | PCR amplification of tetA-sacB cassette |
| Ecoli-tet-sac1338R1 | CGCATTGGCGATAACGTAGCTCAGAATAGAG TCGCCTAAAAATTCTAAACGATCAAAGGGA AAACTGTCCATATGC (SEQ ID NO. 63) | |
| Ecoli-oligo-E38A | G*T*A*G*CTCAGAATAGAGTCGCCTAAAAAT TCGAAGCGGGCATTGTGTTTACTGCTGGCAC TACGATGAGTTAATGC (SEQ ID NO. 64) | Construction of E38A-L40F mutant |
| Ecoli-E38A-1F | AGTAAACACAATGCCCGCTTC (256 bp) (SEQ ID NO. 65) | Identification of E38A-L40F mutant |
| Ecoli-E38A-1R | ATGCTTCGACGGTGTCGG (SEQ ID NO. 66) | |
| Ecoli-tet-sacB117F1 | CTTAAAAGCGGTGGATTTCGTCGTGAGTCAA TTCTCGCCGACACCGTCGAATCCTAATTTTT GTTGACACTCTATC (SEQ ID NO. 67) | PCR amplification of tetA-sacB cassette |
| Ecoli-tet-sacB117R1 | TAATTTCTCGACGGTTTGAATATCACTGTCGA GGAATACGCCACCAATTAATGCATCAAAGG GAAAACTGTCCATATGC (SEQ ID NO. 68) | |
| Ecoli-oligo-E117K | T*T*G*A*ATATCACTGTCGAGGAATACGCCA CCGATGAAAGCCTTCACGGTGTCGGCGAGAA TTGACTCACGACGAAA (SEQ ID NO. 69) | Construction of E117K-L119F mutant |
| Ecoli-E117K-1F | GACACCGTGAAGGCTTTCATC (323 bp) (SEQ ID NO. 70) | Identification of E117K-L119F mutant |
| Ecoli-E117K-1R | TTCAACGCCTGTTCGGC (SEQ ID NO. 71) | |
| Ecoli-oligo-E38A-F2 | G*T*A*G*CTCAGAATAGAGTCGCCTAAAAAT TCCAAGCGGGCATTGTGTTTACTGCTGGCAC TACGATGAGTTAATGC (SEQ ID NO. 72) | Construction of E38A mutant |

TABLE 1-continued

Primers used for RNase III mutant construction.

| Primers | Sequences (5→3) | Purpose |
|---|---|---|
| Ecoli-E38A-2F | AGTAAACACAATGCCCGCTTG (SEQ ID NO. 73) | Identification of E38A mutant |
| Ecoli-oligo-E117K-F2 | T*T*G*A*ATATCACTGTCGAGGAATACGCCACCGATCAAAGCCTTCACGGTGTCGGCGAGAATTGACTCACGACGAAA (SEQ ID NO. 74) | Construction of E117K mutant |
| Ecoli-E117K-2F | GACACCGTGAAGGCTTTGATC (SEQ ID NO. 75) | Identification of E117K mutant |
| Ecoli-tet-sacB E65F1 | AGCTACGTTATCGCCAATGCGCTTTATCACCGTTTCCCTCGTGTGGATGAATCCTAATTTTTGTTGACACTCTATC (SEQ ID NO. 76) | PCR amplification of tetA-sacB cassette |
| Ecoli-tet-sacB E65R1 | CGCCAGCGTATTGCCACGGACCAGCGTGGCGCGCATCCGGCTCATATCGCCATCAAAGGGAAAACTGTCCATATGC (SEQ ID NO. 77) | |
| Ecoli-oligo-E65A-F1 | C*A*G*C*GTGGCGCGCATCCGGCTCATATCGCCGGCGTCGACGCGGGGGAAACGGTGATAAAGCGCATTGGCGATAAC (SEQ ID NO. 78) | Construction of E65A mutant |
| Ecoli-E65A-1F | TTTCCCCCGCGTCGACGC (SEQ ID NO. 79) | Identification of E65A mutant |
| JD-5 | ACCGGTAAACTGAAACTGCA (SEQ ID NO. 80) | Identification of tetA-sacB cassette insertion into the bacterial chromosome |
| Tet-sacB-JD-R1 | TGGCAAGACTGGCATGATAAG (SEQ ID NO. 81) | |
| JD-3 | TGGAGATTTTCTGCCCCAG (SEQ ID NO. 82) | Used for identification of mutants |

Note:
*denoting the phosphorothioated primers.

TABLE 1b

Figure 14:
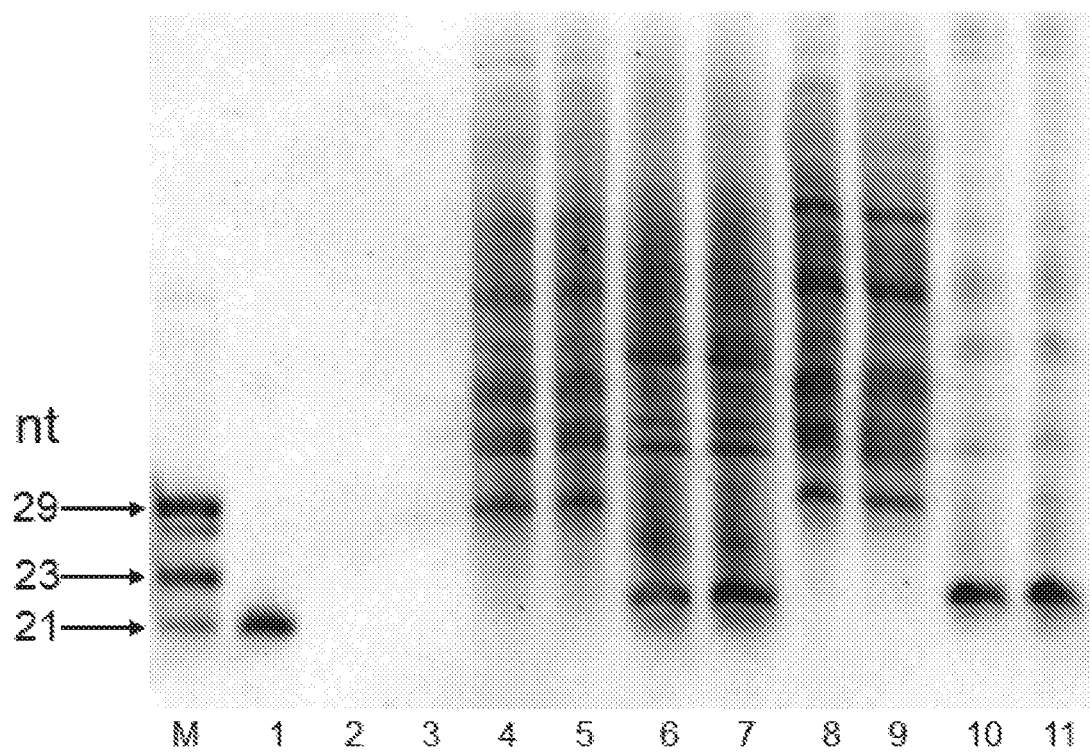
FIG. 14: Northern blot revealing small RNA nucleotides. 5 μg total small RNA was loaded per well. Lanes M: TMV movement protein gene specific single-stranded RNA marker and it consists of five ssRNA: 21, 23, 25, 27 and 29 bases. Lane 1: TMV movement protein gene specific single-stranded RNA marker, 21 base; Lanes 2-3: The total small RNAs extracted from wide-type E. coli JM109 (DE3); Lanes 4-5: The total small RNAs extracted from wide-type E. coli JM109 (DE3) containing pAD-WRKY-GHY7 plasmid; Lanes 6-7: The total small RNAs extracted from HT115-E38A-GHY7 (RNaseIII E38A constructed in the plasmid, code optimization with E. coli K12 strain); Lanes 8-9: The total small RNAs extracted from E. coli E65A mutant containing pAD-WRKY-GHY7 plasmid.

Single-stranded RNAs used for Northern blot of FIG. 14

| TMVU1-MP-F6-RNA21 | CAGUUCAAGGUCGUUCCCAAU (SEQ ID NO. 83) |
|---|---|
| TMVU1-MP-F7-RNA23 | UGAAGAUGUCAGCGGGUUUCUGU (SEQ ID NO. 84) |
| TMVU1-MP-R6-RNA25 | CCAGACGUUUUUCAUCGCGUCCUGG (SEQ ID NO. 85) |
| TMVU1-MP-R7-RNA27 | ACGACUUCUUCUGUAAGUUCCAUGGGC (SEQ ID NO. 86) |
| TMVU1-MP-F6-RNA29 | CAGUUCAAGGUCGUUCCCAAUUAUGCUAU (SEQ ID NO. 87) |

TABLE 2

Primers used for RNase III mutants constructed in a plasmid.

| Primers | Sequences (5→3) | Purpose |
|---|---|---|
| Pveg-F1 | ATCACGAGGCCCTTTCGTCTTCAAGGGAGTTCTGAGAATTGGTATGC (SEQ ID NO. 88) | PCR amplification of Pveg promoter |
| Pveg-R1 | ACACCTCCTTTACTACATTTATTGTACAACACGAGC (SEQ ID NO. 89) | |
| Pveg-F2 | ATCACGAGGCCCTTTCGTCTTCAAGAAGCTTGGAGTTCTGAGAATTGGTATGC (SEQ ID NO. 90) | PCR amplification of Pveg promoter |
| Pveg-R2 | ACGCGATCCCCGGGTACCGAGCTCGCTCGAGACACCTCCTTTACTACATTTATTGTACAACACGAGC (SEQ ID NO. 91) | |
| Bc-E58A-F1 | ACAATAAATGTAGTAAAGGAGGTGTATGCCGTACCGAAAATATAGAG (SEQ ID NO. 92) | PCR amplification of Bc-E58A fragment I |
| Bc-E58A-R1 | GAGGCGGGCGTTGTCTTCATGCGGTTTTTTCG (SEQ ID NO. 93) | |

TABLE 2-continued

Primers used for RNase III mutants constructed in a plasmid.

| Primers | Sequences (5→3) | Purpose |
| --- | --- | --- |
| Bc-E58A-F2 | ACCGCATGAAGACAACGCCCGCCTCGAATTTCTTG GAGATGCAGTATTG (SEQ ID NO. 94) | PCR amplification of Bc-E58A fragment II |
| Bc-E58A-R2 | ACGCGATCCCCGGGTACCGAGCTCGTTATAGTTGT TCTTTTAATTTTTTCAATG (SEQ ID NO. 95) | |
| Bc-E137K-R1 | GATGAAGGCCTTGAAGACATCCGCTAATAAAGCTG G (SEQ ID NO. 96) | PCR amplification of Bc-E137K fragment I |
| Bc-E137K-F1 | AGCGGATGTCTTCAAGGCCTTCATCGGTGCCCTTT ATCTTGATCAAG (SEQ ID NO. 97) | PCR amplification of Bc-E137K fragment II |
| pAD-E58A-F1 | CAATAAATGTAGTAAAGGAGGTGTCATGCCGTACC GAAAATATAGAG (SEQ ID NO. 98) | PCR amplification of Bc-E58A or Bc-137K mutants |
| pAD-E58A-R1 | GCGAGCTCGGTACCCGGGGATCGCGTTATAGTTGT TCTTTTAATTTTTTCAATG (SEQ ID NO. 99) | |
| Eco-F1 | ACGAGGCCCTTTCGTCTTCAA (SEQ ID NO. 100) | pAD43-25 vector primer |
| SglyA-R1 | CATGTTCGCTTGTGCACCA (SEQ ID NO. 101) | pAD43-25 vector primer |
| Ae-JD-5 | AACTAACGACATCCCCTGTCGT (SEQ ID NO. 102) | PCR amplification of bacterial mc gene |
| Ae-JD-3 | CGCAGCTTGTTCAGCACCAT (SEQ ID NO. 103) | |

TABLE 3

Summary of RNase III mutants

| Label | Mutations | Function | References |
| --- | --- | --- | --- |
| M-JM109-GHY7 | E38A-L40F | Mutations in the bacterial chromosome, produced discrete 26-29 bp siRNAs, higher $Mg^{2+}$ | This study |
| M-JM109-GHY7 | Ec-E38A | Mutations in the bacterial chromosome, produced discrete 26-29 bp siRNAs | This study (Xiao et al., 2009) |
| M-JM109-GHY7 | HT115-E38A-K12opt | Mutations constructed in a plasmid, produced discrete 26-29 bp siRNAs | This study |
| M-JM109-GHY7 | HT115-E38A-R107A-R108A | Mutations constructed in a plasmid, produced 22-23 bp siRNA | This study |
| M-JM109-GHY7 | HT115-Ag001-E38A | Mutations constructed in a plasmid, produced discrete 26-29 bp siRNA | This study |
| M-JM109-GHY7 | HT115-Ag001-E38A-R107A-R108A | Mutations constructed in a plasmid, produced 22-23 bp siRNA | This study |
| M-JM109-GHY7 | HT115-Ag1-E38A-R86C-R107A-R108A | Mutations constructed in a plasmid, produced 22-23 bp siRNA, the cleavage efficiency is decreased compared to Ag1-E38A-R107A-R108A | This study |
| M-JM109-GHY7 | HT115-Ae003-E38A | Mutations constructed in a plasmid, produced discrete 26-29 bp siRNA | This study |
| M-JM109-GHY7 | HT115-Ae003-E38A-R107A-R108A | Mutations constructed in a plasmid, produced 22-23 bp siRNA | This study |
| M-JM109-GHY7 | E65A | Mutations in the bacterial chromosome, 26-29 bp siRNAs | This study |
| M-JM109-GHY7 | E117K-L119F | Mutations in the bacterial chromosome, produced dsRNA binding without cleavage | This study |

TABLE 3-continued

Summary of RNase III mutants

| Label | Mutations | Function | References |
|---|---|---|---|
| M-JM109-GHY7 | E117K (rnc70) | Mutations in the bacterial chromosome, not functional in dsRNA cleavage but remained the dsRNA binding activity | (Cao et al., 2013, Dasgupta et al., 1998, Inada et al., 1989, Li & Nicholson, 1996) |
| M-JM109-GHY7 | HT115-E117Q | Mutations constructed in a plasmid, not functional in dsRNA cleavage but remained the dsRNA binding activity | (Sun & Nicholson, 2001) |
| M-JM109-GHY7 | HT115-E117D | Mutations constructed in a plasmid, not functional in dsRNA cleavage and binding | (Sun & Nicholson, 2001) |
| M-JM109-GHY7 | HT115-Q153P | Mutations constructed in a plasmid, not functional in dsRNA cleavage but remained the dsRNA binding activity | (Inada & Nakamura, 1995) |
| M-JM109-GHY7 | HT115-D155E | Mutations constructed in a plasmid, not functional in dsRNA cleavage and binding | (Inada & Nakamura, 1995) |
| M-JM109-GHY7 | HT115-E38A-ΔS33-R107A-R108A | Mutations constructed in a plasmid | This study |
| M-JM109-GHY7 | HT115-E38A-S33A-ΔS34-R107A-R108A | Mutations constructed in a plasmid | This study |
| M-JM109-GHY7 | HT115-E38A-ΔA32-ΔS33-ΔS34 | Mutations constructed in a plasmid | This study |
| M-JM109-GHY7 | HT115-E38A-ΔA32-ΔS33-ΔS34-K35V | Mutations constructed in a plasmid, possible 22-23 bp siRNA, the band is very weak, under the threshold sensitivity of Northern blot analysis | This study |
| M-JM109-GHY7 | HT115-E38A-ΔS33-ΔS34-ΔK35 | Mutations constructed in a plasmid, possible 22-23 bp siRNA, the band is very weak, under the threshold sensitivity of Northern blot analysis | This study |
| M-JM109-GHY7 | HT115-E30A | Mutations constructed in a plasmid, | This study |
| M-JM109-GHY7 | HT115-E30A-K12opt | Mutations constructed in a plasmid, | This study |

TABLE 4

Sequences of probes and primers for Northern blot analysis and qRT-PCR.

| Name | Sequence (5'→3') |
|---|---|
| TMVMP-probe1s | TCTCGGATCTTACTACACAGCAGCTGCAAAGAAAAGATTTCAGTT (SEQ ID NO. 104) |
| TMVMP-probe2as | TCCTGGGTGGTTATAGCATAATTGGGAACGACCTTGAACTGAAAT (SEQ ID NO. 105) |
| TMVMP-probe3s | CACCCAGGACGCGATGAAAAACGTCTGGCAAGTTTTAGTTAATAT (SEQ ID NO. 106) |
| TMVMP-probe4as | AGCGGACAGAAACCCGCTGACATCTTCACATTTCTAATATTAACT (SEQ ID NO. 107) |
| TMVMP-probe5s | CTGTCCGCTTTCTCTGGAGTTTGTGTCGGTGTGTATTGTTTATAG (SEQ ID NO. 108) |
| TMVMP-probe6as | CCCTCCGTCTCTCACGTTTGTAATCTTCTCTCTCAAACCTAATTT (SEQ ID NO. 109) |
| TMVMP-probe8as | CTTTGCAAGCCTGATCGACATAGGGACATCTTCCATGAACTCATC (SEQ ID NO. 110) |
| TMVMP-probe9s | GTTTCGATCTCGAACCGGAAAAAGAGTGATGTCCGCAAAGGGAA (SEQ ID NO. 111) |
| TMVU1-MP-F6-21 | CAGTTCAAGGTCGTTCCCAAT (SEQ ID NO. 112) |
| TMVU1-MP-R6-21 | GTTTTTCATCGCGTCCTGGGT (SEQ ID NO. 113) |
| TMVU1-MP-F7-21 | AAGATGTCAGCGGGTTTCTGT (SEQ ID NO. 114) |
| TMVU1-MP-R7-21 | CTTCTTCTGTAAGTTCCATGG (SEQ ID NO. 115) |
| TMVU1-MP-F4 | CCAGGACGCGATGAAAAACG (SEQ ID NO. 118) |
| TMVU1-MP-R4 | GGACAGAAACCCGCTGACAT (SEQ ID NO. 119) |
| Ec-16SrRNA-F1 | GAATGCCACGGTGAATACGTT (SEQ ID NO. 120) |
| Ec-16SrRNA-R1 | ACCCACTCCCATGGTGTGA (SEQ ID NO. 121) |

TABLE 5 sRNA processed an aligned read information

| Sample | Total_Counts | Aligned_Counts | Prop_aligned | Treatment1 | Treatment2 | Replicate |
|---|---|---|---|---|---|---|
| E38A-GHY7-1 | 19875890 | 1536686 | 0.077314072476755 | dsRNA | E38A | 1 |
| E38A-GHY7-2 | 20887014 | 1892870 | 0.090624251029851 | dsRNA | E38A | 2 |
| E38A-GHY7-3 | 22395853 | 2077999 | 0.092784990149739 | dsRNA | E38A | 3 |
| E38A-R107E-R108E-GHY7-1 | 17856798 | 696574 | 0.039008897339826 | dsRNA | R-mut-E | 1 |
| E38A-R107E-R108E-GHY7-2 | 13744950 | 481533 | 0.035033448648413 | dsRNA | R-mut-E | 2 |
| E38A-R107E-R108E-GHY7-3 | 17651690 | 944198 | 0.053490515639013 | dsRNA | R-mut-E | 3 |
| E38A-R107A-R108A-GHY7-1 | 19176252 | 1940405 | 0.10118791722178 | dsRNA | R-mut-A | 1 |
| E38A-R107A-R108A-GHY7-2 | 20952849 | 1611653 | 0.076918084027618 | dsRNA | R-mut-A | 2 |
| E38A-R107A-R108A-GHY7-3 | 19414442 | 1000029 | 0.051509541196188 | dsRNA | R-mut-A | 3 |
| E65A-GHY7-1 | 23274731 | 2929987 | 0.125887040327126 | dsRNA | E65A | 1 |
| E65A-GHY7-2 | 25562644 | 3354559 | 0.131228952685802 | dsRNA | E65A | 2 |
| E65A-GHY7-3 | 20078044 | 2373409 | 0.118209174160591 | dsRNA | E65A | 3 |
| JM109-1 | 16103261 | 12680 | 0.000787418150895 | no dsRNA | Wild-type | 1 |
| JM109-2 | 16273933 | 15556 | 0.000955884481029 | no dsRNA | Wild-type | 2 |
| JM109-3 | 17383893 | 15654 | 0.00090048874553 | no dsRNA | Wild-type | 3 |
| JM109-GHY7-1 | 13439306 | 413319 | 0.030754489852378 | dsRNA | Wild-type | 1 |
| JM109-GHY7-2 | 14691724 | 435247 | 0.029625318308457 | dsRNA | Wild-type | 2 |
| JM109-GHY7-3 | 18607641 | 476936 | 0.025631190971494 | dsRNA | Wild-type | 3 |

TABLE 6

Manova-type Test Results

| Test Type | Test Statistic | p-value |
|---|---|---|
| PERMANOVA | F = 191.19 | <0.01 |
| ANOSIM | R = ~1 | <0.01 |

TABLE 7

Summary of select RNase III mutations showing increase catalytic activity and preferred sRNA production results.

| SEQ ID NO. | Mutant | Rnase III | Results | Size Preference |
|---|---|---|---|---|
| 3, 4 | E38A | E. coli | Catalytic improvement | 26, 29 nt |
| 5, 6 | E65A | E. coli | Catalytic improvement | 26, 29 nt |
| 17 | E38A-E65A | E. coli | Catalytic improvement | 26, 29 nt |
| 7, 8 | E38A-R107A-R108A | E. coli | Catalytic improvement and cutting enhancement | 22, 23 nt |
| 11, 12 | E38A-R107A-R108A | Enterobacteriaceae Ag001 | Able to cut dsRNA | 22, 23 nt |
| 9, 10 | E38A | Enterobacteriaceae Ag001 | Able to cut dsRNA | 26, 29 nt |
| 15, 16 | E38A-R107A-R108A | Enterobacter Ae003 | Able to cut dsRNA | 22, 23 nt |
| 13, 14 | E38A | Enterobacter Ae003 | Able to cut dsRNA | 26, 29 nt |
| 37, 38 | Q153P | E. coli | Able to cut dsRNA | non-WT |
| 39, 40 | D155E | E. coli | Able to cut dsRNA | non-WT |
| 55, 56 | E58A | B. cereus | Able to cut dsRNA | non-WT* |
| 57, 58 | E59A | B. subtilus | Able to cut dsRNA | non-WT* |
| 27, 28 | E117K | E. coli | Binds but does not cut dsRNA | NA |

*nonWT cutting expected based on homology to E38 in RNase III in E. Coli

TABLE 8

Target pathogens in poultry populations

| Poultry | Viral diseases | Fungal diseases | Parasitic diseases |
|---|---|---|---|
| Chickens Turkeys Ducks | Avian influenza (has multiple strains or types, and is divided into three types: A, B, and C; H5N1 (genus: | Aspergillosis (genus: Aspergillus) | Coccidiosis (genus: Eimeria) |

TABLE 8-continued

Target pathogens in poultry populations

| Poultry | Viral diseases | Fungal diseases | Parasitic diseases |
|---|---|---|---|
| | Influenzavirus A) can cause a 90-100% mortality) | | |
| | Newcastle Disease (genus: Avulavirus) | Candidiasis (genus: *Candida*) | Ascaridia galli (genus: *Ascaridia*) |
| | Poxvirus diseases (mainly genera: Parapoxvirus, orthopoxvirus, yatapoxvirus, molluscipoxvirus) | | Blackhead (genus: *Histomonas*) |
| | Infectious bronchitis virus (IBV) (genus: Gammacoronavirus) | | Mites (genus: *Dermanyssus*) |
| | Laryngotracheitis (genus: Iltovirus) | | Lice (genus: *Menophon*) |
| | Marek's Disease (genus: Mardivirus) | | |
| | Eastern Equine Encephalitis (genus: Alphavirus) | | |
| | Hemorrhagic enteritis (genus: Siadenovirus) | | |
| | Viral arthritis (genus: Reovirus) | | |

TABLE 9

Target pathogens in bee populations

| Bees (*Apis Mellifera*) | Viral diseases | Fungal diseases | Parasitic diseases |
|---|---|---|---|
| | Dicistroviruses: | *Nosema apis* - causing nosemosis, the most common adult honey bees disease. | Varroa mite (*Varroa destructor*). |
| | Israeli acute paralysis virus (CCD (Colony Collapse Syndrom)) | *Ascosphaera apis* (causing Chalkbrood disease) | Honey bee tracheal mites (*Acarapis woodi*) |
| | Kashmir bee virus (CCD) | *Aspegillus* spp (causing Stonebrood disease) | Small hive beetles (*Aethina tumida*) - colonies damage in non-apis bees (bumble bees and stingless bees) |
| | Acute bee paralysis virus (CCD) | | *Tropilaelaps* mites (*Tropilaelaps mercedesae*) |
| | Black queen cell virus (affect pupae but not adults) | | Wax moth (Pyralidae: *Galleria Mellonela* and *Achroia grisella*) |
| | Aphid lethal paralysis virus (possibly CCD) | | |
| | Big sioux river virus (possibly CCD) | | |
| | Iflaviruses: | | |
| | Deformed wing virus | | |
| | Kakugo virus | | |
| | Varroa destructor virus-1 | | |
| | Sacbrood virus | | |
| | Thai/Chinese sacbrood virus | | |
| | Slow bee paralysis virus | | |
| | Baculovirus: | | |
| | Apis iridescent virus (CCD) | | |
| | Unclassified viruses: | | |
| | Cloudy wing virus | | |
| | Bee virus-X | | |
| | Bee virus-Y | | |
| | Lake Sinai virus-1 | | |
| | Lake Sinai virus-2 | | |

TABLE 10

Target pathogens in mammal populations
Mammal Diseases

Bluetongue Virus (BTV): Affects sheep, goats, deer and cattle
Bovine Viral Diarrhoea (BVD): Cattle and other ruminants
Calf Pneumonia: Caused by bovine Respiratory Syncytial Virus (bRSV), Parainfluenza III Virus (PI3)
Infectious Bovine Rhinotracheitis (IBR): Caused by Bovine Herpesvirus-1 (BHV-1)
Trypanosomosis (Sleeping disease): Affects both human and animals. Transmitted through tse-tse fly by flagellated protozoan parasites. The most economically important livestock disease of Africa
Foot-and-mouth disease Virus (FMDV): Highly contagious viral disease that affects cattle and swine. It also affects sheep, goats, deer, and other cloven-hooved ruminants
Rift Valley Fever Virus: viral disease of cattle and sheep. It is spread through infected mosquitoes. It can spread to humans either as airborne and/or by consuming raw milk, handling undercooked meat.
Rotaviral Diarrhoea: Caused by bovine Rotavirus
Parasitic gastro-enteritis (PGE or Gut worms): Affect cattle and is spread through parasites (abomasal worms)
Anaplasmosis: Vector-borne, infectious blood disease in cattle caused by the rickettsial parasites *Anaplasma marginale* and *Anaplasma centrale*. It is also known as yellow-bag or yellow-fever
Bovine Anaemia: Benign theileriosis is a tick-borne disease caused by intracellular blood parasites belonging to the *Theileria orientalis* group (BATOG)
Bovine Babesiosis (BB) (Redwater, Tick Fever): Tick-borne disease of cattle. Caused by single-cell parasites mainly *babesia bovis* and *babesia bigemma*, with *Rhipicephalus* ticks being the major vector
Rabies (Rabies Virus): Affects cattles and other ruminants. It is transmitted through the biting of infected animals such as foxes, dogs, skunks and raccoons, but mostly by bat carrying rabies
Neosporosis: Caused by the protozoan *Neospora caninum*. Affects cattle and sheep. Hosts are canids such as dogs and foxes
Schmallenberg Virus (SBV): New emerging disease. Affects cattle, bison, sheep and goats. Transmitted through midges and vertically from dam to offspring
Epizootic Hemorrhagic Disease Virus (EHDV): Most important infectious disease of white-tailed deer in US. It affects also antelope, mule and other deer species. Cattles are affected uncommonly. It is spread by biting flies (midges, gnats)
Lice: Affects cattle and other ruminants. Two types of lice, biting and sucking lice
Mange: Cattles and other ruminants are infected by mites
Pseudocowpox: Caused by a parapox virus. Most common infectious cause of teat disease in cattle
Ringworm: Skin disease affecting cattles and other ruminants. It is caused by *Trichophyton verrucosum* fungi
Ulcerative mammillitis: Affects cattle. Caused by a herpes virus (BHV-2)
Orf disease: Affects primarily sheep and goats. Caused by a parapox virus
Toxoplasmosis: Affects sheep. Caused by the *Toxoplasma gondii* parasite.
Coccidiosis: Affects cattle, sheep, chicken, dogs. Caused by Coccidian parasites
Myiasis: Parasitic infestation of a live mammal by fly larvae (maggots). Affects a wide range of mammals such as humans, sheep, horse, rabbit
Louping ill: Acute, tick-transmitted viral disease that affects goats, horses, dogs, pigs, sheep, cattle. Caused by louping ill virus
Echinococcosis: Affects sheep goats, cattle, swine, kangaroos, canids such as dogs and foxes, cats and wild felids. Parasitic disease caused by infection with tiny tapeworms of the genus *Echinococcus*
Fasciolosis: Parasitic worm infection caused by the common liver fluke *Fasciola hepatica* as well as by *Fasciola gigantica*. Affects human, sheep and cattle. It is a plant-borne zoonosis
Coenurosis: Parasitic infection that develops in the intermediate hosts of some tapeworm species (*Taenia multiceps*, *T. serialis*, *T. brauni*, or *T. glomerate*) and are caused by the coenurus, the larval stage of these worms. Affects sheep and other ungulates but also humans
Caprine arthritis and encephalitis Virus (CAEV): Affects goats
Chagas (TRYPANOSOMA CRUZI): Affects human, horses, cattle and goats. Caused by the parasites trypanosomes
Myxomatosis: Caused by Myxoma virus, transmitted through insect (mosquito, fly, fur mite) bites. Affects rabbits
Ear mites (canker): Affect rabbits. Caused by the mite *Psoroptes cuniculi*.
Encephalitozoon Cuniculi: Affect rabbits. Caused by single-cell protozoan parasite
Fleas: Ectoparasites
Rabbitpox: Affects rabbits. Caused by rabbitpox virus (RPXV)
Viral Haemorrhagic Disease: Also known as rabbit Haemorrhagic Disease (RHD). Caused by a calicivirus. Affects rabbits
Swine Influenza: Affects pigs. Cause by Swine Influenza virus (SIV)
Japanese B Encephalitis Virus (JE): Affects pigs, transmitted through mosquitoes
Trichinosis: Parasitic disease caused by roundworms of *Trichinella*. Affects pigs
Encephalomyocarditis Virus (EMCV): Affects pigs, transmitted through rats
Swine pox: Caused by Swine pox virus, affects pigs
Porcine Parvovirus Infection (PPV): Most common and important cause of infectious infertility in pigs
Porcine Respiratory Corona Virus Infection (PRCV)
Porcine Cytomegalovirus Infection (PCMV)
Transmissible Gastro Enteritis (TGE): Caused by a coronavirus. Affects pigs
Enteroviruses, SMEDI: gut-borne viruses. Affects pigs
Aujeszky's disease (AD): Caused by a herpes virus, affects pigs
Nipah virus disease: Causes death both in humans and pigs. New disease, first identified in Malaysia in 1998. Caused by a previously unknown paramyxovirus
Swine Fevers; African, Classical, Hog Cholera Viruses: Affects pigs
Teschen Disease: Caused by a porcine enterovirus serotype 1

In one preferred embodiment, the present invention may be applied to one or more of the following non-limiting group of plant viruses, including pathogen gene targets, generally referred to as gene targets, or essential genes, which would be recognized and available to those of ordinary skill in the art without undue experimentation:

TABLE 11

Target plant viral pathogens

| | Plant Pathogens | | |
|---|---|---|---|
| Virus diseases | hosts | Pathogenic genes | References |
| Tobacco mosaic virus (TMV) | Tobacco, tomato, and other solanaceous plants. It can infect well over 350 different species of plants. The typical symptoms are necrosis, mosaic, mottling, stunting, leaf curling, and yellowing of plant tissues, etc. | Replicase gene, movement protein, coat protein | (Scholthof, 2004) |
| Tomato spotted wilt virus (TSWV) | Over 1,000 species in over 85 families, including many vegetables, peanut, and tobacco, are susceptible to TSWV. The Solanaceae and Compositae families contain the largest numbers of susceptible plant species. TSWV also replicates in its insect vector, thrips (Thysanoptera: Thripidae) | glycoproteins (GPs), NSm protein, NSs protein, virus RNA genomic segment L, M, and S. | (Adkins, 2000) |
| Tomato yellow leaf curl virus (TYLCV) | Plants are stunted or dwarfed, can infect about 50 different plant species | V1, V2, C1, C2, C3, and C4. V1 protein | (Czosnek, 2007) |
| Cucumber mosaic virus (CMV) | Over 1,200 species in over 100 families of monocots and dicots, including many vegetables, ornamentals and woody and semi-woody plants | 1a, 2a and 2b protein, 3a and coat protein | (Palukaitis & García-Arenal, 2003) |
| Potato virus Y (PVY) | PVY mostly infects plants in the family Solanaceae. The Solanaceous plants include economically important ones like potato (*Solanum tuberosum*), as well as tomato, tomatillo, green pepper, chili pepper, eggplant, petunia and many weeds, such as the nightshades. Easily spread by aphids | P1, HC-Pro, P3, 6k1, CI, 6k2, NIa, Nib, and CP | (Jakab et al., 1997) |
| Cauliflower mosaic virus (CaMV) | CaMV infects mostly plants of the Brassicaceae family (such as cauliflower and turnip) but some CaMV strains (D4 and W260) are also able to infect Solanaceae species of the genera *Datura* and *Nicotiana*. | Movement protein, two aphid transmission factors (P2 and P3), the precursor of the capsid proteins (P4), and polyprotein precursor of proteinase, P5, and P6 protein. | (Hoh et al., 2010) |

TABLE 11-continued

Target plant viral pathogens

| | Plant Pathogens | | |
|---|---|---|---|
| Virus diseases | hosts | Pathogenic genes | References |
| African cassava mosaic virus (ACMV) | Mosaic, leaf distortion and stunting | AV1, AV2, AC1, AC2, AC3, AC4, BC1, BV1 | (Bock & Harrison, 1985, Fauquet & Fargette, 1990) |
| Plum pox virus (PPV) | *Prunus* species is widespread in most stone fruit-producing countries. Symptoms include chlorotic and necrotic ring patterns or blotches | P1, HC-Pro, P3, 6k1, CI, 6k2, NIa, Nib, and CP | (Cambra et al., 2006, Ilardi & Tavazza, 2015) |
| Brome mosaic virus (BMV) | BMV is cosmopolitan and found virtually wherever wheat is grown. | 1a, 2a, movement protein, coat protein | (Miller et al., 1985, Ahlquist & Janda, 1984) |
| Potato virus X (PVX) | PVX is found mainly in potatoes and is only transmitted mechanically, most infections are transmitted by farm machinery, can also be transmitted by vectors such as grasshoppers or biting insects | Replicase, TGB1, TGB2, TGB3, and coat protein | (Kaniewski et al., 1990, Kutnjak et al., 2014) |

Additional plant pathogens may include: Citrus tristeza virus, Barley yellow dwarf virus, Potato leafroll virus and Tomato and bushy stunt virus.

In one preferred embodiment, the present invention may be applied to one or more of the following non-limiting group of plant fungal pathogens, including pathogen gene targets, generally referred to as gene targets, or essential genes, which would be recognized and available to those of ordinary skill in the art without undue experimentation:

TABLE 12

Target fungal pathogens

| Plant Pathogens | hosts | Pathogenic genes | References |
|---|---|---|---|
| *Maguaporthe oryzae* | Rice (*Oryza sativa*). | MoABC1, MoMAC1 and MoPMK1, pathogenicity-related genes, effectors Iug6, Iug9 and Iug18, secreted proteins: MoMpg1, MoEmp1, MoMhp1, MoMsp1, MC69, and Slp1, etc. | (Zhu et al., 2017, Dong et al., 2015) |
| *Botrytis cinerea* | It can infect over 200 plant species, causing grey mould, evident on the surface as grey fluffy mycelium. Worldwide, it causes annual losses of $10 billion to $100 billion. | pathogenicity-related genes Bcpg1 and BMP1 | (Williamson et al., 2007, Have et al., 1998, Zheng et al., 2000) |
| *Puccinia* spp. | Wheat and barley, common barberry (and some additional *Berberis*, *Mahoberberis*, and *Mahonia* spp.) | pathogenicity-related genes MAPK, cyclophilin, and calcineurin regulatory subunit, and secreted proteins etc. | (Stakman & Levine, 1944, Chen, 2005, Rampitsch et al., 2006, Panwar et al., 2013, Cantu et al., 2013) |
| *Fusarium graminearum* | Wheat (*Triticum aestivum*), Durum Wheat (*Triticum durum*), Barley (*Hordeum vulgare*) and Oat (*Avena sativa*). F. | MAP1, and MAP kinase gpmk1 etc. | (Goswami & Kistler, 2004, Urban et al., 2003, Jenczmionka et al., 2003) |

TABLE 12-continued

Target fungal pathogens

| Plant Pathogens | hosts | Pathogenic genes | References |
|---|---|---|---|
| | *graminearum* parasitizes roots, stems, leaves, and reproductive tissues of many species of cereals and grasses. | | |
| *Fusarium oxysporum* | It can infect many plants including potato, sugarcane, garden bean, cowpea, Prickly pear, cultivated zinnia, pansy, Assam rattlebox, Baby's breath, and *Musa* sp. | MAP kinase, pg1, pathogenicity-related genes, secreted proteins, etc. | (Di Pietro et al., 2001, Michielse & Rep, 2009, Di Pietro & Roncero, 1998) |
| *Blumeria graminis* | Causing powdery mildew on grasses, including cereals. | effector gene Avra10, pathogenicity-related genes, secreted proteins, etc. | (Nowara et al., 2010, Bindschedler et al., 2016) |
| *Mycosphaerella graminicola* | causing septoria leaf blotch, in most years is the second most important disease of wheat in the United States | pathogenicity-related genes, MgSlt2, ABC Transporter Genes MgAtr1 and MgAtr2, secreted proteins, etc. | (Goodwin et al., 2011, Brading et al., 2002, Mehrabi et al., 2006, Zwiers & De Waard, 2000) |
| *Colletotrichum* spp. | black spot disease in the common bean plant | CMK1, and clk1, pathogenesis-related protein 10, secreted proteins, etc. | (Cannon et al., 2012, Takano et al., 2000, Dufresne et al., 1998, Lo et al., 1999) |
| *Ustilago maydis* | causing smut on maize and teosinte | pathogenicity-related genes, Kpp2, ukc1, secreted proteins, etc. | (Kämper et al., 2006, Müller et al., 1999, Dürrenberger & Kronstad, 1999) |
| *Melampsora lini* | flax rust | pathogenicity-related genes, secreted proteins, etc. | (Flor, 1956, Lawrence et al., 1981, Nemri et al., 2014) |

REFERENCES

The following references are hereby incorporated by reference into the specification:

[1] Blaszczyk J, Tropea J E, Bubunenko M, Routzahn K M, Waugh D S, Ji X. 2001. Crystallographic and modeling studies of RNase III suggest a mechanism for double-stranded RNA cleavage. Structure 9(12):1225-1236.

[2] Cao X, Lu Y, Di D, Zhang Z, Liu H, Tian L, Zhang A, Zhang Y, Shi L, Guo B. 2013. Enhanced virus resistance in transgenic maize expressing a dsRNA-specific endoribonuclease gene from *E. coli*. PloS one 8(4):e60829.

[2] Gan J, Tropea J E, Austin B P, Waugh D S, Ji X. 2006. Structural insight into the mechanism of double-stranded RNA processing by ribonuclease III. Cell 124(2):355-366.

[3] Li H, Nicholson A W. 1996. Defining the enzyme binding domain of a ribonuclease III processing signal. Ethylation interference and hydroxyl radical footprinting using catalytically inactive RNase III mutants. The EMBO Journal 15(6):1421.

[4] Sun W, Li G, Nicholson A W. 2004. Mutational analysis of the nuclease domain of *Escherichia coli* ribonuclease III. Identification of conserved acidic residues that are important for catalytic function in vitro. Biochemistry 43(41):13054-13062.

[5] Sun W, Nicholson A W. 2001. Mechanism of action of *Escherichia coli* ribonuclease III. Stringent chemical requirement for the glutamic acid 117 side chain and Mn2+ rescue of the Glu117Asp mutant. Biochemistry 40(16):5102-5110.

[6] Xiao J, Feehery C E, Tzertzinis G, Maina C V. 2009. *E. coli* RNase III (E38A) generates discrete-sized products from long dsRNA. RNA 15(5):984-991.

[7] Dasgupta, S., Fernandez, L., Kameyama, L., Inada, T., Nakamura, Y., Pappas, A. and Court, D. 1998. Genetic uncoupling of the dsRNA-binding and RNA cleavage activities of the *Escherichia coli* endoribonuclease RNase III—the effect of dsRNA binding on gene expression. Molecular Microbiology. 28: 629-640

[8] Doran, John J., Jeff M. Sands, and Richard T. Timmer. "Accurate mRNA size determination in northern analysis using individual lane size markers." Biotechniques 27, no. 2 (1999): 280-282.

[9] Inada, T., Kawakami, K., Chen, S.-M., Takiff, H. and Nakamura, Y. 1989. Temperature-sensitive lethal mutant of era, a G protein in *Escherichia coli*. Journal of Bacteriology. 171: 5017-5024.

[10] Inada, T. and Nakamura, Y. 1995. Lethal double-stranded RNA processing activity of ribonuclease III in the absence of suhB protein of *Escherichia coli*. Biochimie. 77: 294-302.

[11] Li, X.-T., Thomason, L. C., Sawitzke, J. A., Costantino, N. and Court, D. L. 2013. Positive and negative selection using the tetA-sacB cassette: recombineering and P1 transduction in *Escherichia coli*. Nucleic Acids Research. 41:

[12] Schmidt, G. W. and Delaney, S. K. 2010. Stable internal reference genes for normalization of real-time RT-PCR in tobacco (*Nicotiana tabacum*) during development and abiotic stress. Molecular Genetics and Genomics. 283: 233-241.

[13] Bolger, Anthony M., Marc Lohse, and Bjoern Usadel. "Trimmomatic: a flexible trimmer for Illumina sequence data." Bioinformatics 30, no. 15 (2014): 2114-2120.

[14] Bushnell B., Rood J., Singer E. (2017). BBMerge—Accurate paired shotgun read merging via overlap. PLOS ONE 12(10): e0185056.https://doi.org/10.1371/journal.pone.0185056

[15] Dinno, A. (2017). dunn.test: Dunn's Test of Multiple Comparisons Using Rank Sums. R package version 1.3.5. https://CRAN.R-project.org/package=dunn.test

[16] Hoffman G E, Schadt E E (2016). variancePartition: Interpreting drivers of variation in complex gene expression studies. BMC Bioinformatics, 17:483, doi:10.1186/s12859-016-1323-z

[17] Kolde, R., (2018). Pheatmap: pretty heatmaps. R package version, 1.0.10.

[18] Langmead, B. (2010). Aligning short sequencing reads with Bowtie. Current protocols in bioinformatics, 32(1), 11-7

[19] Lawrence, M., Gentleman, R. and Carey, V. (2009). rtracklayer: an R package for interfacing with genome browsers. Bioinformatics, 25(14), pp. 1841-1842.

[20] Lawrence, M., Huber, W., Pages, H., Aboyoun, P., Carlson, M., Gentleman, R., Morgan, M. T. and Carey, V. J. (2013). Software for computing and annotating genomic ranges. PLoS computational biology, 9(8), p. e1003118.

[21] Li, H., Handsaker, B., Wysoker, A., Fennell, T., Ruan, J., Homer, N., Marth, G., Abecasis, G. and Durbin, R., (2009). The sequence alignment/map format and SAMtools. Bioinformatics, 25(16), pp. 2078-2079.

[22] Love, M. I., Huber, W. and Anders, S. (2014). Moderated estimation of fold change and dispersion for RNA-seq data with DESeq2. Genome biology, 15(12), p. 550.

[23] Oksanen, J., Blanchet, F. G., Kindt, R., Legendre, P., Minchin, P. R., O'hara, R. B., Simpson, G. L., Solymos, P., Stevens, M. H. H. and Wagner, H. (2011). vegan: Community ecology package. R package version, pp. 117-118.

[24] Morgan, M., Pages, H., Obenchain, V. and Hayden, N. (2016). Rsamtools: Binary alignment (BAM), FASTA, variant call (BCF), and tabix file import. R package version, 1(0).

[25] R Core Team (2018). R: A language and environment for statistical computing. R Foundation for Statistical Computing, Vienna, Austria. URL https://www.R-project.org/.

[26] Ritchie, M E, Phipson, B, Wu, D, Hu, Y, Law, C W, Shi, W, and Smyth, G K (2015). limma powers differential expression analyses for RNA-sequencing and microarray studies. Nucleic Acids Research 43(7), e47.

[27] Wickham, H. (2016). ggplot2: elegant graphics for data analysis. Springer.

[28] Wu, Martin, Ling V. Sun, Jessica Vamathevan, Markus Riegler, Robert Deboy, Jeremy C. Brownlie, Elizabeth A. McGraw et al. "Phylogenomics of the reproductive parasite *Wolbachia pipientis* wMel (2004). a streamlined genome overrun by mobile genetic elements." PLoS biology 2, no. 3 e69

[29] Åqvist J, Wennerström P, Nervall M, Bjelic S, and Brandsdal B O. (2004). Molecular dynamics simulations of water and biomolecules with a Monte Carlo constant pressure algorithm. Chem Phys Lett. 384: 288-294.

[30] Bondi A. (1964). Can der Waals volumes and radii. J Phys Chem. 68: 441-451.

[31] Case D A, et al. (2017). Amber 2017. University of California, San Francisco.

[32] Chang C E, Chen W, and Gilson M K. (2005). Evaluating the accuracy of the quasiharmonic approximation. J Chem Theory Comput. 1: 1017-1028.

[33] Darden T, York D, and Pedersen L. Particle mesh Ewald: an Nlog(N) method for Ewald sums in large systems. J Chem Phys 98: 10089-10092.

[34] Feenstra K A, Hess B, and Berendsen H J C. (1999). Improving efficiency of large teime-scale molecular dynamics simulations of hydrogen-rich systems. J Comput Chem. 20: 786-798.

[35] Gan J, Shaw G, Tropea J E, Waugh D S, Court D L, and Ji X. (2008). A stepwise model for double-stranded RNA processing by ribonuclease III. Mol Microbiol. 67: 143-154.

[36] Hawkins G D, Cramer C J, and Truhlar D G. (1996). Parametrized models of aqueous free energies of solvation based on pairwise descreening of solute atomic charges from a dielectric medium. J Phys Chem. 100: 19824-19839.

[37] Jorgensen W L, Chandrasekhar J, Madura J D, Impey R W, and Klein M L. (1983). Comparison of simple potential functions for simulating liquid water. J Chem Phys. 79: 926-935.

[38] Kollman, P A, Massova I, Reyes C, Kuhn B, Huo S, Chong L, Lee M, Lee T, Duan Y, Wang W, Donini O, Cieplak P, Srinivasan J, Case D A, and Chetham T E. (2000). Calculating structures and free energies of complex molecules: combining molecular mechanics and continuum models. Acc Chem Res. 33: 889-897.

[39] Lindorff-Larsen K, Piana S, Palmo K, Maragakis P, Klepeis J L, Dror R O, and Shaw D E. (2010). Improved side-chain torsion potentials for the Amber ff99SB protein force field. Protein. 78: 1950-1958.

[40] Miller B R, McGee T D, Swails J m, Homeyer N, Gohlke H, and Roitberg A E. (2012). MMPBSA.py: an efficient program for end-state free energy calculations. J Chem Theory Comput. 8: 3314-3321.

[41] Mongan J, Simmerling C, McCammon J A, Case D A, and Onufriev A. (2007). Generalized Born with a simple, robust molecular volume correction. J Chem Theory Comput. 3: 156-159.

[42] Nguyen, H, Roe D R, and Simmerling C. (2013). Improved generalized Born solvent model parameters for protein simulations. J Chem Theory Comput. 9: 2020-2034.

[43] Onufriev A, Bashford D, and Case D A. (2004). Exploring protein native states and large-scale conformational changes with a modified generalized Born model. Proteins. 55: 383-394.

[44] Pastor R W, Brooks B R, and Szabo A. (1988). An analysis of the accuracy of Langevin and molecular dynamics algorithms. Mol Phys. 65: 1409-1419.

[45] Ryckaert J P, Cicotti G, and Berendsen H J C. (1977). Numerical integration of the Cartesian equations of motion with. Constraints: molecular dynamics of n-alkanes. J Comput Phys. 23: 327-341.

[46] Sali A and Blundell T L. (1993). Comparative protein modeling by satisfaction of spatial restraints. J Mol Biol. 234: 779-815.
[47] Salomon-Ferrer R, Case D A, and Walker R C. (2013). An overview of the Amber biomolecular simulation package. WIREs Comput Mol Sci. 3: 198-210.
[48] Shen M and Sali A. (2006). Statistical potential for assessment and prediction of protein structures. Protein Sci. 15: 2507-2524.
[49] Srinivasan J, Chetham T E, Cieplak P, Kollman P A, and Case D A. (1998). Continuum solvent studies of the stability of DNA, RNA, and phosphoramidate-DNA helices. J Am Chem Soc. 120: 9401-9409.
[50] Sun H, Duan L, Chen F, Liu H, Wang Z, Pan P, Zhu F, Zhang J Z H, and Hou T. (2018). Assessing the performance of MM/PBSA and MM/GBSA methods. 7. Entropy effects on the performance of end-point binding free energy calculation approaches. Phys Chem Chem Phys. 20: 14450-14460.
[51] The PyMOL Molecular Graphics System, version 2.3. (2018). Schrödinger, LLC.
[52] Tsui V and Case D A. (2001). Theory and application of the generalized Born solvation model in macromolecular simulations. Biopolymers. 56: 275-291.
[53] Wang J, Cieplak P, and Kollman P A. (2000). How well does a restrained electrostatic potential (RESP) model perform in calculating conformational energies of organic and biological molecules? J Comp Chem. 21: 1049-1074.
[54] Webb B and Sali A. (2016). Comparative protein structure modeling using MODELLER. Curr Protoc Bioinformatics. 54: 5.6.1-5.6.37.
[55] Weiser J, Shenkin P S, and Still W C. (1999). Approximate atomic surfaces from linear combinations of pairwise overlaps (LCPO). J Comput Chem. 20: 217-230.
[58] U.S. Pat. No. 7,695,964

```
                        SEQUENCE LISTINGS
         As noted above, the instant application contains a full Sequence
         Listing which has been submitted electronically in ASCII format
           and is hereby incorporated by reference in its entirety. The
           following sequences are further provided herewith and are hereby
                incorporated into the specification in their entirety:

SEQ ID NO. 1
DNA
E. coli-TM109(DE3)-wild-type-681bp
E. coli
ATGAACCCCATCGTAATTAATCGGCTTCAACGGAAGCTGGGCTACACTTTTAATCATCAGGAACTGTTGC
AGCAGGCATTAACTCATCGTAGTGCCAGCAGTAAACATAACGAGCGTTTAGAATTTTTAGGCGACTCTAT
TCTGAGCTACGTTATCGCCAATGCGCTTTATCACCGTTTCCCTCGTGTGGATGAAGGCGATATGAGCCGG
ATGCGCGCCACGCTGGTCCGTGGCAATACGCTGGCGGAACTGGCGCGCGAATTTGAGTTAGGCGAGTGCT
TACGTTTAGGGCCAGGTGAACTTAAAAGCGGTGGATTTCGTCGTGAGTCAATTCTCGCCGACACCGTCGA
AGCATTAATTGGTGGCGTATTCCTCGACAGTGATATTCAAACCGTCGAGAAATTAATCCTCAACTGGTAT
CAAACTCGTTTGGACGAAATTAGCCCAGGCGATAAACAAAAAGATCCGAAAACGCGCTTGCAAGAATATT
TGCAGGGTCGCCATCTGCCGCTGCCGACTTATCTGGTAGTCCAGGTACGTGGCGAAGCGCACGATCAGGA
ATTTACTATCCACTGCCAGGTCAGCGGCCTGAGTGAACCGGTGGTTGGCACAGGTTCAAGCCGTCGTAAG
GCTGAGCAGGCTGCCGCCGAACAGGCGTTGAAAAAACTGGAGCTGGAATGA SEQ ID NO. 2
Amino Acid
E. coli-JM109(DE3)-wild-type-226aa
E. coli
MNPIVINRLQRKLGYTFNHQELLQQALTHRSASSKHNERLEFLGDSILSYVIANALYHRFPRVDEGDMSR
MRATLVRGNTLAELAREFELGECLRLGPGELKSGGFRRESILADTVEALIGGVFLDSDIQTVEKLILNWY
QTRLDEISPGDKQKDPKTRLQEYLQGRHLPLPTYLVVQVRGEAHDQEFTIHCQVSGLSEPVVGTGSSRRK
AEQAAAEQALKKLELE SEQ ID NO. 3
DNA
M-JM109-GHY7-Ec-E38A
E. coli
ATGAACCCCATCGTAATTAATCGGCTTCAACGGAAGCTGGGCTACACTTTTAATCATCAGGAACTGTTGC
AGCAGGCATTAACTCATCGTAGTGCCAGCAGTAAACACAATGCCCGCTTGGAATTTTTAGGCGACTCTAT
TCTGAGCTACGTTATCGCCAATGCGCTTTATCACCGTTTCCCTCGTGTGGATGAAGGCGATATGAGCCGG
ATGCGCGCCACGCTGGTCCGTGGCAATACGCTGGCGGAACTGGCGCGCGAATTTGAGTTAGGCGAGTGCT
TACGTTTAGGGCCAGGTGAACTTAAAAGCGGTGGATTTCGTCGTGAGTCAATTCTCGCCGACACCGTCGA
AGCATTAATTGGTGGCGTATTCCTCGACAGTGATATTCAAACCGTCGAGAAATTAATCCTCAACTGGTAT
CAAACTCGTTTGGACGAAATTAGCCCAGGCGATAAACAAAAAGATCCGAAAACGCGCTTGCAAGAATATT
TGCAGGGTCGCCATCTGCCGCTGCCGACTTATCTGGTAGTCCAGGTACGTGGCGAAGCGCACGATCAGGA
ATTTACTATCCACTGCCAGGTCAGCGGCCTGAGTGAACCGGTGGTTGGCACAGGTTCAAGCCGTCGTAAG
GCTGAGCAGGCTGCCGCCGAACAGGCGTTGAAAAAACTGGAGCTGGAATGA SEQ ID NO. 4
Amino Acid
M-JM109-GHY7-Ec-E38A-aa
E. coli
MNPIVINRLQRKLGYTFNHQELLQQALTHRSASSKHNARLEFLGDSILSYVIANALYHRFPRVDEGDMSR
MRATLVRGNTLAELAREFELGECLRLGPGELKSGGFRRESILADTVEALIGGVFLDSDIQTVEKLILNWY
QTRLDEISPGDKQKDPKTRLQEYLQGRHLPLPTYLVVQVRGEAHDQEFTIHCQVSGLSEPVVGTGSSRRK
AEQAAAEQALKKLELE
```

SEQUENCE LISTINGS
As noted above, the instant application contains a full Sequence Listing which has been submitted electronically in ASCII format and is hereby incorporated by reference in its entirety. The following sequences are further provided herewith and are hereby incorporated into the specification in their entirety:

SEQ ID NO. 5
DNA
M-JM109-GHY7-E65A
E. coli
ATGAACCCCATCGTAATTAATCGGCTTCAACGGAAGCTGGGCTACACTTTTAATCATCAGGAACTGTTGC
AGCAGGCATTAACTCATCGTAGTGCCAGCAGTAAACATAACGAGCGTTTAGAATTTTTAGGCGACTCTAT
TCTGAGCTACGTTATCGCCAATGCGCTTTATCACCGTTTCCCCCGCGTCGACGCCGGCGATATGAGCCGG
ATGCGCGCCACGCTGGTCCGTGGCAATACGCTGGCGGAACTGGCGCGCGAATTTGAGTTAGGCGAGTGCT
TACGTTTAGGGCCAGGTGAACTTAAAAGCGGTGGATTTCGTCGTGAGTCAATTCTCGCCGACACCGTCGA
AGCATTAATTGGTGGCGTATTCCTCGACAGTGATATTCAAACCGTCGAGAAATTAATCCTCAACTGGTAT
CAAACTCGTTTGGACGAAATTAGCCCAGGCGATAAACAAAAGATCCGAAAACGCGCTTGCAAGAATATT
TGCAGGGTCGCCATCTGCCGCTGCCGACTTATCTGGTAGTCCAGGTACGTGGCGAAGCGCACGATCAGGA
ATTTACTATCCACTGCCAGGTCAGCGGCCTGAGTGAACCGGTGGTTGGCACAGGTTCAAGCCGTCGTAAG
GCTGAGCAGGCTGCCGCCGAACAGGCGTTGAAAAAACTGGAGCTGGAATGA SEQ ID NO. 6
Amino Acid
M-JM109-GHY7-E65A-aa
E. coli
MNPIVINRLQRKLGYTFNHQELLQQALTHRSASSKHNERLEFLGDSILSYVIANALYHRFPRVDAGDMSR
MRATLVRGNTLAELAREFELGECLRLGPGELKSGGFRRESILADTVEALIGGVFLDSDIQTVEKLILNWY
QTRLDEISPGDKQKDPKTRLQEYLQGRHLPLPTYLVVQVRGEAHDQEFTIHCQVSGLSEPVVGTGSSRRK
AEQAAAEQALKKLELE SEQ ID NO. 7
DNA
HT115-E38A-R107A-R108A
E. coli
ATGAACCCCATCGTAATTAATCGGCTTCAACGGAAGCTGGGCTACACTTTTAATCATCAGGAACTGTTGC
AGCAGGCATTAACTCATCGTAGTGCCAGCAGTAAACACAATGCCCGCTTGGAATTTTTAGGCGACTCTAT
TCTGAGCTACGTTATCGCCAATGCGCTTTATCACCGTTTCCCTCGTGTGGATGAAGGCGATATGAGCCGG
ATGCGCGCCACGCTGGTCCGTGGCAATACGCTGGCGGAACTGGCGCGCGAATTTGAGTTAGGCGAGTGCT
TACGTTTAGGGCCAGGTGAACTTAAAAGCGGTGGATTTGCCGCCGAGTCAATTCTCGCCGACACCGTCGA
AGCATTAATTGGTGGCGTATTCCTCGACAGTGATATTCAAACCGTCGAGAAATTAATCCTCAACTGGTAT
CAAACTCGTTTGGACGAAATTAGCCCAGGCGATAAACAAAAGATCCGAAAACGCGCTTGCAAGAATATT
TGCAGGGTCGCCATCTGCCGCTGCCGACTTATCTGGTAGTCCAGGTACGTGGCGAAGCGCACGATCAGGA
ATTTACTATCCACTGCCAGGTCAGCGGCCTGAGTGAACCGGTGGTTGGCACAGGTTCAAGCCGTCGTAAG
GCTGAGCAGGCTGCCGCCGAACAGGCGTTGAAAAAACTGGAGCTGGAATGA SEQ ID NO. 8
Amino Acid
HT115-E38A-R107A-R108A-aa
E. coli
MNPIVINRLQRKLGYTFNHQELLQQALTHRSASSKHNARLEFLGDSILSYVIANALYHRFPRVDEGDMSR
MRATLVRGNTLAELAREFELGECLRLGPGELKSGGFAAESILADTVEALIGGVFLDSDIQTVEKLILNWY
QTRLDEISPGDKQKDPKTRLQEYLQGRHLPLPTYLVVQVRGEAHDQEFTIHCQVSGLSEPVVGTGSSRRK
AEQAAAEQALKKLELE SEQ ID NO. 9
DNA
HT115-Ag001-E38A
Enterobacteriaceae Ag001
ATGAATCCCATCGTAATAAATAGGCTGCAGCGTAAGCTGGGCTACACTTTTCAACATCAGGATCTGTTGC
AACAGGCATTAACCCATCGGAGTGCCAGCAGCAAGCATAATGCCCGCTTGGAGTTTTTGGGTGACTCCAT
TCTCAGTTATGTCATCGCGAATGCGCTGTATCATCGTTTTCCTCGCGTAGATGAAGGCGACATGAGCCGC
ATGCGTGCGACGCTGGTGCGCGGCAATACGCTGGCGGAAATCGCCCGCGAGTTCGAACTGGGTGAGTGTC
TGCGTCTTGGGCCGGGTGAACTGAAAAGTGGCGGTTTCCGTCGCGAGTCGATTCTTGCTGATACCGTGGA
AGCGTTGATCGGTGGCGTCTTCCTCGACAGCGACATTCAGAACGTTGAGCGTTTGATTCTCTCGTGGTAT
CAGACCCGTCTCGACGAAATCAGTCCAGGCGACAAGCAAAAGATCCGAAAACGCGTCTGCAGGAGTACC
TGCAGGGTCGCCATCTGCCGCTGCCGTCGTATCTGGTGGTGCAGGTGCGTGGTGAAGCGCACGATCAAGA
ATTTACCATTCACTGTCAGGTGAGTGGCCTGCCTGAGCCTGTCGTAGGGACGGGCTCAAGCCGCCGTAAA
GCGGAACAGGCTGCGGCTGAGCAGGCACTGAAAAAGCTGGAGCTGGAATGA SEQ ID NO. 10
Amino Acid
HT115-Ag001-E38A-aa
Enterobacteriaceae Ag001
MNPIVINRLQRKLGYTFQHQDLLQQALTHRSASSKHNARLEFLGDSILSYVIANALYHRFPRVDEGDMSR
MRATLVRGNTLAEIAREFELGECLRLGPGELKSGGFRRESILADTVEALIGGVFLDSDIQNVERLILSWY
QTRLDEISPGDKQKDPKTRLQEYLQGRHLPLPSYLVVQVRGEAHDQEFTIHCQVSGLPEPVVGTGSSRRK
AEQAAAEQALKKLELE

SEQUENCE LISTINGS

As noted above, the instant application contains a full Sequence Listing which has been submitted electronically in ASCII format and is hereby incorporated by reference in its entirety. The following sequences are further provided herewith and are hereby incorporated into the specification in their entirety:

SEQ ID NO. 11
DNA
HT115-Ag001-E38A-R107A-R108A
Enterobacteriaceae Ag001
ATGAATCCCATCGTAATAAATAGGCTGCAGCGTAAGCTGGGCTACACTTTTCAACATCAGGATCTGTTGC
AACAGGCATTAACCCATCGGAGTGCCAGCAGCAAGCATAATGCCCGCTTGGAGTTTTTGGGTGACTCCAT
TCTCAGTTATGTCATCGCGAATGCGCTGTATCATCGTTTTCCTCGCGTAGATGAAGGCGACATGAGCCGC
ATGCGTGCGACGCTGGTGCGCGGCAATACGCTGGCGGAAATCGCCCGCGAGTTCGAACTGGGTGAGTGTC
TGCGTCTTGGGCCGGGTGAACTGAAAAGTGGCGGTTTCGCCGCCGAGTCGATTCTTGCTGATACCGTGGA
AGCGTTTGATCGGTGGCGTCTTCCTCGACAGCGACATTCAGAACGTTGAGCGTTTGATTCTCTCGTGGTAT
CAGACCCGTCTCGACGAAATCAGTCCAGGCGACAAGCAAAAAGATCCGAAAACGCGTCTGCAGGAGTACC
TGCAGGGTCGCCATCTGCCGCTGCCGTCGTATCTGGTGGTGCAGGTGCGTGGTGAAGCGCACGATCAAGA
ATTTACCATTCACTGTCAGGTGAGTGGCCTGCCTGAGCCTGTCGTAGGGACGGGCTCAAGCCGCCGTAAA
GCGGAACAGGCTGCGGCTGAGCAGGCACTGAAAAAGCTGGAGCTGGAATGA SEQ ID NO. 12
Amino Acid
HT115-Ag001-E38A-R107A-R108A-aa
Enterobacteriaceae Ag001
MNPIVINRLQRKLGYTFQHQDLLQQALTHRSASSKHNARLEFLGDSILSYVIANALYHRFPRVDEGDMSR
MRATLVRGNTLAEIAREFELGECLRLGPGELKSGGFAAESILADTVEALIGGVFLDSDIQNVERLILSWY
QTRLDEISPGDKQKDPKTRLQEYLQGRHLPLPSYLVVQVRGEAHDQEFTIHCQVSGLPEPVVGTGSSRRK
AEQAAAEQALKKLELE SEQ ID NO. 13
DNA
HT115-Ae003-E38A
Enterobacter Ae003
ATGAACCCCATCGTAATTAATCGGCTTCAACGGAAGCTGGGCTACACTTTTCATCATCAGGAGTTGTTGC
AACAGGCATTAACCCACCGCAGTGCCAGCAGCAAGCACAACGCCCGCCTGGAGTTTTTAGGCGACTCTAT
TTTAAGTTTCGTGATTGCGAATGCGCTTTATCATCGTTTCCCGCGCGTGGATGAAGGTGATATGAGCCGC
ATGCGTGCCACGCTGGTTCGGGGTAACACCCTTGCGGAAATCGCGCGCGAATTTGAACTGGGCGAATGTC
TGCGTCTTGGGCCGGGTGAACTGAAAAGCGGCGGCTTCCGTCGTGAATCTATTCTTGCCGATACGGTCGA
AGCATTAATTGGTGGTGTGTTCCTGGACAGCGATATCCAGACCGTCGAAAAGCTGATCCTGAACTGGTAT
CAGACCCGTCTGGACGAAATCAGCCCGGGCGATAAACAAAAAGATCCCAAAACGCGTCTGCAGGAATATT
TGCAGGGCCGTCATCTGCCGCTGCCATCTTATCTGGTGGTGCAGGTTCGTGGCGAAGCGCACGATCAGGA
ATTTACCATCCATTGCCAGGTCAGTGGCCTGAGTGAACCGGTGGTGGGCACAGGTTCAAGCCGTCGTAAG
GCTGAACAGGCTGCCGCCGAACAGGCGTTAAAAATGCTGGAGCTGGAATGA SEQ ID NO. 14
Amino Acid
HT115-Ae003-E38A-aa
Enterobacter Ae003
MNPIVINRLQRKLGYTFHHQELLQQALTHRSASSKHNARLEFLGDSILSFVIANALYHRFPRVDEGDMSR
MRATLVRGNTLAEIAREFELGECLRLGPGELKSGGFRRESILADTVEALIGGVFLDSDIQTVEKLILNWY
QTRLDEISPGDKQKDPKTRLQEYLQGRHLPLPSYLVVQVRGEAHDQEFTIHCQVSGLSEPVVGTGSSRRK
AEQAAAEQALKMLELE SEQ ID NO. 15
DNA
HT115-Ae003-E38A-R107A-R108A
Enterobacter Ae003
ATGAACCCCATCGTAATTAATCGGCTTCAACGGAAGCTGGGCTACACTTTTCATCATCAGGAGTTGTTGC
AACAGGCATTAACCCACCGCAGTGCCAGCAGCAAGCACAACGCCCGCCTGGAGTTTTTAGGCGACTCTAT
TTTAAGTTTCGTGATTGCGAATGCGCTTTATCATCGTTTCCCGCGCGTGGATGAAGGTGATATGAGCCGC
ATGCGTGCCACGCTGGTTCGGGGTAACACCCTTGCGGAAATCGCGCGCGAATTTGAACTGGGCGAATGTC
TGCGTCTTGGGCCGGGTGAACTGAAAAGCGGCGGCTTCGCCGCCGAATCTATTCTTGCCGATACGGTCGA
AGCATTAATTGGTGGTGTGTTCCTGGACAGCGATATCCAGACCGTCGAAAAGCTGATCCTGAACTGGTAT
CAGACCCGTCTGGACGAAATCAGCCCGGGCGATAAACAAAAAGATCCCAAAACGCGTCTGCAGGAATATT
TGCAGGGCCGTCATCTGCCGCTGCCATCTTATCTGGTGGTGCAGGTTCGTGGCGAAGCGCACGATCAGGA
ATTTACCATCCATTGCCAGGTCAGTGGCCTGAGTGAACCGGTGGTGGGCACAGGTTCAAGCCGTCGTAAG
GCTGAACAGGCTGCCGCCGAACAGGCGTTAAAAATGCTGGAGCTGGAATGA SEQ ID NO. 16
Amino Acid
HT115-Ae003-E38A-R107A-R108A-aa
Enterobacter Ae003
MNPIVINRLQRKLGYTFHHQELLQQALTHRSASSKHNARLEFLGDSILSFVIANALYHRFPRVDEGDMSR
MRATLVRGNTLAEIAREFELGECLRLGPGELKSGGFAAESILADTVEALIGGVFLDSDIQTVEKLILNWY
QTRLDEISPGDKQKDPKTRLQEYLQGRHLPLPSYLVVQVRGEAHDQEFTIHCQVSGLSEPVVGTGSSRRK
AEQAAAEQALKMLELE

SEQUENCE LISTINGS

As noted above, the instant application contains a full Sequence Listing which has been submitted electronically in ASCII format and is hereby incorporated by reference in its entirety. The following sequences are further provided herewith and are hereby incorporated into the specification in their entirety:

SEQ ID NO. 17
Amino Acid
RNase III E38A-E65A mutant
*E. coli*
MNPIVINRLQRKLGYTFNHQELLQQALTHRSASSKHNARLEFLGDSILSYVIANALYHRFPRVDAGDMSR
MRATLVRGNTLAELAREFELGECLRLGPGELKSGGFRRESILADTVEALIGGVFLDSDIQTVEKLILNWY
QTRLDEISPGDKQKDPKTRLQEYLQGRHLPLPTYLVVQVRGEAHDQEFTIHCQVSGLSEPVVGTGSSRRK
AEQAAAEQALKKLELE SEQ ID NO. 18
DNA
Ae003-mc
Enterobacteria
AACTAACGACATCCCCTGTCGTTGTGTATAGAATATTCCCCCGAAGTTTAAGGTTGGCCCTGCAAGGGTG
CCACGGCACACGAAACCGCGTTGGTTTTCTCAGGTCGGTTTCGTGTGCTGCATTTTTGACGCATTCATTT
ATTGGTATCGCATGAACCCCATCGTAATTAATCGGCTTCAACGGAAGCTGGGCTACACTTTTCATCATCA
GGAGTTGTTGCAACAGGCATTAACCCACCGCAGTGCCAGCAGCAAACATAATGAGCGTCTCGAGTTTTTA
GGCGACTCTATTTTAAGTTTCGTGATTGCGAATGCGCTTTATCATCGTTTCCCGCGCGTGGATGAAGGTG
ATATGAGCCGCATGCGTGCCACGCTGGTTCGGGGTAACACCCTTGCGGAAATCGCGCGCGAATTTGAACT
GGGCGAATGTCTGCGTCTTGGGCCGGGTGAACTGAAAAGCGGCGGCTTCCGTCGTGAATCTATTCTTGCC
GATACGGTCGAAGCATTAATTGGTGGTGTGTTCCTGGACAGCGATATCCAGACCGTCGAAAAGCTGATCC
TGAACTGGTATCAGACCCGTCTGGACGAAATCAGCCCGGGCGATAAACAAAAAGATCCCAAAACGCGTCT
GCAGGAATATTTGCAGGGCCGTCATCTGCCGCTGCCATCTTATCTGGTGGTGCAGGTTCGTGGCGAAGCG
CACGATCAGGAATTTACCATCCATTGCCAGGTCAGTGGCCTGAGTGAACCGGTGGTGGGCACAGGTTCAA
GCCGTCGTAAGGCTGAACAGGCTGCCGCCGAACAGGCGTTAAAAATGCTGGAGCTGGAATGAGCGAAGAA
AAGACCTATTGCGGATTTATTGCCATCGTCGGACGTCCGAACGTCGGCAAATCCACCCTGTTGAATAATC
TGCTTGGGCAGAAGATTTCTATCACCTCGCGTAAGGCTCAGACCACGCGTCACCGCATCGTCGGTATCCA
TACTGAAGGCGCGTATCAGGCGATCTACGTCGATACCCCGGGCCTGCACATGGAAGAGAAGCGTGCCATC
AACCGTCTGATGAACAAGGCGGCGAGCAGCTCGATTGGCGACGTGGAGCTGGTGATTTTCGTTGTGGAAG
GCACCCGCTGGACGCCTGACGACGAGATGGTGCTGAACAAGCTGCG SEQ ID NO. 19
DNA
Ae073-rnc
Enterobacteria
AACTAACGACATCCCCTGTCGTTGTGTATAGAATATTCCCCCGAAGTTTAAGGTTGGCCCTGCAAGGGTG
CCACGGCACACGAAACCGCGTTGGTTTTCTCAGGTCGGTTTCGTGTGCTGCATTTTTGACGCATTCATTT
ATTGGTATCGCATGAACCCCATCGTAATTAATCGGCTTCAACGGAAGCTGGGCTACACTTTTCATCATCA
GGAGTTGTTGCAACAGGCATTAACCCACCGCAGTGCCAGCAGCAAACATAATGAGCGTCTCGAGTTTTTA
GGCGACTCTATTTTAAGTTTCGTGATTGCGAATGCGCTTTATCATCGTTTCCCGCGCGTGGATGAAGGTG
ATATGAGCCGCATGCGTGCCACGCTGGTTCGGGGTAATACCCTTGCGGAAATCGCGCGCGAATTTGAGCT
GGGCGAATGTCTGCGTCTTGGGCCGGGTGAACTGAAAAGCGGCGGCTTCCGTCGTGAATCTATTCTTGCC
GATACGGTCGAAGCATTAATTGGTGGTGTGTTCCTGGACAGCGATATCCAGACCGTCGAAAAGCTGATCC
TGAACTGGTATCAGACCCGTCTGGACGAAATCAGCCCGGGCGATAAACAAAAAGATCCCAAAACGCGTCT
GCAGGAATATTTGCAGGGCCGTCATCTGCCGCTGCCATCTTATCTGGTGGTGCAGGTTCGTGGCGAAGCG
CACGATCAGGAATTTACCATCCATTGCCAGGTCAGTGGCCTGAGTGAACCGGTGGTGGGCACAGGTTCAA
GCCGTCGTAAGGCTGAACAGGCTGCCGCCGAACAGGCGTTAAAAATGCTGGAGCTGGAATGAGCGAAGAA
AAGACCTATTGCGGATTTATTGCCATCGTCGGACGTCCGAACGTCGGCAAATCCACCCTGTTGAATAATC
TGCTTGGGCAGAAGATTTCTATCACCTCGCGTAAGGCGCAGACCACGCGTCACCGCATCGTCGGTATCCA
TACTGAAGGCGCGTATCAGGCGATCTACGTCGATACACCGGGCCTGCACATGGAAGAGAAGCGTGCCATC
AACCGTCTGATGAACAAGGCGGCGAGCAGCTCAATTGGCGACGTGGAGCTGGTGATTTTCGTTGTGGAAG
GCACCCGCTGGACGCCGGACGACGAGATGGTGCTGAACAAGCTGCG SEQ ID NO. 20
DNA
Ag001-rnc
Enterobacteria
AACTAACGACATCCCCTGTCGTTGTGTATAGAATATTCCCGCCTTTAAAGATTGGCTCCCGAAAGGGAGC
CACGGCACACGAAACAGCGTTGGTTTCCTTTTTTCAGGTCTGTTCCGTGTGCTGAATAGTTGACGCATTC
ATTAATTTTGGTATCGCATGAATCCCATCGTAATAAATAGGCTGCAGCGTAAGCTGGCTACACTTTTCA
ACATCAGGATCTGTTGCAACAGGCATTAACCCATCGGAGTGCCAGCAGCAAACACAACGAGCGTCTTGAG
TTTTTGGGTGACTCCATTCTCAGTTATGTCATCGCGAATGCGCTGTATCATCGTTTTCCTCGCGTAGATG
AAGGCGACATGAGCCGCATGCGTGCGACGCTGGTGCGCGGCAATACGCTGGCGGAAATCGCCCGCGAGTT
CGAACTGGGTGAGTGTCTGCGTCTTGGGCCGGGTGAACTGAAAAGTGGCGGTTTCCGTCGCGAGTCGATT
CTTGCTGATACCGTGGAAGCGTTGATCGGTGGCGTCTTCCTCGACAGCGACATTCAGAACGTTGAGCGTT
TGATTCTCTCGTGGTATCAGACCCGTCTCGACGAAATCAGTCCAGGCGACAAGCAAAAAGATCCGAAAAC
GCGTCTGCAGGAGTACCTGCAGGGTCGCCATCTGCCGCTGCCGTCGTATCTGGTGGTGCAGGTGCGTGGT
GAAGCGCACGATCAAGAATTTACCATTCACTGTCAGGTGAGTGGCCTGCCTGAGCCTGTCGTAGGGACGG
GCTCAAGCCGCCGTAAAGCGGAACAGGCTGCGGCTGAGCAGGCACTGAAAAAGCTGGAGCTGGAATGAGC
GAAGAAAAAACGTATTGCGGCTTCGCGGCCATTGTTGGTCGCCCGAACGTCGGCAAATCCACGCTGCTGA
ATCAGCTGCTTGGGCAAAAAGTTTCCATTACCTCGCGTAAGGCGCAAACCACGCGCCACCGCATCATGGG

```
CATCCATACCGAAGGGCCATATCAGGCGATTTACGTCGATACCCCGGGGCTGCACATGGAAGAAAAACGC
GCCATTAACCGCCTGATGAACCGCGCGGCAAGCAGCTCCATCGGTGACGTTGAGCTGGTTATCTTCGTGG
TTGAAGGCACCCGCTGGACGCCGGATGATGAAATGGTGCTGAACAAGCTGCG
```

SEQ ID NO. 21
Amino Acid
Ag001-rnc
Enterobacteria

```
MNPIVINRLQRKLGYTFQHQDLLQQALTHRSASSKHNERLEFLGDSILSYVIANALYHRFPRVDEGDMSR
MRATLVRGNTLAEIAREFELGECLRLGPGELKSGGFRRESILADTVEALIGGVFLDSDIQNVERLILSWY
QTRLDEISPGDKQKDPKTRLQEYLQGRHLPLPSYLVVQVRGEAHDQEFTIHCQVSGLPEPVVGTGSSRRK
AEQAAAEQALKKLELE
```

SEQ ID NO. 22
Amino Acid
Ae003-rnc
Enterobacteria

```
MNPIVINRLQRKLGYTFHHQELLQQALTHRSASSKHNERLEFLGDSILSFVIANALYHRFPRVDEGDMSR
MRATLVRGNTLAEIAREFELGECLRLGPGELKSGGFRRESILADTVEALIGGVFLDSDIQTVEKLILNWY
QTRLDEISPGDKQKDPKTRLQEYLQGRHLPLPSYLVVQVRGEAHDQEFTIHCQVSGLSEPVVGTGSSRRK
AEQAAAEQALKMLELE
```

SEQ ID NO. 23
DNA
*Verrucomicrobia*-rnc-wide-type
*Verrucomicrobia*

```
ATGAATCCGCTCGAAGACCGCATCGGTTACAAGTTCCGCAACGCGCTGTTGCTGGAAGAAGCGCTCACGC
ATCCCAGTGTGAGGCACGAGCGCCTGGAGTTTTTGGGCGATGCGGTCCTGCAGCTCGTGATGACGGAACA
CCTGTTCGGGCATTTTAAGAAAGAAGCCGAAGGGACGCTGACGAAACTGCGCTCGCGGCTTGTTTCGCGG
GAGGCCCTCGCCGTTCATGCGGCGACGCTCGAACTGGGACGCTATCTGGCCGTCGGCCGCGGTGAGGACG
CGAGCGGCGGTCGCGAACGCAATTCGACGCTCGCCGACGCTTTCGAGGCGCTCGTCGGAGCGATCTATCT
CGATAGCGATCTGGCCACGGTGCGTCGCTTTATCCTGGATCAGGCAGCGGGCGATCTGGCGCAACTCGTC
GACGAACCGACCGATATCAACCCGAAGGGTCACCTGCAGGAATTGCTCCAGGCGATTTCGCCCCGCAGCC
CGGTTTACGAAGTGATTTCGCAGACCGGGCCGGAGCACGAAAAGACGTTTGTGATTCGCGCGGTTTGGGA
GGGCATCACGCTCGGGGAGGGAACCGGGCGAAGCAAGAAACAGGCGGAAACGGCCGCCGCCGAGGAGGCG
ATGCGGCAAAAGCGGTGGGAAACGGAAAAGACGTCGACCGCACCTTCTCGGTAG
```

SEQ ID NO. 24
Amino Acid
*Verrucomicrobia*-rnc-wide-type-aa
*Verrucomicrobia*

```
MNPLEDRIGYKFRNALLLEEALTHPSVRHERLEFLGDAVLQLVMTEHLFGHFKKEAEGTLTKLRSRLVSR
EALAVHAATLELGRYLAVGRGEDASGGRERNSTLADAFEALVGAIYLDSDLATVRRFILDQAAGDLAQLV
DEPTDINPKGHLQELLQAISPRSPVYEVISQTGPEHEKTFVIRAVWEGITLGEGTGRSKKQAETAAAEEA
MRQKRWETEKTSTAPSR
```

SEQ ID NO. 25
DNA
M-JM109-GHY7-E117K-L119F
*E. coli*

```
ATGAACCCCATCGTAATTAATCGGCTTCAACGGAAGCTGGGCTACACTTTTAATCATCAGGAACTGTTGC
AGCAGGCATTAACTCATCGTAGTGCCAGCAGTAAACATAACGAGCGTTTAGAATTTTTAGGCGACTCTAT
TCTGAGCTACGTTATCGCCAATGCGCTTTATCACCGTTTCCCTCGTGGATGAAGGCGATATGAGCCGG
ATGCGCGCCACGCTGGTCCGTGGCAATACGCTGGCGGAACTGGCGCGCGAATTTGAGTTAGGCGAGTGCT
TACGTTAGGGCCAGGTGAACTTAAAAGCGGTGGATTTCGTCGTGAGTCAATTCTCGCCGACACCGTGAA
GGCTTTCATCGGTGGCGTATTCCTCGACAGTGATATTCAAACCGTCGAGAAATTAATCCTCAACTGGTAT
CAAACTCGTTTGGACGAAATTAGCCCAGGCGATAAACAAAAGATCCGAAAACGCGCTTGCAAGAATATT
TGCAGGGTCGCCATCTGCCGCTGCCGACTTATCTGGTAGTCCAGGTACGTGGCGAAGCGCACGATCAGGA
ATTTACTATCCACTGCCAGGTCAGCGGCCTGAGTGAACCGGTGGTTGGCACAGGTTCAAGCCGTCGTAAG
GCTGAGCAGGCTGCCGCCGAACAGGCGTTGAAAAAACTGGAGCTGGAATGA
```

SEQ ID NO. 26
Amino Acid
M-JM109-GHY7-E117K-L119F-aa
*E. coli*

```
MNPIVINRLQRKLGYTFNHQELLQQALTHRSASSKHNERLEFLGDSILSYVIANALYHRFPRVDEGDMSR
MRATLVRGNTLAELAREFELGECLRLGPGELKSGGFRRESILADTVKAFIGGVFLDSDIQTVEKLILNWY
QTRLDEISPGDKQKDPKTRLQEYLQGRHLPLPTYLVVQVRGEAHDQEFTIHCQVSGLSEPVVGTGSSRRK
AEQAAAEQALKKLELE
```

SEQUENCE LISTINGS
As noted above, the instant application contains a full Sequence Listing which has been submitted electronically in ASCII format and is hereby incorporated by reference in its entirety. The following sequences are further provided herewith and are hereby incorporated into the specification in their entirety:

SEQ ID NO. 27
DNA
M-JM109-GHY7-Ec-E117K
*E. coli*
ATGAACCCCATCGTAATTAATCGGCTTCAACGGAAGCTGGGCTACACTTTTAATCATCAGGAACTGTTGC
AGCAGGCATTAACTCATCGTAGTGCCAGCAGTAAACATAACGAGCGTTTAGAATTTTTAGGCGACTCTAT
TCTGAGCTACGTTATCGCCAATGCGCTTTATCACCGTTTCCCTCGTGTGGATGAAGGCGATATGAGCCGG
ATGCGCGCCACGCTGGTCCGTGGCAATACGCTGGCGGAACTGGCGCGCGAATTTGAGTTAGGCGAGTGCT
TACGTTTAGGGCCAGGTGAACTTAAAAGCGGTGGATTTCGTCGTGAGTCAATTCTCGCCGACACCGTGAA
GGCTTTGATCGGTGGCGTATTCCTCGACAGTGATATTCAAACCGTCGAGAAATTAATCCTCAACTGGTAT
CAAACTCGTTTGGACGAAATTAGCCCAGGCGATAAACAAAAGATCCGAAAACGCGCTTGCAAGAATATT
TGCAGGGTCGCCATCTGCCGCTGCCGACTTATCTGGTAGTCCAGGTACGTGGCGAAGCGCACGATCAGGA
ATTTACTATCCACTGCCAGGTCAGCGGCCTGAGTGAACCGGTGGTTGGCACAGGTTCAAGCCGTCGTAAG
GCTGAGCAGGCTGCCGCCGAACAGGCGTTGAAAAAACTGGAGCTGGAATGA SEQ ID NO. 28
Amino Acid
M-JM109-GHY7-Ec-E117K-aa
*E. coli*
MNPIVINRLQRKLGYTFNHQELLQQALTHRSASSKHNERLEFLGDSILSYVIANALYHRFPRVDEGDMSR
MRATLVRGNTLAELAREFELGECLRLGPGELKSGGFRRESILADTVKALIGGVFLDSDIQTVEKLILNWY
QTRLDEISPGDKQKDPKTRLQEYLQGRHLPLPTYLVVQVRGEAHDQEFTIHCQVSGLSEPVVGTGSSRRK
AEQAAAEQALKKLELE SEQ ID NO. 29
DNA
HT115-E38A-K12opt
*E. coli*
ATGAATCCCATCGTGATCAACCGTTTGCAGCGTAAATTGGGTTACACTTTTAATCACCAAGAATTGCTGC
AGCAGGCATTGACCCACCGCTCCGCTTCGTCTAAACACAACGCCCGTCTGGAATTTTTAGGAGATTCGAT
CCTGTCTTACGTGATCGCCAATGCACTGTATCACCGCTTTCCCCGCTGGATGAAGGAGATATGAGCCGT
ATGCGTGCGACACTTGTGCGCGGAAATACCCTGGCAGAACTGGCGCGCGAGTTCGAACTGGGAGAGTGCT
TACGCCTTGGTCCCGGTGAGCTGAAGTCCGGGGGCTTTCGTCGTGAGTCTATCCTTGCTGATACGGTTGA
AGCTTTAATCGGGGGTGTATTTTTAGACTCAGACATCCAAACAGTGGAAAAGCTTATCTTGAACTGGTAC
CAAACCCGTTTAGATGAGATCAGCCCGGGGGACAAACAAAAGGACCCAAAGACACGTTTGCAGGATACC
TTCAAGGGCGTCACCTGCCCTTGCCAACATACTTAGTAGTCCAGGTACGTGGAGAAGCACACGATCAGGA
GTTCACCATTCACTGTCAAGTTAGTGGGTTATCCGAACCTGTAGTGGGGACGGGCTCCTCACGTCGCAAA
GCGGAACAAGCTGCGGCTGAACAGGCATTGAAAAAATTGGAGCTTGAGTAA SEQ ID NO. 30
Amino Acid
HT115-E38A-K12opt-aa
*E. coli*
MNPIVINRLQRKLGYTFNHQELLQQALTHRSASSKHNARLEFLGDSILSYVIANALYHRFPRVDEGDMSR
MRATLVRGNTLAELAREFELGECLRLGPGELKSGGFRRESILADTVEALIGGVFLDSDIQTVEKLILNWY
QTRLDEISPGDKQKDPKTRLQEYLQGRHLPLPTYLVVQVRGEAHDQEFTIHCQVSGLSEPVVGTGSSRRK
AEQAAAEQALKKLELE SEQ ID NO. 31
DNA
Ag001-E38A-R86C-R107A-R108A
Enterobacteriaceae
ATGAATCCCATCGTAATAAATAGGCTGCAGCGTAAGCTGGGCTACACTTTTCAACATCAGGATCTGTTGC
AACAGGCATTAACCCATCGGAGTGCCAGCAGCAAGCATAATGCCCGCTTGGAGTTTTTGGGTGACTCCAT
TCTCAGTTATGTCATCGCGAATGCGCTGTATCATCGTTTTCCTCGCGTAGATGAAGGCGACATGAGCCGC
ATGCGTGCGACGCTGGTCGCGGCAATACGCTGGCGGAAATCGCCTGCGAGTTCGAACTGGGTGAGTGTC
TGCGTCTTGGGCCGGGTGAACTGAAAAGTGGCGGTTTCGCCGCCGAGTCGATTCTTGCTGATACCGTGGA
AGCGTTGATCGGTGGCGTCTTCCTCGACAGCGACATTCAGAACGTTGAGCGTTTGATTCTCTCGTGGTAT
CAGACCCGTCTCGACGAAATCAGTCCAGGCGACAAGCAAAAAGATCCGAAAACGCGTCTGCAGGAGTACC
TGCAGGGTCGCCATCTGCCGCTGCCGTCGTATCTGGTGGTGCAGGTGCGTGGTGAAGCGCACGATCAAGA
ATTTACCATTCACTGTCAGGTGAGTGGCCTGCCTGAGCCTGTCGTAGGGACGGGCTCAAGCCGCCGTAAA
GCGGAACAGGCTGCGGCTGAGCAGGCACTGAAAAAGCTGGAGCTGGAATGA SEQ ID NO. 32
Amino Acid
Ag001-E38A-R86C-R107A-R108A-aa
Enterobacteriaceae
MNPIVINRLQRKLGYTFQHQDLLQQALTHRSASSKHNARLEFLGDSILSYVIANALYHRFPRVDEGDMSR
MRATLVRGNTLAEIACEFELGECLRLGPGELKSGGFAAESILADTVEALIGGVFLDSDIQNVERLILSWY
QTRLDEISPGDKQKDPKTRLQEYLQGRHLPLPSYLVVQVRGEAHDQEFTIHCQVSGLPEPVVGTGSSRRK
AEQAAAEQALKKLELE -continued SEQUENCE LISTINGS
As noted above, the instant application contains a full Sequence Listing which has been submitted electronically in ASCII format and is hereby incorporated by reference in its entirety. The following sequences are further provided herewith and are hereby incorporated into the specification in their entirety:

SEQ ID NO. 33
DNA
HT115-E117Q
E. coli
ATGAACCCCATCGTAATTAATCGGCTTCAACGGAAGCTGGGCTACACTTTTAATCATCAGGAACTGTTGC
AGCAGGCATTAACTCATCGTAGTGCCAGCAGTAAACATAACGAGCGTTTAGAATTTTTAGGCGACTCTAT
TCTGAGCTACGTTATCGCCAATGCGCTTTATCACCGTTTCCCTCGTGTGGATGAAGGCGATATGAGCCGG
ATGCGCGCCACGCTGGTCCGTGGCAATACGCTGGCGGAACTGGCGCGCGAATTTGAGTTAGGCGAGTGCT
TACGTTTAGGGCCAGGTGAACTTAAAAGCGGTGGATTTCGTCGTGAGTCAATTCTCGCCGACACGGTGCA
GGCTTTGATCGGTGGCGTATTCCTCGACAGTGATATTCAAACCGTCGAGAAATTAATCCTCAACTGGTAT
CAAACTCGTTTGGACGAAATTAGCCCAGGCGATAAACAAAAGATCCGAAAACGCGCTTGCAAGAATATT
TGCAGGGTCGCCATCTGCCGCTGCCGACTTATCTGGTAGTCCAGGTACGTGGCGAAGCGCACGATCAGGA
ATTTACTATCCACTGCCAGGTCAGCGGCCTGAGTGAACCGGTGGTTGGCACAGGTTCAAGCCGTCGTAAG
GCTGAGCAGGCTGCCGCCGAACAGGCGTTGAAAAAACTGGAGCTGGAATGA SEQ ID NO. 34
Amino Acid
HT115-E117Q-aa
E. coli
MNPIVINRLQRKLGYTFNHQELLQQALTHRSASSKHNERLEFLGDSILSYVIANALYHRFPRVDEGDMSR
MRATLVRGNTLAELAREFELGECLRLGPGELKSGGFRRESILADTVQALIGGVFLDSDIQTVEKLILNWY
QTRLDEISPGDKQKDPKTRLQEYLQGRHLPLPTYLVVQVRGEAHDQEFTIHCQVSGLSEPVVGTGSSRRK
AEQAAAEQALKKLELE SEQ ID NO. 35
DNA
HT115-E117D
E. coli
ATGAACCCCATCGTAATTAATCGGCTTCAACGGAAGCTGGGCTACACTTTTAATCATCAGGAACTGTTGC
AGCAGGCATTAACTCATCGTAGTGCCAGCAGTAAACATAACGAGCGTTTAGAATTTTTAGGCGACTCTAT
TCTGAGCTACGTTATCGCCAATGCGCTTTATCACCGTTTCCCTCGTGTGGATGAAGGCGATATGAGCCGG
ATGCGCGCCACGCTGGTCCGTGGCAATACGCTGGCGGAACTGGCGCGCGAATTTGAGTTAGGCGAGTGCT
TACGTTTAGGGCCAGGTGAACTTAAAAGCGGTGGATTTCGTCGTGAGTCAATTCTCGCCGACACGGTGGA
CGCTTTGATCGGTGGCGTATTCCTCGACAGTGATATTCAAACCGTCGAGAAATTAATCCTCAACTGGTAT
CAAACTCGTTTGGACGAAATTAGCCCAGGCGATAAACAAAAGATCCGAAAACGCGCTTGCAAGAATATT
TGCAGGGTCGCCATCTGCCGCTGCCGACTTATCTGGTAGTCCAGGTACGTGGCGAAGCGCACGATCAGGA
ATTTACTATCCACTGCCAGGTCAGCGGCCTGAGTGAACCGGTGGTTGGCACAGGTTCAAGCCGTCGTAAG
GCTGAGCAGGCTGCCGCCGAACAGGCGTTGAAAAAACTGGAGCTGGAATGA SEQ ID NO. 36
Amino Acid
HT115-E117D-aa
E. coli
MNPIVINRLQRKLGYTFNHQELLQQALTHRSASSKHNERLEFLGDSILSYVIANALYHRFPRVDEGDMSR
MRATLVRGNTLAELAREFELGECLRLGPGELKSGGFRRESILADTVDALIGGVFLDSDIQTVEKLILNWY
QTRLDEISPGDKQKDPKTRLQEYLQGRHLPLPTYLVVQVRGEAHDQEFTIHCQVSGLSEPVVGTGSSRRK
AEQAAAEQALKKLELE SEQ ID NO. 37
DNA
HT115-Q153P
E. coli
ATGAACCCCATCGTAATTAATCGGCTTCAACGGAAGCTGGGCTACACTTTTAATCATCAGGAACTGTTGC
AGCAGGCATTAACTCATCGTAGTGCCAGCAGTAAACATAACGAGCGTTTAGAATTTTTAGGCGACTCTAT
TCTGAGCTACGTTATCGCCAATGCGCTTTATCACCGTTTCCCTCGTGTGGATGAAGGCGATATGAGCCGG
ATGCGCGCCACGCTGGTCCGTGGCAATACGCTGGCGGAACTGGCGCGCGAATTTGAGTTAGGCGAGTGCT
TACGTTTAGGGCCAGGTGAACTTAAAAGCGGTGGATTTCGTCGTGAGTCAATTCTCGCCGACACCGTCGA
AGCATTAATTGGTGGCGTATTCCTCGACAGTGATATTCAAACCGTCGAGAAATTAATCCTCAACTGGTAT
CAAACTCGTTTGGACGAAATTAGCCCAGGCGACAAGCCCAAGGACCCGAAAACGCGCTTGCAAGAATATT
TGCAGGGTCGCCATCTGCCGCTGCCGACTTATCTGGTAGTCCAGGTACGTGGCGAAGCGCACGATCAGGA
ATTTACTATCCACTGCCAGGTCAGCGGCCTGAGTGAACCGGTGGTTGGCACAGGTTCAAGCCGTCGTAAG
GCTGAGCAGGCTGCCGCCGAACAGGCGTTGAAAAAACTGGAGCTGGAATGA SEQ ID NO. 38
Amino Acid
HT115-Q153P-aa
E. coli
MNPIVINRLQRKLGYTFNHQELLQQALTHRSASSKHNERLEFLGDSILSYVIANALYHRFPRVDEGDMSR
MRATLVRGNTLAELAREFELGECLRLGPGELKSGGFRRESILADTVEALIGGVFLDSDIQTVEKLILNWY
QTRLDEISPGDKPKDPKTRLQEYLQGRHLPLPTYLVVQVRGEAHDQEFTIHCQVSGLSEPVVGTGSSRRK
AEQAAAEQALKKLELE

SEQUENCE LISTINGS

As noted above, the instant application contains a full Sequence Listing which has been submitted electronically in ASCII format and is hereby incorporated by reference in its entirety. The following sequences are further provided herewith and are hereby incorporated into the specification in their entirety:

SEQ ID NO. 39
DNA
HT115-D155E
E. coli
ATGAACCCCATCGTAATTAATCGGCTTCAACGGAAGCTGGGCTACACTTTTAATCATCAGGAACTGTTGC
AGCAGGCATTAACTCATCGTAGTGCCAGCAGTAAACATAACGAGCGTTTAGAATTTTTAGGCGACTCTAT
TCTGAGCTACGTTATCGCCAATGCGCTTTATCACCGTTTCCCTCGTGTGGATGAAGGCGATATGAGCCGG
ATGCGCGCCACGCTGGTCCGTGGCAATACGCTGGCGGAACTGGCGCGCGAATTTGAGTTAGGCGAGTGCT
TACGTTTAGGGCCAGGTGAACTTAAAAGCGGTGGATTTCGTCGTGAGTCAATTCTCGCCGACACCGTCGA
AGCATTAATTGGTGGCGTATTCCTCGACAGTGATATTCAAACCGTCGAGAAATTAATCCTCAACTGGTAT
CAAACTCGTTTGGACGAAATTAGCCCAGGCGACAAGCAGAAGGAGCCCAAAACGCGCTTGCAAGAATATT
TGCAGGGTCGCCATCTGCCGCTGCCGACTTATCTGGTAGTCCAGGTACGTGGCGAAGCGCACGATCAGGA
ATTTACTATCCACTGCCAGGTCAGCGGCCTGAGTGAACCGGTGGTTGGCACAGGTTCAAGCCGTCGTAAG
GCTGAGCAGGCTGCCGCCGAACAGGCGTTGAAAAAACTGGAGCTGGAATGA SEQ ID NO. 40
Amino Acid
HT115-D155E-aa
E. coli
MNPIVINRLQRKLGYTFNHQELLQQALTHRSASSKHNERLEFLGDSILSYVIANALYHRFPRVDEGDMSR
MRATLVRGNTLAELAREFELGECLRLGPGELKSGGFRRESILADTVEALIGGVFLDSDIQTVEKLILNWY
QTRLDEISPGDKQKEPKTRLQEYLQGRHLPLPTYLVVQVRGEAHDQEFTIHCQVSGLSEPVVGTGSSRRK
AEQAAAEQALKKLELE SEQ ID NO. 41
DNA
HT115-E38A-ΔS33-R107A-R108A
E. coli
ATGAACCCCATCGTAATTAATCGGCTTCAACGGAAGCTGGGCTACACTTTTAATCATCAGGAACTGTTGC
AGCAGGCATTAACTCATCGTAGTGCCAGTAAACACAATGCCCGCTTGGAATTTTTAGGCGACTCTATTCT
GAGCTACGTTATCGCCAATGCGCTTTATCACCGTTTCCCTCGTGTGGATGAAGGCGATATGAGCCGGATG
CGCGCCACGCTGGTCCGTGGCAATACGCTGGCGGAACTGGCGCGCGAATTTGAGTTAGGCGAGTGCTTAC
GTTTAGGGCCAGGTGAACTTAAAAGCGGTGGATTTGCCGCCGAGTCAATTCTCGCCGACACCGTCGAAGC
ATTAATTGGTGCGTATTCCTCGACAGTGATATTCAAACCGTCGAGAAATTAATCCTCAACTGGTATCAA
ACTCGTTTGGACGAAATTAGCCCAGGCGATAAACAAAAGATCCGAAAACGCGCTTGCAAGAATATTTGC
AGGGTCGCCATCTGCCGCTGCCGACTTATCTGGTAGTCCAGGTACGTGGCGAAGCGCACGATCAGGAATT
TACTATCCACTGCCAGGTCAGCGGCCTGAGTGAACCGGTGGTTGGCACAGGTTCAAGCCGTCGTAAGGCT
GAGCAGGCTGCCGCCGAACAGGCGTTGAAAAAACTGGAGCTGGAATGA SEQ ID NO. 42
Amino Acid
HT115-E38A-ΔS33-R107A-R108A-aa
E. coli
MNPIVINRLQRKLGYTFNHQELLQQALTHRSASKHNARLEFLGDSILSYVIANALYHRFPRVDEGDMSRM
RATLVRGNTLAELAREFELGECLRLGPGELKSGGFAAESILADTVEALIGGVFLDSDIQTVEKLILNWYQ
TRLDEISPGDKQKDPKTRLQEYLQGRHLPLPTYLVVQVRGEAHDQEFTIHCQVSGLSEPVVGTGSSRRKA
EQAAAEQALKKLELE SEQ ID NO. 43
DNA
HT115-E38A-S33A-ΔS34-R107A-R108A
E. coli
ATGAACCCCATCGTAATTAATCGGCTTCAACGGAAGCTGGGCTACACTTTTAATCATCAGGAACTGTTGC
AGCAGGCATTAACTCATCGTAGTGCCGCCAAACACAATGCCCGCTTGGAATTTTTAGGCGACTCTATTCT
GAGCTACGTTATCGCCAATGCGCTTTATCACCGTTTCCCTCGTGTGGATGAAGGCGATATGAGCCGGATG
CGCGCCACGCTGGTCCGTGGCAATACGCTGGCGGAACTGGCGCGCGAATTTGAGTTAGGCGAGTGCTTAC
GTTTAGGGCCAGGTGAACTTAAAAGCGGTGGATTTGCCGCCGAGTCAATTCTCGCCGACACCGTCGAAGC
ATTAATTGGTGGCGTATTCCTCGACAGTGATATTCAAACCGTCGAGAAATTAATCCTCAACTGGTATCAA
ACTCGTTTGGACGAAATTAGCCCAGGCGATAAACAAAAGATCCGAAAACGCGCTTGCAAGAATATTTGC
AGGGTCGCCATCTGCCGCTGCCGACTTATCTGGTAGTCCAGGTACGTGGCGAAGCGCACGATCAGGAATT
TACTATCCACTGCCAGGTCAGCGGCCTGAGTGAACCGGTGGTTGGCACAGGTTCAAGCCGTCGTAAGGCT
GAGCAGGCTGCCGCCGAACAGGCGTTGAAAAAACTGGAGCTGGAATGA SEQ ID NO. 44
Amino Acid
HT115-E38A-S33A-ΔS34-R107A-R108A-aa
E. coli
MNPIVINRLQRKLGYTFNHQELLQQALTHRSAAKHNARLEFLGDSILSYVIANALYHRFPRVDEGDMSRM
RATLVRGNTLAELAREFELGECLRLGPGELKSGGFAAESILADTVEALIGGVFLDSDIQTVEKLILNWYQ
TRLDEISPGDKQKDPKTRLQEYLQGRHLPLPTYLVVQVRGEAHDQEFTIHCQVSGLSEPVVGTGSSRRKA
EQAAAEQALKKLELE SEQUENCE LISTINGS
As noted above, the instant application contains a full Sequence Listing which has been submitted electronically in ASCII format and is hereby incorporated by reference in its entirety. The following sequences are further provided herewith and are hereby incorporated into the specification in their entirety:

SEQ ID NO. 45
DNA
HT115-E38A-ΔA32-ΔS33-ΔS34
*E. coli*
ATGAACCCCATCGTAATTAATCGGCTTCAACGGAAGCTGGGCTACACTTTTAATCATCAGGAACTGTTGC
AGCAGGCATTAACTCATCGTAGTAAACACAATGCCCGCTTGGAATTTTTAGGCGACTCTATTCTGAGCTA
CGTTATCGCCAATGCGCTTTATCACCGTTTCCCTCGTGTGGATGAAGGCGATATGAGCCGGATGCGCGCC
ACGCTGGTCCGTGGCAATACGCTGGCGGAACTGGCGCGCGAATTTGAGTTAGGCGAGTGCTTACGTTTAG
GGCCAGGTGAACTTAAAAGCGGTGGATTTCGTCGTGAGTCAATTCTCGCCGACACCGTCGAAGCATTAAT
TGGTGGCGTATTCCTCGACAGTGATATTCAAACCGTCGAGAAATTAATCCTCAACTGGTATCAAACTCGT
TTGGACGAAATTAGCCCAGGCGATAAACAAAAAGATCCGAAAACGCGCTTGCAAGAATATTTGCAGGGTC
GCCATCTGCCGCTGCCGACTTATCTGGTAGTCCAGGTACGTGGCGAAGCGCACGATCAGGAATTTACTAT
CCACTGCCAGGTCAGCGGCCTGAGTGAACCGGTGGTTGGCACAGGTTCAAGCCGTCGTAAGGCTGAGCAG
GCTGCCGCCGAACAGGCGTTGAAAAAACTGGAGCTGGAATGA SEQ ID NO. 46
Amino Acid
HT115-E38A-ΔA32-ΔS33-ΔS34-aa
*E. coli*
MNPIVINRLQRKLGYTFNHQELLQQALTHRSKHNARLEFLGDSILSYVIANALYHRFPRVDEGDMSRMRA
TLVRGNTLAELAREFELGECLRLGPGELKSGGFRRESILADTVEALIGGVFLDSDIQTVEKLILNWYQTR
LDEISPGDKQKDPKTRLQEYLQGRHLPLPTYLVVQVRGEAHDQEFTIHCQVSGLSEPVVGTGSSRRKAEQ
AAAEQALKKLELE SEQ ID NO. 47
DNA
HT115-E38A-ΔA32-ΔS33-ΔS34-K35V
*E. coli*
ATGAACCCCATCGTAATTAATCGGCTTCAACGGAAGCTGGGCTACACTTTTAATCATCAGGAACTGTTGC
AGCAGGCATTAACTCATCGTAGTGTACACAATGCCCGCTTGGAATTTTTAGGCGACTCTATTCTGAGCTA
CGTTATCGCCAATGCGCTTTATCACCGTTTCCCTCGTGTGGATGAAGGCGATATGAGCCGGATGCGCGCC
ACGCTGGTCCGTGGCAATACGCTGGCGGAACTGGCGCGCGAATTTGAGTTAGGCGAGTGCTTACGTTTAG
GGCCAGGTGAACTTAAAAGCGGTGGATTTCGTCGTGAGTCAATTCTCGCCGACACCGTCGAAGCATTAAT
TGGTGGCGTATTCCTCGACAGTGATATTCAAACCGTCGAGAAATTAATCCTCAACTGGTATCAAACTCGT
TTGGACGAAATTAGCCCAGGCGATAAACAAAAAGATCCGAAAACGCGCTTGCAAGAATATTTGCAGGGTC
GCCATCTGCCGCTGCCGACTTATCTGGTAGTCCAGGTACGTGGCGAAGCGCACGATCAGGAATTTACTAT
CCACTGCCAGGTCAGCGGCCTGAGTGAACCGGTGGTTGGCACAGGTTCAAGCCGTCGTAAGGCTGAGCAG
GCTGCCGCCGAACAGGCGTTGAAAAAACTGGAGCTGGAATGA SEQ ID NO. 48
Amino Acid
HT115-E38A-ΔA32-ΔS33-ΔS34-K35V-aa
*E. coli*
MNPIVINRLQRKLGYTFNHQELLQQALTHRSVHNARLEFLGDSILSYVIANALYHRFPRVDEGDMSRMRA
TLVRGNTLAELAREFELGECLRLGPGELKSGGFRRESILADTVEALIGGVFLDSDIQTVEKLILNWYQTR
LDEISPGDKQKDPKTRLQEYLQGRHLPLPTYLVVQVRGEAHDQEFTIHCQVSGLSEPVVGTGSSRRKAEQ
AAAEQALKKLELE SEQ ID NO. 49
DNA
HT115-E38A-ΔS33-ΔS34-ΔK35
*E. coli*
ATGAACCCCATCGTAATTAATCGGCTTCAACGGAAGCTGGGCTACACTTTTAATCATCAGGAACTGTTGC
AGCAGGCATTAACTCATCGTAGTGCCCACAATGCCCGCTTGGAATTTTTAGGCGACTCTATTCTGAGCTA
CGTTATCGCCAATGCGCTTTATCACCGTTTCCCTCGTGTGGATGAAGGCGATATGAGCCGGATGCGCGCC
ACGCTGGTCCGTGGCAATACGCTGGCGGAACTGGCGCGCGAATTTGAGTTAGGCGAGTGCTTACGTTTAG
GGCCAGGTGAACTTAAAAGCGGTGGATTTCGTCGTGAGTCAATTCTCGCCGACACCGTCGAAGCATTAAT
TGGTGGCGTATTCCTCGACAGTGATATTCAAACCGTCGAGAAATTAATCCTCAACTGGTATCAAACTCGT
TTGGACGAAATTAGCCCAGGCGATAAACAAAAAGATCCGAAAACGCGCTTGCAAGAATATTTGCAGGGTC
GCCATCTGCCGCTGCCGACTTATCTGGTAGTCCAGGTACGTGGCGAAGCGCACGATCAGGAATTTACTAT
CCACTGCCAGGTCAGCGGCCTGAGTGAACCGGTGGTTGGCACAGGTTCAAGCCGTCGTAAGGCTGAGCAG
GCTGCCGCCGAACAGGCGTTGAAAAAACTGGAGCTGGAATGA SEQ ID NO. 50
Amino Acid
HT115-E38A-ΔS33-ΔS34-ΔK35-aa
*E. coli*
MNPIVINRLQRKLGYTFNHQELLQQALTHRSAHNARLEFLGDSILSYVIANALYHRFPRVDEGDMSRMRA
TLVRGNTLAELAREFELGECLRLGPGELKSGGFRRESILADTVEALIGGVFLDSDIQTVEKLILNWYQTR
LDEISPGDKQKDPKTRLQEYLQGRHLPLPTYLVVQVRGEAHDQEFTIHCQVSGLSEPVVGTGSSRRKAEQ
AAAEQALKKLELE -continued SEQUENCE LISTINGS
As noted above, the instant application contains a full Sequence
Listing which has been submitted electronically in ASCII format
and is hereby incorporated by reference in its entirety. The
following sequences are further provided herewith and are hereby
incorporated into the specification in their entirety:

SEQ ID NO. 51
DNA
HT115-E30A
*Verrucomicrobia*
ATGAATCCGCTCGAAGACCGCATCGGTTACAAGTTCCGCAACGCGCTGTTGCTGGAAGAAGCGCTCACGC
ATCCCAGTGTGAGGCACGCGCGCCTGGAGTTTTTGGGCGATGCGGTCCTGCAGCTCGTGATGACGGAACA
CCTGTTCGGGCATTTTAAGAAAGAAGCCGAAGGGACGCTGACGAAACTGCGCTCGCGGCTTGTTTCGCGG
GAGGCCCTCGCCGTTCATGCGGCGACGCTCGAACTGGGACGCTATCTGGCCGTCGGCCGCGGTGAGGACG
CGAGCGGCGGTCGCGAACGCAATTCGACGCTCGCCGACGCTTTCGAGGCGCTCGTCGGAGCGATCTATCT
CGATAGCGATCTGGCCACGGTGCGTCGCTTTATCCTGGATCAGGCAGCGGGCGATCTGGCGCAACTCGTC
GACGAACCGACCGATATCAACCCCGAAGGGTCACCTGCAGGAATTGCTCCAGGCGATTTCGCCCCGCAGCC
CGGTTTACGAAGTGATTTCGCAGACCGGGCCGGAGCACGAAAAGACGTTTGTGATTCGCGCGGTTTGGGA
GGGCATCACGCTCGGGGAGGGAACCGGGCGAAGCAAGAAACAGGCGGAAACGGCCGCCGCCGAGGAGGCG
ATGCGGCAAAAGCGGTGGGAAACGGAAAAGACGTCGACCGCACCTTCTCGGTAG SEQ ID NO. 52
Amino Acid
HT115-E30A-aa
*Verrucomicrobia*
MNPLEDRIGYKFRNALLLEEALTHPSVRHARLEFLGDAVLQLVMTEHLFGHFKKEAEGTLTKLRSRLVSR
EALAVHAATLELGRYLAVGRGEDASGGRERNSTLADAFEALVGAIYLDSDLATVRRFILDQAAGDLAQLV
DEPTDINPKGHLQELLQAISPRSPVYEVISQTGPEHEKTFVIRAVWEGITLGEGTGRSKKQAETAAAEEA
MRQKRWETEKTSTAPSR SEQ ID NO. 53
DNA
HT115-E30A-K12opt
*Verrucomicrobia*
ATGAATCCTTTAGAAGACCGTATTGGGTATAAGTTTCGTAATGCTTTACTGCTGGAAGAAGCTTTGACCC
ACCCATCTGTGCGCCACGCTCGTTTGGAGTTCTTGGGAGACGCGGTGTTACAATTAGTAATGACAGAACA
CCTGTTCGGGCACTTTAAGAAAGAAGCTGAAGGGACTTTAACGAAACTTCGTAGCCGTTTGGTTTCCCGC
GAGGCTCTGGCTGTCCACGCTGCCACTTTGGAACTTGGACGTTATTTGGCTGTGGGCCGTGGCGAGGACG
CATCCGGCGACGTGAGCGTAACTCAACGTTAGCGGACGCCTTCGAGGCTCTGGTGGGCGCGATTTATCT
TGATTCAGACCTGGCAACCGTTCGTCGCTTTATTCTTGATCAGGCTGCAGGGGATTTGGCACAGTTGGTA
GATGAACCGACCGATATTAACCCTAAAGGTCATTTACAGGAACTTTTGCAGGCTATCTCCCCTCGTTCCC
CAGTATATGAAGTTATCTCTCAAACTGGTCCAGAACACGAAAAGACATTCGTAATCCGCGCAGTATGGGA
GGGTATCACTTTAGGGGAGGGAACGGGACGCAGTAAAAAACAAGCTGAGACGGCAGCTGCTGAGGAAGCT
ATGCGCCAAAAGCGTTGGGAGACGGAGAAAACTTCCACGGCCCCTTCCCGTTAA SEQ ID NO. 54
Amino Acid
HT115-E30A-K12opt-aa
*Verrucomicrobia*
MNPLEDRIGYKFRNALLLEEALTHPSVRHARLEFLGDAVLQLVMTEHLFGHFKKEAEGTLTKLRSRLVSR
EALAVHAATLELGRYLAVGRGEDASGGRERNSTLADAFEALVGAIYLDSDLATVRRFILDQAAGDLAQLV
DEPTDINPKGHLQELLQAISPRSPVYEVISQTGPEHEKTFVIRAVWEGITLGEGTGRSKKQAETAAAEEA
MRQKRWETEKTSTAPSR SEQ ID NO. 55
DNA
B. cereus-E58A
*B. cereus*
ATGCCGTACCGAAAATATAGAGAAAAAAAATACGAAACAAAATATCGTGAAGCATTTAAAGTGTTTCAAG
AAAAGATAGGTATTACGTTTACAGATGAAAAATTATTGATTCAAGCATTTACGCATTCATCGTATGTGAA
TGAGCATCGAAAAAAACCGCATGAAGACAACGCCCGCCTCGAATTTCTTGGAGATGCAGTATTGGAACTT
ACTGTATCGCAGTATCTGTTTCAAAAATATCCGACAATGAGCGAAGGAGAGTTAACAAAACTACGTGCAG
CTATTGTATGTGAGCCATCTCTTGTTCGTTTTGCGAACGAATTGTCATTTGGTAGCCTTGTTTTATTAGG
AAAAGGTGAAGAAATGACAGGTGGACGTGAACGACCAGCTTTATTAGCGGATGTCTTTGAAGCGTTTATT
GGTGCCCTTTATCTTGATCAAGGGTTAGAAACAGTTTGGGAATTCTTAAAAGAAATTGTATATCCGAAAA
TTAATGAGGGTGCTTTTTCTCATGTGATGGATTATAAGAGTCAGTTACAAGAATTGATTCAGCGTGATGG
TAGTGGCAATGTTGAGTATCAAATTTTGCAAGAAAAAGGACCAGCTCACAATCGAGAATTTGTGTCACGT
GTTACGTTAAATAACGTAGCTTTAGGTCTTGGTAGTGGTAAGTCGAAAAAAGAAGCAGAGCAACAAGCTG
CTGCAGAAGCATTGAAAAAATTAAAAGAACAACTATAA -continued

| SEQUENCE LISTINGS |
| --- |
| As noted above, the instant application contains a full Sequence Listing which has been submitted electronically in ASCII format and is hereby incorporated by reference in its entirety. The following sequences are further provided herewith and are hereby incorporated into the specification in their entirety: |

SEQ ID NO. 56
Amino Acid
*B. cereus*-E58A-aa
*B. cereus*
MPYRKYREKKYETKYREAFKVFQEKIGITFTDEKLLIQAFTHSSYVNEHRKKPHEDNARLEFLGDAVLEL
TVSQYLFQKYPTMSEGELTKLRAAIVCEPSLVRFANELSFGSLVLLGKGEEMTGGRERPALLADVFEAFI
GALYLDQGLETVWEFLKEIVYPKINEGAFSHVMDYKSQLQELIQRDGSGNVEYQILQEKGPAHNREFVSR
VTLNNVALGLGSGKSKKEAEQQAAAEALKKLKEQL SEQ ID NO. 57
DNA
*B. subtilis*-E59A
*B. cereus*
ATGTCAAAACACTCACATTATAAAGATAAAAAAAAGTTCTATAAAAAAGTAGAACAATTTAAAGAGTTTC
AAGAACGGATTTCGGTTCACTTTCAAAATGAAAAGCTTTTGTATCAAGCATTTACACATTCATCTTATGT
GAATGAGCATCGGAAAAAGCCGTATGAGGACAACGCTAGACTTGAATTTTTAGGTGACGCTGTTTTGGAA
CTGACGATCTCCAGATTCTTATTTGCCAAATACCCGGCTATGAGTGAAGGAGATTTGACGAAATTGAGAG
CCGCAATTGTTTGCGAACCGTCTCTCGTTTCATTGGCTCACGAGCTGTCATTCGGCGATCTTGTCCTGTT
GGGTAAAGGCGAGGAAATGACAGGCGGAAGAAAGCGTCCTGCTCTATTGGCGGATGTTTTTGAGGCATTT
ATCGGAGCCTTGTACCTTGACCAAGGATTAGAGCCGGTCGAAAGTTTCTTAAAAGTTTATGTGTTCCCTA
AAATTAACGATGGTGCTTTTTCTCATGTGATGGATTTCAAAAGCCAGCTGCAGGAATACGTGCAGCGGGA
CGGCAAAGGCTCTCTGGAGTATAAAATCTCCAACGAAAAAGGACCTGCGCACAACCGTGAATTTGAAGCC
ATCGTATCTCTAAAAGGTGAACCACTCGGAGTCGGAAACGGCCGTTCAAAGAAAGAAGCCGAACAGCACG
CTGCTCAGGAAGCTTTAGCTAAATTGCAAAAACACCATACGAAACAATAA SEQ ID NO. 58
Amino Acid
*B. subtilis*-E59A-aa
*B. subtilis*
MSKHSHYKDKKKFYKKVEQFKEFQERISVHFQNEKLLYQAFTHSSYVNEHRKKPYEDNARLEFLGDAVLE
LTISRFLFAKYPAMSEGDLTKLRAAIVCEPSLVSLAHELSFGDLVLLGKGEEMTGGRKRPALLADVFEAF
IGALYLDQGLEPVESFLKVYVFPKINDGAFSHVMDFKSQLQEYVQRDGKGSLEYKISNEKGPAHNREFEA
IVSLKGEPLGVGNGRSKKEAEQHAAQEALAKLQKHHTKQ SEQ ID NO. 59
DNA
*B. cereus*-E137K
*B. cereus*
ATGCCGTACCGAAAATATAGAGAAAAAAAATACGAAACAAAATATCGTGAAGCATTTAAAGTGTTTCAAG
AAAAGATAGGTATTACGTTTACAGATGAAAAATTATTGATTCAAGCATTTACGCATTCATCGTATGTGAA
TGAGCATCGAAAAAAACCGCATGAAGATAATGAGCGTCTTGAATTTCTTGGAGATGCAGTATTGGAACTT
ACTGTATCGCAGTATCTGTTTCAAAAATATCCGACAATGAGCGAAGGAGAGTTAACAAAACTACGTGCAG
CTATTGTATGTGAGCCATCTCTTGTTCGTTTTGCGAACGAATTGTCATTTGGTAGCCTTGTTTTATTAGG
AAAAGGTGAAGAAATGACAGGTGGACGTGAACGACCAGCTTTATTAGCGGATGTCTTCAAGGCCTTCATC
GGTGCCCTTTATCTTGATCAAGGGTTAGAAACAGTTTGGGAATTCTTAAAAGAAATTGTATATCCGAAAA
TTAATGAGGGTGCTTTTTCTCATGTGATGGATTATAAGAGTCAGTTACAAGAATTGATTCAGCGTGATGG
TAGTGGCAATGTTGAGTATCAAATTTTGCAAGAAAAAGGACCAGCTCACAATCGAGAATTTGTGTCACGT
GTTACGTTAAATAACGTAGCTTTAGGTCTTGGTAGTGGTAAGTCGAAAAAAGAAGCAGAGCAACAAGCTG
CTGCAGAAGCATTGAAAAAATTAAAAGAACAACTATAA SEQ ID NO. 60
Amino Acid
*B. cereus*-E137K-aa
*B. cereus*
MPYRKYREKKYETKYREAFKVFQEKIGITFTDEKLLIQAFTHSSYVNEHRKKPHEDNERLEFLGDAVLEL
TVSQYLFQKYPTMSEGELTKLRAAIVCEPSLVRFANELSFGSLVLLGKGEEMTGGRERPALLADVFKAFI
GALYLDQGLETVWEFLKEIVYPKINEGAFSHVMDYKSQLQELIQRDGSGNVEYQILQEKGPAHNREFVSR
VTLNNVALGLGSGKSKKEAEQQAAAEALKKLKEQL SEQ ID NO. 62
DNA
*Ecoli*-tetsac
Artificial
GAACTGTTGCAGCAGGCATTAACTCATCGTAGTGCCAGCAGTAAACATAACGAGTCCTAATTTTTGTTGA
CACTCTATC SEQUENCE LISTINGS
As noted above, the instant application contains a full Sequence Listing which has been submitted electronically in ASCII format and is hereby incorporated by reference in its entirety. The following sequences are further provided herewith and are hereby incorporated into the specification in their entirety:

SEQ ID NO. 63
DNA
*Ecoli*-tet-sacB38R1
Artificial
CGCATTGGCGATAACGTAGCTCAGAATAGAGTCGCCTAAAAATTCTAAACGATCAAAGGGAAAACTGTCC
ATATGC SEQ ID NO. 64
DNA
*Ecoli*-oligo-E38A
Artificial
GTAGCTCAGAATAGAGTCGCCTAAAAATTCGAAGCGGGCATTGTGTTTACTGCTGGCACTACGATGAGTT
AATGC SEQ ID NO. 65
DNA
*Ecoli*-E38A-1F
Artificial
AGTAAACACAATGCCCGCTTC SEQ ID NO. 66
DNA
*Ecoli*-E38A-1R
Artificial
ATGCTTCGACGGTGTCGG SEQ ID NO. 67
DNA
*Ecoli*-tet-sacB117F1
Artificial
CTTAAAAGCGGTGGATTTCGTCGTGAGTCAATTCTCGCCGACACCGTCGAATCCTAATTTTTGTTGACAC
TCTATC SEQ ID NO. 68
DNA
*Ecoli*-tet-sacB117R1
Artificial
TAATTTCTCGACGGTTTGAATATCACTGTCGAGGAATACGCCACCAATTAATGCATCAAAGGGAAAACTG
TCCATATGC SEQ ID NO. 69
DNA
*Ecoli*-oligo-E117K
Artificial
TTGAATATCACTGTCGAGGAATACGCCACCGATGAAAGCCTTCACGGTGTCGGCGAGAATTGACTCACGA
CGAAA SEQ ID NO. 70
DNA
*Ecoli*-E117K-1F
Artificial
GACACCGTGAAGGCTTTCATC SEQ ID NO. 71
DNA
*Ecoli*-E117K-1R
Artificial
TTCAACGCCTGTTCGGC SEQ ID NO. 72
DNA
*Ecoli*-oligo-E38A-F2
Artificial
GTAGCTCAGAATAGAGTCGCCTAAAAATTCCAAGCGGGCATTGTGTTTACTGCTGGCACTACGATGAGTT
AATGC SEQ ID NO. 73
DNA
*Ecoli*-E38A-2F
Artificial
AGTAAACACAATGCCCGCTTG

SEQUENCE LISTINGS

As noted above, the instant application contains a full Sequence Listing which has been submitted electronically in ASCII format and is hereby incorporated by reference in its entirety. The following sequences are further provided herewith and are hereby incorporated into the specification in their entirety:

SEQ ID NO. 74
DNA
*Ecoli*-oligo-E117K-F2
Artificial
TTGAATATCACTGTCGAGGAATACGCCACCGATCAAAGCCTTCACGGTGTCGGCGAGAATTGACTCACGA
CGAAA SEQ ID NO. 75
DNA
*Ecoli*-E117K-2F
Artificial
GACACCGTGAAGGCTTTGATC SEQ ID NO. 76
DNA
*Ecoli*-tet-sacB-E65F1
Artificial
AGCTACGTTATCGCCAATGCGCTTTATCACCGTTTCCCTCGTGTGGATGAATCCTAATTTTTGTTGACAC
TCTATC SEQ ID NO. 77
DNA
*Ecoli*-tet-sacB-E65R1
Artificial
CGCCAGCGTATTGCCACGGACCAGCGTGGCGCGCATCCGGCTCATATCGCCATCAAAGGGAAAACTGTCC
ATATGC SEQ ID NO. 78
DNA
*Ecoli*-oligo-E65A-F1
Artificial
CAGCGTGGCGCGCATCCGGCTCATATCGCCGGCGTCGACGCGGGGGAAACGGTGATAAAGCGCATTGGCG
ATAAC SEQ ID NO. 79
DNA
*Ecoli*-E65A-1F
Artificial
TTTCCCCCGCGTCGACGC SEQ ID NO. 80
DNA
JD-5
Artificial
ACCGGTAAACTGAAACTGCA SEQ ID NO. 81
DNA
Tet-sacB-JD-R1
Artificial
TGGCAAGACTGGCATGATAAG SEQ ID NO. 82
DNA
JD-3
Artificial
TGGAGATTTTCTGCCCCAG SEQ ID NO. 83
RNA
TMVU1-MP-F6-RNA21
Artificial
CAGUUCAAGGUCGUUCCCAAU SEQ ID NO. 84
RNA
TMVU1-MP-F7-RNA23
Artificial
UGAAGAUGUCAGCGGGUUUCUGU -continued SEQUENCE LISTINGS
As noted above, the instant application contains a full Sequence Listing which has been submitted electronically in ASCII format and is hereby incorporated by reference in its entirety. The following sequences are further provided herewith and are hereby incorporated into the specification in their entirety:

SEQ ID NO. 85
RNA
TMVU1-MP-R6-RNA25
Artificial
CCAGACGUUUUUCAUCGCGUCCUGG

SEQ ID NO. 86
RNA
TMVU1-MP-R7-RNA27
Artificial
ACGACUUCUUCUGUAAGUUCCAUGGGC

SEQ ID NO. 87
RNA
TMVU1-MP-F6-RNA29
Artificial
CAGUUCAAGGUCGUUCCCAAUUAUGCUAU

SEQ ID NO. 88
DNA
Pveg-F1
Artificial
ATCACGAGGCCCTTTCGTCTTCAAGGGAGTTCTGAGAATTGGTATGC SEQ ID NO. 89
DNA
Pveg-R1
Artificial
ACACCTCCTTTACTACATTTATTGTACAACACGAGC SEQ ID NO. 90
DNA
Pveg-F2
Artificial
ATCACGAGGCCCTTTCGTCTTCAAGAAGCTTGGAGTTCTGAGAATTGGTATGC SEQ ID NO. 91
DNA
Pveg-R2
Artificial
ACGCGATCCCCGGGTACCGAGCTCGCTCGAGACACCTCCTTTACTACATTTATTGTACAACACGAGC SEQ ID NO. 92
DNA
Bc-E58A-F1
Artificial
ACAATAAATGTAGTAAAGGAGGTGTATGCCGTACCGAAAATATAGAG SEQ ID NO. 93
DNA
Bc-E58A-R1
Artificial
GAGGCGGGCGTTGTCTTCATGCGGTTTTTTCG SEQ ID NO. 94
DNA
Bc-E58A-F2
Artificial
ACCGCATGAAGACAACGCCCGCCTCGAATTTCTTGGAGATGCAGTATTG SEQ ID NO. 95
DNA
Bc-E58A-R2
Artificial
ACGCGATCCCCGGGTACCGAGCTCGTTATAGTTGTTCTTTTAATTTTTTCAATG SEQ ID NO. 96
DNA
Bc-E137K-R1
Artificial
GATGAAGGCCTTGAAGACATCCGCTAATAAAGCTGG

SEQUENCE LISTINGS

As noted above, the instant application contains a full Sequence Listing which has been submitted electronically in ASCII format and is hereby incorporated by reference in its entirety. The following sequences are further provided herewith and are hereby incorporated into the specification in their entirety:

SEQ ID NO. 97
DNA
Bc-E137K-F1
Artificial
AGCGGATGTCTTCAAGGCCTTCATCGGTGCCCTTTATCTTGATCAAG SEQ ID NO. 98
DNA
pAD-E58A-F1
Artificial
CAATAAATGTAGTAAAGGAGGTGTCATGCCGTACCGAAAATATAGAG SEQ ID NO. 99
DNA
pAD-E58A-Artificial
GCGAGCTCGGTACCCGGGGATCGCGTTATAGTTGTTCTTTTAATTTTTTCAATG SEQ ID NO. 100
DNA
Eco-F1
Artificial
ACGAGGCCCTTTCGTCTTCAA SEQ ID NO. 101
DNA
SglyA-R1
Artificial
CATGTTCGCTTGTGCACCA SEQ ID NO. 102
DNA
Ae-JD-5
Artificial
AACTAACGACATCCCCTGTCGT SEQ ID NO. 103
DNA
Ae-JD-3
Artificial
CGCAGCTTGTTCAGCACCAT SEQ ID NO. 104
DNA
TMVMP-probe1s
Artificial
TCTCGGATCTTACTACACAGCAGCTGCAAAGAAAAGATTTCAGTT SEQ ID NO. 105
DNA
TMVMP-probe2as
Artificial
TCCTGGGTGGTTATAGCATAATTGGGAACGACCTTGAACTGAAAT SEQ ID NO. 106
DNA
TMVMP-probe3s
Artificial
CACCCAGGACGCGATGAAAAACGTCTGGCAAGTTTTAGTTAATAT SEQ ID NO. 107
DNA
TMVMP-probe4as
Artificial
AGCGGACAGAAACCCGCTGACATCTTCACATTTCTAATATTAACT SEQ ID NO. 108
DNA
TMVMP-probe5s
Artificial
CTGTCCGCTTTCTCTGGAGTTTGTGTCGGTGTGTATTGTTTATAG SEQUENCE LISTINGS
As noted above, the instant application contains a full Sequence Listing which has been submitted electronically in ASCII format and is hereby incorporated by reference in its entirety. The following sequences are further provided herewith and are hereby incorporated into the specification in their entirety:

SEQ ID NO. 109
DNA
TMVMP-probe6as
Artificial
CCCTCCGTCTCTCACGTTTGTAATCTTCTCTCTCAAACCTAATTT SEQ ID NO. 110
DNA
TMVMP-probe8as
Artificial
CTTTGCAAGCCTGATCGACATAGGGACATCTTCCATGAACTCATC SEQ ID NO. 111
DNA
TMVMP-probe9s
Artificial
GTTTCGATCTCGAACCGGAAAAAAGAGTGATGTCCGCAAAGGGAA SEQ ID NO. 112
DNA
TMVU1-MP-F6-21
Artificial
CAGTTCAAGGTCGTTCCCAAT

SEQ ID NO. 113
DNA
TMVU1-MP-R6-21
GTTTTTCATCGCGTCCTGGGT

SEQ ID NO. 114
DNA
TMVU1-MP-F7-21
Artificial
AAGATGTCAGCGGGTTTCTGT

SEQ ID NO. 115
DNA
TMVU1-MP-R7-21
Artificial
CTTCTTCTGTAAGTTCCATGG

SEQ ID NO. 116
DNA
TMVU1-MP-F7-21
Artificial
AAGATGTCAGCGGGTTTCTGT

SEQ ID NO. 117
DNA
TMVU1-MP-R7-21
Artificial
CTTCTTCTGTAAGTTCCATGG

SEQ ID NO. 118
DNA
TMVU1-MP-F4
Artificial
CCAGGACGCGATGAAAAACG

SEQ ID NO. 119
DNA
TMVU1-MP-R4
Artificial
GGACAGAAACCCGCTGACAT

SEQ ID NO. 120
DNA
Ec-16SrRNA-F1
Artificial
GAATGCCACGGTGAATACGTT

SEQUENCE LISTINGS
As noted above, the instant application contains a full Sequence Listing which has been submitted electronically in ASCII format and is hereby incorporated by reference in its entirety. The following sequences are further provided herewith and are hereby incorporated into the specification in their entirety:

SEQ ID NO. 121
DNA
Ec-16SrRNA-R1
Artificial
ACCCACTCCCATGGTGTGA

---

What is claimed is:

1. A genetically modified cell expressing a heterologous polynucleotide sequence operably linked to a promoter sequence encoding an RNase III mutant from *E. coli* or *Enterobacter* adapted for enhanced generation of small RNA (sRNA) from catalytic cutting of double stranded RNA (dsRNA), wherein said RNase III mutant comprises:
an E38A-R107A-R108A RNase III mutant, wherein a glutamic acid is replaced with an alanine at residue 38, and an arginine is replaced with an alanine at residue 107, and an arginine is replaced with an alanine at residue 108, or a homologous RNase III mutant thereof, wherein the homologous RNase III's wild-type sequence includes the conserved residues E38, R107 and R108.

2. The genetically modified cell of claim 1, wherein said genetically modified cell is selected from the group consisting of: a genetically modified prokaryotic cell, and a genetically modified eukaryotic cell.

3. The genetically modified cell of claim 1, wherein said heterologous polynucleotide sequence operably linked to a promoter sequence encoding an RNase III mutant is selected from:
a heterologous polynucleotide sequence, operably linked to a promoter sequence encoding an E38A-R107A-R108A RNase III mutant according to SEQ ID NO. 7, or a fragment thereof;
a heterologous polynucleotide sequence, operably linked to a promoter sequence encoding an E38A-R107A-R108A RNase III mutant according to SEQ ID NO. 11, or a fragment thereof; and
a heterologous polynucleotide sequence, operably linked to a promoter sequence encoding an E38A-R107A-R108A RNase III mutant according to SEQ ID NO. 15, or a fragment thereof.

4. The genetically modified cell of claim 1, wherein said heterologous polynucleotide sequence operably linked to a promoter sequence encoding an RNase III mutant is selected from:
a heterologous polynucleotide sequence, operably linked to a promoter sequence encoding an E38A-R107A-R108A RNase III mutant polypeptide according to SEQ ID NO. 8, or a fragment thereof;
a heterologous polynucleotide sequence, operably linked to a promoter sequence encoding an E38A-R107A-R108A RNase III mutant polypeptide according to SEQ ID NO. 12, or a fragment thereof; and
a heterologous polynucleotide sequence, operably linked to a promoter sequence encoding an E38A-R107A-R108A RNase III mutant polypeptide according to SEQ ID NO. 16, or a fragment thereof.

5. The genetically modified cell of claim 1, wherein the E38A-R107A-R108A RNase III mutant exhibits discrete dsRNA cutting size preferences of 22 and 23 nucleotides (nt).

6. The genetically modified cell of claim 1, wherein said genetically modified cell co-expresses a heterologous polynucleotide sequence operably linked to a promoter sequence encoding a dsRNA.

7. The genetically modified cell of claim 6, wherein said co-expressed dsRNA comprises a dsRNA directed to an essential pathogen gene.

8. The genetically modified cell of claim 7, wherein said essential pathogen gene comprises an essential viral pathogen gene.

9. The genetically modified cell of claim 1, wherein said genetically modified cell is introduced to a target host and cuts said co-expressed dsRNA into sRNA which initiates an RNA interference (RNAi) response pathway in said target host.

10. The genetically modified cell of claim 9, wherein said RNAi response pathway in said target host is initiated independently of said DICER enzyme.

11. A composition comprising an E38A-R107A-R108A RNase III mutant from *E. coli* or *Enterobacter*, wherein a glutamic acid is replaced with an alanine at residue 38, and an arginine is replaced with an alanine at residue 107, and an arginine is replaced with an alanine at residue 108.

12. The composition of claim 11, wherein said E38A-R107A-R108A RNase III mutant exhibits at least one of the following enhanced characteristics compared to a wild type RNase III:
a discrete dsRNA cutting size preferences of 22, and 23 nucleotides (nt);
enhanced stabilization of dsRNA cutting patterns; and
enhanced catalytic efficiency of dsRNA cutting.

13. The composition of claim 11, wherein said E38A-R107A-R108A RNase III mutant comprises at least one of the following:
a polynucleotide sequence encoding an E38A-R107A-R108A RNase III mutant according to SEQ ID NO. 7;
a polynucleotide sequence encoding an E38A-R107A-R108A RNase III mutant according to SEQ ID NO. 11;
a polynucleotide sequence encoding an E38A-R107A-R108A RNase III mutant according to SEQ ID NO. 15;
an amino acid sequence encoding an E38A-R107A-R108A RNase III mutant according to SEQ ID NO. 8;
an amino acid sequence encoding E38A-R107A-R108A RNase III mutant according to SEQ ID NO. 12; and
an amino acid sequence encoding E38A-R107A-R108A RNase III mutant according to SEQ ID NO. 16.

14. The composition of claim 11, wherein said E38A-R107A-R108A RNase III mutant is co-expressed in a prokaryotic or eukaryotic cell with a heterologous polynucleotide sequence operably linked to a promoter sequence encoding a dsRNA.

15. The composition of claim 14, wherein said co-expressed dsRNA comprises a dsRNA directed to an essential pathogen gene.

16. The composition of claim 15, wherein said essential pathogen gene comprises an essential viral pathogen gene.

17. The composition of claim 16, wherein the cell comprises a bacteria that is introduced to a target host and wherein the RNase III mutant cuts said co-expressed dsRNA into 22 and 23 nucleotides (nt) sRNA fragments that initiate an RNA interference (RNAi) response pathway in said target host.

18. The composition of claim 17, wherein said RNAi response pathway in said target host is initiated independently of a DICER enzyme.

19. A composition comprising polynucleotide sequence operably linked to a promoter sequence encoding an E38A-R107A-R108A RNase III mutant selected from:
an E38A-R107A-R108A RNase III mutant according to SEQ ID NO. 7, or a fragment thereof;
an E38A-R107A-R108A RNase III mutant according to SEQ ID NO. 11, or a fragment thereof;
an E38A-R107A-R108A RNase III mutant according to SEQ ID NO. 15, or a fragment thereof.

20. A composition comprising an E38A-R107A-R108A RNase III mutant polypeptide mutant selected from:
an E38A-R107A-R108A RNase III mutant polypeptide according to SEQ ID NO. 12, or a fragment thereof;

an E38A-R107A-R108A RNase III mutant polypeptide according to SEQ ID NO. 16, or a fragment thereof;

an E38A-R107A-R108A RNase III mutant polypeptide according to SEQ ID NO. 8 or a fragment thereof.

\* \* \* \* \*